United States Patent
Bang et al.

(10) Patent No.: US 11,180,496 B2
(45) Date of Patent: Nov. 23, 2021

(54) 1H-PYRAZOLOPYRIDINE DERIVATIVE AND PHARMACEUTICAL COMPOSITION COMPRISING THE SAME

(71) Applicant: Daewoong Pharmaceutical Co., Ltd., Gyeonggi-do (KR)

(72) Inventors: Keuk-Chan Bang, Gyeonggi-do (KR); Deok Ki Eom, Gyeonggi-do (KR); Joon Seok Park, Gyeonggi-do (KR)

(73) Assignee: Daewoong Pharmaceutical Co., Ltd., Gyeonggi-do (KR)

( * ) Notice: Subject to any disclaimer, the term of this patent is extended or adjusted under 35 U.S.C. 154(b) by 0 days.

(21) Appl. No.: 16/629,392

(22) PCT Filed: Jul. 12, 2018

(86) PCT No.: PCT/KR2018/007885
§ 371 (c)(1),
(2) Date: Jan. 8, 2020

(87) PCT Pub. No.: WO2019/013562
PCT Pub. Date: Jan. 17, 2019

(65) Prior Publication Data
US 2020/0140432 A1 May 7, 2020

(30) Foreign Application Priority Data

Jul. 12, 2017 (KR) .................. 10-2017-0088679
Jul. 9, 2018 (KR) .................. 10-2018-0079611

(51) Int. Cl.
*C07D 471/04* (2006.01)

(52) U.S. Cl.
CPC ................. *C07D 471/04* (2013.01)

(58) Field of Classification Search
CPC .................................................. C07D 471/04
See application file for complete search history.

(56) References Cited

U.S. PATENT DOCUMENTS

| 10,870,652 | B2* | 12/2020 | Hudson | .................. A61P 35/00 |
| 2014/0221333 | A1 | 8/2014 | De Man et al. | |
| 2017/0008899 | A1 | 1/2017 | De Man et al. | |
| 2019/0315758 | A1 | 10/2019 | Li et al. | |
| 2019/0367524 | A1 | 12/2019 | Cai et al. | |

FOREIGN PATENT DOCUMENTS

| CN | 106588937 A | 4/2017 |
| CN | 106831787 A | 6/2017 |
| KR | 2014-0068020 | 6/2014 |
| WO | WO-02/50071 A1 | 6/2002 |
| WO | WO-2005/056785 | 6/2005 |
| WO | WO-2005/066335 | 7/2005 |
| WO | WO-2008/039218 A2 | 4/2008 |
| WO | WO-2010/065898 A2 | 6/2010 |
| WO | WO-2013/010380 A1 | 1/2013 |
| WO | WO-2014/022569 A1 | 2/2014 |
| WO | WO-2014/036016 A1 | 3/2014 |
| WO | WO-2014/055934 A2 | 4/2014 |
| WO | WO-2015/061247 A2 | 4/2015 |
| WO | WO-2015/095099 A1 | 6/2015 |
| WO | 2016/210165 | * 12/2016 |
| WO | WO-2016/210165 | 12/2016 |
| WO | WO-2017/077507 | 5/2017 |
| WO | WO-2018/092047 | 5/2018 |

OTHER PUBLICATIONS

Leipe et al., "Role of Th17 Cells in Human Autoimmune Arthritis" Arthritis & Rheumatism, vol. 62, No. 10, Oct. 2010, pp. 2876-2885.
Sahu et al., "ITK Inhibitors in Inflammation and Immune-Mediated Disorders", Current Topics in Medicinal Chemistry, 9, 2009, pp. 690-703.
Horwood et al., "Bruton's Tyrosine Kinase is Required for Lipopolysaccharide-induced Tumor Necrosis Factor α Production", J. Exp. Med. Vol. 197, 2003, pp. 1603-1611.
Fowell et al., "Impaired NFATc Translocation and Failure of Th2 Development in Itk-Deficient CD4+ T Cells", Immunity, vol. 11, Oct. 1999, pp. 399-409.
Zhong et al., "Targeting Interleukin-2-inducible T-cell Kinase (ITK) and Resting Lymphocyte Kinase (RLK) Using a Novel Covalent Inhibitor PRN694", The Journal of Biological Chemistry, vol. 290, No. 10, Mar. 6, 2015, pp. 5960-5978.
Ho Yin Lo, "Itk Inhibitors: A Patent Review", Expert Opinion on Therapeutic Patents, vol. 20, Issue 4, pp. 459-469.
Schaeffer et al., "Mutation of Tec Family Kinases Alters T Helper Cell Differentiation", Nature Immunology, vol. 2, 2001, pp. 1183-1188.
Iwaki et al., "Btk Plays a Crucial Role in the Amplification of FcεRi-mediated Mast Cell Activation by Kit", The Journal of Biological Chemistry, vol. 280, No. 48, Dec. 2, 2005, pp. 40261-40270.
Gomez-Rodriguez et al., "Itk-mediated Integration of T Cell Receptor and Cytokine Signaling Regulates the Balance Between Th17 and Regulatory T Cells", J. Exp. Med., vol. 211, No. 3, pp. 529-543.
Search Report and Written Opinion in International Application No. PCT/KR2018/007885 dated Oct. 26, 2018, 14 pages (English translation of Search Report only).
Office Action in JP Application No. 2020-501212 dated Jan. 12, 2021, 6 pages.
Extended European Search Report in EP Application No. 18832639.1 dated Feb. 25, 2021, 9 pages.

* cited by examiner

*Primary Examiner* — D Margaret M Seaman
(74) *Attorney, Agent, or Firm* — Marshall, Gerstein & Borun LLP

(57) ABSTRACT

The present invention relates to a novel 1H-pyrazolopyridine derivative and a pharmaceutical composition containing the same. The 1H-pyrazolopyridine derivative and the pharmaceutical composition containing the same can be usefully used for the prevention or treatment of autoimmune diseases or cancer.

9 Claims, No Drawings

1H-PYRAZOLOPYRIDINE DERIVATIVE AND PHARMACEUTICAL COMPOSITION COMPRISING THE SAME

CROSS-REFERENCE TO RELATED APPLICATION(S)

This application claims priority to or the benefit of Korean Patent Application No. 10-2017-0088679 filed with the Korean Intellectual Property Office on Jul. 12, 2017, and Korean Patent Application No. 10-2018-0079611 filed with the Korean Intellectual Property Office on Jul. 9, 2018, the disclosures of which are incorporated herein by reference in their entirety.

TECHNICAL FIELD

The present invention relates to a novel 1H-pyrazolopyridine derivative useful as a BTK (Bruton's Tyrosince Kinase) inhibitor and a pharmaceutical composition comprising the same.

BACKGROUND ART

BTK (Bruton's Tyrosince Kinase) and ITK (Interleukin-2 Tyrosine Kinase) are a type of tyrosine kinase that does not have TEC family receptors, together with Tec (tyrosine kinase expressed in hepatocellular carcinoma) and RLK (Resting Lymphocyte Kinase) and BMX (Bone-Marrow tyrosine kinase gene on chromosome X), which act on various immune responses.

BTK functions as a regulator of mature B-cell activation, signaling, and survival as well as early B-cell development. The B-cells are signaled by a B-cell receptor (BCR) that recognizes an antigen attached to the surface of an antigen-presenting cell and activated into mature antibody-producing cells. However, abnormal signaling by BCR may lead to abnormal B-cell proliferation and pathological autoantibody formation, which can induce cancer, autoimmune and/or inflammatory diseases. Thus, in abnormal B-cell proliferation, BTK deficiency can block signaling through BCR. Consequently, inhibition of BTK may block the B-cell mediated disease process, and thus the use of BTK inhibitors may be a useful approach to the treatment of B-cell mediated diseases.

In addition, BTK can be expressed by B-cells as well as other cells that may be associated with the diseases. As one example, BTK is an important component of Fc-gamma signaling in bone marrow cells, which is expressed by mast cells. Specifically, it is known that BTK-deficient bone marrow-derived mast cells exhibit impaired antigen-induced degranulation, and thus inhibition of BTK activity is useful for treating pathological mast cell responses such as allergy and asthma (Iwaki et al. J. Biol. Chem. 2005 280: 40261). Further, it is known that monocytes from XLA patients, in which BTK activity is absent, show decreased TNF alpha production following stimulation, and TNF alpha-mediated inflammation can be suppressed by BTK inhibitors (see Horwood et al. J. Exp. Med. 197: 1603, 2003).

ITK is expressed not only in T cells but also in NK cells and mast cells, and plays an important role in the production of important cytokines such as IL-2, IL-4, IL-5, IL-10, IL-13 and IL-17 and T-cell proliferation (Schaeffer et al. Nat. Immune 2001, 2, 1183; Fowell et al. Immunity, 1999, 11, 399). T cells are activated by TCR signaling, and the activated T cells produce inflammatory cytokines and activate B cells and macrophages to cause autoimmune diseases such as rheumatoid arthritis (RA) (Sahu N. et al. Curr Top Med Chem. 2009, 9, 690). Previously, it has been known that T cells are activated as Th1 cells, causing RA disease, but recently, it has been reported that Th17/Treg as well as Th1 cells play a role in the pathogenesis of RA (J Leipe J. et al. Arthritis Rheum. 2010, 62, 2876). Further, ITK has been previously developed as an immunotherapeutic drug target such as asthma, but it has not developed as a therapeutic for RA (Lo H. Y Expert Opin Ther Pat. 2010, 20, 459). However, it has recently been reported that the development of Th17 and Treg cells is regulated via ITK−/− mice, and it offers sufficient potential as a therapeutic target for RA. (Gomez-Rodriguez J. et al. J. Exp. Med. 2014, 211, 529).

In studies using the ITK inhibitor PRN694, it has been reported on the reduction of TNF-α, which is a representative inflammatory cytokine of RA disease, confirming that it is likely to be developed as a therapeutic agent by regulating Th17 expression via ITK inhibition (Zhong Y. ey al. THE JOURNAL OF BIOLOGICAL CHEMISTRY 2015, 290, 5960).

At present, there is no case that has been developed as a substance that double-inhibits BTK and ITK, but as a BTK inhibitor, WO2008/039218 discloses 4-aminopyrazolo[3,4-d]pyrimidinylpiperidine derivatives, WO2015/061247 discloses hetero compounds such as pyridine, pyrimidine, pyrazine and pyridazine compounds, and WO2014/055934 discloses pyrimidinylphenylacrylamide derivatives. As an ITK inhibitor, WO2005/066335 discloses aminobenzimidazoles, WO2005/056785 discloses pyridones, WO2002/050071 discloses aminothiazole derivatives, and recently, WO2014/036016 discloses benzimidazole derivatives.

Therefore, the present inventors have studied to develop a novel compound, and as a result, it was confirmed that a compound having a chemical structure different from that of BTK and ITK inhibitors reported so far has excellent BTK and ITK dual-activity inhibitory effects, thereby completing the present invention. The compounds belonging to the present invention mainly have BTK and ITK inhibitory activity by themselves, but after being absorbed into the body, the possibility of exhibiting pharmacological action by a specific body environment or a metabolic process product as an agonist is not excluded.

DETAILED DESCRIPTION OF THE INVENTION

Technical Problem

It is an object of the present invention to provide a 1H-pyrazolopyridine derivative useful as a BTK inhibitor and a pharmaceutical composition comprising the same.

Technical Solution

In order to achieve the above objects, one embodiment of the present invention provides a compound represented by the following Chemical Formula 1, or a pharmaceutically acceptable salt thereof.

[Chemical Formula 1]

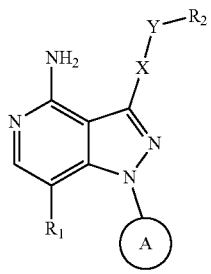

in Chemical Formula 1,
X is a bond, or,
Y is a bond, O, NH, COO, CONH, or CONCO($C_{2-4}$ alkenyl),
A is

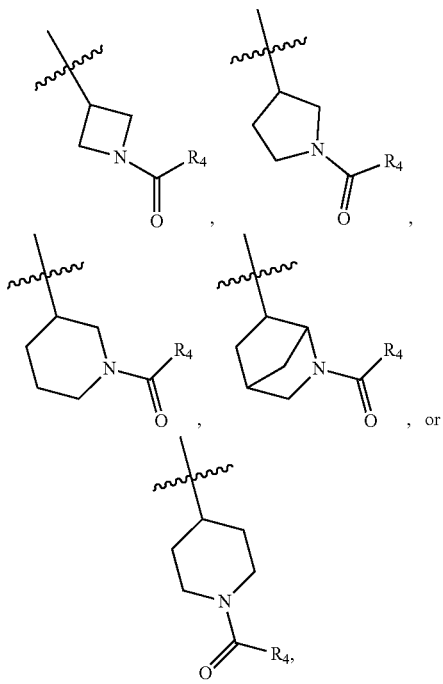

$R_1$ is hydrogen, halogen, $C_{1-4}$ alkyl, $C_{1-4}$ alkyl substituted with hydroxy, $C_{2-4}$ alkenyl, cyano, or -L-R', wherein L is a bond, NH, $C_{1-4}$ alkylene, or $C_{2-4}$ alkenylene; R' is $C_{6-10}$ aryl, pyrazolyl, thiophenyl, or thiazolyl, R' is unsubstituted or substituted with halogen, $C_{1-4}$ alkyl, $C_{1-4}$ haloalkyl, tetrahydropyranyl, piperidinyl substituted with $C_{1-4}$ alkyl, —($C_{1-4}$ alkylene) —N($C_{1-4}$ alkyl)$_2$, —($C_{1-4}$ alkylene)-pyrrolidinyl, or —($C_{1-4}$ alkylene)-morpholino, $R_2$ is halogen, $C_{1-4}$ alkyl, $C_{6-10}$ aryl, or $C_{4-10}$ heteroaryl containing one or two heteroatoms selected from the group consisting of N and O, wherein $R_2$ is unsubstituted or substituted with halogen or $C_{3-6}$ cycloalkyl, $R_3$ is hydrogen, halogen, or $C_{1-4}$ alkoxy, and
$R_4$ is $C_{2-4}$ alkenyl, or $C_{2-4}$ alkynyl.

Preferably, Y is a bond, O, NH, COO, CONH, or CONCO(CH=CH$_2$).

Preferably, $R_1$, is hydrogen, bromo, chloro, iodo, methyl, ethyl, hydroxymethyl, vinyl, cyano, or -L-R', wherein L is a bond, NH, CH$_2$, CH=CH, or CH=CHCH$_2$, R' is phenyl unsubstituted or substituted with fluoro; unsubstituted thiophenyl; thiazolyl substituted with methyl; or pyrazolyl unsubstituted or substituted with methyl, difluoromethyl, tetrahydropyranyl, methylpiperidinyl, dimethylaminoethyl, pyrrolidinylethyl, or morpholinoethyl.

Preferably, $R_2$ is bromo, tert-butyl, unsubstituted phenyl, pyrazolyl substituted with cyclopropyl, unsubstituted benzoxazolyl, benzoxazolyl substituted with halogen, unsubstituted dihydrobenzodioxinyl, unsubstituted pyridinyl, or pyridinyl substituted with fluoro.

Preferably, $R_3$ is hydrogen, fluoro, chloro, or methoxy.
Preferably, $R_4$ is —CH=CH$_2$, —C(CH$_3$)=CH$_2$, —C≡CH, or —C≡CCH$_3$.

In addition, the compounds of the present invention may exist in the form of salts, in particular pharmaceutically acceptable salts. As the salt, salts commonly used in the art may be used without limitation, such as acid addition salts formed by pharmaceutically acceptable free acid. The term "pharmaceutically acceptable salt" used herein refers to any organic or inorganic addition salt of the compound represented by Chemical Formula 1, in which the adverse effect caused by the salt does not impair the beneficial effect of the compound at a concentration exhibiting relatively non-toxic and non-harmful effective activity to a patient.

As the free acid, an inorganic acid or an organic acid can be used. Examples of the inorganic acids include, but are not limited to, hydrochloric acid, phosphoric acid, sulfuric acid, nitric acid, stannic acid and the like. Examples of the organic acids include, but are not limited to, methanesulfonic acid, p-toluenesulfonic acid, acetic acid, trifluoroacetic acid, maleic acid, succinic acid, oxalic acid, benzoic acid, tartaric acid, fumaric acid, mandelic acid, propionic acid, citric acid, lactic acid, glycolic acid, gluconic acid, galacturonic acid, glutamic acid, glutaric acid, glucuronic acid, aspartic acid, ascorbic acid, carbonic acid, vanillic acid, hydroiodic acid, and the like. Preferably, the salt may be hydrochloride.

In addition, a pharmaceutically acceptable metal salt may be prepared using a base. Alkali metal or alkaline earth metal salt may be obtained, for example, by dissolving a compound represented by Chemical Formula 1 in an excess amount of alkali metal hydroxide or alkaline earth metal hydroxide solution, filtering the undissolved compound salt, and then evaporating the filtrate until dry. At this time, it is desirable to produce a sodium salt, potassium salt or calcium salt as the metal salt.

Other pharmaceutically unacceptable salts or solvates of the compound represented by Chemical Formula 1 can be used as intermediates in the preparation of the compound represented by Chemical Formula 1, a pharmaceutically acceptable salt or a solvate thereof.

In addition, the compounds represented by Chemical Formula 1 according to the present invention include, but are not limited thereto, not only pharmaceutically acceptable salts thereof, but also all solvates or hydrates and all possible stereoisomers that can be prepared therefrom. The solvate and stereoisomer of the compound represented by Chemical Formula 1 may be prepared from the compound represented by Chemical Formula 1 using methods known in the art.

Furthermore, the compound represented by Chemical Formula 1 according to the present invention may be prepared either in a crystalline form or in a non-crystalline form. When the compound is prepared in a crystalline form, it may be optionally hydrated or solvated. In the present invention, the compound of Chemical Formula 1 may not only include a stoichiometric hydrate, but also include a compound containing various amounts of water. The solvate of the compound of Chemical Formula 1 according to the present invention includes both stoichiometric solvates and non-stoichiometric solvates.

Representative examples of the compound represented by Chemical Formula 1, or a pharmaceutically acceptable salt thereof are as follows:
1) 1-(3-(4-amino-3-(4-phenoxyphenyl)-1H-pyrazolo[4,3-c]pyridin-1-yl)piperidin-1-yl)prop-2-en-1-one,
2) 1-(3-(4-amino-3-(4-phenoxyphenyl)-1H-pyrazolo[4,3-c]pyridin-1-yl)piperidin-1-yl)prop-2-yn-1-one,
3) 1-(4-(4-amino-3-(4-phenoxyphenyl)-1H-pyrazolo[4,3-c]pyridin-1-yl)piperidin-1-yl)prop-2-en-1-one,
4) 1-(4-(4-amino-3-(4-phenoxyphenyl)-1H-pyrazolo[4,3-c]pyridin-1-yl)piperidin-1-yl)prop-2-yn-1-one,
5) 1-(3-(4-amino-7-iodo-3-(4-phenoxyphenyl)-1H-pyrazolo[4,3-c]pyridin-1-yl)piperidin-1-yl)prop-2-en-1-one,
6) 1-(3-(4-amino-7-benzyl-3-(4-phenoxyphenyl)-1H-pyrazolo[4,3-c]pyridin-1-yl)piperidin-1-yl)prop-2-en-1-one,
7) 1-(3-(4-amino-7-(1-methyl-1H-pyrazol-4-yl)-3-(4-phenoxyphenyl)-1H-pyrazolo[4,3-c]pyridin-1-yl)piperidin-1-yl)prop-2-en-1-one,
8) 1-(6-(4-amino-7-(1-methyl-1H-pyrazol-4-yl)-3-(4-phenoxyphenyl)-1H-pyrazolo[4,3-c]pyridin-1-yl)-2-azabicyclo[2.2.1]heptan-2-yl)prop-2-en-1-one,
9) 1-(3-(4-amino-7-chloro-3-(4-phenoxyphenyl)-1H-pyrazolo[4,3-c]pyridin-1-yl)piperidin-1-yl)prop-2-en-1-one,
10) 1-(3-(4-amino-7-bromo-3-(4-phenoxyphenyl)-1H-pyrazolo[4,3-c]pyridin-1-yl)piperidin-1-yl)prop-2-en-1-one,
11) 1-(3-(4-amino-3-(4-phenoxyphenyl)-7-phenyl-1H-pyrazolo[4,3-c]pyridin-1-yl)piperidin-1-yl)prop-2-en-1-one,
12) 1-(4-(4-amino-7-iodo-3-(4-phenoxyphenyl)-1H-pyrazolo[4,3-c]pyridin-1-yl)piperidin-1-yl)prop-2-en-1-one,
13) 1-(4-(4-amino-7-(1-methyl-1H-pyrazol-4-yl)-3-(4-phenoxyphenyl)-1H-pyrazolo[4,3-c]pyridin-1-yl)piperidin-1-yl)prop-2-en-1-one,
14) (E)-1-(3-(4-amino-7-(4-fluorostyryl)-3-(4-phenoxyphenyl)-1H-pyrazolo[4,3-c]pyridin-1-yl)piperidin-1-yl)prop-2-en-1-one,
15) (E)-1-(4-(4-amino-7-(4-fluorostyryl)-3-(4-phenoxyphenyl)-1H-pyrazolo[4,3-c]pyridin-1-yl)piperidin-1-yl)prop-2-en-1-one,
16) (R)-1-(3-(4-amino-7-iodo-3-(4-phenoxyphenyl)-1H-pyrazolo[4,3-c]pyridin-1-yl)piperidin-1-yl)prop-2-en-1-one,
17) (E)-1-(3-(4-amino-3-(4-phenoxyphenyl)-7-(3-phenylprop-1-enyl)-1H-pyrazolo[4,3-c]pyridin-1-yl)piperidin-1-yl)prop-2-en-1-one,
18) (R)-4-(1-(1-acryloylpiperidin-3-yl)-4-amino-1H-pyrazolo[4,3-c]pyridin-3-yl)-N-(pyridin-2-yl)benzamide,
19) (R)-4-(1-(1-acryloylpiperidin-3-yl)-4-amino-7-chloro-1H-pyrazolo[4,3-c]pyridin-3-yl)-N-(pyridin-2-yl)benzamide,
20) (R)-4-(1-(1-acryloylpiperidin-3-yl)-4-amino-7-bromo-1H-pyrazolo[4,3-c]pyridin-3-yl)-N-(pyridin-2-yl)benzamide,
21) (R)-4-(1-(1-acryloylpiperidin-3-yl)-4-amino-7-iodo-1H-pyrazolo[4,3-c]pyridin-3-yl)-N-(pyridin-2-yl)benzamide,
22) (R)-4-(1-(1-acryloylpiperidin-3-yl)-4-amino-1H-pyrazolo[4,3-c]pyridin-3-yl)-N-phenylbenzamide,
23) (R)-4-(1-(1-acryloylpiperidin-3-yl)-4-amino-7-chloro-1H-pyrazolo[4,3-c]pyridin-3-yl)-N-phenylbenzamide,
24) (R)-4-(1-(1-acryloylpiperidin-3-yl)-4-amino-7-bromo-1H-pyrazolo[4,3-c]pyridin-3-yl)-N-phenylbenzamide,
25) (R)-4-(1-(1-acryloylpiperidin-3-yl)-4-amino-7-iodo-1H-pyrazolo[4,3-c]pyridin-3-yl)-N-phenylbenzamide,
26) (R)-4-(1-(1-acryloylpiperidin-3-yl)-4-amino-7-(1-methyl-1H-pyrazol-4-yl)-1H-pyrazolo[4,3-c]pyridin-3-yl)-N-phenylbenzamide,
27) (R)-4-(1-(1-acryloylpiperidin-3-yl)-4-amino-7-(hydroxymethyl)-1H-pyrazolo[4,3-c]pyridin-3-yl)-N-phenylbenzamide,
28) (R)-4-(1-(1-acryloylpiperidin-3-yl)-4-amino-7-(1H-pyrazol-4-yl)-1H-pyrazolo[4,3-c]pyridin-3-yl)-N-phenylbenzamide,
29) (R)-4-(1-(1-acryloylpiperidin-3-yl)-4-amino-7-(1H-pyrazol-3-yl)-1H-pyrazolo[4,3-c]pyridin-3-yl)-N-phenylbenzamide,
30) (R)-4-(1-(1-acryloylpiperidin-3-yl)-4-amino-7-(1H-pyrazol-5-yl)-1H-pyrazolo[4,3-c]pyridin-3-yl)-N-phenylbenzamide,
31) (R)-4-(1-(1-acryloylpiperidin-3-yl)-4-amino-7-(thiophen-3-yl)-1H-pyrazolo[4,3-c]pyridin-3-yl)-N-phenylbenzamide,
32) (R)-4-(1-(1-acryloylpiperidin-3-yl)-4-amino-7-(2-methylthiazol-5-yl)-1H-pyrazolo[4,3-c]pyridin-3-yl)-N-phenylbenzamide,
33) (R)-4-(1-(1-acryloylpiperidin-3-yl)-4-amino-7-(1-(difluoromethyl)-1H-pyrazol-4-yl)-1H-pyrazolo[4,3-c]pyridin-3-yl)-N-phenylbenzamide,
34) (R)-4-(1-(1-acryloylpiperidin-3-yl)-4-amino-7-(1-(tetrahydro-2H-pyran-4-yl)-1H-pyrazol-4-yl)-1H-pyrazolo[4,3-c]pyridin-3-yl)-N-phenylbenzamide,
35) (R)-4-(1-(1-acryloylpiperidin-3-yl)-4-amino-7-(1-(1-methylpiperidin-4-yl)-1H-pyrazol-4-yl)-1H-pyrazolo[4,3-c]pyridin-3-yl)-N-phenylbenzamide,
36) (R)-4-(1-(1-acryloylpiperidin-3-yl)-4-amino-7-(1-(2-(dimethylamino)ethyl)-1H-pyrazol-4-yl)-1H-pyrazolo[4,3-c]pyridin-3-yl)-N-phenylbenzamide,
37) (R)-4-(1-(1-acryloylpiperidin-3-yl)-4-amino-7-(1-(2-(pyrrolidin-1-yl)ethyl)-1H-pyrazol-4-yl)-1H-pyrazolo[4,3-c]pyridin-3-yl)-N-phenylbenzamide,
38) (R)-4-(1-(1-acryloylpiperidin-3-yl)-4-amino-7-(1-(2-morpholinoethyl)-1H-pyrazol-4-yl)-1H-pyrazolo[4,3-c]pyridin-3-yl)-N-phenylbenzamide,
39) (S)-4-(1-(1-acryloylpiperidin-3-yl)-4-amino-1H-pyrazolo[4,3-c]pyridin-3-yl)-N-(pyridin-2-yl)benzamide,
40) (R)-4-(1-(1-acryloylpiperidin-3-yl)-4-amino-1H-pyrazolo[4,3-c]pyridin-3-yl)-3-fluoro-N-(pyridin-2-yl)benzamide,
41) (R)-4-(1-(1-acryloylpiperidin-3-yl)-4-amino-1H-pyrazolo[4,3-c]pyridin-3-yl)-N-(4-fluoropyridin-2-yl)benzamide,
42) (R)—N-acryloyl-4-(1-(1-acryloylpiperidin-3-yl)-4-amino-1H-pyrazolo[4,3-c]pyridin-3-yl)-N-(4-fluoropyridin-2-yl)benzamide,
43) (R)-4-(1-(1-acryloylpiperidin-3-yl)-4-amino-7-(phenylamino)-1H-pyrazolo[4,3-c]pyridin-3-yl)-N-(pyridin-2-yl)benzamide,
44) (R)-4-(1-(1-acryloylpiperidin-3-yl)-4-amino-7-methyl-1H-pyrazolo[4,3-c]pyridin-3-yl)-N-phenylbenzamide,
45) (R)-4-(1-(1-acryloylpiperidin-3-yl)-4-amino-7-methyl-1H-pyrazolo[4,3-c]pyridin-3-yl)-N-(pyridin-2-yl)benzamide,
46) 4-(1-(1-acryloylpyrrolidin-3-yl)-4-amino-7-(1-(difluoromethyl)-1H-pyrazol-4-yl)-1H-pyrazolo[4,3-c]pyridin-3-yl)-N-phenylbenzamide,
47) 4-(1-(1-acryloylpyrrolidin-3-yl)-4-amino-1H-pyrazolo[4,3-c]pyridin-3-yl)-N-phenylbenzamide,
48) 4-(4-amino-1-(1-but-2-ynoylpyrrolidin-3-yl)-1H-pyrazolo[4,3-c]pyridin-3-yl)-N-phenylbenzamide, 49) (R)-4-(1-(1-acryloylpiperidin-3-yl)-4-amino-7-chloro-1H-pyrazolo[4,3-c]pyridin-3-yl)-3-fluoro-N-(pyridin-2-yl)benzamide,
50) (R)-4-(1-(1-acryloylpiperidin-3-yl)-4-amino-7-iodo-1H-pyrazolo[4,3-c]pyridin-3-yl)-3-fluoro-N-(pyridin-2-yl)benzamide,
51) 4-(1-((6R)-2-acryloyl-2-azabicyclo[2.2.1]heptan-6-yl)-4-amino-1H-pyrazolo[4,3-c]pyridin-3-yl)-3-fluoro-N-(pyridin-2-yl)benzamide,
52) 4-(1-(1-acryloylazetidin-3-yl)-4-amino-7-chloro-1H-pyrazolo[4,3-c]pyridin-3-yl)-3-fluoro-N-(pyridin-2-yl)benzamide,
53) (R)-4-(1-(1-acryloylpiperidin-3-yl)-4-amino-7-cyano-1H-pyrazolo[4,3-c]pyridin-3-yl)-3-fluoro-N-(pyridin-2-yl)benzamide,
54) (R)-4-(4-amino-1-(1-methacryloylpiperidin-3-yl)-1H-pyrazolo[4,3-c]pyridin-3-yl)-3-fluoro-N-(pyridin-2-yl)benzamide,
55) (R)-4-(4-amino-7-chloro-1-(1-methacryloylpiperidin-3-yl)-1H-pyrazolo[4,3-c]pyridin-3-yl)-3-fluoro-N-(pyridin-2-yl)benzamide,
56) (R)-4-(1-(1-acryloylpiperidin-3-yl)-4-amino-1H-pyrazolo[4,3-c]pyridin-3-yl)-3-chloro-N-(pyridin-2-yl)benzamide,
57) (R)-4-(1-(1-acryloylpiperidin-3-yl)-4-amino-1H-pyrazolo[4,3-c]pyridin-3-yl)-3-methoxy-N-(pyridin-2-yl)benzamide,
58) (R)-4-(1-(1-acryloylpiperidin-3-yl)-4-amino-7-chloro-1H-pyrazolo[4,3-c]pyridin-3-yl)-3-chloro-N-(pyridin-2-yl)benzamide,
59) (R)-4-(1-(1-acryloylpiperidin-3-yl)-4-amino-7-chloro-1H-pyrazolo[4,3-c]pyridin-3-yl)-3-methoxy-N-(pyridin-2-yl)benzamide,
60) 4-(1-(1-acryloylazetidin-3-yl)-4-amino-7-chloro-1H-pyrazolo[4,3-c]pyridin-3-yl)-3-fluoro-N-(pyridin-2-yl)benzamide,
61) (R)-1-(3-(4-amino-3-(1-cyclopropyl-1H-pyrazol-4-ylamino)-1H-pyrazolo[4,3-c]pyridin-1-yl)piperidin-1-yl)prop-2-en-1-one,
62) (R)-1-(3-(4-amino-3-bromo-1H-pyrazolo[4,3-c]pyridin-1-yl)piperidin-1-yl)prop-2-en-1-one,
63) 4-(1-(1-acryloylazetidin-3-yl)-4-amino-1H-pyrazolo[4,3-c]pyridin-3-yl)-3-chloro-N-(pyridin-2-yl)benzamide,
64) 4-(1-(1-acryloylazetidin-3-yl)-4-amino-7-chloro-1H-pyrazolo[4,3-c]pyridin-3-yl)-3-chloro-N-(pyridin-2-yl)benzamide,
65) (R)-4-(1-(1-acryloylpiperidin-3-yl)-4-amino-7-iodo-1H-pyrazolo[4,3-c]pyridin-3-yl)-3-chloro-N-(pyridin-2-yl)benzamide,
66) (R)-4-(1-(1-acryloylpiperidin-3-yl)-4-amino-7-cyano-1H-pyrazolo[4,3-c]pyridin-3-yl)-3-chloro-N-(pyridin-2-yl)benzamide,
67) (R)-4-(1-(1-acryloylpiperidin-3-yl)-4-amino-7-(1-methyl-1H-pyrazol-4-yl)-1H-pyrazolo[4,3-c]pyridin-3-yl)-3-chloro-N-(pyridin-2-yl)benzamide,
68) (R)-4-(1-(1-acryloylpiperidin-3-yl)-4-amino-7-ethyl-1H-pyrazolo[4,3-c]pyridin-3-yl)-3-chloro-N-(pyridin-2-yl)benzamide,
69) (R)-4-(1-(1-acryloylpiperidin-3-yl)-4-amino-7-vinyl-1H-pyrazolo[4,3-c]pyridin-3-yl)-3-chloro-N-(pyridin-2-yl)benzamide,
70) (R)-4-(1-(1-acryloylpiperidin-3-yl)-4-amino-7-(1H-pyrazol-4-yl)-1H-pyrazolo[4,3-c]pyridin-3-yl)-3-chloro-N-(pyridin-2-yl)benzamide,
71) (R)-1-(1-acryloylpiperidin-3-yl)-4-amino-N-(5-chlorobenzo[d]oxazol-2-yl)-1H-pyrazolo[4,3-c]pyridine-3-carboxamide,
72) (R)-tert-butyl 1-(1-acryloylpiperidin-3-yl)-4-amino-1H-pyrazolo[4,3-c]pyridine-3-carboxylate,
73) (R)-1-(1-acryloylpiperidin-3-yl)-4-amino-N-(6-bromobenzo[d]oxazol-2-yl)-1H-pyrazolo[4,3-c]pyridine-3-carboxamide,
74) (R)-1-(1-acryloylpiperidin-3-yl)-4-amino-7-chloro-N-(5-chlorobenzo[d]oxazol-2-yl)-1H-pyrazolo[4,3-c]pyridine-3-carboxamide,
75) (R)-1-(1-acryloylpiperidin-3-yl)-4-amino-N-(benzo[d]oxazol-2-yl)-7-chloro-1H-pyrazolo[4,3-c]pyridine-3-carboxamide,
76) (R)-1-(1-acryloylpiperidin-3-yl)-4-amino-7-chloro-N-(5-fluorobenzo[d]oxazol-2-yl)-1H-pyrazolo[4,3-c]pyridine-3-carboxamide,
77) (R)-1-(1-acryloylpiperidin-3-yl)-4-amino-N-(benzo[d]oxazol-2-yl)-1H-pyrazolo[4,3-c]pyridine-3-carboxamide,
78) (R)-1-(1-acryloylpiperidin-3-yl)-4-amino-7-chloro-N-phenyl-1H-pyrazolo[4,3-c]pyridine-3-carboxamide, and
79) (R)-1-(1-acryloylpiperidin-3-yl)-4-amino-7-chloro-N-(2,3-dihydrobenzo[b][1,4]dioxin-6-yl)-1H-pyrazolo[4,3-c]pyridine-3-carboxamide In addition, in one example of the present invention, a compound represented by Chemical Formula 1 can be prepared through the following Reaction Scheme 1.

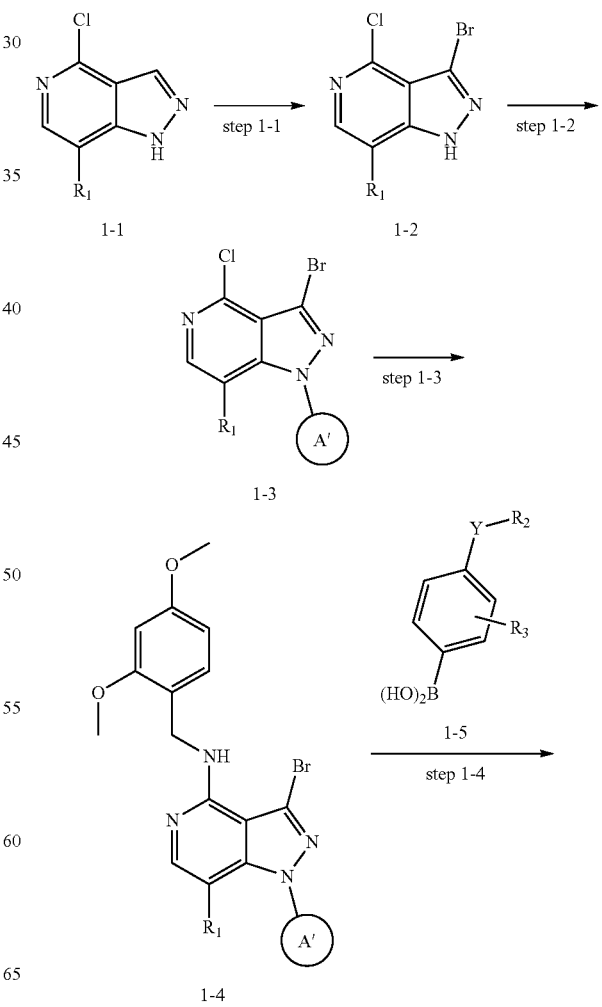

[Reaction Scheme 1]

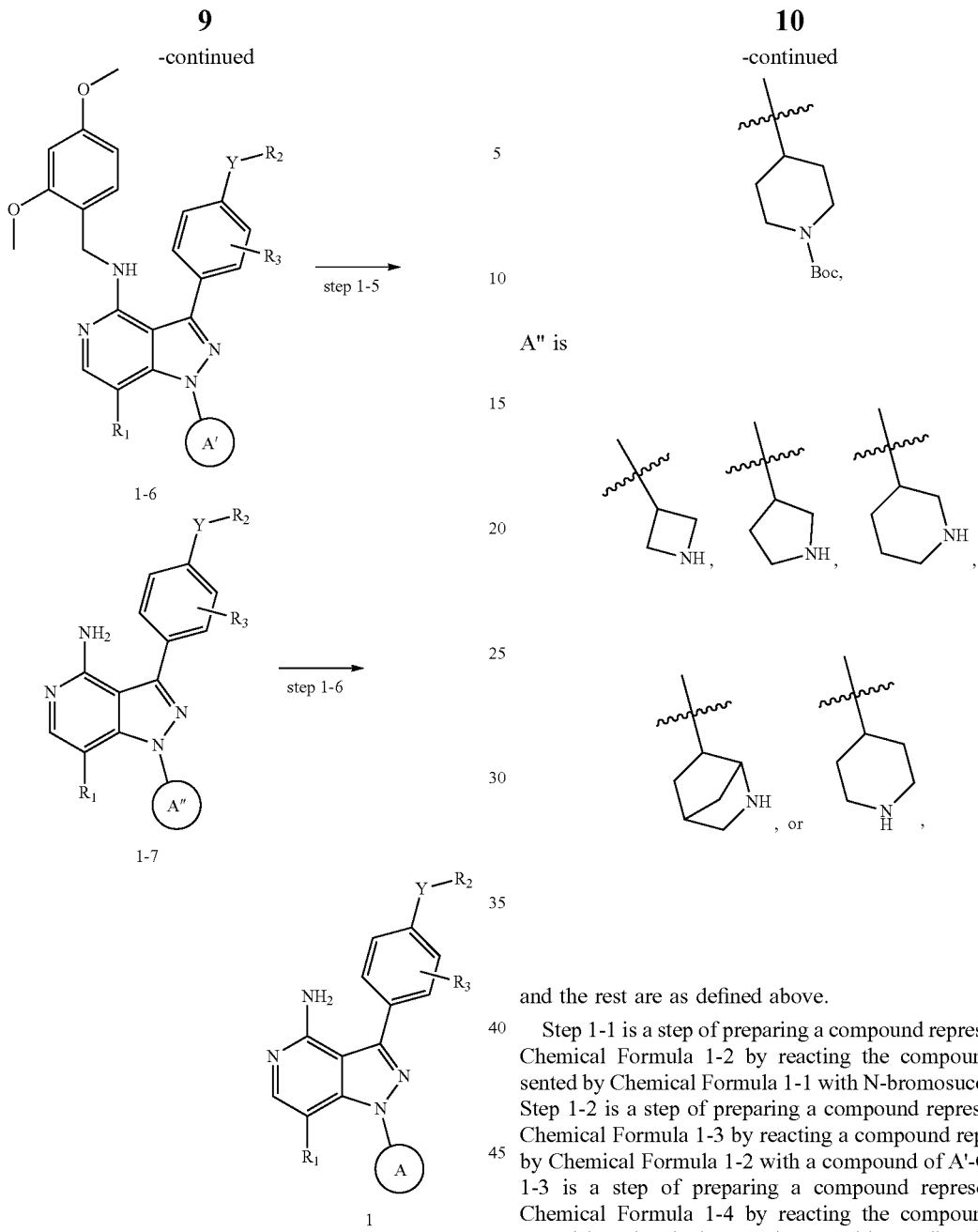

in Reaction Scheme 1, A' is,

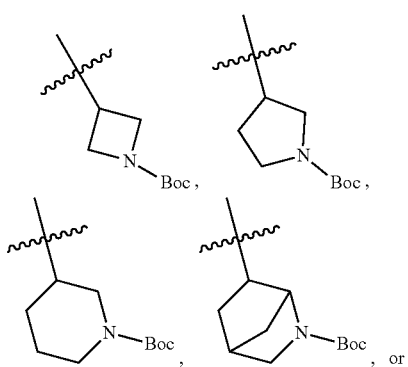

A" is

[structures shown]

and the rest are as defined above.

Step 1-1 is a step of preparing a compound represented by Chemical Formula 1-2 by reacting the compound represented by Chemical Formula 1-1 with N-bromosuccinimide. Step 1-2 is a step of preparing a compound represented by Chemical Formula 1-3 by reacting a compound represented by Chemical Formula 1-2 with a compound of A'-OH. Step 1-3 is a step of preparing a compound represented by Chemical Formula 1-4 by reacting the compound represented by Chemical Formula 1-3 with 2,4-dimethoxybenzylamine. Step 1-4 is a step of preparing a compound represented by Chemical Formula 1-6 by reacting the compound represented by Chemical Formula 1-4 with the compound represented by Chemical Formula 1-5. Step 1-5 is a step of preparing a compound represented by Chemical Formula 1-7 by reacting the compound represented by Chemical Formula 1-6 with triethylsilane. Step 1-6 is a step of preparing a compound represented by Chemical Formula 1 by reacting a compound represented by Chemical Formula 1-7 with a compound of R'—COCl.

The preparation method of each step mentioned above can be more embodied in Examples described hereinafter.

In another example of the present invention, a compound represented by Chemical Formula 1 can be prepared through the following Reaction Scheme 2. The Reaction Scheme 2 is a reaction similar to Reaction Scheme 1 above but different in the order of introducing substituents.

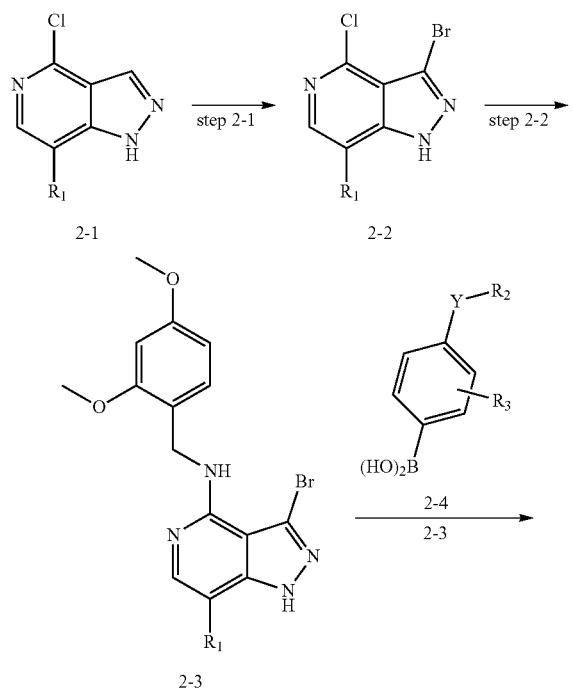
in Reaction Scheme 2,
A″ is
and the rest are as defined above.
Steps 2-1 and 2-2 are the same as steps 1-1 and 1-3 of Reaction Scheme 1, respectively. Step 2-3 corresponds to steps 1-4 of Reaction Scheme 1 and is a step of preparing the compound represented by Chemical Formula 2-5 by reacting the compound represented by Chemical Formula 2-3 with the compound represented by Chemical Formula 2-4. Step 2-4 corresponds to step 1-2 of Reaction Scheme 1 and is a step of preparing a compound represented by Chemical Formula 2-6 by reacting the compound represented by Formula 1-5 with a compound of A'-OH. Steps 2-5 and 2-6 are the same as steps 1-5 and 1-6 of Reaction Scheme 1, respectively.

The preparation method of each step described above can be further embodied in the Example mentioned hereinbelow.

In addition, in one example of the present invention, when $R_1$ is not hydrogen, the compound represented by Chemical Formula 1 can be prepared through the following Reaction Scheme 3.

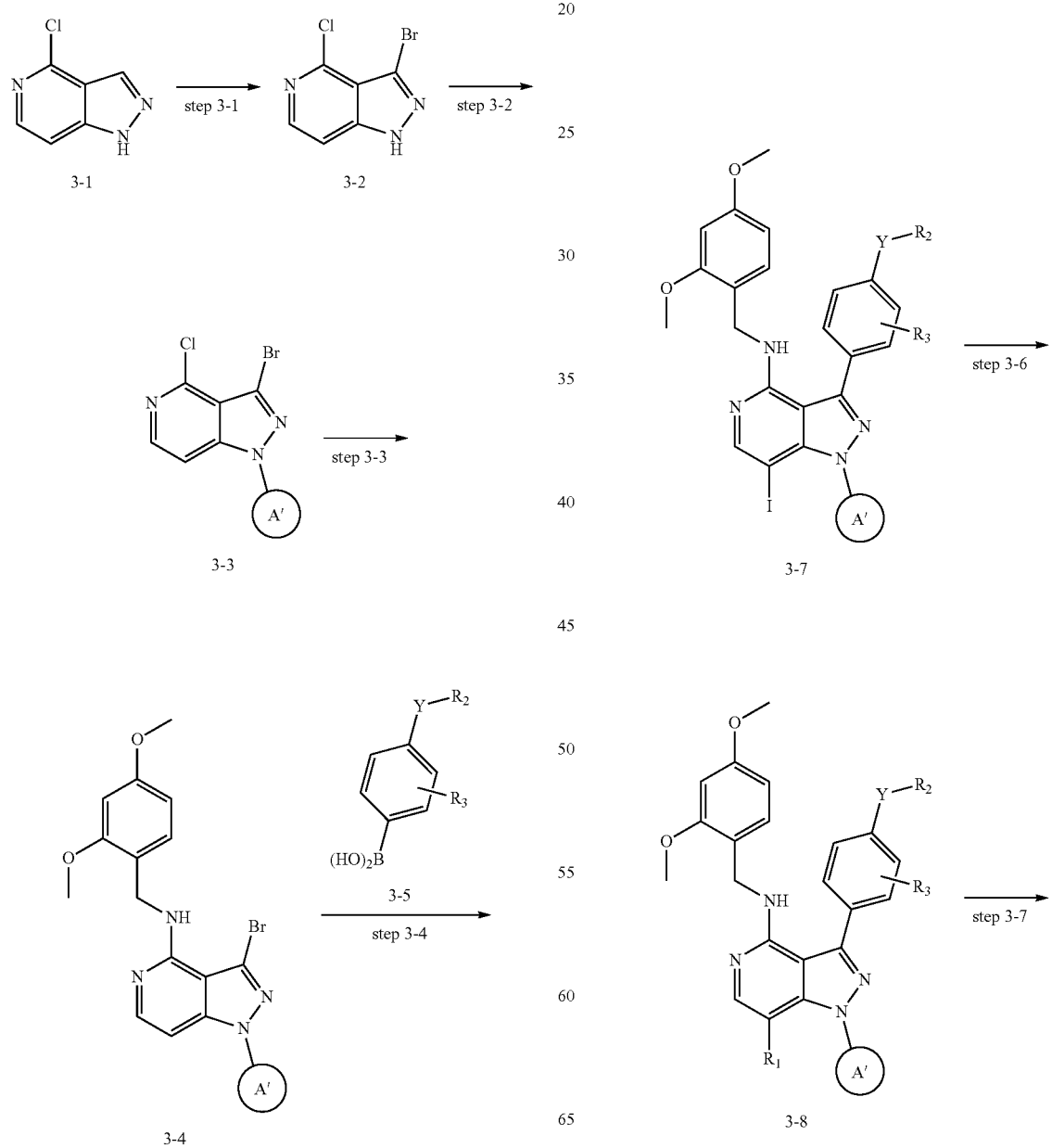

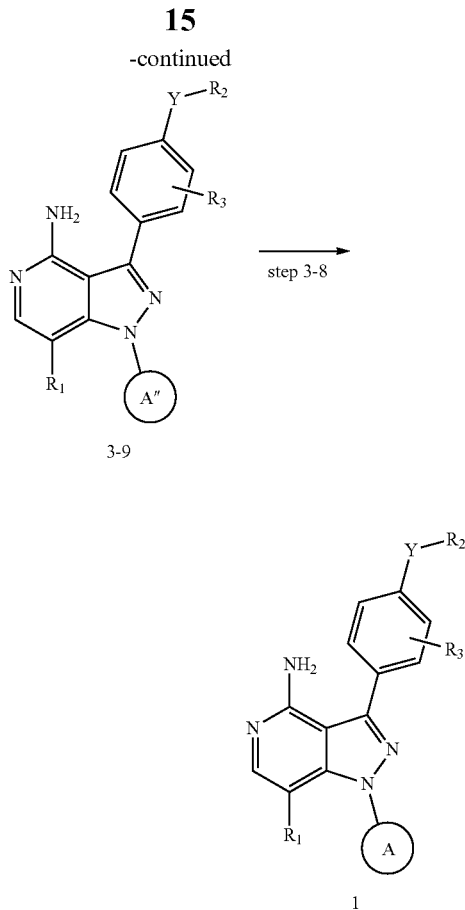

3-9 step 3-8

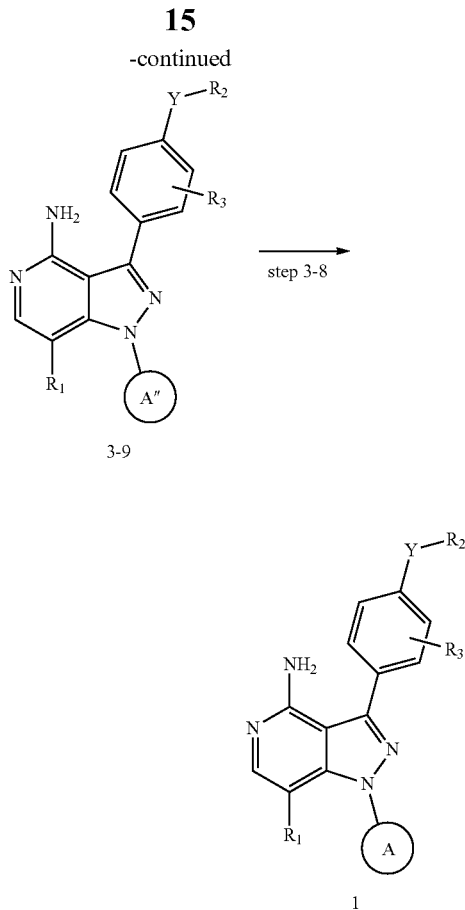

1 in Reaction Scheme 3, A'

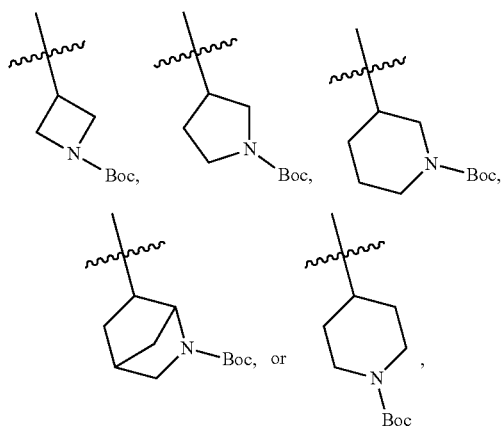

A" is

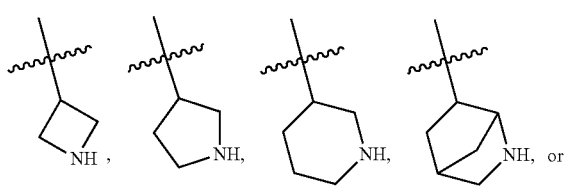

and the rest are as defined above.

Steps 3-1, 3-2, 3-3, and 3-4 are steps 1-1, 1-2, 1-3 and 1-4 of Reaction Scheme 1, respectively, except that $R_1$ of each reactant is not substituted. Step 3-5 is a step of preparing a compound represented by Chemical Formula 3-7 by reacting the compound represented by Chemical Formula 3-6 with N-iodosuccinimide. Step 3-6 is a step of preparing a compound represented by Chemical Formula 3-8 by reacting a compound represented by Chemical Formula 3-7 with a compound capable of substituting $R_1$. As the compound capable of substituting $R_1$, there may be mentioned $R_1$—ZnBr, $R_1$—B(OH)$_2$, or $R_1$—(BO$_2$C$_6$H$_{12}$). Steps 3-7 and 3-8 are the same as steps 1-5 and 1-6 of Reaction Scheme 1, respectively.

The preparation method of each step described above can be further embodied in the Examples mentioned hereinbelow.

Another embodiment of the present invention provides a pharmaceutical composition for the prevention or treatment of autoimmune disease or cancer disease which is beneficial for the BTK inhibitory action, comprising the compound represented by Chemical Formula 1, or a pharmaceutically acceptable salt, hydrate, solvate or isomer thereof as an active ingredient.

In this case, the autoimmune diseases are rheumatoid arthritis, systemic lupus erythematosus, childhood diabete, psoriasis, aphthous stomatitis, chronic thyroiditis, some acquired aplastic anemia, primary biliary cirrhosis, ulcerative colitis, Behcet's disease, Crohn's disease, silicosis, asbestosis, Sjogren's syndrome, Guillain-Barre syndrome, dermatomyositis, polymyositis, multiple sclerosis, autoimmune hemolytic anemia, autoimmune encephalomyelitis, myasthenia gravis, Graves' hyperthyroidism, polyarteritis nodosa, ankylosing spondylitis, fibrositis, temporal arteritis, Wilson's disease, asthma, or Fanconi syndrome.

The cancer may be hematologic malignancy, extranodal marginal zone B-cell lymphoma, glioblastoma, lymphoplasmacytic lymphoma, acute myeloid leukemia, macroglobulinemia, B cell lymphoma, chronic lymphocytic leukemia, follicular lymphoma, non-Hodgkin lymphoma, diffuse large B-cell lymphoma, hairy cell leukemia, mantle cell lymphoma, glioblastoma, bladder cancer, pancreatic cancer, ovarian cancer, colon cancer, kidney cancer, gastric cancer, transitional cell carcinoma, carcinoid tumor, breast cancer, non-small cell lung cancer, or multiple myeloma.

As used herein, the term "prevention" refers to any act to delay or inhibit occurrence, spread or recurrence of the above diseases by administration of the composition of the present invention, and the term "treatment" refers to any act to improve or change the symptoms of the above diseases for the better by administration of the composition of the present invention.

The pharmaceutical composition according to the present invention can be formulated in types for oral or parenteral administrations according to standard pharmaceutical practice. These formulations may contain additives such as pharmaceutically acceptable carrier, adjuvant or diluent in addition to the active ingredient.

Suitable carriers include, for example, physiological saline, polyethylene glycol, ethanol, vegetable oil, isopropyl myristate and the like. Diluents include, for example, lactose, dextrose, sucrose, mannitol, sorbitol, cellulose and/or glycine and the like, but are not limited thereto. Further, the compounds of the present invention can be dissolved in oils, propylene glycol or other solvents commonly used in the preparation of injection solutions. Furthermore, the compounds of the present invention can be formulated in ointments or creams for topical application.

A preferred dose of the compound of the present invention may be varied according to the condition and weight of a patient, the severity of a disease, the type of a drug, and the route and duration of administration, but it may be suitably selected by those skilled in the art. In order to achieve the desirable effects, however, the compound of the present invention may be administered daily at a dose of 0.0001 to 100 mg/kg (body weight), and preferably 0.001 to 100 mg/kg (body weight). The administration may be performed once a day or in divided doses each day through an oral or parenteral route.

Depending on the method of administration, the pharmaceutical composition may contain the compound of the present invention in an amount of 0.001 to 99% by weight, preferably 0.01 to 60% by weight.

The pharmaceutical composition according to the present invention may be administered to mammals such as a rat, a mouse, a domestic animal and a human, through various routes. The administration may be carried out through all possible methods, for example, oral, rectal, intravenous, intramuscular, subcutaneous, intra-endometrial, intracerebroventricular injection.

Advantageous Effects

The compound represented by Chemical Formula 1, or a pharmaceutically acceptable salt, hydrate, solvate or isomer thereof according to the present invention can be usefully used for the prevention or treatment of disease which is beneficial for the BTK inhibitory action.

Detailed Description of the Embodiments

Below, the present invention will be described in more detail with reference to the following Examples. However, these examples are for illustrative purposes only and the scope of the present invention is not limited thereby.

Example 1: Preparation of 1-(3-(4-amino-3-(4-phenoxyphenyl)-1H-pyrazolo[4,3-c]pyridin-1-yl)piperidin-1-yl)prop-2-en-1-one Step 1-1: Preparation of 3-bromo-4-chloro-1H-pyrazolo[4,3-c]pyridine

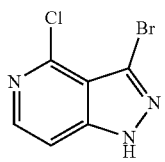 [SMILES: Clc1nccc2[nH]nc(Br)c12]

After 4-chloro-1H-pyrazolo [4,3-c]pyridine (1.0 g, 1.0 eq) was dissolved in acetonitrile (20.0 mL), N-bromosuccinimide (1.2 g, 1.0 eq) was added thereto at room temperature. The reaction mixture was allowed to react at 80° C. for 2 hours, then water was added and the mixture was extracted with ethyl acetate. The separated organic layer was dried over magnesium sulfate, then filtered through a pad of silica gel, and then concentrated under reduced pressure to obtain 1.2 g (yield: 79.3%) of the title compound.

Step 1-2: Preparation of tert-butyl 3-(3-bromo-4-chloro-1H-pyrazolo[4,3-c]pyridin-1-yl)piperidine-1-carboxylate

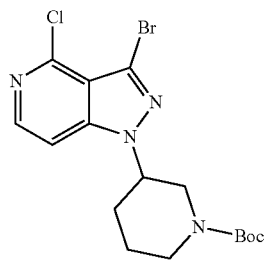 [SMILES: CC(C)(C)OC(=O)N1CCCC(n2nc(Br)c3c(Cl)nccc32)C1]

After tert-butyl 3-hydroxypiperidine-1-carboxylate (1.9 g, 1.0 eq) was dissolved in tetrahydrofuran (65.0 mL), triphenylphosphine (2.4 g, 1.0 eq) was added at room temperature and diisopropyl azadicarboxylate (1.8 g, 1.0 eq) was added at 0° C. The reaction mixture was allowed to react at room temperature for 10 minutes, and then 3-bromo-4-chloro-1H-pyrazolo[4,3-c]pyridine (1.4 g, 1.0 eq) obtained in step 1-1 was added thereto. The reaction mixture was allowed to react at room temperature for 1 day, then water was added and the mixture was extracted with ethyl acetate. The separated organic layer was dried over magnesium sulfate and then concentrated under reduced pressure. The resulting residue was purified by column chromatography (ethyl acetate:hexane=1:1) to obtain 1.9 g (yield: 77.1%) of the title compound.

Step 1-3: Preparation of tert-butyl 3-(3-bromo-4-((2,4-dimethoxybenzyl)amino)-1H-pyrazolo[4,3-c]pyridin-1-yl)piperidine-1-carboxylate

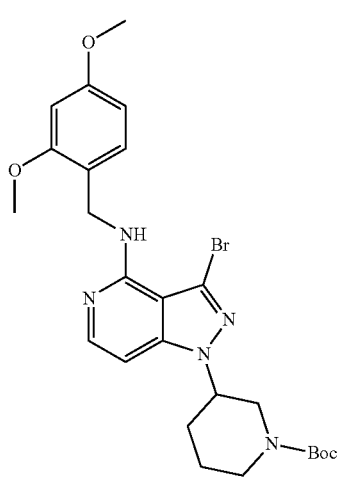 [SMILES: COc1ccc(CNc2nccc3c2c(Br)nn3C2CCCN(C(=O)OC(C)(C)C)C2)c(OC)c1]

After tert-butyl 3-(3-bromo-4-chloro-1H-pyrazolo[4,3-c]pyridin-1-yl)piperidine-1-carboxylate (1.7 g, 1.0 eq) obtained in step 1-2 was dissolved in acetonitrile (10.0 mL), 2,4-dimethoxybenzylamine (3.0 mL, 5.0 eq) and diisopropylethylamine (3.4 mL, 5.0 eq) were added thereto at room temperature. The reaction mixture was allowed to react at 80° C. for 2 days and then concentrated under reduced pressure. The resulting residue was purified by column chromatography (ethyl acetate:hexane=1:1) to obtain 0.5 g (yield: 23.9%) of the title compound.

Steps 1-4: Preparation of tert-butyl 3-(4-((2,4-dimethoxybenzyl)amino)-3-(4-phenoxyphenyl)-1H-pyrazolo[4,3-c]pyridin-1-yl)piperidine-1-carboxylate

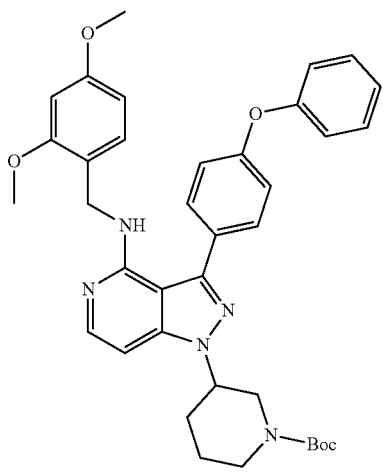 [SMILES: COc1ccc(CNc2nccc3c2c(-c2ccc(Oc4ccccc4)cc2)nn3C2CCCN(C(=O)OC(C)(C)C)C2)c(OC)c1]

After tert-butyl 3-(3-bromo-4-((2,4-dimethoxybenzyl)amino)-1H-pyrazolo[4,3-c]pyridin-1-yl)piperidine-1-carboxylate (350.0 mg, 1.0 eq) obtained in step 1-3 was dissolved in 1,4-dioxane (12.5 mL) and water (2.5 mL), (4-phenoxyphenyl)boronic acid (171.3 mg, 1.25 eq), [1,1'-bis(diphenylphosphino)ferrocene]dichloropalladium(II) (46.9 mg, 0.1 eq) and potassium carbonate (442.6 mg, 5.0 eq) were added thereto at room temperature. The reaction mixture was allowed to react at 80° C. for 3 hours, then water was added and the mixture was extracted with ethyl acetate. The separated organic layer was dried over magnesium sulfate and then concentrated under reduced pressure. The resulting residue was purified by column chromatography (dichloromethane:methanol=10:1) to obtain 152.0 mg (yield: 37.3%) of the title compound.

Step 1-5: Preparation of 3-(4-phenoxyphenyl)-1-(piperidin-3-yl)-1H-pyrazolo[4,3-c]pyridin-4-amine

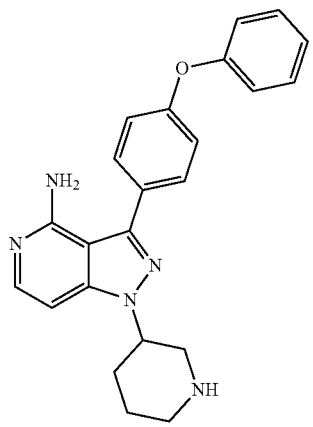 [SMILES: Nc1nccc2c1c(-c1ccc(Oc3ccccc3)cc1)nn2C1CCCNC1]

After tert-butyl 3-(4-((2,4-dimethoxybenzyl)amino)-3-(4-phenoxyphenyl)-1H-pyrazolo[4,3-c]pyridin-1-yl)piperidine-1-carboxylate (150.0 mg, 1.0 eq) obtained in step 1-4 was dissolved in trifluoroacetic acid (3.0 mL), triethylsilane (75.2 uL, 2.0 eq) was added thereto at room temperature. The reaction mixture was allowed to react at 80° C. for 2 hours and then concentrated under reduced pressure. Saturated aqueous sodium hydrogen carbonate solution was added to the resulting residue, and the mixture was extracted with ethyl acetate. The separated organic layer was dried over magnesium sulfate and then concentrated under reduced pressure. The obtained compound was used in a mixture state in the next reaction without purification.

Step 1-6: Preparation of 1-(3-(4-amino-3-(4-phenoxyphenyl)-1H-pyrazolo[4,3-c]pyridin-1-yl)piperidin-1-yl)prop-2-en-1-one

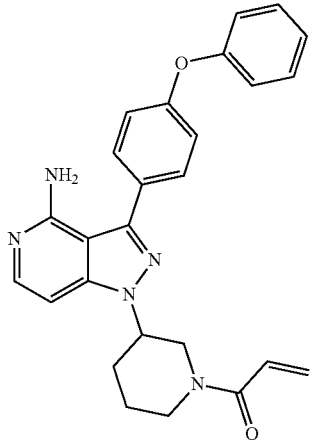 [SMILES: C=CC(=O)N1CCCC(n2nc(-c3ccc(Oc4ccccc4)cc3)c3c(N)nccc32)C1]

After 3-(4-phenoxyphenyl)-1-(piperidin-3-yl)-1H-pyrazolo[4,3-c]pyridin-4-amine (40.0 mg, 1.0 eq) obtained in step 1-5 was dissolved in tetrahydrofuran (4.0 mL) and water (1.0 mL), sodium hydrogen carbonate (17.4 mg, 2.0 eq) and acryloyl chloride (10.2 uL, 1.2 eq) were added thereto at 0° C. The reaction mixture was allowed to react at 0° C. for 10 minutes, then water was added and the mixture was extracted with ethyl acetate. The separated organic layer was dried over magnesium sulfate and then concentrated under reduced pressure. The resulting residue was purified by column chromatography (dichloromethane:methanol=10:1) to obtain 9.4 mg (yield: 13.4%) of the title compound.

$^1$H NMR (500 MHz, CDCl$_3$): 7.60-7.57 (m, 2H), 7.40 (t, 2H), 7.34 (t, 1H), 7.19 (t, 1H), 7.14 (d, 2H), 7.06 (d, 2H), 7.05 (d, 2H), 6.68-6.67 (m, 1H), 6.19-6.14 (m, 1H), 5.77-5.70 (m, 1H), 4.92-4.90 (m, 1H), 4.56-4.52 (m, 1H), 4.42-4.25 (m, 2H), 4.09-4.02 (m, 1H), 3.22-3.17 (m, 1H), 2.78-2.75 (m, 1H), 2.60-2.52 (m, 1H), 1.81-1.62 (m, 1H)

MS M/z: 440.38 [m+1]

Example 2: Preparation of 1-(3-(4-amino-3-(4-phenoxyphenyl)-1H-pyrazolo[4,3-c]pyridin-1-yl)piperidin-1-yl)prop-2-yn-1-one

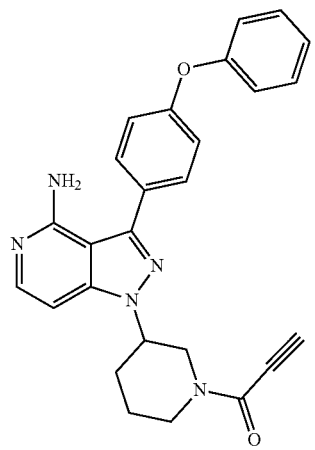 [SMILES: C#CC(=O)N1CCCC(n2nc(-c3ccc(Oc4ccccc4)cc3)c3c(N)nccc32)C1]

A reaction was performed in the same manner as in step 1-6 of Example 1 by using 3-(4-phenoxyphenyl)-1-(piperidin-3-yl)-1H-pyrazolo[4,3-c]pyridin-4-amine (44.0 mg, 1.0 eq) obtained in step 1-5 and propionyl chloride (18.4 mg, 2.0 eq) to obtain 9.0 mg (yield: 37.4%) of the title compound.

$^1$H NMR (500 MHz, CDCl$_3$): 7.65-7.56 (m, 3H), 7.42-7.39 (m, 3H), 7.21 (t, 1H), 7.14 (d, 2H), 7.09 (d, 2H), 6.76 (d, 1H), 4.82-4.79 (m, 1H), 4.59-4.53 (m, 1H), 4.47-4.09 (m, 1H), 4.38-4.33 (m, 1H), 3.81-3.76 (m, 1H), 3.33-3.28 (m, 1H), 3.26-3.19 (m, 1H), 2.43-2.37 (m, 1H), 2.32-2.24 (m, 1H), 1.82-1.68 (m, 1H)

MS M/z: 438.36 [m+1]

Example 3: Preparation of 1-(4-(4-amino-3-(4-phenoxyphenyl)-1H-pyrazolo[4,3-c]pyridin-1-yl)piperidin-1-yl)prop-2-en-1-one Step 3-1: Preparation of 3-bromo-N-(2,4-dimethoxybenzyl)-1H-pyrazolo[4,3-c]pyridin-4-amine

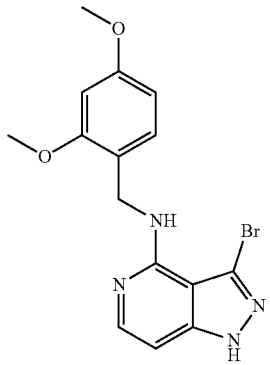 [SMILES: COc1ccc(CNc2nccc3[nH]nc(Br)c23)c(OC)c1]

After 3-bromo-4-chloro-1H-pyrazolo[4,3-c]pyridine (3.0 g, 1.0 eq) obtained in step 1-1 was dissolved in acetonitrile (120.0 mL), 2,4-dimethoxybenzylamine (9.7 mL, 5.0 eq) and diisopropylethylamine (11.0 mL, 5.0 eq) were added thereto at room temperature. The reaction mixture was allowed to react at 80° C. for 1 day and then concentrated under reduced pressure. The resulting residue was purified by column chromatography (ethyl acetate:hexane=1:1) to obtain 2.7 g (yield: 56.5%) of the title compound.

Step 3-2: Preparation of N-(2,4-dimethoxybenzyl)-3-(4-phenoxyphenyl)-1H-pyrazolo[4,3-c]pyridin-4-amine

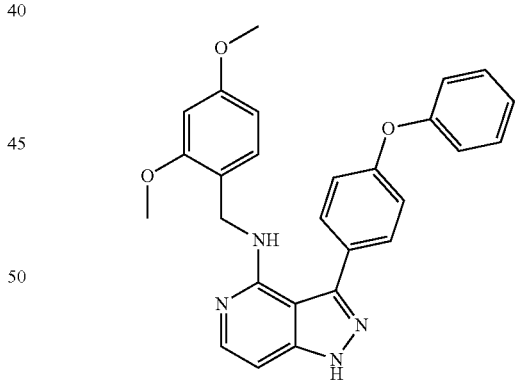

After 3-bromo-N-(2,4-dimethoxybenzyl)-1H-pyrazolo[4,3-c]pyridin-4-amine (1.0 g, 1.0 eq) obtained in step 3-1 was dissolved in 1,4-dioxane (12.5 mL) and water (2.5 mL), (4-phenoxyphenyl)boronic acid (0.7 g, 1.25 eq), [1,1'-(diphenylphosphino)ferrocene]dichloropalladium (II) (0.2 g, 0.1 eq) and potassium carbonate (1.1 g, 3.0 eq) were added thereto at room temperature. The reaction mixture was allowed to react at 100° C. for 20 minutes using a microwave reactor, then water was added and the mixture was extracted with ethyl acetate. The separated organic layer was dried over magnesium sulfate and then concentrated under reduced pressure. The resulting residue was purified by column chromatography (ethyl acetate:hexane=1:1) to obtain 0.3 g (yield: 21.0%) of the title compound.

Step 3-3: Preparation of tert-butyl 4-(4-((2,4-dimethoxybenzyl)amino)-3-(4-phenoxyphenyl)-1H-pyrazolo[4,3-c]pyridine-1-yl)piperidine-1-carboxylate

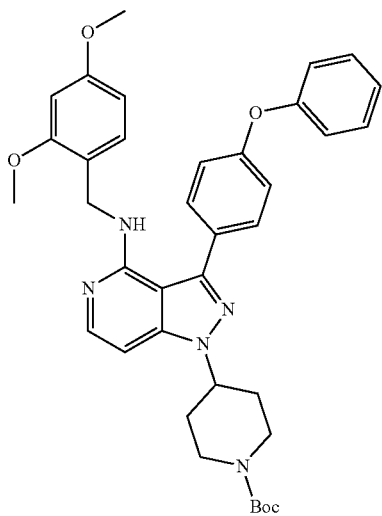 [SMILES: COc1ccc(CNc2nccc3c2c(-c2ccc(Oc4ccccc4)cc2)nn3C2CCN(C(=O)OC(C)(C)C)CC2)c(OC)c1]

After tert-butyl 4-hydroxypiperidine-1-carboxylate (166.8 mg, 1.0 eq) was dissolved in tetrahydrofuran (5.0 mL), triphenylphosphine (217.4 mg, 1.5 eq) and diisopropyl azadicarboxylate (163.2 uL, 1.5 eq) were added thereto at 0° C. The reaction mixture was allowed to react at 0° C. for 10 minutes, and then N-(2,4-dimethoxybenzyl)-3-(4-phenoxyphenyl)-1H-pyrazolo[4,3-c]pyridin-4-amine (250.1 mg, 1.0 eq) obtained in step 3-2 was added thereto. The reaction mixture was allowed to react at room temperature for 1 day, then water was added and the mixture was extracted with ethyl acetate. The separated organic layer was dried over magnesium sulfate and then concentrated under reduced pressure. The resulting residue was purified by column chromatography (dichloromethane:methanol=10:1) to obtain 158.0 mg (yield: 45.0%) of the title compound.

Step 3-4: Preparation of 3-(4-phenoxyphenyl)-1-(piperidin-4-yl)-1H-pyrazolo[4,3-c]pyridin-4-amine

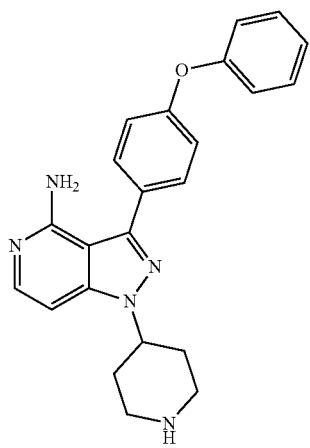 [SMILES: Nc1nccc2c1c(-c1ccc(Oc3ccccc3)cc1)nn2C1CCNCC1]

After tert-butyl 4-(4-((2,4-dimethoxybenzyl)amino)-3-(4-phenoxyphenyl)-1H-pyrazolo[4,3-c]pyridine-1-yl)piperidine-1-carboxylate (150.0 mg, 1.0 eq) obtained in step 3-3 was dissolved in trifluoroacetic acid (3.0 mL), triethylsilane (75.2 uL, 2.0 eq) was added thereto at room temperature. The reaction mixture was allowed to react at 80° C. for 2 hours and then concentrated under reduced pressure. The saturated aqueous sodium hydrogen carbonate solution was added to the resulting residue, and the mixture was extracted with ethyl acetate. The separated organic layer was dried over magnesium sulfate and then concentrated under reduced pressure. The obtained compound was used in a mixture state in the next reaction without purification.

Step 3-5: Preparation of 1-(4-(4-amino-3-(4-phenoxyphenyl)-1H-pyrazolo[4,3-c]pyridin-1-yl)piperidin-1-yl)prop-2-en-1-one

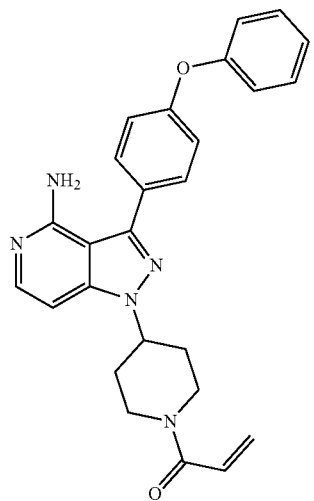 [SMILES: C=CC(=O)N1CCC(n2nc(-c3ccc(Oc4ccccc4)cc3)c3c(N)nccc32)CC1]

After 3-(4-phenoxyphenyl)-1-(piperidin-4-yl)-1H-pyrazolo[4,3-c]pyridin-4-amine (40.0 mg, 1.0 eq) obtained in step 3-4 was dissolving in tetrahydrofuran (4.0 mL) and water (1.0 mL), sodium hydrogen carbonate (17.4 mg, 2.0 eq) and acryloyl chloride (16.9 uL, 2.0 eq) were added thereto at 0° C. The reaction mixture was allowed to react at 0° C. for 10 minutes, then water was added and the mixture was extracted with ethyl acetate. The separated organic layer was dried over magnesium sulfate and then concentrated under reduced pressure. The resulting residue was purified by column chromatography (dichloromethane:methanol=10:1) to obtain 2.3 mg (yield: 5.0%) of the title compound.

$^1$H NMR (500 MHz, MeOD): 7.72 (d, 2H), 7.66-7.60 (m, 2H), 7.46-7.39 (m, 2H), 7.28-7.01 (m, 6H), 6.38 (dd, 1H), 6.24 (d, 1H), 5.77 (d, 1H), 4.73-4.71 (m, 1H), 4.32-4.29 (m, 1H), 3.48-3.30 (m, 2H), 3.05-3.01 (m, 1H), 2.35-2.08 (m, 3H), 1.34-1.29 (m, 1H)

MS M/z: 440.38 [m+1]

Example 4: Preparation of 1-(4-(4-amino-3-(4-phenoxyphenyl)-1H-pyrazolo[4,3-c]pyridin-1-yl)piperidin-1-yl)prop-2-yn-1-one

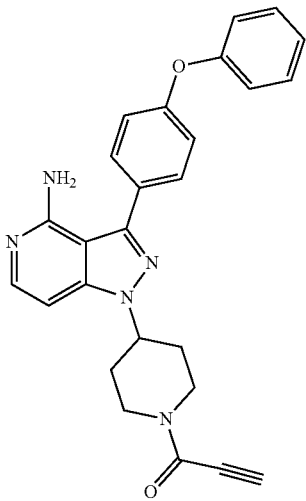 [SMILES: C#CC(=O)N1CCC(n2nc(-c3ccc(Oc4ccccc4)cc3)c3c(N)nccc32)CC1]

A reaction was performed in the same manner as in step 1-6 of Example 1 by using 3-(4-phenoxyphenyl)-1-(piperidin-4-yl)-1H-pyrazolo[4,3-c]pyridin-4-amine (44.0 mg, 1.0 eq) obtained in step 3-4 and propionyl chloride (18.4 mg, 2.0 eq) to obtain 8.4 mg (yield: 40.0%) of the title compound.

$^1$H NMR (500 MHz, MeOD): 7.71 (d, 1H), 7.67-7.63 (m, 2H), 7.46-7.40 (m, 2H), 7.27 (d, 1H), 7.22-7.09 (m, 5H), 4.64-4.59 (m, 2H), 3.56-3.48 (m, 2H), 3.31-3.24 (m, 1H), 2.32-2.08 (m, 4H), 1.42-1.28 (m, 1H)

MS m/z: 438.36 [m+1]

Example 5: Preparation of 1-(3-(4-amino-7-iodo-3-(4-phenoxyphenyl)-1H-pyrazolo[4,3-c]pyridin-1-yl)piperidin-1-yl)prop-2-en-1-one

Step 5-1: Preparation of tert-butyl 3-(4-((2,4-dimethoxybenzyl)amino)-7-iodo-3-(4-phenoxyphenyl)-1H-pyrazolo[4,3-c]pyridin-1-yl)piperidine-1-carboxylate

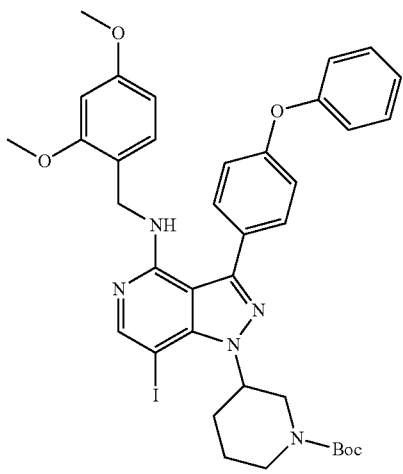 [SMILES: COc1ccc(CNc2ncc(I)c3c2c(-c2ccc(Oc4ccccc4)cc2)nn3C2CCCN(C(=O)OC(C)(C)C)C2)c(OC)c1]

After tert-butyl 3-(3-bromo-4-((2,4-dimethoxybenzyl)amino)-1H-pyrazolo[4,3-c]pyridin-1-yl)piperidine-1-carboxylate (560.0 mg, 1.0 eq) obtained in step 1-3 was dissolved in formamide (400.0 mL), N-iodosuccinimide (198.2 mg, 1.0 eq) was added thereto at room temperature. The reaction mixture was allowed to react at room temperature for 1 hour and then concentrated under reduced pressure. The resulting residue was purified by column chromatography (ethyl acetate:hexane=1:1) to obtain 536.0 mg (yield: 80.0%) of the title compound.

Step 5-2: Preparation of 7-iodo-3-(4-phenoxyphenyl)-1-(piperidin-3-yl)-1H-pyrazolo[4,3-c]pyridine-4-amine

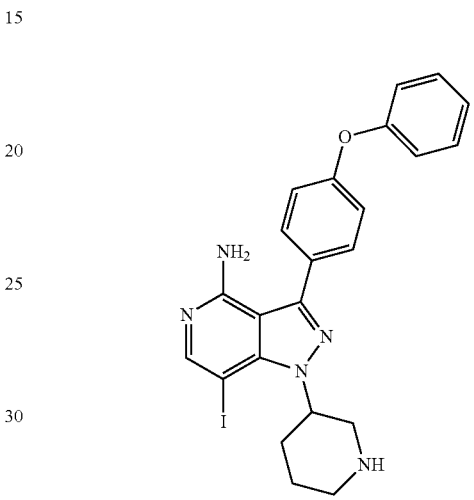

A reaction was performed in the same manner as in step 3-4 of Example 3 by using tert-butyl 3-(4-((2,4-dimethoxybenzyl)amino)-7-iodo-3-(4-phenoxyphenyl)-1H-pyrazolo[4,3-c]pyridin-1-yl)piperidine-1-carboxylate (130.0 mg, 1.0 eq) obtained in step 5-1, trifluoroacetic acid (1.7 mL) and triethylsilane (54.4 uL, 2.0 eq) to obtain the title compound, which was used in the next reaction without purification.

Step 5-3: Preparation of 1-(3-(4-amino-7-iodo-3-(4-phenoxyphenyl)-1H-pyrazolo[4,3-c]pyridin-1-yl)piperidin-1-yl)prop-2-en-1-one

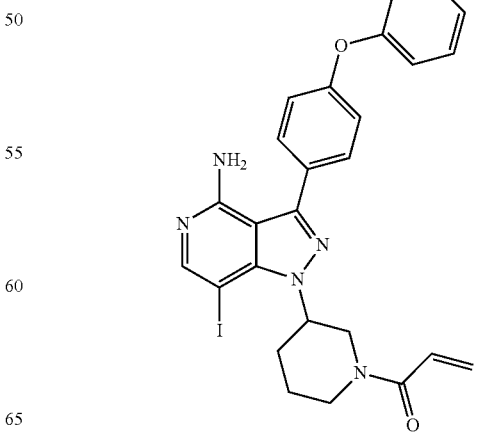

A reaction was performed in the same manner as in Step 3-5 of Example 3 by using 7-iodo-3-(4-phenoxyphenyl)-1-(piperidin-3-yl)-1H-pyrazolo[4,3-c]pyridin-4-amine (86.9 mg, 1.0 eq) obtained in step 5-2, sodium hydrogen carbonate (14.3 mg, 1.0 eq) and acryloyl chloride (13.8 uL, 1.0 eq) to obtain 5.0 mg (yield: 5.2%) of the title compound.

$^{1}$H NMR (500 MHz, MeOD): 8.02 (s, 1H), 7.62 (d, 1H), 7.46-7.39 (m, 2H), 7.18 (t, 1H), 7.14 (d, 2H), 7.06 (d, 1H), 6.85-6.74 (m, 1H), 6.23-6.15 (m, 1H), 5.78-5.67 (m, 1H), 4.43-4.41 (m, 1H), 4.35-4.31 (m, 1H), 4.16-4.12 (m, 1H), 3.86-3.81 (m, 1H), 3.55-3.45 (m, 1H), 3.11-3.02 (m, 1H), 2.40-2.21 (m, 1H), 2.10-2.45 (m, 1H), 1.78-1.60 (m, 1H)

MS m/z: 566.37 [m+1]

Example 6: Preparation of 1-(3-(4-amino-7-benzyl-3-(4-phenoxyphenyl)-1H-pyrazolo[4,3-c]pyridin-1-yl)piperidin-1-yl)prop-2-en-1-one Step 6-1: Preparation of tert-butyl 3-(7-benzyl-4-((2,4-dimethoxybenzyl)amino)-3-(4-phenoxyphenyl)-1H-pyrazolo[4,3-c]pyridin-1-yl)piperidine-1-carboxylate

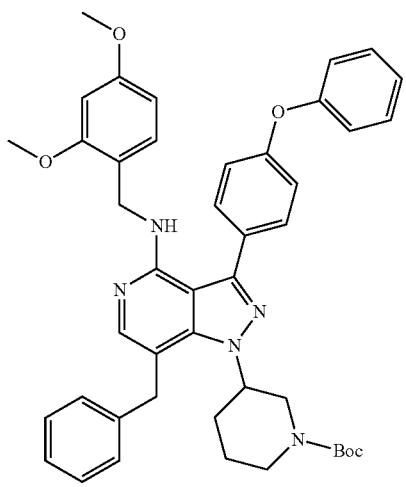 [SMILES: COc1ccc(CNc2ncc(Cc3ccccc3)c3c2c(-c2ccc(Oc4ccccc4)cc2)nn3C2CCCN(C(=O)OC(C)(C)C)C2)c(OC)c1]

After tert-butyl 3-(4-((2,4-dimethoxybenzyl)amino)-7-iodo-3-(4-phenoxyphenyl)-1H-pyrazolo[4,3-c]pyridin-1-yl)piperidine-1-carboxylate (200.0 mg, 1.0 eq) obtained in step 5-1 was dissolved in tetrahydrofuran (5.0 mL), tetrakis(triphenylphosphine)palladium (0) (30.3 mg, 0.1 eq) and benzylzinc bromide (0.8 mL, 1.5 eq) were added thereto at room temperature. The reaction mixture was allowed to react at 100° C. for 10 minutes using a microwave reactor, then water was added and the mixture was extracted with ethyl acetate. The separated organic layer was dried over magnesium sulfate and then concentrated under reduced pressure. The resulting residue was purified by column chromatography (ethyl acetate:hexane=1:1) to obtain 86.0 mg (yield: 45.6%) of the title compound.

Step 6-2: Preparation of 7-benzyl-3-(4-phenoxyphenyl)-1-(piperidin-3-yl)-1H-pyrazolo[4,3-c]pyridine-4-amine

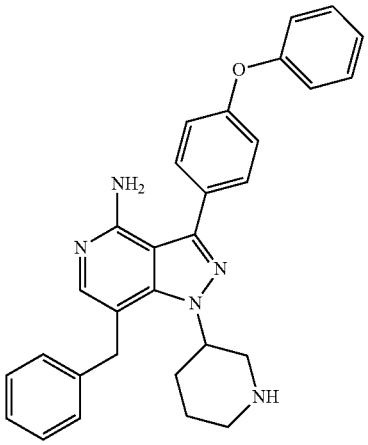 [SMILES: Nc1ncc(Cc2ccccc2)c2c1c(-c1ccc(Oc3ccccc3)cc1)nn2C1CCCNC1]

A reaction was performed in the same manner as in step 3-4 of Example 3 by using tert-butyl 3-(7-benzyl-4-((2,4-dimethoxybenzyl)amino)-3-(4-phenoxyphenyl)-1H-pyrazolo[4,3-c]pyridin-1-yl)piperidine-1-carboxylate obtained in step 6-1, trifluoroacetic acid (1.7 mL) and triethylsilane (35.1 uL, 2.0 eq) to obtain the title compound, which was used in the next reaction without purification.

Step 6-3: Preparation of 1-(3-(4-amino-7-benzyl-3-(4-phenoxyphenyl)-1H-pyrazolo[4,3-c]pyridin-1-yl)piperidin-1-yl)prop-2-en-1-one

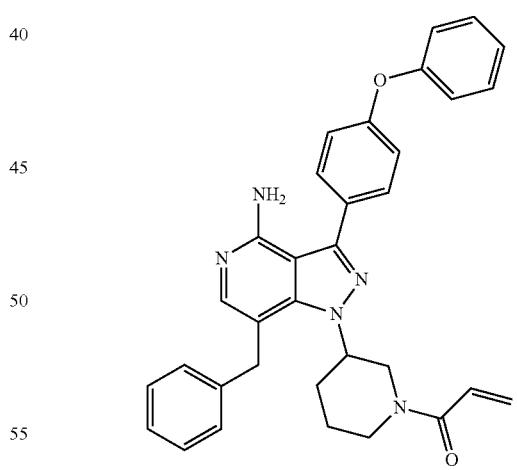

A reaction was performed in the same manner as step 3-5 of Example 3 by using 7-benzyl-3-(4-phenoxyphenyl)-1-(piperidin-3-yl)-1H-pyrazolo[4,3-c]pyridin-4-amine (52.3 mg, 1.0 eq) obtained in step 6-2, sodium hydrogen carbonate (9.2 mg, 1.0 eq) and acryloyl chloride (8.9 uL, 1.0 eq) to obtain 15.0 mg (yield: 25.7%) of the title compound.

$^{1}$H NMR (500 MHz, MeOD): 7.65-7.62 (m, 2H), 7.57-7.42 (m, 2H), 7.33-7.27 (m, 2H), 7.23-7.18 (m, 1H), 7.17-7.07 (m, 4H), 6.81-6.76 (m, 1H), 6.31 (d, 1H), 5.82 (d, 1H), 4.62-4.60 (m, 1H), 4.48-4.39 (m, 1H), 4.35-4.22 (m, 1H), 4.06-3.98 (m, 1H), 3.69-3.64 (m, 1H), 3.15-3.07 (m, 1H), 2.81-2.76 (m, 1H)

MS m/z: 530.49 [m+1]

Example 7: Preparation of 1-(3-(4-amino-7-(1-methyl-1H-pyrazol-4-yl)-3-(4-phenoxyphenyl)-1H-pyrazolo[4,3-c]pyridin-1-yl)piperidin-1-yl)prop-2-en-1-one Step 7-1: Preparation of tert-butyl 3-(4-((2,4-dimethoxybenzyl)amino)-7-(1-methyl-1H-pyrazolo-4-yl)-3-(4-phenoxyphenyl)-1H-pyrazolo[4,3-c]pyridin-1-yl)piperidine-1-carboxylate

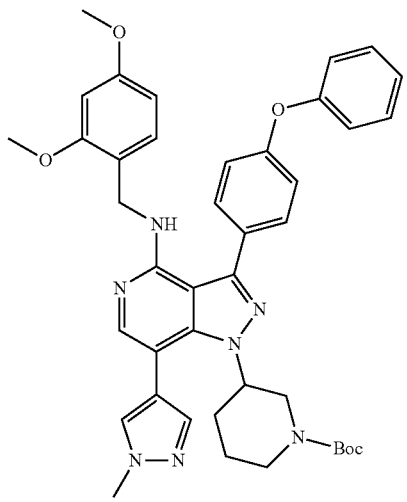 [SMILES: COc1ccc(CNc2ncc(-c3cnn(C)c3)c3c2c(-c2ccc(Oc4ccccc4)cc2)nn3C2CCCN(C(=O)OC(C)(C)C)C2)c(OC)c1]

After tert-butyl 3-(4-((2,4-dimethoxybenzyl)amino)-7-iodo-3-(4-phenoxyphenyl)-1H-pyrazolo[4,3-c]pyridin-1-yl)piperidine-1-carboxylate (200.0 mg, 1.0 eq) obtained in step 5-1 was dissolved in 1,4-dioxane (54.2 mL) and water (10.8 mL), 1-methyl-4-(4,4,5,5-tetramethyl-1,3,2-dioxaborolan-2-yl)-1H-pyrazole (81.9 mg, 1.5 eq), [1,1'-bis(diphenylphosphino)ferrocene]dichloropalladium (II) (19.2 mg, 0.1 eq) and potassium carbonate (108.9 mg, 5.0 eq) were added thereto at room temperature. The reaction mixture was allowed to react at 130° C. for 10 minutes using a microwave reactor, then water was added and the mixture was extracted with ethyl acetate. The separated organic layer was dried over magnesium sulfate and then concentrated under reduced pressure. The resulting residue was purified by column chromatography (ethyl acetate:hexane=1:1) to obtain 155.0 mg (yield: 83.3%) of the title compound.

Step 7-2: Preparation of 7-(1-methyl-1H-pyrazolo-4-yl)-3-(4-phenoxyphenyl)-1-(piperidin-3-yl)-1H-pyrazolo[4,3-c]pyridin-4-amine

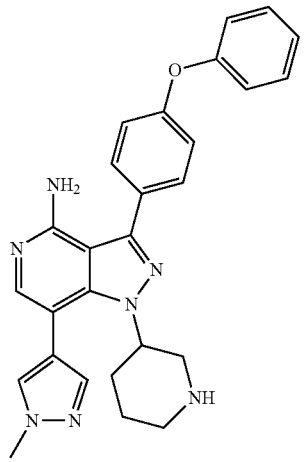 [SMILES: Cn1cc(-c2cnc(N)c3c(-c4ccc(Oc5ccccc5)cc4)nn(C4CCCNC4)c23)cn1]

After tert-butyl 3-(4-((2,4-dimethoxybenzyl)amino)-7-(1-methyl-1H-pyrazolo-4-yl)-3-(4-phenoxyphenyl)-1H-pyrazolo[4,3-c]pyridin-1-yl)piperidine-1-carboxylate (150.0 mg, 1.0 eq) obtained in step 7-1 was dissolved trifluoroacetic acid (2.0 mL) at room temperature, triethylsilane (66.8 uL, 2.0 eq) was added thereto. The reaction mixture was allowed to react at 80° C. for 2 hours and then concentrated under reduced pressure. Saturated aqueous sodium hydrogen carbonate solution was added to the resulting residue, and the mixture was extracted with ethyl acetate. The separated organic layer was dried over magnesium sulfate and then concentrated under reduced pressure. The resulting residue was purified by column chromatography (dichloromethane:methanol=10:1) to obtain 72.0 mg (yield: 73.6%) of the title compound as a white solid.

Step 7-3: Preparation of 1-(3-(4-amino-7-(1-methyl-1H-pyrazol-4-yl)-3-(4-phenoxyphenyl)-1H-pyrazolo[4,3-c]pyridin-1-yl)piperidin-1-yl)prop-2-en-1-one

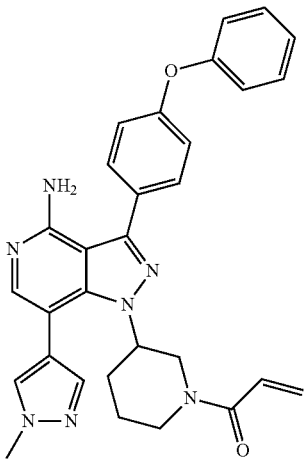 [SMILES: C=CC(=O)N1CCCC(n2nc(-c3ccc(Oc4ccccc4)cc3)c3c(N)ncc(-c4cnn(C)c4)c32)C1]

After 7-(1-methyl-1H-pyrazolo-4-yl)-3-(4-phenoxyphenyl)-1-(piperidin-3-yl)-1H-pyrazolo[4,3-c]pyridin-4-amine (65.0 mg, 1.0 eq) obtained in step 7-2 was dissolved in tetrahydrofuran (10.0 mL) and water (2.0 mL), sodium hydrogen carbonate (11.7 mg, 1.0 eq) was added thereto at 0° C., and the reaction mixture was allowed to react at 0° C. for 10 minutes. Acryloyl chloride (11.4 uL, 1.0 eq) was added thereto at 0° C. The reaction mixture was allowed to react at 0° C. for 10 minutes, then water was added and the mixture was extracted with ethyl acetate. The separated organic layer was dried over magnesium sulfate and then concentrated under reduced pressure. The resulting residue was purified by column chromatography (dichloromethane:methanol=10:1) to obtain 13.9 mg (yield: 19.1%) of the title compound.

$^1$H NMR (500 MHz, CDCl$_3$): 7.74 (s, 1H), 7.62 (d, 2H), 7.58 (s, 1H), 7.51 (s, 1H), 7.41-7.37 (m, 2H), 7.19-7.08 (m, 5H), 6.57-6.52 (m, 1H), 6.32-6.25 (m, 1H), 5.74-5.68 (m, 1H), 4.80 (d, 1H), 4.30-4.23 (m, 1H), 3.95 (s, 3H), 3.12-2.60 (m, 3H), 2.45-2.28 (m, 2H), 1.89-1.79 (m, 1H), 1.71-1.62 (m, 1H)

MS m/z: 520.60 [m+1]

Example 8: Preparation of 1-(6-(4-amino-7-(1-methyl-1H-pyrazol-4-yl)-3-(4-phenoxyphenyl)-1H-pyrazolo[4,3-c]pyridin-1-yl)-2-azabicyclo[2.2.1]heptan-2-yl)prop-2-en-1-one Step 8-1: Preparation of tert-butyl 6-(3-bromo-4-((2,4-dimethoxybenzyl)amino)-1H-pyrazolo[4,3-c]pyridin-1-yl)-2-azabicyclo[2.2.1]heptane-2-carboxylate

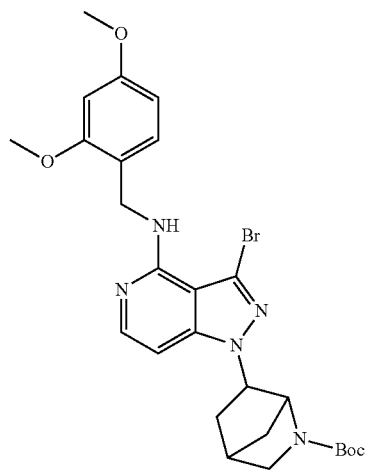 [SMILES: COc1ccc(CNc2nccc3c2c(Br)nn3C2CC3CC2N(C(=O)OC(C)(C)C)C3)c(OC)c1]

After tert-butyl 6-hydroxy-2-azabicyclo[2.2.1]heptan-2-carboxylate (500.0 mg, 1.5 eq) was dissolved in tetrahydrofuran (15.0 mL), triphenylphosphine (614.9 mg, 1.5 eq) was added at room temperature and diisopropyl azadicarboxylate (461.2 uL, 1.5 eq) was added at 0° C. The reaction mixture was allowed to react at room temperature for 10 minutes and then 3-bromo-N-(2,4-dimethoxybenzyl)-1H-pyrazolo[4,3-c]pyridin-4-amine (363.3 mg, 1.0 eq) obtained in step 3-1 was added thereto. The reaction mixture was allowed to react at room temperature for 2 days, then water was added and the mixture was extracted with ethyl acetate. The separated organic layer was dried over magnesium sulfate and then concentrated under reduced pressure. The resulting residue was purified by column chromatography (ethyl acetate:hexane=1:1) to obtain 372.0 mg (yield: 42.7%) of the title compound.

Step 8-2: Preparation of tert-butyl 6-(4-((2,4-dimethoxybenzyl)amino)-3-(4-phenoxyphenyl)-1H-pyrazolo[4,3-c]pyridin-1-yl)-2-azabicyclo[2.2.1]heptane-2-carboxylate

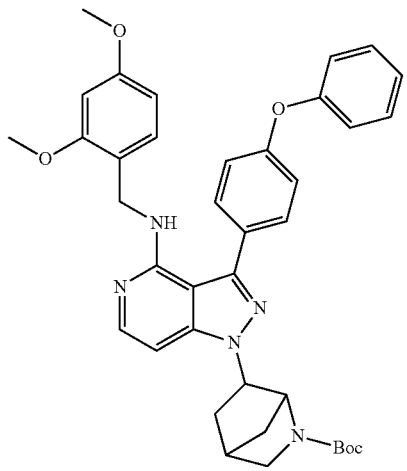 [SMILES: COc1ccc(CNc2nccc3c2c(-c2ccc(Oc4ccccc4)cc2)nn3C2CC3CC2N(C(=O)OC(C)(C)C)C3)c(OC)c1]

After tert-butyl 6-(3-bromo-4-((2,4-dimethoxybenzyl)amino)-1H-pyrazolo[4,3-c]pyridin-1-yl)-2-azabicyclo[2.2.1]heptane-2-carboxylate (370.0 mg, 1.0 eq) obtained in step 8-1 was dissolved in 1,4-dioxane (8.3 mL) and water (1.7 mL), (4-phenoxyphenyl) boronic acid (177.2 mg, 1.25 eq), [1,1'-bis(diphenylphosphino)ferrocene]dichloropalladium(II) (48.5 mg, 0.1 eq) and potassium carbonate (274.7 mg, 5.0 eq) were added thereto at room temperature. The reaction mixture was allowed to react at 110° C. for 20 minutes using a microwave reactor, then water was added and the mixture was extracted with ethyl acetate. The separated organic layer was dried over magnesium sulfate and then concentrated under reduced pressure. The resulting residue was purified by column chromatography (ethyl acetate:hexane=1:1) to obtain 245.0 mg (yield: 57.3%) of the title compound.

Step 8-3: Preparation of tert-butyl 6-(4-((2,4-dimethoxybenzyl)amino)-7-iodo-3-(4-phenoxyphenyl)-1H-pyrazolo[4,3-c]pyridin-1-yl)-2-azabicyclo[2.2.1]heptane-2-carboxylate

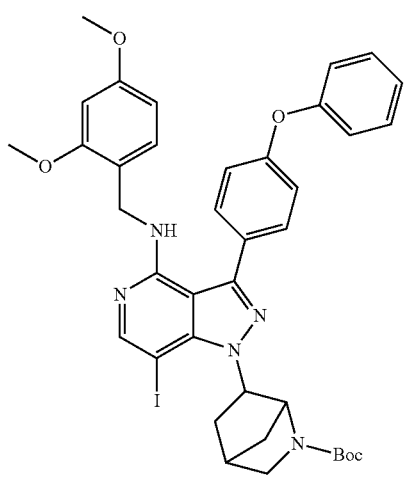 [SMILES: COc1ccc(CNc2ncc(I)c3c2c(-c2ccc(Oc4ccccc4)cc2)nn3C2CC3CC2N(C(=O)OC(C)(C)C)C3)c(OC)c1]

After tert-butyl 6-(4-((2,4-dimethoxybenzyl)amino)-3-(4-phenoxyphenyl)-1H-pyrazolo[4,3-c]pyridin-1-yl)-2-azabicyclo[2.2.1]heptane-2-carboxylate (240 mg, 1.0 eq) obtained in step 8-2 was dissolved in formamide (50.0 mL), N-iodosuccinimide (83.4 mg, 1.0 eq) was added thereto at room temperature. The reaction mixture was allowed to react at room temperature for 1 hour and then concentrated under reduced pressure. The resulting residue was purified by column chromatography (ethyl acetate:hexane=1:1) to obtain 150.0 mg (yield: 52.4%) of the title compound.

Step 8-4: Preparation of tert-butyl 6-(4-((2,4-dimethoxybenzyl)amino)-7-(1-methyl-1H-pyrazolo-4-yl)-3-(4-phenoxyphenyl)-1H-pyrazolo[4,3-c]pyridin-1-yl)-2-azabicyclo[2.2.1]heptan-2-carboxylate

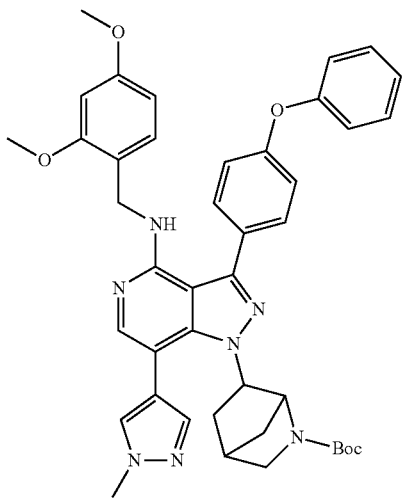 [SMILES: COc1ccc(CNc2ncc(-c3cnn(C)c3)c3c2c(-c2ccc(Oc4ccccc4)cc2)nn3C2CC3CC2N(C(=O)OC(C)(C)C)C3)c(OC)c1]

After tert-butyl 6-(4-((2,4-dimethoxybenzyl)amino)-7-iodo-3-(4-phenoxyphenyl)-1H-pyrazolo[4,3-c]pyridin-1-yl)-2-azabicyclo[2.2.1]heptan-2-carboxylate (140 mg, 1.0 eq) obtained in step 8-3 was dissolved in 1,4-dioxane (5.0 mL) and water (1.0 mL), 1-methyl-4-(4,4,5,5-tetramethyl-1,3,2-dioxaborolan-2-yl)-1H-pyrazole (56.5 mg, 1.5 eq), [1,1'-bis(diphenylphosphino)ferrocene]dichloropalladium (II) (13.2 mg, 0.1 eq) and potassium carbonate (75.0 mg, 3.0 eq) were added thereto at room temperature. The reaction mixture was allowed to react at 100° C. for 12 hours, then water was added and the mixture was extracted with ethyl acetate. The separated organic layer was dried over magnesium sulfate and then concentrated under reduced pressure. The resulting residue was purified by column chromatography (ethyl acetate:hexane=1:1) to obtain 83.1 mg (yield: 71.3%) of the title compound.

Step 8-5: Preparation of 1-(2-azabicyclo[2.2.1]heptan-6-yl)-7-(1-methyl-1H-pyrazolo-4-yl)-3-(4-phenoxyphenyl)-1H-pyrazolo[4,3-c]pyridin-4-amine

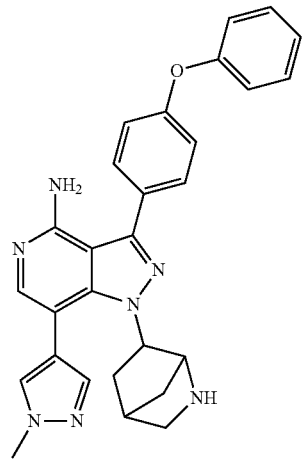 [SMILES: Cn1cc(-c2cnc(N)c3c(-c4ccc(Oc5ccccc5)cc4)nn(C4CC5CNC4C5)c23)cn1]

A reaction was performed in the same manner as in step 7-2 of Example 7 by using tert-butyl 6-(4-((2,4-dimethoxybenzyl)amino)-7-(1-methyl-1H-pyrazolo-4-yl)-3-(4-phenoxyphenyl)-1H-pyrazolo[4,3-c]pyridin-1-yl)-2-azabicyclo[2.2.1]heptan-2-carboxylate (70.0 mg, 1.0 eq) obtained in step 8-4, trifluoroacetic acid (2.0 mL) and triethylsilane (34.4 uL, 2.0 eq) to obtain 14.0 mg (yield: 7.9%) of the title compound.

Step 8-6: Preparation of 1-(6-(4-amino-7-(1-methyl-1H-pyrazol-4-yl)-3-(4-phenoxyphenyl)-1H-pyrazolo[4,3-c]pyridin-1-yl)-2-azabicyclo[2.2.1]heptan-2-yl)prop-2-en-1-one

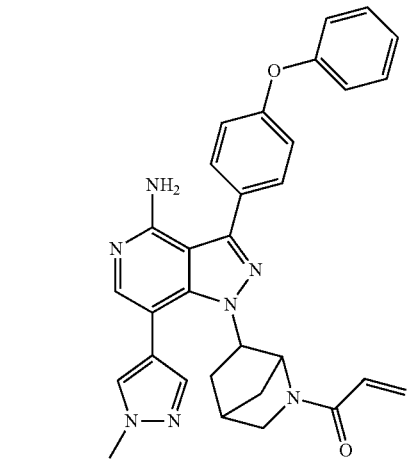 [SMILES: C=CC(=O)N1CC2CC1C(n1nc(-c3ccc(Oc4ccccc4)cc3)c3c(N)ncc(-c4cnn(C)c4)c31)C2]

A reaction was performed in the same manner as in step 3-5 of Example 3 by using 1-(2-azabicyclo[2.2.1]heptan-6-yl)-7-(1-methyl-1H-pyrazolo-4-yl)-3-(4-phenoxyphenyl)-1H-pyrazolo[4,3-c]pyridin-4-amine (33.5 mg, 1.0 eq) obtained in step 8-5, sodium hydrogen carbonate (5.9 mg, 1.0 eq) and acryloyl chloride (5.6 uL, 1.0 eq) to obtain 12.0 mg (yield: 32.2%) of the title compound.

<sup>1</sup>H NMR (500 MHz, CDCl<sub>3</sub>): 7.86 (s, 1H), 7.61-7.60 (m, 2H), 7.51-7.48 (m, 2H), 7.42-7.38 (m, 2H), 7.18 (t, 1H), 7.14 (d, 2H), 7.10 (d, 2H), 6.43 (d, 1H), 6.31-6.25 (m, 1H), 5.75-5.71 (m, 1H), 4.76-4.67 (m, 2H), 3.92-3.90 (m, 1H), 3.46-3.40 (m, 1H), 3.07-3.05 (m, 1H), 2.79-2.68 (m, 2H), 2.44-2.41 (m, 1H), 1.88-1.83 (m, 1H), 1.56-1.54 (m, 1H)

MS m/z: 532.57 [m+1]

Example 9: Preparation of 1-(3-(4-amino-7-chloro-3-(4-phenoxyphenyl)-1H-pyrazolo[4,3-c]pyridin-1-yl)piperidin-1-yl)prop-2-en-1-one Step 9-1: Preparation of tert-butyl 3-(7-chloro-4-((2,4-dimethoxybenzyl)amino)-3-(4-phenoxyphenyl)-1H-pyrazolo[4,3-c]pyridin-1-yl)piperidine-1-carboxylate

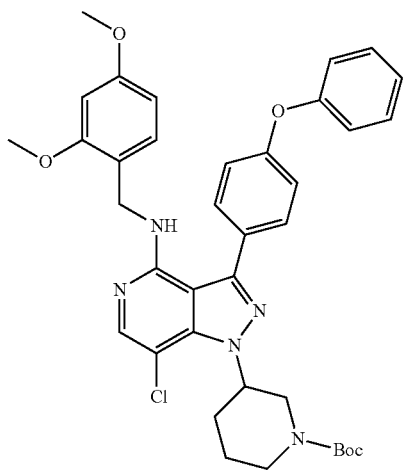 [SMILES: COc1ccc(CNc2ncc(Cl)c3c2c(-c2ccc(Oc4ccccc4)cc2)nn3C2CCCN(C(=O)OC(C)(C)C)C2)c(OC)c1]

After tert-butyl 3-(3-bromo-4-((2,4-dimethoxybenzyl)amino)-1H-pyrazolo[4,3-c]pyridin-1-yl)piperidine-1-carboxylate (130.0 mg, 1.0 eq) obtained in step 1-3 was dissolved in formamide (5.0 mL), N-chlorosuccinimide (27.3 mg, 1.0 eq) was added thereto at room temperature. The reaction mixture was allowed to react at 80° C. for 1 hour and then concentrated under reduced pressure. The resulting residue was purified by column chromatography (ethyl acetate:hexane=1:1) to obtain 136.0 mg (yield: 99.5%) of the title compound.

Step 9-2: Preparation of 7-chloro-3-(4-phenoxyphenyl)-1-(piperidin-3-yl)-1H-pyrazolo[4,3-c]pyridin-4-amine

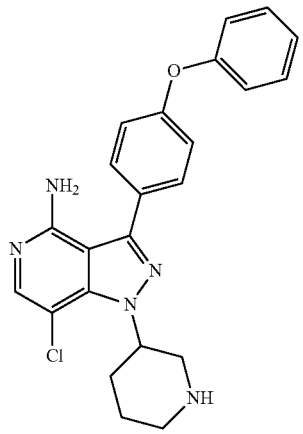 [SMILES: Nc1ncc(Cl)c2c1c(-c1ccc(Oc3ccccc3)cc1)nn2C1CCCNC1]

A reaction was performed in the same manner as in step 3-4 of Example 3 by using tert-butyl 3-(7-chloro-4-((2,4-dimethoxybenzyl)amino)-3-(4-phenoxyphenyl)-1H-pyrazolo[4,3-c]pyridin-1-yl)piperidine-1-carboxylate (120.0 mg, 1.0 eq) obtained in step 9-1, trifluoroacetic acid (2.0 mL) and triethylsilane (57.0 uL, 2.0 eq) to obtain the title compound, which was used in the next reaction without purification.

Step 9-3: Preparation of 1-(3-(4-amino-7-chloro-3-(4-phenoxyphenyl)-1H-pyrazolo[4,3-c]pyridin-1-yl)piperidin-1-yl)prop-2-en-1-one

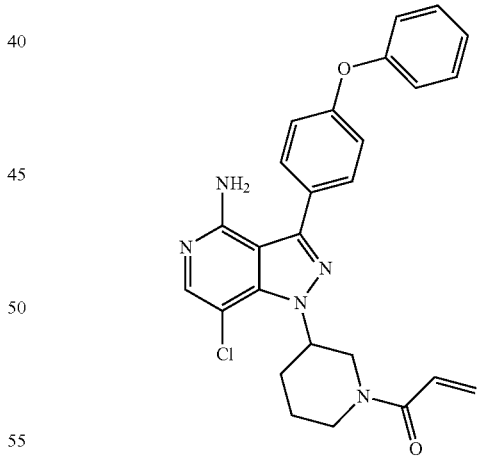

A reaction was performed in the same manner as in step 3-5 of Example 3 by using 7-chloro-3-(4-phenoxyphenyl)-1-(piperidin-3-yl)-1H-pyrazolo[4,3-c]pyridin-4-amine (46.3 mg, 1.0 eq) obtained in step 9-2 and acryloyl chloride (8.9 uL, 1.0 eq) to obtain 42.0 mg (yield: 80.6%) of the title compound.

<sup>1</sup>H NMR (500 MHz, CDCl<sub>3</sub>): 7.79-7.76 (m, 1H), 7.59-7.56 (m, 2H), 7.46-7.38 (m, 2H), 7.18 (t, 1H), 7.16-7.08 (m, 4H), 6.65-6.59 (m, 1H), 6.35-6.28 (m, 1H), 5.34-5.67 (m, 1H), 5.01-4.99 (m, 1H), 4.68-4.66 (m, 1H), 4.31-4.28 (m, 1H), 4.05-4.03 (m, 1H), 3.69-3.65 (m, 1H), 3.18-3.13 (m, 1H), 2.78-2.75 (m, 1H), 2.43-2.41 (m, 1H)

MS m/z: 472.37 [m+1]

Example 10: Preparation of 1-(3-(4-amino-7-bromo-3-(4-phenoxyphenyl)-1H-pyrazolo[4,3-c]pyridin-1-yl)piperidin-1-yl)prop-2-en-1-one Step 10-1: Preparation of tert-butyl 3-(7-bromo-4-((2,4-dimethoxybenzyl)amino)-3-(4-phenoxyphenyl)-1H-pyrazolo[4,3-c]pyridin-1-yl)piperidine-1-carboxylate

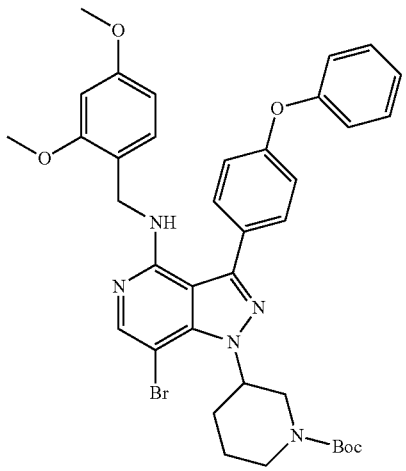 [SMILES: COc1ccc(CNc2ncc(Br)c3c2c(-c2ccc(Oc4ccccc4)cc2)nn3C2CCCN(C(=O)OC(C)(C)C)C2)c(OC)c1]

After tert-butyl 3-(3-bromo-4-((2,4-dimethoxybenzyl)amino)-1H-pyrazolo[4,3-c]pyridin-1-yl)piperidine-1-carboxylate (130.0 mg, 1.0 eq) obtained in step 1-3 was dissolving in formamide (5.0 mL), N-bromosuccinimide (36.4 mg, 1.0 eq) was added thereto at room temperature. The reaction mixture was allowed to react at 80° C. for 1 hour and then concentrated under reduced pressure. The resulting residue was purified by column chromatography (ethyl acetate:hexane=1:1) to obtain 143.0 mg (yield: 100.0%) of the title compound.

Step 10-2: Preparation of 7-bromo-3-(4-phenoxyphenyl)-1-(piperidin-3-yl)-1H-pyrazolo[4,3-c]pyridin-4-amine

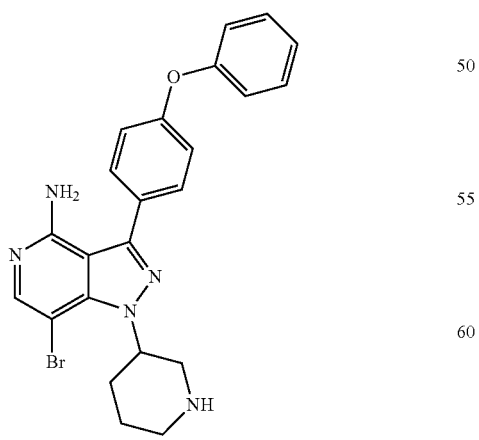

The title compound was obtained in the same manner as in step 3-4 of Example 3, by using tert-butyl 3-(7-bromo-4-((2,4-dimethoxybenzyl)amino)-3-(4-phenoxyphenyl)-1H-pyrazolo[4,3-c]pyridin-1-yl)piperidine-1-carboxylate (135.0 mg, 1.0 eq) obtained in step 10-1, trifluoroacetic acid (2.0 mL) and triethylsilane (60.2 uL, 2.0 eq).

Step 10-3: Preparation of 1-(3-(4-amino-7-bromo-3-(4-phenoxyphenyl)-1H-pyrazolo[4,3-c]pyridin-1-yl)piperidin-1-yl)prop-2-en-1-one

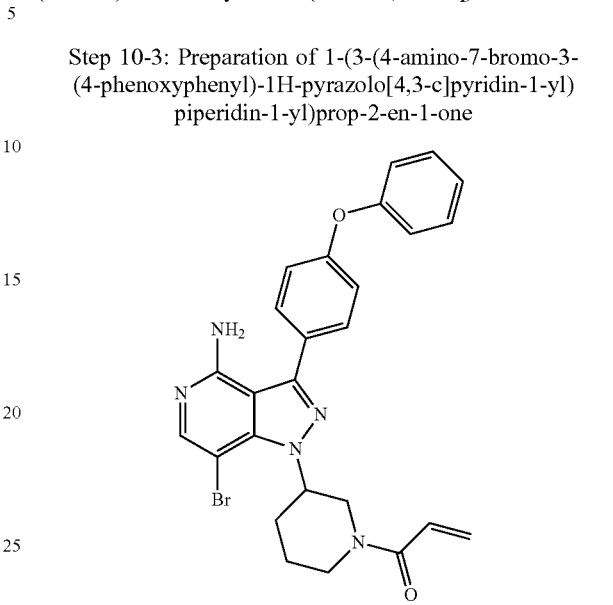

A reaction was performed in the same manner as in step 3-5 of Example 3 by using 7-bromo-3-(4-phenoxyphenyl)-1-(piperidin-3-yl)-1H-pyrazolo[4,3-c]pyridin-4-amine (50.0 mg, 1.0 eq) obtained in step 10-2, sodium hydrogen carbonate (9.1 mg, 1.0 eq) and acryloyl chloride (8.8 uL, 1.0 eq) to obtain 43.0 mg (yield: 75.4%) of the title compound.

$^1$H NMR (500 MHz, CDCl$_3$): 7.89-7.85 (m, 1H), 7.58-7.55 (m, 2H), 7.41-7.38 (m, 2H), 7.20-7.18 (m, 1H), 7.17-7.00 (m, 4H), 6.66-6.61 (m, 1H), 6.35-6.28 (m, 1H), 5.72-5.68 (m, 1H), 5.01-4.99 (m, 1H), 4.69-4.67 (m, 1H), 4.30-4.28 (m, 1H), 4.05-4.03 (m, 1H), 3.68-3.66 (m, 1H), 3.42-3.38 (m, 1H), 3.20-3.10 (m, 1H), 2.84-2.72 (m, 1H), 2.48-2.37 (m, 1H)

MS m/z: 518.52 [m+1]

Example 11: Preparation of 1-(3-(4-amino-3-(4-phenoxyphenyl)-7-phenyl-1H-pyrazolo[4,3-c]pyridin-1-yl)piperidin-1-yl)prop-2-en-1-one Step 11-1: Preparation of tert-butyl 3-(4-((2,4-dimethoxybenzyl)amino)-3-(4-phenoxyphenyl)-7-phenyl-1H-pyrazolo[4,3-c]pyridin-1-yl)piperidine-1-carboxylate

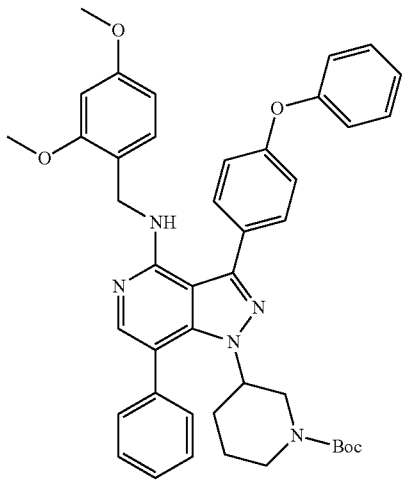 [SMILES: COc1ccc(CNc2ncc(-c3ccccc3)c3c2c(-c2ccc(Oc4ccccc4)cc2)nn3C2CCCN(C(=O)OC(C)(C)C)C2)c(OC)c1]

After tert-butyl 3-(4-((2,4-dimethoxybenzyl)amino)-7-iodo-3-(4-phenoxyphenyl)-1H-pyrazolo[4,3-c]pyridine-1-yl)piperidine-1-carboxylate (200.0 mg, 1.0 eq) obtained in step 5-1 of Example 5 was dissolved in 1,4-dioxane (5.0 mL) and water (1.0 mL), phenylboronic acid (48.0 mg, 1.5 eq), [1,1'-bis(diphenylphosphino)ferrocene]dichloropalladium (II) (19.2 mg, 0.1 eq) and potassium carbonate (108.9 mg, 3.0 eq) were added thereto at room temperature. The reaction mixture was allowed to react at 130° C. for 20 minutes using a microwave reactor, then water was added and the mixture was extracted with ethyl acetate. The separated organic layer was dried over magnesium sulfate and then concentrated under reduced pressure. The resulting residue was purified by column chromatography (ethyl acetate: hexane=1:1) to obtain 167.0 mg (yield: 90.2%) of the title compound.

Step 11-2: Preparation of 3-(4-phenoxyphenyl)-7-phenyl-1-(piperidin-3-yl)-1H-pyrazolo[4,3-c]pyridin-4-amine

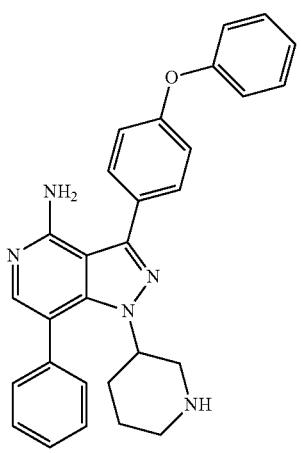 [SMILES: Nc1ncc(-c2ccccc2)c2c1c(-c1ccc(Oc3ccccc3)cc1)nn2C1CCCNC1]

A reaction was performed in the same manner as in step 7-2 of Example 7 by using tert-butyl 3-(4-((2,4-dimethoxybenzyl)amino)-3-(4-phenoxyphenyl)-7-phenyl-1H-pyrazolo[4,3-c]pyridin-1-yl)piperidine-1-carboxylate (130.0 mg, 1.0 eq) obtained in step 11-1, trifluoroacetic acid (3.0 mL) and triethylsilane (58.2 uL, 2.0 eq) to obtain 65.5 mg (yield: 77.5%) of the title compound.

Step 11-3: Preparation of 1-(3-(4-amino-3-(4-phenoxyphenyl)-7-phenyl-1H-pyrazolo[4,3-c]pyridin-1-yl)piperidin-1-yl)prop-2-en-1-one

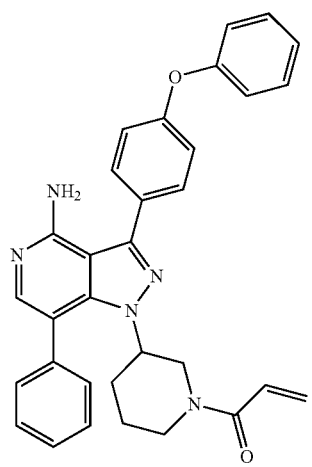 [SMILES: C=CC(=O)N1CCCC(n2nc(-c3ccc(Oc4ccccc4)cc3)c3c(N)ncc(-c4ccccc4)c32)C1]

A reaction was performed in the same manner as in step 3-5 of Example 3 by using 3-(4-phenoxyphenyl)-7-phenyl-1-(piperidin-3-yl)-1H-pyrazolo[4,3-c]pyridin-4-amine (60.0 mg, 1.0 eq) obtained in step 11-2, sodium hydrogen carbonate (10.9 mg, 1.0 eq) and acryloyl chloride (10.6 uL, 1.0 eq) to obtain 38.0 mg (yield: 56.7%) of the title compound.

$^1$H NMR (500 MHz, CDCl$_3$): 7.64-7.62 (m, 3H), 7.48-7.38 (m, 6H), 7.19-7.15 (m, 3H), 7.09 (d, 2H), 6.45-6.43 (m, 1H), 6.36-3.60 (m, 1H), 6.21-6.13 (m, 1H), 5.43-5.28 (m, 1H), 4.76-4.66 (m, 1H), 4.52-4.44 (m, 1H), 3.90-3.77 (m,

2H), 3.62-3.59 (m, 1H), 3.25-3.15 (m, 1H), 3.02-2.91 (m, 1H), 2.62-2.51 (m, 1H), 2.22-2.08 (m, 1H)

MS m/z: 516.44 [m+1]

Example 12: Preparation of 1-(4-(4-amino-7-iodo-3-(4-phenoxyphenyl)-1H-pyrazolo[4,3-c]pyridin-1-yl)piperidin-1-yl)prop-2-en-1-one

Step 12-1: Preparation of tert-butyl 4-(3-bromo-4-chloro-1H-pyrazolo[4,3-c]pyridin-1-yl)piperidine-1-carboxylate

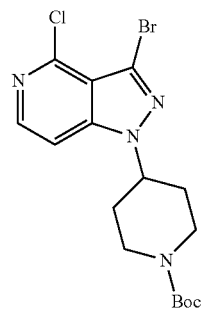 [SMILES: CC(C)(C)OC(=O)N1CCC(n2nc(Br)c3c(Cl)nccc32)CC1]

After 1-(tert-butoxycarbonyl)-4-hydroxypiperidine (13.0 g, 1.5 eq) was dissolved in tetrahydrofuran (100.0 mL), triphenylphosphine (16.9 mg, 1.5 eq) was added at room temperature and diisopropyl azadicarboxylate (12.7 mL, 1.5 eq) was added at 0° C. The reaction mixture was allowed to react at room temperature for 10 minutes, and then 3-bromo-4-chloro-1H-pyrazolo[4,3-c]pyridine (10.0 g, 1.0 eq) obtained in step 1-1 of Example 1 was added. The reaction mixture was allowed to react at room temperature for 2 days, then water was added and the mixture was extracted with ethyl acetate. The separated organic layer was dried over magnesium sulfate and then concentrated under reduced pressure. The resulting residue was purified by column chromatography (ethyl acetate:hexane=1:1) to obtain 1.8 g (yield: 10.1%) of the title compound.

Step 12-2: Preparation of tert-butyl 4-(3-bromo-4-((2,4-dimethoxybenzyl)amino)-1H-pyrazolo[4,3-c]pyridin-1-yl)piperidine-1-carboxylate

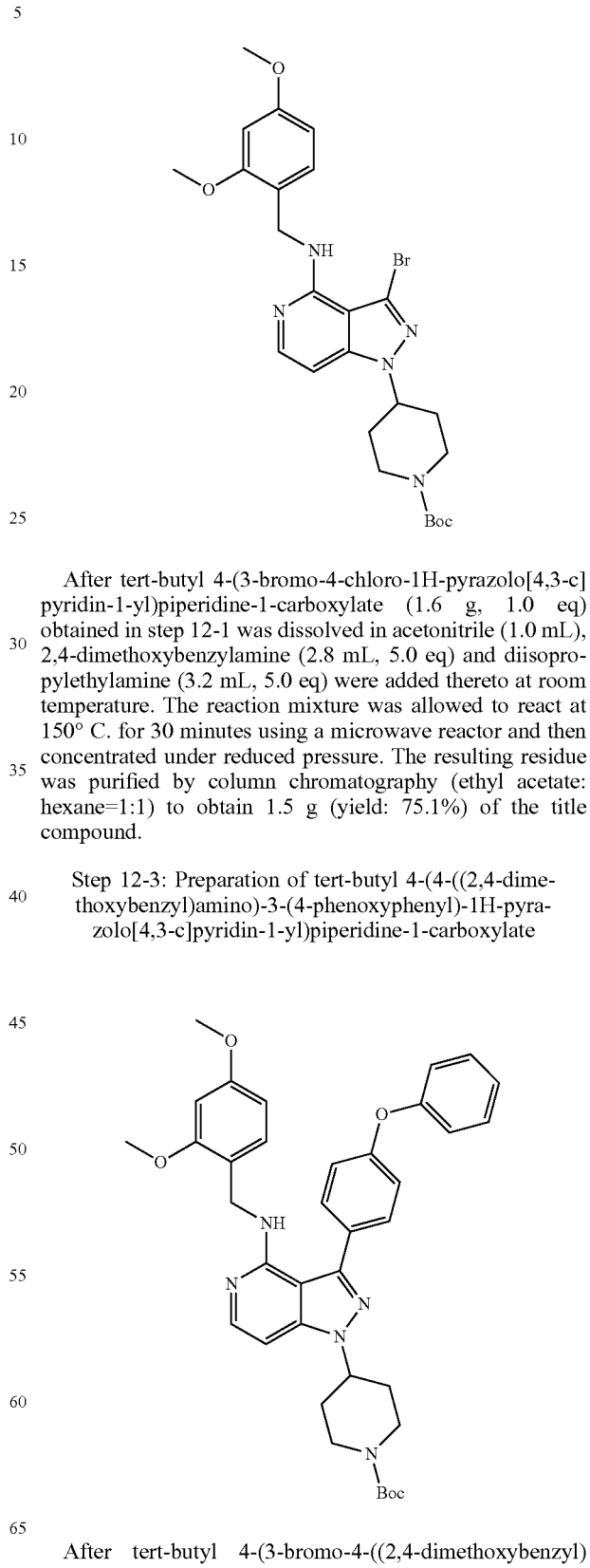

After tert-butyl 4-(3-bromo-4-chloro-1H-pyrazolo[4,3-c]pyridin-1-yl)piperidine-1-carboxylate (1.6 g, 1.0 eq) obtained in step 12-1 was dissolved in acetonitrile (1.0 mL), 2,4-dimethoxybenzylamine (2.8 mL, 5.0 eq) and diisopropylethylamine (3.2 mL, 5.0 eq) were added thereto at room temperature. The reaction mixture was allowed to react at 150° C. for 30 minutes using a microwave reactor and then concentrated under reduced pressure. The resulting residue was purified by column chromatography (ethyl acetate:hexane=1:1) to obtain 1.5 g (yield: 75.1%) of the title compound.

Step 12-3: Preparation of tert-butyl 4-(4-((2,4-dimethoxybenzyl)amino)-3-(4-phenoxyphenyl)-1H-pyrazolo[4,3-c]pyridin-1-yl)piperidine-1-carboxylate

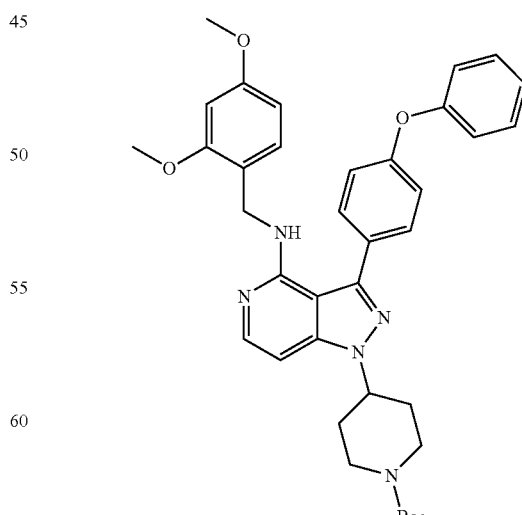

After tert-butyl 4-(3-bromo-4-((2,4-dimethoxybenzyl)amino)-1H-pyrazolo[4,3-c]pyridin-1-yl)piperidine-1-carboxylate (1.5 g, 1.0 eq) obtained in step 12-2 was dissolved in 1,4-dioxane (15.0 mL) and water (3.0 mL), (4-phenoxyphenyl)boronic acid (0.7 g, 1.25 eq), [1,1'-bis(diphenylphosphino)ferrocene]dichloropalladium (II) (0.2 g, 0.1 eq) and potassium carbonate (1.14 g, 3.0 eq) were added thereto at room temperature. The reaction mixture was allowed to react at 130° C. for 20 minutes using a microwave reactor, then water was added and the mixture was extracted with ethyl acetate. The separated organic layer was dried over magnesium sulfate and then concentrated under reduced pressure. The resulting residue was purified by column chromatography (ethyl acetate:hexane=1:1) to obtain 1.6 g (yield: 89.2%) of the title compound.

Step 12-4: Preparation of tert-butyl 4-(4-((2,4-dimethoxybenzyl)amino)-7-iodo-3-(4-phenoxyphenyl)-1H-pyrazolo[4,3-c]pyridin-1-yl)piperidine-1-carboxylate

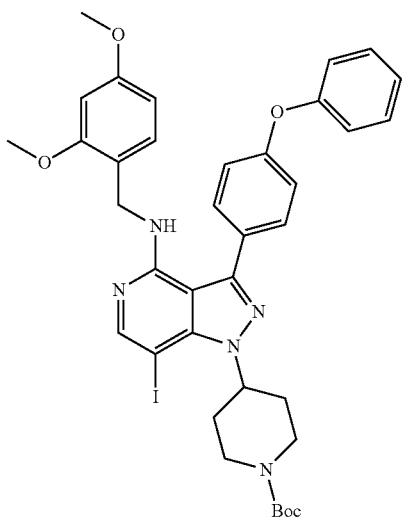 [SMILES: COc1ccc(CNc2ncc(I)c3c2c(-c2ccc(Oc4ccccc4)cc2)nn3C2CCN(C(=O)OC(C)(C)C)CC2)c(OC)c1]

A reaction was performed in the same manner as in step 5-1 of Example 5 by using tert-butyl 4-(4-((2,4-dimethoxybenzyl)amino)-3-(4-phenoxyphenyl)-1H-pyrazolo[4,3-c]pyridin-1-yl)piperidine-1-carboxylate (800.0 mg, 1.0 eq) obtained in step 12-3, formamide (15.0 mL) and N-iodosuccinimide (283.1 mg, 1.0 eq) to obtain 710.0 mg (yield: 74.0%) of the title compound.

Step 12-5: Preparation of 7-iodo-3-(4-phenoxyphenyl)-1-(piperidin-4-yl)-1H-pyrazolo[4,3-c]pyridine-4-amine

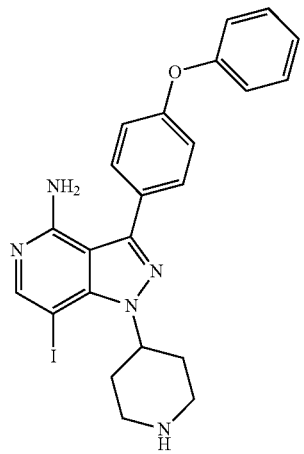 [SMILES: Nc1ncc(I)c2c1c(-c1ccc(Oc3ccccc3)cc1)nn2C1CCNCC1]

A reaction was performed in the same manner as in step 3-4 of Example 3 by using tert-butyl 4-(4-((2,4-dimethoxybenzyl)amino)-7-iodo-3-(4-phenoxyphenyl)-1H-pyrazolo[4,3-c]pyridin-1-yl)piperidine-1-carboxylate (700.0 mg, 1.0 eq) obtained in step 12-4, trifluoroacetic acid (5.0 mL) and triethylsilane (293.0 uL, 2.0 eq) to obtain the title compound, which was used in the next reaction without purification.

Step 12-6: Preparation of 1-(4-(4-amino-7-iodo-3-(4-phenoxyphenyl)-1H-pyrazolo[4,3-c]pyridin-1-yl)piperidin-1-yl)prop-2-en-1-one

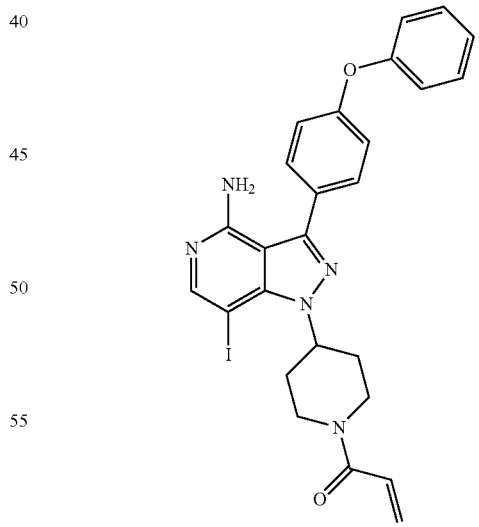

A reaction was performed in the same manner as in Example 3-5 of Example 3 by using 7-iodo-3-(4-phenoxyphenyl)-1-(piperidin-4-yl)-1H-pyrazolo[4,3-c]pyridine-4-amine (470.5 mg, 1.0 eq) obtained in step 12-5, sodium hydrogen carbonate (77.3 mg, 1.0 eq) and acryloyl chloride (10.6 uL, 1.0 eq) to obtain 83.0 mg (yield: 16.0%) of the title compound.

$^1$H NMR (500 MHz, CDCl$_3$): 8.10 (s, 1H), 7.56 (d, 1H), 7.40-7.37 (m, 2H), 7.17 (t, 1H), 7.13 (d, 2H), 6.63-6.58 (m, 1H), 6.31-6.27 (m, 1H), 5.78-5.74 (m, 1H), 5.71 (d, 1H), 5.35-5.21 (m, 1H), 4.85-4.83 (m, 1H), 4.20-4.11 (m, 1H), 3.34-3.25 (m, 1H), 2.98-2.86 (m, 1H), 2.35-2.29 (m, 2H), 2.17-2.15 (m, 1H)

MS m/z 566.50 [m+1]

Example 13: Preparation of 1-(4-(4-amino-7-(1-methyl-1H-pyrazol-4-yl)-3-(4-phenoxyphenyl)-1H-pyrazolo[4,3-c]pyridin-1-yl)piperidin-1-yl)prop-2-en-1-one

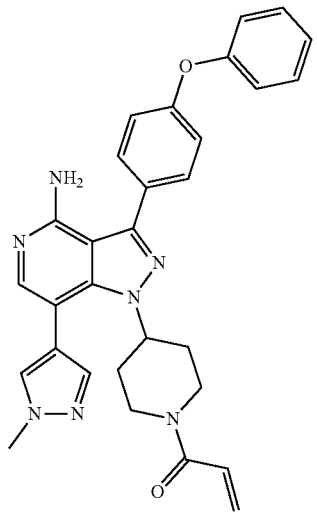 [SMILES: C=CC(=O)N1CCC(n2nc(-c3ccc(Oc4ccccc4)cc3)c3c(N)ncc(-c4cnn(C)c4)c32)CC1]

After 1-(4-(4-amino-7-iodo-3-(4-phenoxyphenyl)-1H-pyrazolo[4,3-c]pyridin-1-yl)piperidin-1-yl)prop-2-en-1-one (30.0 mg, 1.0 eq) obtained in step 12-6 of Example 12 was dissolved in 1,4-dioxane (1.6 mL) and water (0.4 mL), 1-methyl-4-(4,4,5,5-tetramethyl-1,3,2-dioxaborolan-2-yl)-1H-pyrazole(14.4 mg, 1.3 eq), [1,1'-bis(diphenylphosphino)ferrocene]dichloropalladium(II) (3.9 mg, 0.1 eq) and potassium carbonate (22.0 mg, 3.0 eq) were added thereto at room temperature. The reaction mixture was allowed to react at 130° C. for 20 minutes using a microwave reactor, then water was added and the mixture was extracted with ethyl acetate. The separated organic layer was dried over magnesium sulfate and then concentrated under reduced pressure. The resulting residue was purified by column chromatography (dichloromethane:methanol=1:1) to obtain 9.8 mg (yield: 35.6%) of the title compound.

$^1$H NMR (500 MHz, CDCl$_3$): 7.60-7.55 (m, 4H), 7.47 (s, 1H), 7.40-7.37 (m, 2H), 7.17 (t, 1H), 7.14 (d, 2H), 7.08 (d, 2H), 6.56-6.50 (m, 1H), 6.24 (d, 1H), 5.85-5.71 (m, 1H), 5.67 (d, 1H), 4.76-4.65 (m, 1H), 4.48-4.42 (m, 1H), 4.10-4.03 (m, 1H), 2.98-2.87 (m, 1H), 2.58-2.43 (m, 1H), 2.29-2.10 (m, 2H)

MS m/z: 520.47 [m+1]

Example 14: Preparation of (E)-1-(3-(4-amino-7-(4-fluorostyryl)-3-(4-phenoxyphenyl)-1H-pyrazolo[4,3-c]pyridin-1-yl)piperidin-1-yl)prop-2-en-1-one Step 14-1: Preparation of tert-butyl (E)-3-(4-((2,4-dimethoxybenzyl)amino)-7-(4-fluorostyryl)-3-(4-phenoxyphenyl)-1H-pyrazolo[4,3-c]pyridin-1-yl)piperidine-1-carboxylate

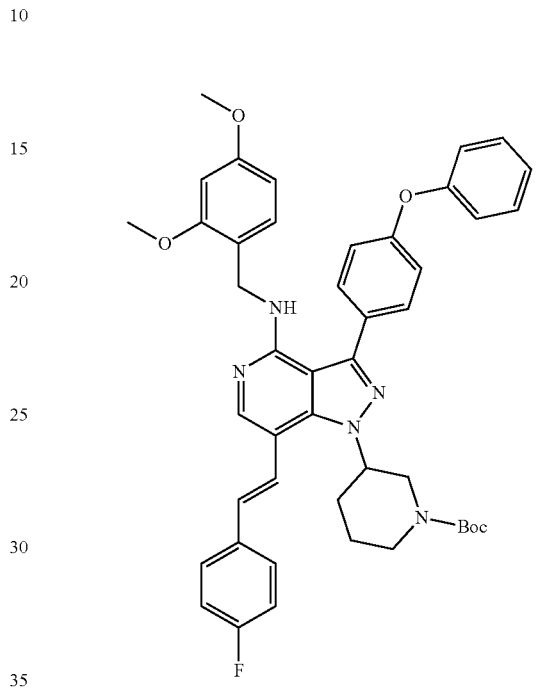

After tert-butyl 3-(4-((2,4-dimethoxybenzyl)amino)-7-iodo-3-(4-phenoxyphenyl)-1H-pyrazolo[4,3-c]pyridine-1-yl)piperidine-1-carboxylate (200.0 mg, 1.0 eq) obtained in step 5-1 of Example 5 was dissolved in 1,4-dioxane (10.0 mL) and water (2.0 mL), (E)-(4-fluorostyryl)boronic acid (56.6 mg, 1.3 eq), [1,1'-bis(diphenylphosphino)ferrocene]dichloropalladium(II) (19.2 mg, 0.1 eq) and potassium carbonate (108.9 mg, 3.0 eq) were added thereto at room temperature. The reaction mixture was allowed to react at 130° C. for 20 minutes using a microwave reactor, then water was added and the mixture was extracted with ethyl acetate. The separated organic layer was dried over magnesium sulfate and then concentrated under reduced pressure. The resulting residue was purified by column chromatography (ethyl acetate:hexane=1:1) to obtain 156.0 mg (yield: 79.4%) of the title compound.

Step 14-2: Preparation of (E)-7-(4-fluorostyryl)-3-(4-phenoxyphenyl)-1-(piperidin-3-yl)-1H-pyrazolo[4,3-c]pyridine-4-amine

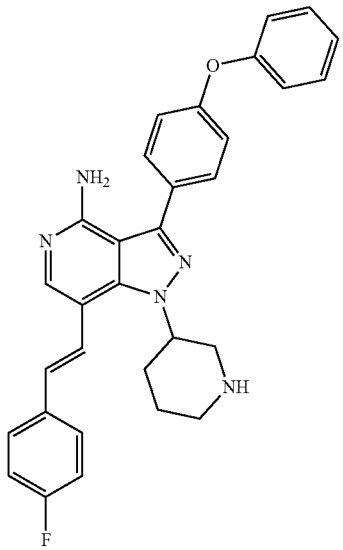 [SMILES: Nc1ncc(/C=C/c2ccc(F)cc2)c2c1c(-c1ccc(Oc3ccccc3)cc1)nn2C1CCCNC1]

A reaction was performed in the same manner as in step 3-4 of Example 3 by using tert-butyl (E)-3-(4-((2,4-dimethoxybenzyl)amino)-7-(4-fluorostyryl)-3-(4-phenoxyphenyl)-1H-pyrazolo[4,3-c]pyridin-1-yl)piperidine-1-carboxylate (150.0 mg, 1.0 eq) obtained in step 14-1, trifluoroacetic acid (2.0 mL) and triethylsilane (63.2 uL, 2.0 eq) to obtain the title compound, which was used in the next reaction without purification.

Step 14-3: Preparation of (E)-1-(3-(4-amino-7-(4-fluorostyryl)-3-(4-phenoxyphenyl)-1H-pyrazolo[4,3-c]pyridin-1-yl)piperidin-1-yl)prop-2-en-1-one

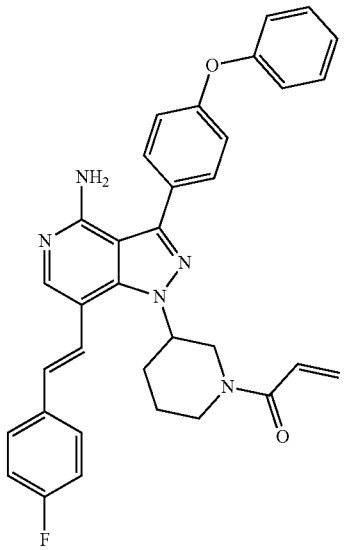 [SMILES: C=CC(=O)N1CCCC(n2nc(-c3ccc(Oc4ccccc4)cc3)c3c(N)ncc(/C=C/c4ccc(F)cc4)c32)C1]

A reaction was performed in the same manner as in step 3-5 of Example 3 by using (E)-7-(4-fluorostyryl)-3-(4-phenoxyphenyl)-1-(piperidin-3-yl)-1H-pyrazolo[4,3-c]pyridine-4-amine (100.1 mg, 1.0 eq) obtained in step 14-2, sodium hydrogen carbonate (16.6 mg, 1.0 eq) and acryloyl chloride (16.1 uL, 1.0 eq) to obtain 6.0 mg (yield: 5.4%) of the title compound.

$^1$H NMR (500 MHz, CDCl$_3$): 7.68-7.58 (m, 4H), 7.57-7.52 (m, 1H), 7.46-7.38 (m, 3H), 7.20 (t, 1H), 7.17 (d, 2H), 7.10 (d, 2H), 7.07-7.01 (m, 2H), 6.84-6.81 (m, 1H), 6.66-6.60 (m, 1H), 6.44-6.41 (m, 1H), 5.82-5.80 (m, 1H), 5.09-5.07 (m, 1H), 4.76-4.68 (m, 1H), 4.05-4.03 (m, 1H), 3.21-3.10 (m, 2H), 2.64-2.49 (m, 1H), 2.27-2.21 (m, 1H), 2.04-1.98 (m, 1H)

MS m/z: 560.28 [m+1]

Example 15: Preparation of (E)-1-(4-(4-amino-7-(4-fluorostyryl)-3-(4-phenoxyphenyl)-1H-pyrazolo[4,3-c]pyridin-1-yl)piperidin-1-yl)prop-2-en-1-one

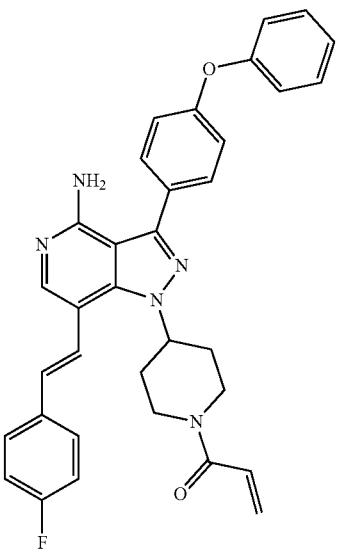 [SMILES: C=CC(=O)N1CCC(n2nc(-c3ccc(Oc4ccccc4)cc3)c3c(N)ncc(/C=C/c4ccc(F)cc4)c32)CC1]

A reaction was performed in the same manner as in step 14-3 of Example 14 by using 1-(4-(4-amino-7-iodo-3-(4-phenoxyphenyl)-1H-pyrazolo[4,3-c]pyridin-1-yl)piperidin-1-yl)prop-2-en-1-one (30.0 mg, 1.0 eq) obtained in step 12-6 of Example 12, 1,4-dioxane (2.5 mL), water (0.5 mL), (E)-(4-fluorostyryl)boronic acid (12.7 mg, 1.3 eq), [1,1'-bis(diphenylphosphino)ferrocene]dichloropalladium(II) (4.3 mg, 0.1 eq), and potassium carbonate (24.3 mg, 3.0 eq) to obtain 13.6 mg (yield: 41.2%) of the title compound.

$^1$H NMR (500 MHz, CDCl$_3$): 7.78 (s, 1H), 7.60-7.58 (m, 2H), 7.56-7.46 (m, 2H), 7.43-7.38 (m, 2H), 7.23-7.11 (m, 4H), 7.09-7.04 (m, 3H), 6.88 (d, 1H), 6.60-6.55 (m, 1H), 6.28 (d, 1H), 5.96-5.78 (m, 1H), 5.70 (d, 1H), 4.93-4.88 (m, 1H), 4.78-4.76 (m, 1H), 4.22-4.14 (m, 1H), 3.24-3.08 (m, 1H), 2.86-2.69 (m, 1H), 2.48-2.32 (m, 2H), 2.19-2.06 (m, 1H)

MS m/z: 560.60 [m+1]

Example 16: Preparation of (R)-1-(3-(4-amino-7-iodo-3-(4-phenoxyphenyl)-1H-pyrazolo[4,3-c]pyridin-1-yl)piperidin-1-yl)prop-2-en-1-one

Step 16-1: Preparation of tert-butyl (R)-3-(3-bromo-4-chloro-1H-pyrazolo[4,3-c]pyridin-1-yl)piperidine-1-carboxylate

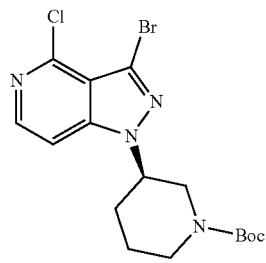 [SMILES: CC(C)(C)OC(=O)N1CCC[C@@H](n2nc(Br)c3c(Cl)nccc32)C1]

A reaction was performed in the same manner as in step 1-2 of Example 1 by using (S)-1-(tert-butoxycarbonyl)-3-hydroxypiperidine (1.00 g, 1.5 eq), tetrahydrofuran (30.0 mL), triphenylphosphine (1.30 g, 1.5 eq), diisopropyl azadicarboxylate (1.0 mL, 1.5 eq), and 3-bromo-4-chloro-1H-pyrazolo[4,3-c]pyridine (0.77 g, 1.0 eq) obtained in step 1-1 of Example 1 to obtain 730.0 mg (yield: 53.2%) of the title compound.

Step 16-2: Preparation of tert-butyl (R)-3-(3-bromo-4-((2,4-dimethoxybenzyl)amino)-1H-pyrazolo[4,3-c]pyridin-1-yl)piperidine-1-carboxylate

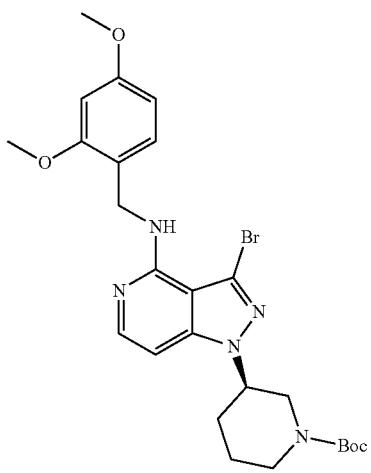 [SMILES: COc1ccc(CNc2nccc3c2c(Br)nn3[C@@H]2CCCN(C(=O)OC(C)(C)C)C2)c(OC)c1]

A reaction was performed in the same manner as in step 1-3 of Example 1 by using tert-butyl (R)-3-(3-bromo-4-chloro-1H-pyrazolo[4,3-c]pyridin-1-yl)piperidine-1-carboxylate (700.0 mg, 1.0 eq) obtained in step 16-1, acetonitrile (10.0 mL), 2,4-dimethoxybenzylamine (1.3 mL, 5.0 eq) and diisopropylethylamine (1.4 mL, 5.0 eq) to obtain 619.0 mg (yield: 66.4%) of the title compound.

Step 16-3: Preparation of tert-butyl (R)-3-(4-((2,4-dimethoxybenzyl)amino)-3-(4-phenoxyphenyl)-1H-pyrazolo[4,3-c]pyridin-1-yl)piperidine-1-carboxylate

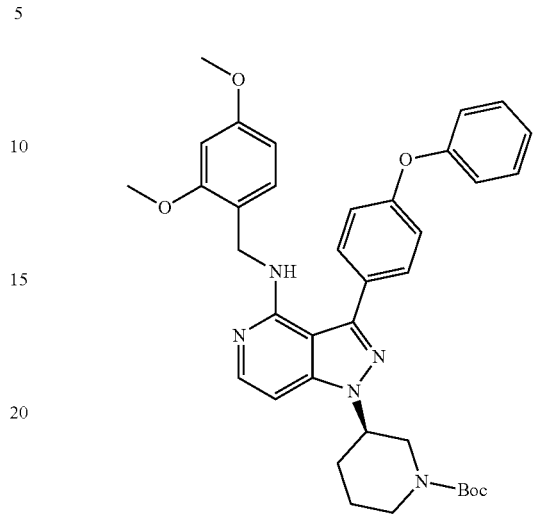

After tert-butyl (R)-3-(3-bromo-4-((2,4-dimethoxybenzyl)amino)-1H-pyrazolo[4,3-c]pyridin-1-yl)piperidine-1-carboxylate (600.0 mg, 1.0 eq) obtained in step 16-2 was dissolved in 1,4-dioxane (10.0 mL) and water (2.0 mL), (4-phenoxyphenyl)boronic acid (305.5 mg, 1.3 eq), [1,1'-bis(diphenylphosphino)ferrocene]dichloropalladium(II) (80.3 mg, 0.1 eq) and potassium carbonate (455.3 mg, 3.0 eq) were added thereto at room temperature. The reaction mixture was allowed to react at 130° C. for 20 minutes using a microwave reactor, then water was added and the mixture was extracted with ethyl acetate. The separated organic layer was dried over magnesium sulfate and then concentrated under reduced pressure. The resulting residue was purified by column chromatography (ethyl acetate:hexane=1:1) to obtain 352.0 mg (yield: 50.3%) of the title compound.

Step 16-4: Preparation of tert-butyl (R)-3-(4-((2,4-dimethoxybenzyl)amino)-7-iodo-3-(4-phenoxyphenyl)-1H-pyrazolo[4,3-c]pyridin-1-yl)piperidine-1-carboxylate

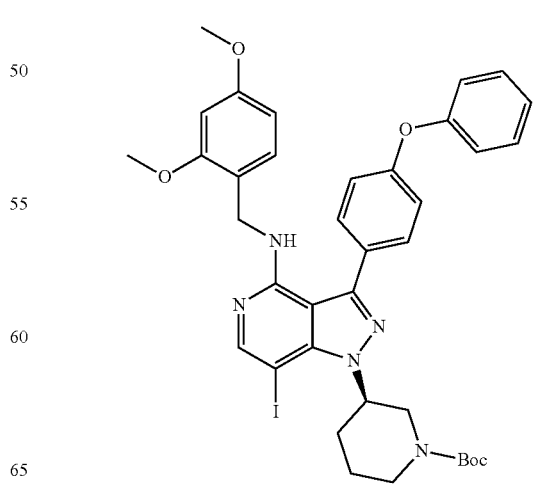

A reaction was performed in the same manner as in step 5-1 of Example 5 by using tert-butyl (R)-3-(4-((2,4-dimethoxybenzyl)amino)-3-(4-phenoxyphenyl)-1H-pyrazolo[4,3-c]pyridin-1-yl)piperidine-1-carboxylate (300.0 mg, 1.0 eq) obtained in step 16-3, formamide (10.0 mL) and N-iodosuccinimide (106.2 mg, 1.0 eq) to obtain 280.0 mg (yield 78.2%) of the title compound.

Step 16-5: Preparation of (R)-7-iodo-3-(4-phenoxyphenyl)-1-(piperidin-3-yl)-1H-pyrazolo[4,3-c]pyridine-4-amine

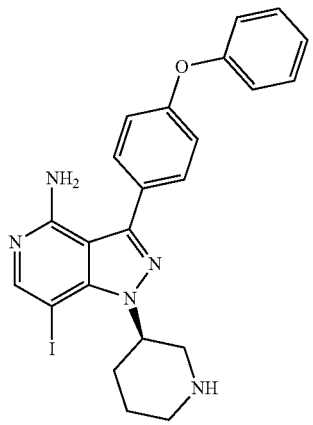 [SMILES: Nc1ncc(I)c2c1c(-c1ccc(Oc3ccccc3)cc1)nn2[C@@H]1CCCNC1]

A reaction was performed in the same manner as in step 7-2 of Example 7 by using tert-butyl (R)-3-(4-((2,4-dimethoxybenzyl)amino)-7-iodo-3-(4-phenoxyphenyl)-1H-pyrazolo[4,3-c]pyridin-1-yl)piperidine-1-carboxylate (280.0 mg, 1.0 eq) obtained in step 16-4, trifluoroacetic acid (2.0 mL) and triethylsilane (117.1 uL, 2.0 eq) to obtain 203.0 mg (yield: 100.0%) of the title compound.

Step 16-6: Preparation of (R)-1-(3-(4-amino-7-iodo-3-(4-phenoxyphenyl)-1H-pyrazolo[4,3-c]pyridin-1-yl)piperidin-1-yl)prop-2-en-1-one

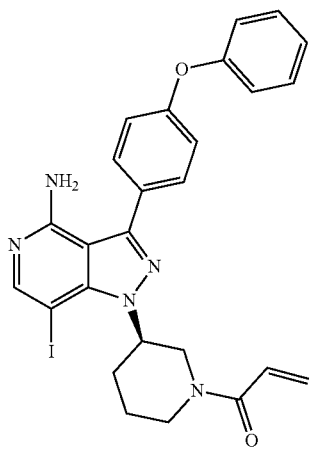 [SMILES: C=CC(=O)N1CCC[C@@H](n2nc(-c3ccc(Oc4ccccc4)cc3)c3c(N)ncc(I)c32)C1]

The reaction was performed in the same method as in step 3-5 of Example 3 by using (R)-7-iodo-3-(4-phenoxyphenyl)-1-(piperidin-3-yl)-1H-pyrazolo[4,3-c]pyridine-4-amine (189.2 mg, 1.0 eq) obtained in step 16-5, sodium hydrogen carbonate (31.1 mg, 1.0 eq) and acryloyl chloride (30.1 uL, 1.0 eq) to obtain 4.6 mg (yield: 27.1%) of the title compound.

$^1$H NMR (500 MHz, CDCl$_3$): 8.14-8.07 (m, 1H), 7.57 (d, 2H), 7.40-7.37 (m, 2H), 7.17 (t, 1H), 7.13 (d, 2H), 7.08 (d, 2H), 6.69-6.61 (m, 1H), 6.34-6.28 (m, 1H), 5.78-5.50 (m, 1H), 5.00-4.97 (m, 1H), 4.72-4.69 (m, 1H), 4.28-4.25 (m, 1H), 2.79-2.45 (m, 1H), 2.40-2.15 (m, 1H)

MS m/z: 566.39 [m+1]

Example 17: Preparation of (E)-1-(3-(4-amino-3-(4-phenoxyphenyl)-7-(3-phenylprop-1-enyl)-1H-pyrazolo[4,3-c]pyridin-1-yl)piperidin-1-yl)prop-2-en-1-one

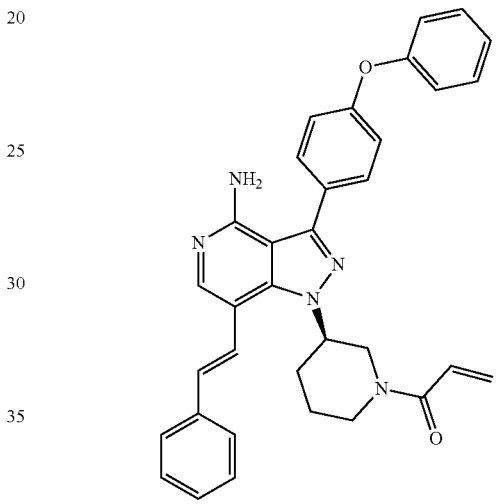

After (R)-1-(3-(4-amino-7-iodo-3-(4-phenoxyphenyl)-1H-pyrazolo[4,3-c]pyridin-1-yl)piperidin-1-yl)prop-2-en-1-one (30.0 mg, 1.0 eq) obtained in step 16-6 of Example 16 was dissolved in 1,4-dioxane (2.5 mL) and water (0.5 mL), (E)-styrylboronic acid (11.2 mg, 1.3 eq), [1,1'-bis(diphenylphosphino)ferrocene]dichloropalladium(II) (3.9 mg, 0.1 eq) and potassium carbonate (22.0 mg, 3.0 eq) were added thereto at room temperature. The reaction mixture was allowed to react at 100° C. for 4 hours, then water was added and the mixture was extracted with ethyl acetate. The separated organic layer was dried over magnesium sulfate and then concentrated under reduced pressure. The resulting residue was purified by column chromatography (ethyl acetate:hexane=1:1) to obtain 6.7 mg (yield: 22.7%) of the title compound.

$^1$H NMR (500 MHz, CDCl$_3$): 7.68-7.61 (m, 1H), 7.58 (d, 1H), 7.43-7.37 (m, 2H), 7.36-7.28 (m, 2H), 7.27-7.19 (m, 2H), 7.17 (t, 1H), 7.13 (d, 2H), 7.06 (d, 2H), 6.77-6.74 (m, 1H), 6.68-6.61 (m, 1H), 6.54-6.43 (m, 1H), 6.43-6.18 (m, 2H), 5.80-5.75 (m, 1H), 4.97-4.95 (m, 1H), 4.71-4.58 (m, 1H), 4.08-4.02 (m, 1H), 3.61-3.52 (m, 1H), 3.26-3.22 (m, 1H), 3.18-3.07 (m, 1H), 2.78-2.70 (m, 1H), 2.41-2.28 (m, 1H)

MS m/z: 566.30 [m+1]

Example 18: Preparation of (R)-4-(1-(1-acryloylpiperidin-3-yl)-4-amino-1H-pyrazolo[4,3-c]pyridin-3-yl)-N-(pyridin-2-yl)benzamide

Step 18-1: Preparation of tert-butyl (R)-3-(4-((2,4-dimethoxybenzyl)amino)-3-(4-(pyridin-2-ylcarbamoyl)phenyl)-1H-pyrazolo[4,3-c]pyridin-1-yl)piperidine-1-carboxylate

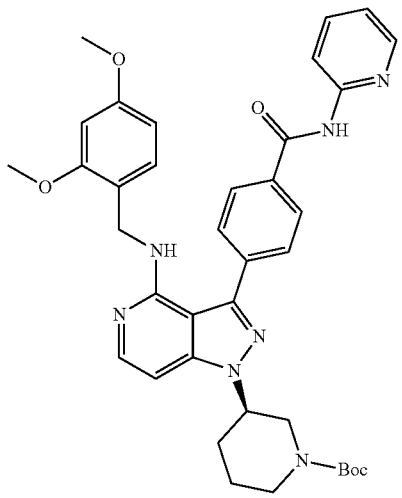 [SMILES: COc1ccc(CNc2nccc3c2c(-c2ccc(C(=O)Nc4ccccn4)cc2)nn3[C@@H]2CCCN(C(=O)OC(C)(C)C)C2)c(OC)c1]

After tert-butyl (R)-3-(3-bromo-4-((2,4-dimethoxybenzyl)amino)-1H-pyrazolo[4,3-c]pyridin-1-yl)piperidine-1-carboxylate (500.0 mg, 1.0 eq) obtained in step 16-2 of Example 16 was dissolved in 1,4-dioxane (10.0 mL) and water (2.0 mL), (4-(pyridin-2-ylcarbamoyl)phenyl)boronic acid (287.8 mg, 1.3 eq), [1,1'-bis(diphenylphosphino)ferrocene]dichloropalladium (II) (66.9 mg, 0.1 eq) and potassium carbonate (379.4 mg, 3.0 eq) were added thereto at room temperature. The reaction mixture was allowed to react at 110° C. for 2 hours, then water was added and the mixture was extracted with ethyl acetate. The separated organic layer was dried over magnesium sulfate and then concentrated under reduced pressure. The resulting residue was purified by column chromatography (ethyl acetate:hexane=1:1) to obtain 260.0 mg (yield: 42.6%) of the title compound.

Step 18-2: Preparation of (R)-4-(4-amino-1-(piperidin-3-yl)-1H-pyrazolo[4,3-c]pyridin-3-yl)-N-(pyridin-2-yl)benzamide

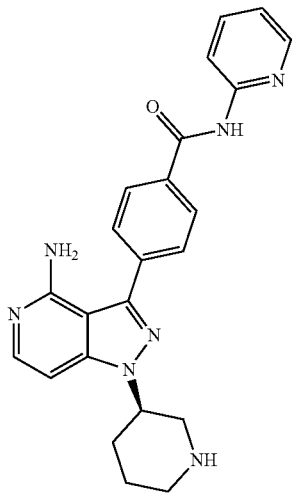 [SMILES: Nc1nccc2c1c(-c1ccc(C(=O)Nc3ccccn3)cc1)nn2[C@@H]1CCCNC1]

After tert-butyl (R)-3-(4-((2,4-dimethoxybenzyl)amino)-3-(4-(pyridine-2-ylcarbamoyl)phenyl)-1H-pyrazolo[4,3-c]pyridin-1-yl)piperidine-1-carboxylate (100.0 mg, 1.0 eq) obtained in step 18-1 was dissolved in trifluoroacetic acid (1.0 mL), triethylsilane (48.0 uL, 2.0 eq) was added thereto at room temperature. The reaction mixture was allowed to react at room temperature for 12 hours and then concentrated under reduced pressure. Saturated aqueous sodium hydrogen carbonate solution was added to the resulting residue and extracted with ethyl acetate. The separated organic layer was dried over magnesium sulfate and then concentrated under reduced pressure. The obtained title compound was used in a mixture state in the next reaction without purification.

Step 18-3: Preparation of (R)-4-(1-(1-acryloylpiperidin-3-yl)-4-amino-1H-pyrazolo[4,3-c]pyridin-3-yl)-N-(pyridine-2-yl)benzamide

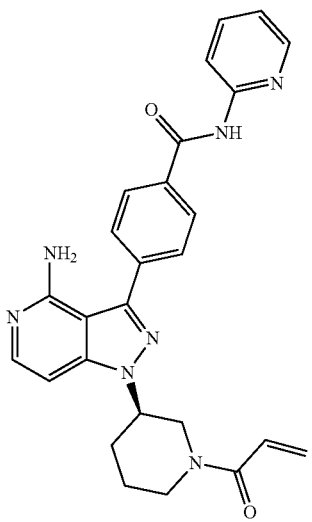 [SMILES: C=CC(=O)N1CCC[C@@H](n2nc(-c3ccc(C(=O)Nc4ccccn4)cc3)c3c(N)nccc32)C1]

After (R)-4-(4-amino-1-(piperidin-3-yl)-1H-pyrazolo[4,3-c]pyridin-3-yl)-N-(pyridin-2-yl)benzamide (62.0 mg, 1.0 eq) obtained in step 18-2 was dissolved in tetrahydrofuran (2.5 mL) and water (0.5 mL), sodium hydrogen carbonate (12.6 mg, 1.0 eq) was added thereto at 0° C. and the mixture was allowed to react at 0° C. for 10 minutes. Acryloyl chloride (12.1 uL, 1.0 eq) was added thereto at 0° C. The reaction mixture was allowed to react at 0° C. for 10 minutes, then water was added and the mixture was extracted with ethyl acetate. The separated organic layer was dried over magnesium sulfate and then concentrated under reduced pressure. The resulting residue was purified by column chromatography (dichloromethane:methanol=10:1) to obtain 36.0 mg (yield: 51.3%) of the title compound.

$^1$H NMR (500 MHz, CDCl$_3$): 9.40 (s, 1H), 8.46 (d, 1H), 8.40 (d, 1H), 8.16 (d, 1H), 7.83-7.61 (m, 4H), 7.14-7.09 (m, 1H), 6.41-6.37 (m, 1H), 6.18-6.13 (m, 1H), 5.83-5.76 (m, 1H), 4.98-4.80 (m, 1H), 4.49-4.39 (m, 1H), 4.32-4.26 (m, 1H), 4.13-4.04 (m, 1H), 3.26-3.18 (m, 1H), 2.90-2.25 (m, 3H)

MS m/z: 468.60 [m+1]

Example 19: Preparation of (R)-4-(1-(1-acryloylpiperidin-3-yl)-4-amino-7-chloro-1H-pyrazolo[4,3-c]pyridin-3-yl)-N-(pyridin-2-yl)benzamide Step 19-1: Preparation of tert-butyl (R)-3-(7-chloro-4-((2,4-dimethoxybenzyl)amino)-3-(4-(pyridin-2-ylcarbamoyl)phenyl)-1H-pyrazolo[4,3-c]pyridin-1-yl)piperidine-1-carboxylate

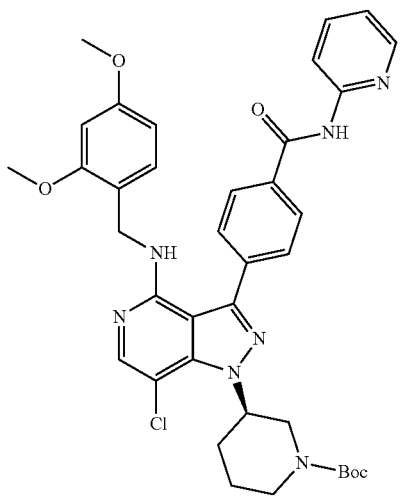 [SMILES: COc1ccc(CNc2ncc(Cl)c3c2c(-c2ccc(C(=O)Nc4ccccn4)cc2)nn3[C@@H]2CCCN(C(=O)OC(C)(C)C)C2)c(OC)c1]

After tert-butyl (R)-3-(4-((2,4-dimethoxybenzyl)amino)-3-(4-(pyridin-2-ylcarbamoyl)phenyl)-1H-pyrazolo[4,3-c]pyridin-1-yl)piperidine-1-carboxylate (60.0 mg, 1.0 eq) obtained in step 18-1 of Example 18 was dissolved in formamide (3.0 mL), N-chlorosuccinimide (12.6 mg, 1.1 eq) was added thereto at room temperature. The reaction mixture was allowed to react at 80° C. for 1 hour and then concentrated under reduced pressure. The resulting residue was purified by column chromatography (ethyl acetate:hexane=1:1) to obtain 42.6 mg (yield: 67.8%) of the title compound.

Step 19-2: Preparation of (R)-4-(4-amino-7-chloro-1-(piperidin-3-yl)-1H-pyrazolo[4,3-c]pyridin-3-yl)-N-(pyridin-2-yl)benzamide

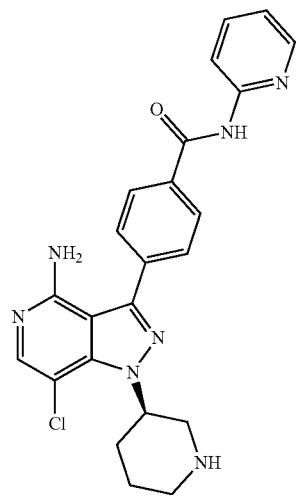 [SMILES: Nc1ncc(Cl)c2c1c(-c1ccc(C(=O)Nc3ccccn3)cc1)nn2[C@@H]1CCCNC1]

A reaction was performed in the same manner as in step 18-2 of Example 18 by using tert-butyl (R)-3-(7-chloro-4-((2,4-dimethoxybenzyl)amino)-3-(4-(pyridin-2-ylcarbamoyl)phenyl)-1H-pyrazolo[4,3-c]pyridin-1-yl)piperidine-1-carboxylate (40.0 mg, 1.0 eq) obtained in step 19-1, trifluoroacetic acid (1.7 mL) and triethylsilane (18.3 uL, 2.0 eq) to obtain the title compound, which was used in the next reaction without purification.

Step 19-3: Preparation of (R)-4-(1-(1-acryloylpiperidin-3-yl)-4-amino-7-chloro-1H-pyrazolo[4,3-c]pyridin-3-yl)-N-(pyridin-2-yl)benzamide

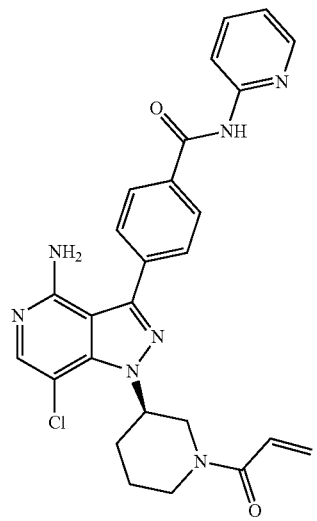

A reaction was performed in the same manner as in step 3-5 of Example 3 by using (R)-4-(4-amino-7-chloro-1-(piperidin-3-yl)-1H-pyrazolo[4,3-c]pyridin-3-yl)-N-(pyridin-2-yl)benzamide obtained in step 19-2, sodium hydrogen carbonate (8.3 mg, 1.1 eq) and acryloyl chloride (8.0 uL, 1.1 eq) to obtain 36.0 mg (yield: 51.3%) of the title compound.

¹H NMR (500 MHz, CDCl₃): 8.81 (s, 1H), 8.43 (d, 1H), 8.33 (d, 1H), 8.12 (d, 1H), 7.82-7.73 (m, 4H), 7.13-7.04 (m, 1H), 6.65-6.60 (m, 1H), 6.35-6.29 (m, 1H), 5.75-5.68 (m, 1H), 5.05-4.95 (m, 1H), 4.72-4.62 (m, 1H), 4.35-4.28 (m, 1H), 4.09-4.02 (m, 1H), 3.73-3.62 (m, 1H), 3.48-3.35 (m, 1H), 3.23-3.12 (m, 1H), 2.88-2.73 (m, 1H), 2.40-2.23 (m, 1H)

MS m/z: 502.36 [m+1]

Example 20: Preparation of (R)-4-(1-(1-acryloylpiperidin-3-yl)-4-amino-7-bromo-1H-pyrazolo[4,3-c]pyridin-3-yl)-N-(pyridin-2-yl)benzamide Step 20-1: Preparation of tert-butyl (R)-3-(7-bromo-4-((2,4-dimethoxybenzyl)amino)-3-(4-(pyridin-2-ylcarbamoyl)phenyl)-1H-pyrazolo[4,3-c]pyridin-1-yl)piperidine-1-carboxylate

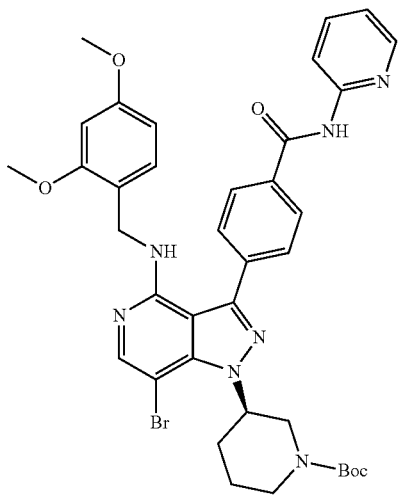

After tert-butyl (R)-3-(4-((2,4-dimethoxybenzyl)amino)-3-(4-(pyridin-2-ylcarbamoyl)phenyl)-1H-pyrazolo[4,3-c]pyridin-1-yl)piperidine-1-carboxylate (60.0 mg, 1.0 eq) obtained in step 18-1 of Example 18 was dissolved in formamide (3.0 mL), N-bromosuccinimide (16.9 mg, 1.1 eq) was added thereto at room temperature. The reaction mixture was allowed to react at room temperature for 1 hour and then concentrated under reduced pressure. The resulting residue was purified by column chromatography (ethyl acetate:hexane=1:1) to obtain 46.0 mg (yield: 68.8%) of the title compound.

Step 20-2: Preparation of (R)-4-(4-amino-7-bromo-1-(piperidin-3-yl)-1H-pyrazolo[4,3-c]pyridin-3-yl)-N-(pyridin-2-yl)benzamide

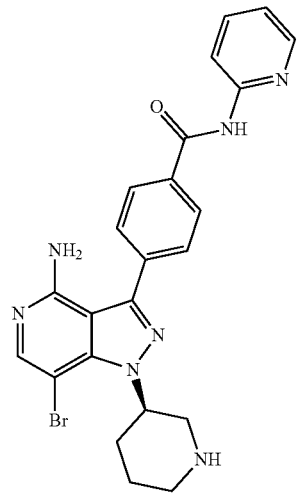 [SMILES: Nc1ncc(Br)c2c1c(-c1ccc(C(=O)Nc3ccccn3)cc1)nn2[C@@H]1CCCNC1]

A reaction was performed in the same manner as in step 18-2 of Example 18 by using tert-butyl (R)-3-(7-bromo-4-((2,4-dimethoxybenzyl)amino)-3-(4-(pyridin-2-ylcarbamoyl)phenyl)-1H-pyrazolo[4,3-c]pyridin-1-yl)piperidine-1-carboxylate (42.5 mg, 1.0 eq), trifluoroacetic acid (1.7 mL) and triethylsilane (18.3 uL, 2.0 eq) to obtain the title compound, which was used in the next reaction without purification.

Step 20-3: Preparation of (R)-4-(1-(1-acryloylpiperidin-3-yl)-4-amino-7-bromo-1H-pyrazolo[4,3-c]pyridin-3-yl)-N-(pyridin-2-yl)benzamide

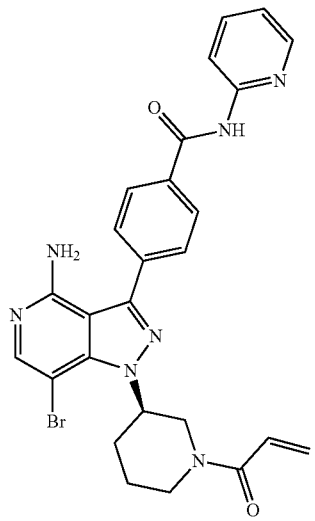 [SMILES: C=CC(=O)N1CCC[C@@H](n2nc(-c3ccc(C(=O)Nc4ccccn4)cc3)c3c(N)ncc(Br)c32)C1]

A reaction was performed in the same manner as in 18-3 of Example 18 by using (R)-4-(4-amino-7-bromo-1-(piperidin-3-yl)-1H-pyrazolo[4,3-c]pyridin-3-yl)-N-(pyridin-2-yl)benzamide (44.0 mg, 1.0 eq) obtained in step 20-2, sodium hydrogen carbonate (8.3 mg, 1.1 eq) and acryloyl chloride (8.0 uL, 1.1 eq) to obtain 26.0 mg (yield: 52.9%) of the title compound.

¹H NMR (500 MHz, CDCl₃): 8.44-8.40 (m, 1H), 8.34-8.32 (m, 1H), 8.18-8.07 (m, 2H), 7.86-7.65 (m, 4H), 7.18-7.10 (m, 1H), 6.08-5.96 (m, 1H), 5.67-5.54 (m, 1H), 5.38-5.32 (m, 1H), 5.02-4.95 (m, 1H), 4.66-4.60 (m, 1H), 4.38-4.32 (m, 3H), 3.82-3.78 (m, 1H), 3.76-3.62 (m, 1H), 3.57-3.45 (m, 1H), 3.20-3.07 (m, 1H), 2.40-2.15 (m, 2H)

MS m/z: 548.39 [m+1]

Example 21: Preparation of (R)-4-(1-(1-acryloylpiperidin-3-yl)-4-amino-7-iodo-1H-pyrazolo[4,3-c]pyridin-3-yl)-N-(pyridin-2-yl)benzamide Step 21-1: Preparation of tert-butyl (R)-3-(4-((2,4-dimethoxybenzyl)amino)-7-iodo-3-(4-(pyridin-2-ylcarbamoyl)phenyl)-1H-pyrazolo[4,3-c]pyridin-1-yl)piperidine-1-carboxylate

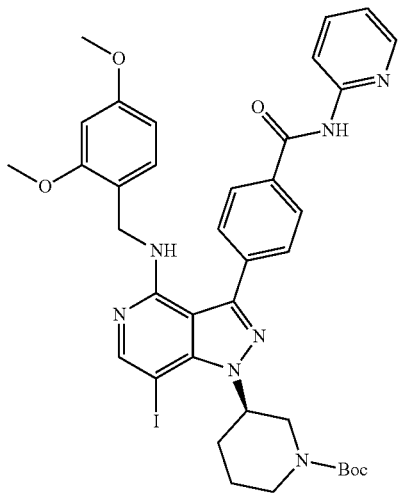 [SMILES: COc1ccc(CNc2ncc(I)c3c2c(-c2ccc(C(=O)Nc4ccccn4)cc2)nn3[C@@H]2CCCN(C(=O)OC(C)(C)C)C2)c(OC)c1]

After tert-butyl (R)-3-(4-((2,4-dimethoxybenzyl)amino)-3-(4-(pyridin-2-ylcarbamoyl)phenyl)-1H-pyrazolo[4,3-c]pyridin-1-yl)piperidine-1-carboxylate (60.0 mg, 1.0 eq) obtained in step 18-1 of Example 18 was dissolved in formamide (3.0 mL), N-iodosuccinimide (21.3 mg, 1.1 eq) was added thereto at room temperature. The reaction mixture was allowed to react at room temperature for 1 hour and then concentrated under reduced pressure. The resulting residue was purified by column chromatography (ethyl acetate:hexane=1:1) to obtain 50.0 mg (yield: 70.4%) of the title compound.

Step 21-2: Preparation of (R)-4-(4-amino-7-iodo-1-(piperidin-3-yl)-1H-pyrazolo[4,3-c]pyridin-3-yl)-N-(pyridin-2-yl)benzamide

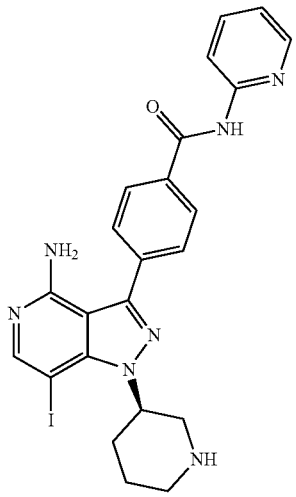 [SMILES: Nc1ncc(I)c2c1c(-c1ccc(C(=O)Nc3ccccn3)cc1)nn2[C@@H]1CCCNC1]

A reaction was performed in the same manner as in step 18-2 of Example 18 by using tert-butyl (R)-3-(4-((2,4-dimethoxybenzyl)amino)-7-iodo-3-(4-(pyridin-2-ylcarbamoyl)phenyl)-1H-pyrazolo[4,3-c]pyridin-1-yl)piperidine-1-carboxylate (45.2 mg, 1.0 eq) obtained in step 21-1, trifluoroacetic acid (2.0 mL) and triethylsilane (18.3 uL, 2.0 eq) to obtain the title compound, which was used in the next reaction without purification.

Step 21-3: Preparation of (R)-4-(1-(1-acryloylpiperidin-3-yl)-4-amino-7-iodo-1H-pyrazolo[4,3-c]pyridin-3-yl)-N-(pyridin-2-yl)benzamide

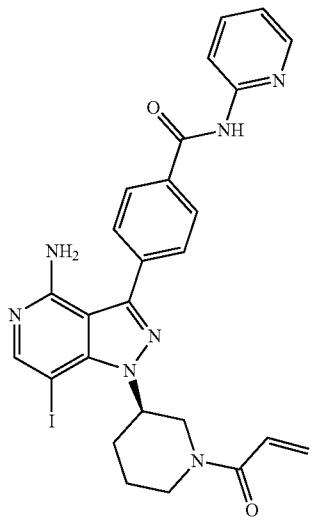 [SMILES: C=CC(=O)N1CCC[C@@H](n2nc(-c3ccc(C(=O)Nc4ccccn4)cc3)c3c(N)ncc(I)c32)C1]

A reaction was performed in the same manner as in step 18-3 of Example 18 by using (R)-4-(4-amino-7-iodo-1-(piperidin-3-yl)-1H-pyrazolo[4,3-c]pyridin-3-yl)-N-(pyridin-2-yl)benzamide (48.2 mg, 1.0 eq) obtained in step 21-2, sodium hydrogen carbonate (8.3 mg, 1.1 eq) and acryloyl chloride (8.0 uL, 1.1 eq) to obtain 19.3 mg (yield: 36.1%) of the title compound.

¹H NMR (500 MHz, CDCl₃): 9.40 (s, 1H), 8.42 (d, 1H), 8.32-8.31 (m, 1H), 8.08 (d, 2H), 8.04-8.03 (m, 1H), 7.82-7.75 (m, 3H), 7.11-7.09 (m, 1H), 5.80-5.68 (m, 1H), 5.21-5.10 (m, 2H), 3.53-3.50 (m, 1H), 3.48-3.33 (m, 1H), 3.24-3.18 (m, 1H), 2.90-2.61 (m, 2H), 2.30-2.28 (m, 2H), 1.99-1.82 (m, 1H)

MS m/z: 594.49 [m+1]

Example 22: Preparation of (R)-4-(1-(1-acryloylpiperidin-3-yl)-4-amino-1H-pyrazolo[4,3-c]pyridin-3-yl)-N-phenyl benzamide Step 22-1: Preparation of tert-butyl (R)-3-(4-((2,4-dimethoxybenzyl)amino)-3-(4-(phenylcarbamoyl)phenyl)-1H-pyrazolo[4,3-c]pyridin-1-yl)piperidine-1-carboxylate

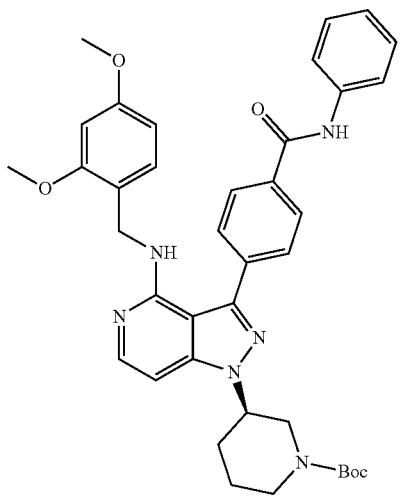 [SMILES: COc1ccc(CNc2nccc3c2c(-c2ccc(C(=O)Nc4ccccc4)cc2)nn3[C@@H]2CCCN(C(=O)OC(C)(C)C)C2)c(OC)c1]

After tert-butyl (R)-3-(3-bromo-4-((2,4-dimethoxybenzyl)amino)-1H-pyrazolo[4,3-c]pyridin-1-yl)piperidine-1-carboxylate (3,000.0 mg, 1.0 eq) obtained in step 16-2 of Example 16 was dissolved in 1,4-dioxane (25.0 mL) and water (5.0 mL), N-phenyl-4-(4,4,5,5-tetramethyl-1,3,2-dioxaborolan-2-yl)benzamide (2,310.0 mg, 1.3 eq), [1,1'-bis(diphenylphosphino)ferrocene]dichloropalladium (II) (400.0 mg, 0.1 eq) and potassium carbonate (2,280.0 mg, 3.0 eq) were added thereto at room temperature. The reaction mixture was allowed to react at 110° C. for 2 hours, then water was added and the mixture was extracted with ethyl acetate. The separated organic layer was dried over magnesium sulfate and then concentrated under reduced pressure. The resulting residue was purified by column chromatography (ethyl acetate:hexane=1:1) to obtain 2,200.0 mg (yield: 60.5%) of the title compound.

Step 22-2: Preparation of (R)-4-(4-amino-1-(piperidin-3-yl)-1H-pyrazolo[4,3-c]pyridin-3-yl)-N-phenyl benzamide

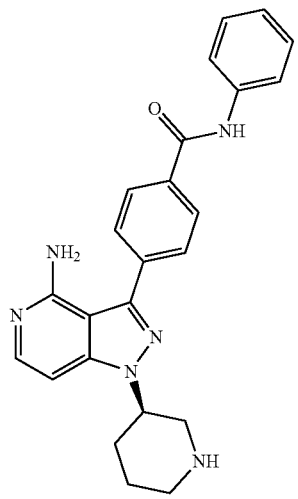 [SMILES: Nc1nccc2c1c(-c1ccc(C(=O)Nc3ccccc3)cc1)nn2[C@@H]1CCCNC1]

A reaction was performed in the same manner as Step 18-2 of Example 18 by using tert-butyl (R)-3-(4-((2,4-dimethoxybenzyl)amino)-3-(4-(phenylcarbamoyl)phenyl)-1H-pyrazolo[4,3-c]pyridin-1-yl)piperidine-1-carboxylate (100.0 mg, 1.0 eq) obtained in step 22-1, trifluoroacetic acid (2.0 mL) and triethylsilane (35.1 uL, 2.0 eq) to obtain the title compound, which was used in the next reaction without purification.

Step 22-3: Preparation of (R)-4-(1-(1-acryloylpiperidin-3-yl)-4-amino-1H-pyrazolo[4,3-c]pyridin-3-yl)-N-phenyl benzamide

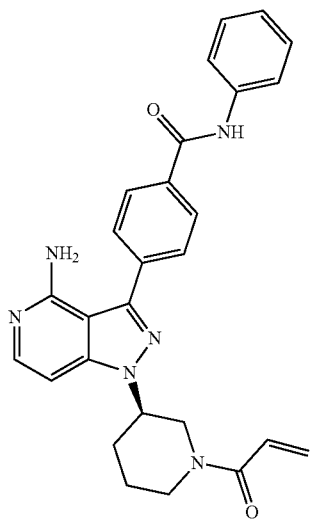

A reaction was performed in the same manner as in step 18-3 of Example 18 by using (R)-4-(4-amino-1-(piperidin-3-yl)-1H-pyrazolo[4,3-c]pyridin-3-yl)-N-phenylbenzamide (53.8 mg, 1.0 eq) obtained in step 22-2, sodium hydrogen carbonate (25.4 mg, 2.0 eq) and acryloyl chloride (24.5 uL, 2.0 eq) to obtain 58.0 mg (yield: 82.9%) of the title compound.

¹H NMR (500 MHz, CDCl₃): 8.16-8.02 (m, 2H), 7.78 (d, 2H), 7.76-7.62 (m, 4H), 7.45-7.33 (m, 2H), 7.17 (t, 1H), 6.42-6.30 (m, 1H), 6.20-6.11 (m, 1H), 5.78-5.75 (m, 1H), 5.38-5.32 (m, 1H), 4.98-4.91 (m, 1H), 4.68-4.60 (m, 1H), 4.46-4.38 (m, 1H), 4.11-4.05 (m, 1H), 3.28-3.17 (m, 1H), 2.80-2.20 (m, 2H)

MS m/z: 467.44 [m+1]

Example 23: Preparation of (R)-4-(1-(1-acryloylpiperidin-3-yl)-4-amino-7-chloro-1H-pyrazolo[4,3-c]pyridin-3-yl)-N-phenyl benzamide Step 23-1: Preparation of tert-butyl (R)-3-(7-chloro-4-((2,4-dimethoxybenzyl)amino)-3-(4-(phenylcarbamoyl)phenyl)-1H-pyrazolo[4,3-c]pyridin-1-yl)piperidine-1-carboxylate

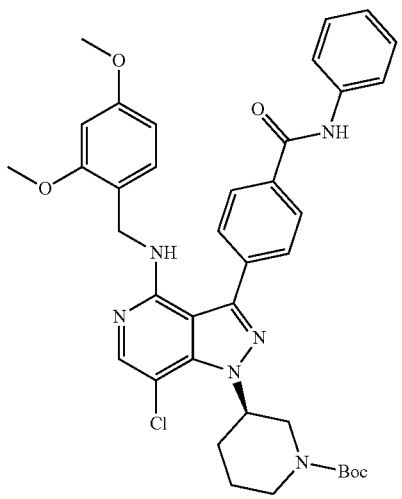 [SMILES: COc1ccc(CNc2ncc(Cl)c3c2c(-c2ccc(C(=O)Nc4ccccc4)cc2)nn3[C@@H]2CCCN(C(=O)OC(C)(C)C)C2)c(OC)c1]

A reaction was performed in the same manner as in Step 19-1 of Example 19 by using tert-butyl (R)-3-(4-((2,4-dimethoxybenzyl)amino)-3-(4-(phenylcarbamoyl)phenyl)-1H-pyrazolo[4,3-c]pyridin-1-yl)piperidine-1-carboxylate (100.0 mg, 1.0 eq) obtained in step 22-1 of Example 22, formamide (3.0 mL) and N-chlorosuccinimide (23.4 mg, 1.1 eq) to obtain 85.0 mg (yield 76.2%) of the title compound.

Step 23-2: Preparation of (R)-4-(4-amino-7-chloro-1-(piperidin-3-yl)-1H-pyrazolo[4,3-c]pyridin-3-yl)-N-phenyl benzamide

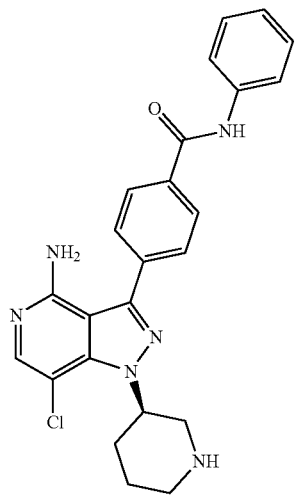 [SMILES: Nc1ncc(Cl)c2c1c(-c1ccc(C(=O)Nc3ccccc3)cc1)nn2[C@@H]1CCCNC1]

A reaction was performed in the same manner as in step 18-2 of Example 18 by using tert-butyl (R)-3-(7-chloro-4-((2,4-dimethoxybenzyl)amino)-3-(4-(phenylcarbamoyl)phenyl)-1H-pyrazolo[4,3-c]pyridin-1-yl)piperidine-1-carboxylate (69.7 mg, 1.0 eq) obtained in step 23-1, trifluoroacetic acid (1.0 mL) and triethylsilane (32.0 uL, 2.0 eq) to obtain the title compound, which was used in the next reaction without purification.

Step 23-3: Preparation of (R)-4-(1-(1-acryloylpiperidin-3-yl)-4-amino-7-chloro-1H-pyrazolo[4,3-c]pyridin-3-yl)-N-phenyl benzamide

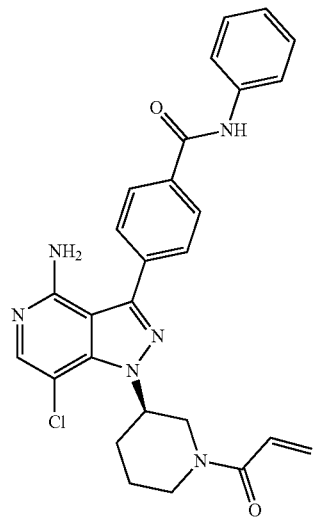 [SMILES: C=CC(=O)N1CCC[C@@H](n2nc(-c3ccc(C(=O)Nc4ccccc4)cc3)c3c(N)ncc(Cl)c32)C1]

A reaction was performed in the same manner as in step 18-3 of Example 18 by using (R)-4-(4-amino-7-chloro-1-(piperidin-3-yl)-1H-pyrazolo[4,3-c]pyridin-3-yl)-N-phenyl-benzamide (44.7 mg, 1.0 eq) obtained in step 23-2, sodium hydrogen carbonate (9.3 mg, 1.1 eq) and acryloyl chloride (10.0 uL, 1.1 eq) to obtain 26.7 mg (yield: 53.3%) of the title compound.

¹H NMR (500 MHz, CDCl₃): 8.07-7.98 (m, 2H), 7.71-7.66 (m, 5H), 7.64-7.39 (m, 2H), 7.19 (t, 1H), 6.63-6.02 (m, 1H), 6.35-6.28 (m, 1H), 5.76-5.68 (m, 1H), 5.03-4.95 (m, 1H), 4.65-4.63 (m, 1H), 4.32-4.29 (m, 1H), 4.05-4.03 (m, 1H), 3.75-3.68 (m, 1H), 3.48-3.88 (m, 1H), 3.23-3.18 (m, 1H), 2.90-2.81 (m, 1H), 2.48-2.28 (m, 1H)

MS m/z: 501.33 [m+1]

Example 24: Preparation of (R)-4-(1-(1-acryloylpiperidin-3-yl)-4-amino-7-bromo-1H-pyrazolo[4,3-c]pyridin-3-yl)-N-phenyl benzamide Step 24-1: Preparation of tert-butyl (R)-3-(7-bromo-4-((2,4-dimethoxybenzyl)amino)-3-(4-(phenylcarbamoyl)phenyl)-1H-pyrazolo[4,3-c]pyridin-1-yl)piperidine-1-carboxylate

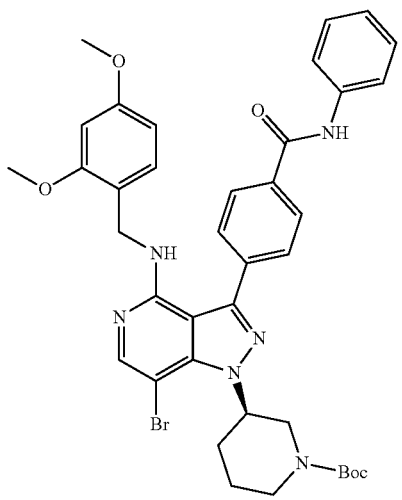

A reaction was performed in the same manner as in step 20-2 of Example 22 by using tert-butyl (R)-3-(4-((2,4-dimethoxybenzyl)amino)-3-(4-(phenylcarbamoyl)phenyl)-1H-pyrazolo[4,3-c]pyridin-1-yl)piperidine-1-carboxylate (100.0 mg, 1.0 eq) obtained in step 22-1 of Example 22, formamide (3.0 mL) and N-bromosuccinimide (31.5 mg, 1.1 eq) to obtain 94.0 mg (yield: 79.2%) of the title compound.

Step 24-2: Preparation of (R)-4-(4-amino-7-bromo-1-(piperidin-3-yl)-1H-pyrazolo[4,3-c]pyridin-3-yl)-N-phenylbenzaminde

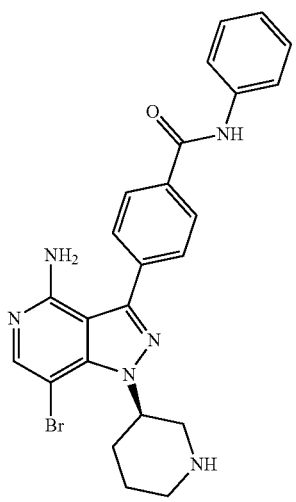 [SMILES: Nc1ncc(Br)c2c1c(-c1ccc(C(=O)Nc3ccccc3)cc1)nn2[C@@H]1CCCNC1]

A reaction was performed in the same manner as in step 18-2 of Example 18 by using tert-butyl (R)-3-(7-bromo-4-((2,4-dimethoxybenzyl)amino)-3-(4-(phenylcarbamoyl)phenyl)-1H-pyrazolo[4,3-c]pyridin-1-yl)piperidine-1-carboxylate (74.2 mg, 1.0 eq) obtained in step 24-1, trifluoroacetic acid (1.0 mL) and triethylsilane (32.0 uL, 2.0 eq) to obtain the title compound, which was used in the next reaction without purification.

Step 24-3: Preparation of (R)-4-(1-(1-acryloylpiperidin-3-yl)-4-amino-7-bromo-1H-pyrazolo[4,3-c]pyridin-3-yl)-N-phenyl benzamide

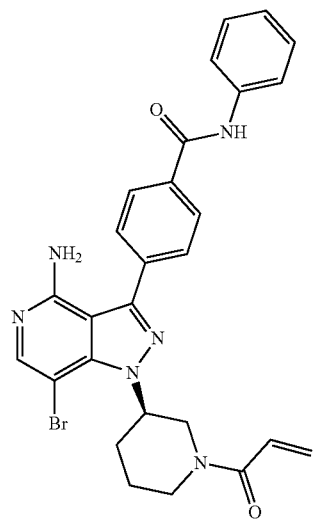 [SMILES: C=CC(=O)N1CCC[C@@H](n2nc(-c3ccc(C(=O)Nc4ccccc4)cc3)c3c(N)ncc(Br)c32)C1]

A reaction was performed in the same manner as in step 18-3 of Example 18 by using (R)-4-(4-amino-7-bromo-1-(piperidin-3-yl)-1H-pyrazolo[4,3-c]pyridin-3-yl)-N-phenylbenzaminde (49.1 mg, 1.0 eq) obtained in step 24-2, sodium hydrogen carbonate (9.3 mg, 1.1 eq) and acryloyl chloride (10.0 uL, 1.1 eq) to obtain 22.0 mg (yield: 40.3%) of the title compound.

¹H NMR (500 MHz, CDCl₃): 8.08-7.68 (m, 7H), 7.46-7.39 (m, 2H), 7.19 (t, 1H), 6.65-6.60 (m, 1H), 6.35-6.29 (m, 1H), 5.46-5.69 (m, 1H), 4.98-4.96 (m, 1H), 4.71-4.62 (m, 1H), 4.37-4.27 (m, 1H), 4.12-4.06 (m, 1H), 3.79-3.69 (m, 1H), 3.49-3.39 (m, 1H), 3.28-3.18 (m, 1H), 2.89-2.80 (m, 1H), 2.48-2.28 (m, 1H)

MS m/z: 547.36 [m+1]

Example 25: Preparation of (R)-4-(1-(1-acryloylpiperidin-3-yl)-4-amino-7-iodo-1H-pyrazolo[4,3-c]pyridin-3-yl)-N-phenyl benzamide Step 25-1: Preparation of tert-butyl (R)-3-(4-((2,4-dimethoxybenzyl)amino)-7-iodo-3-(4-(phenylcarbamoyl)phenyl)-1H-pyrazolo[4,3-c]pyridin-1-yl)piperidine-1-carboxylate

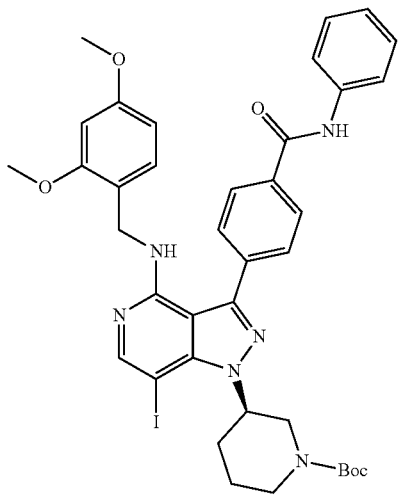 [SMILES: COc1ccc(CNc2ncc(I)c3c2c(-c2ccc(C(=O)Nc4ccccc4)cc2)nn3[C@@H]2CCCN(C(=O)OC(C)(C)C)C2)c(OC)c1]

A reaction was performed in the same manner as in step 21-1 of Example 21 by using tert-butyl (R)-3-(4-((2,4-dimethoxybenzyl)amino)-3-(4-(phenylcarbamoyl)phenyl)-1H-pyrazolo[4,3-c]pyridin-1-yl)piperidine-1-carboxylate (1000.0 mg, 1.0 eq) obtained in step 22-1 of Example 22, formamide (15.0 mL) and N-iodosuccinimide (410.0 mg, 1.1 eq) to obtain 820.0 mg (yield: 68.9%) of the title compound.

Step 25-2: Preparation of (R)-4-(4-amino-7-iodo-1-(piperidin-3-yl)-1H-pyrazolo[4,3-c]pyridin-3-yl)-N-phenyl benzamide

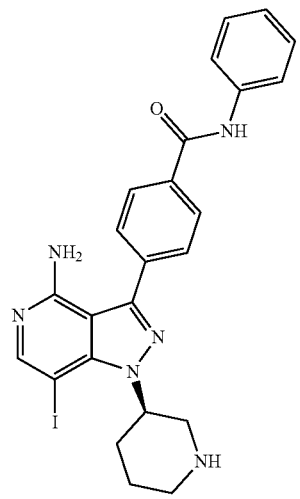 [SMILES: Nc1ncc(I)c2c1c(-c1ccc(C(=O)Nc3ccccc3)cc1)nn2[C@@H]1CCCNC1]

A reaction was performed in the same manner as Step 18-2 of Example 18 by using tert-butyl (R)-3-(4-((2,4-dimethoxybenzyl)amino)-7-iodo-3-(4-(phenylcarbamoyl)phenyl)-1H-pyrazolo[4,3-c]pyridin-1-yl)piperidine-1-carboxylate (78.9 mg, 1.0 eq) obtained in step 25-1, trifluoroacetic acid (1.0 mL) and triethylsilane (32.0 uL, 2.0 eq) to obtain the title compound, which was used in the next reaction without purification.

Step 25-3: Preparation of (R)-4-(1-(1-acryloylpiperidin-3-yl)-4-amino-7-iodo-1H-pyrazolo[4,3-c]pyridin-3-yl)-N-phenyl benzamide

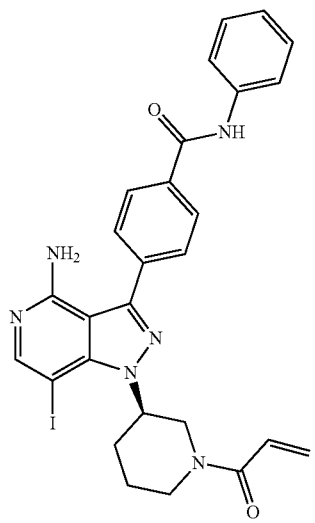 [SMILES: C=CC(=O)N1CCC[C@@H](n2nc(-c3ccc(C(=O)Nc4ccccc4)cc3)c3c(N)ncc(I)c32)C1]

A reaction was performed in the same manner as in step 18-3 of Example 18 by using (R)-4-(4-amino-7-iodo-1-(piperidin-3-yl)-1H-pyrazolo[4,3-c]pyridin-3-yl)-N-phenyl-benzamide (53.8 mg, 1.0 eq) obtained in step 25-2, sodium hydrogen carbonate (9.3 mg, 1.1 eq) and acryloyl chloride (10.0 uL, 1.1 eq) to obtain 30.2 mg (yield: 51.0%) of the title compound.

¹H NMR (500 MHz, CDCl₃): 8.10-7.95 (m, 3H), 7.75 (d, 2H), 7.69 (d, 2H), 7.46-7.39 (m, 2H), 7.19 (t, 1H), 6.70-6.60 (m, 1H), 6.38-6.28 (m, 1H), 5.81-5.53 (m, 1H), 5.02-4.92 (m, 1H), 4.74-4.65 (m, 1H), 4.33-4.27 (m, 1H), 4.13-4.05 (m, 1H), 3.31-3.20 (m, 1H), 3.49-3.40 (m, 1H), 3.25-3.16 (m, 1H), 2.88-2.80 (m, 1H), 2.40-2.31 (m, 1H)

MS m/z: 593.26 [m+1]

Example 26: Preparation of (R)-4-(1-(1-acryloylpiperidin-3-yl)-4-amino-7-(1-methyl-1H-pyrazol-4-yl)-1H-pyrazolo[4,3-c]pyridin-3-yl)-N-phenyl benzamide Step 26-1: Preparation of tert-butyl (R)-3-(4-((2,4-dimethoxybenzyl)amino)-7-(1-methyl-1H-pyrazolo-4-yl)-3-(4-(phenylcarbamoyl)phenyl)-1H-pyrazolo[4,3-c]pyridin-1-yl)piperidine-1-carboxylate

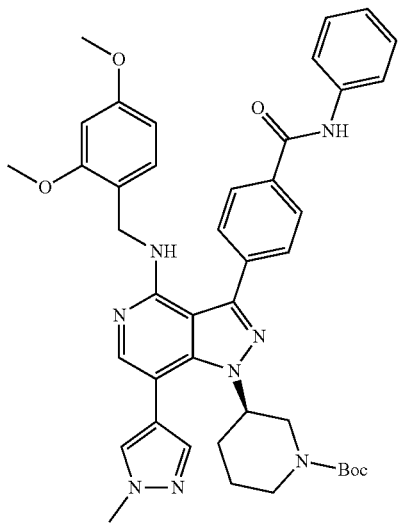 [SMILES: COc1ccc(CNc2ncc(-c3cnn(C)c3)c3c2c(-c2ccc(C(=O)Nc4ccccc4)cc2)nn3[C@@H]2CCCN(C(=O)OC(C)(C)C)C2)c(OC)c1]

After tert-butyl (R)-3-(4-((2,4-dimethoxybenzyl)amino)-7-iodo-3-(4-(phenylcarbamoyl)phenyl)-1H-pyrazolo[4,3-c]pyridin-1-yl)piperidine-1-carboxylate (130.0 mg, 1.0 eq) obtained in step 25-1 of Example 25 was dissolved in 1,4-dioxane (5.0 mL) and water (1.0 mL), 1-methyl-4-(4,4,5,5-tetramethyl-1,3,2-dioxaborolan-2-yl)-1H-pyrazole (50.9 mg, 1.3 eq), [1,1'-bis(diphenylphosphino)ferrocene]dichloropalladium (II) (13.8 mg, 0.1 eq), and potassium carbonate (78.0 mg, 3.0 eq) were added thereto at room temperature. The reaction mixture was allowed to react at 110° C. for 2 hours, then water was added and the mixture was extracted with ethyl acetate. The separated organic layer was dried over magnesium sulfate and then concentrated under reduced pressure. The resulting residue was purified by column chromatography (ethyl acetate:hexane=1:1) to obtain 105.0 mg (yield: 75.2%) of the title compound.

Step 26-2: Preparation of (R)-4-(4-amino-7-(1-methyl-1H-pyrazolo-4-yl)-1-(piperidin-3-yl)-1H-pyrazolo[4,3-c]pyridin-3-yl)-N-phenylbenzamide

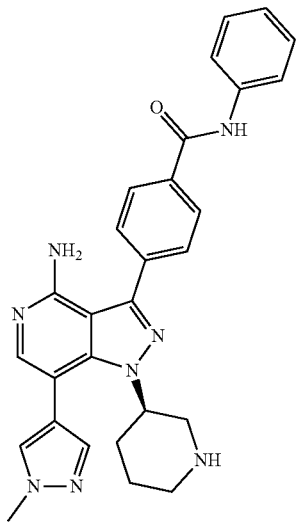 [SMILES: Cn1cc(-c2cnc(N)c3c(-c4ccc(C(=O)Nc5ccccc5)cc4)nn([C@@H]4CCCNC4)c23)cn1]

A reaction was performed in the same manner as in step 18-2 of Example 18 by using tert-butyl (R)-3-(4-((2,4-dimethoxybenzyl)amino)-7-(1-methyl-1H-pyrazolo-4-yl)-3-(4-(phenylcarbamoyl)phenyl)-1H-pyrazolo[4,3-c]pyridin-1-yl)piperidine-1-carboxylate (105.0 mg, 1.0 eq) obtained in step 26-1, trifluoroacetic acid (2.0 mL) and triethylsilane (67.6 uL, 3.0 eq) to obtain the title compound, which was used in the next reaction without purification.

Step 26-3: Preparation of (R)-4-(1-(1-acryloylpiperidin-3-yl)-4-amino-7-(1-methyl-1H-pyrazol-4-yl)-1H-pyrazolo[4,3-c]pyridin-3-yl)-N-phenyl benzamide

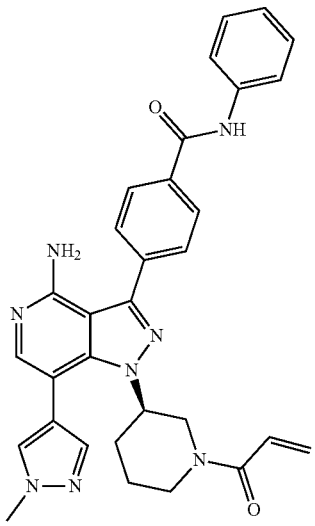 [SMILES: C=CC(=O)N1CCC[C@@H](n2nc(-c3ccc(C(=O)Nc4ccccc4)cc3)c3c(N)ncc(-c4cnn(C)c4)c32)C1]

A reaction was performed in the same manner as in step 18-3 of Example 18 by using (R)-4-(4-amino-7-(1-methyl-1H-pyrazolo-4-yl)-1-(piperidin-3-yl)-1H-pyrazolo[4,3-c]

pyridin-3-yl)-N-phenylbenzamide (68.9 mg, 1.0 eq) obtained in step 26-2, sodium hydrogen carbonate (23.0 mg, 2.0 eq) and acryloyl chloride (22.7 uL, 2.0 eq) to obtain 16.0 mg (yield: 20.9%) of the title compound.

$^1$H NMR (500 MHz, CDCl$_3$): 8.19-8.08 (m, 3H), 7.84-7.69 (m, 4H), 7.53 (s, 1H), 7.46-7.34 (m, 3H), 7.19 (t, 1H), 6.57-6.52 (m, 1H), 6.37-6.29 (m, 1H), 5.79-5.70 (m, 1H), 4.79-4.75 (m, 1H), 4.30-4.21 (m, 1H), 4.05-3.92 (m, 2H), 3.16-3.05 (m, 2H), 2.48-2.37 (m, 1H), 2.08-2.01 (m, 1H), 1.98-1.87 (m, 1H)

Example 27: Preparation of (R)-4-(1-(1-acryloylpiperidin-3-yl)-4-amino-7-(hydroxymethyl)-1H-pyrazolo[4,3-c]pyridin-3-yl)-N-phenylbenzamide Step 27-1: Preparation of tert-butyl (R)-3-(4-((2,4-dimethoxybenzyl)amino)-7-formyl-3-(4-(phenylcarbamoyl)phenyl)-1H-pyrazolo[4,3-c]pyridin-1-yl)piperidine-1-carboxylate

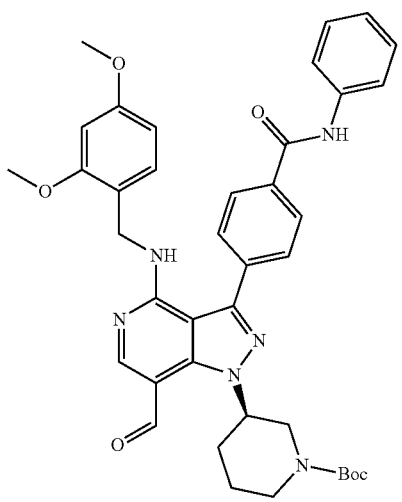 [SMILES: COc1ccc(CNc2ncc(C=O)c3c2c(-c2ccc(C(=O)Nc4ccccc4)cc2)nn3[C@@H]2CCCN(C(=O)OC(C)(C)C)C2)c(OC)c1]

After tert-butyl (R)-3-(4-((2,4-dimethoxybenzyl)amino)-7-iodo-3-(4-(phenylcarbamoyl)phenyl)-1H-pyrazolo[4,3-c]pyridin-1-yl)piperidine-1-carboxylate (1,000.0 mg, 1.0 eq) obtained in step 25-1 of Example 25 was dissolved in formamide (10.0 mL) and water (0.013 mL), iron (0) pentacarbonyl (179.8 uL, 1.1 eq), palladium (II) chloride (22.5 mg, 0.1 eq) and triethylamine (530.2 uL, 3.0 eq) were added thereto at room temperature. The reaction mixture was allowed to react at 110° C. for 2 hours, then water was added and the mixture was extracted with ethyl acetate. The separated organic layer was dried over magnesium sulfate and then concentrated under reduced pressure. The resulting residue was purified by column chromatography (ethyl acetate:hexane=1:1) to obtain 250.0 mg (yield: 28.5%) of the title compound.

Step 27-2: Preparation of tert-butyl (R)-3-(4-((2,4-dimethoxybenzyl)amino)-7-(hydroxymethyl)-3-(4-(phenylcarbamoyl)phenyl)-1H-pyrazolo[4,3-c]pyridin-1-yl)piperidine-1-carboxylate

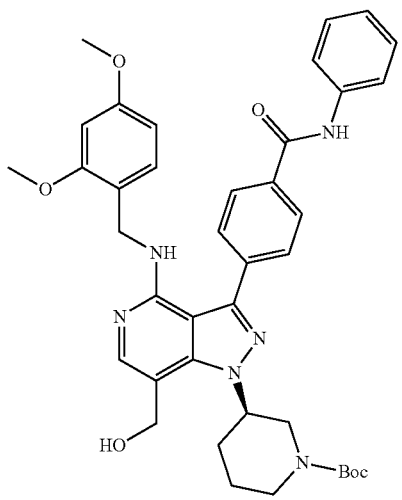 [SMILES: COc1ccc(CNc2ncc(CO)c3c2c(-c2ccc(C(=O)Nc4ccccc4)cc2)nn3[C@@H]2CCCN(C(=O)OC(C)(C)C)C2)c(OC)c1]

After tert-butyl (R)-3-(4-((2,4-dimethoxybenzyl)amino)-7-formyl-3-(4-(phenylcarbamoyl)phenyl)-1H-pyrazolo[4,3-c]pyridin-1-yl)piperidine-1-carboxylate (160.0 mg, 1.0 eq) obtained in step 27-1 was dissolved in methanol (5.0 mL), sodium borohydride (35.0 mg, 4.0 eq) was added thereto, allowed to react for 30 minutes, then water was added and the mixture was extracted with ethyl acetate. The reaction mixture was allowed to react for 30 minutes, then water was added and the mixture was extracted with ethyl acetate. The separated organic layer was dried over magnesium sulfate and then concentrated under reduced pressure. The resulting residue was purified by column chromatography (ethyl acetate:hexane=1:1) to obtain 135.0 mg (yield: 84.7%) of the title compound.

Step 27-3: Preparation of (R)-4-(4-amino-7-(hydroxymethyl)-1-(piperidin-3-yl)-1H-pyrazolo[4,3-c]pyridin-3-yl)-N-phenyl benzamide

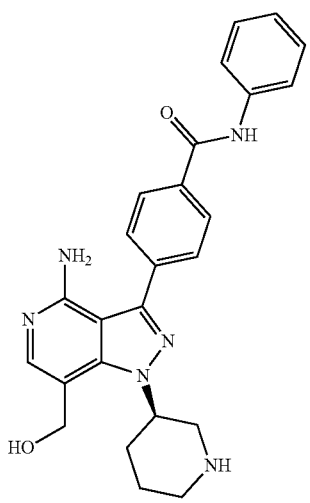 [SMILES: Nc1ncc(CO)c2c1c(-c1ccc(C(=O)Nc3ccccc3)cc1)nn2[C@@H]1CCCNC1]

A reaction was performed in the same manner as in step 18-2 of Example 18 by using tert-butyl (R)-3-(4-((2,4-dimethoxybenzyl)amino)-7-(hydroxymethyl)-3-(4-(phenylcarbamoyl)phenyl)-1H-pyrazolo[4,3-c]pyridin-1-yl)piperidine-1-carboxylate (40.0 mg, 1.0 eq) obtained in step 27-2, trifluoroacetic acid (2.0 mL) and triethylsilane (18.5 uL, 2.0 eq) to obtain the title compound, which was used in the next reaction without purification.

Step 27-4: Preparation of (R)-4-(1-(1-acryloylpiperidin-3-yl)-4-amino-7-(hydroxymethyl)-1H-pyrazolo[4,3-c]pyridin-3-yl)-N-phenyl benzamide

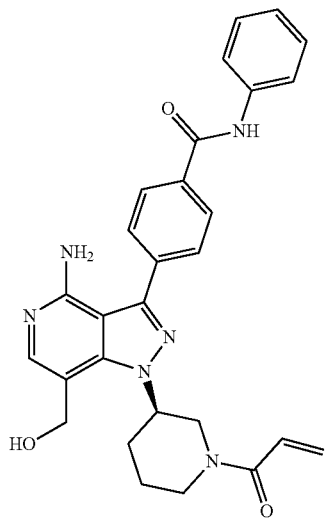 [SMILES: C=CC(=O)N1CCC[C@@H](n2nc(-c3ccc(C(=O)Nc4ccccc4)cc3)c3c(N)ncc(CO)c32)C1]

After (R)-4-(4-amino-7-(hydroxymethyl)-1-(piperidin-3-yl)-1H-pyrazolo[4,3-c]pyridin-3-yl)-N-phenylbenzamide (34.8 mg, 1.0 eq) obtained in step 27-3 was dissolved in tetrahydrofuran (5.0 mL) and water (1.0 mL), acryloyl chloride (9.8 uL, 2.0 eq) was added thereto at room temperature. The reaction mixture was allowed to react for 10 minutes, then water was added and the mixture was extracted with ethyl acetate. The separated organic layer was dried over magnesium sulfate and then concentrated under reduced pressure. The resulting residue was purified by column chromatography (dichloromethane:methanol=10:1) to obtain 5.9 mg (yield: 19.8%) of the title compound.

$^1$H NMR (500 MHz, CDCl$_3$): 8.04-7.88 (m, 2H), 7.78-7.71 (m, 2H), 7.68-7.54 (m, 2H), 7.49-7.32 (m, 3H), 7.16 (t, 1H), 6.67-6.54 (m, 1H), 6.35-6.18 (m, 1H), 5.79-5.68 (m, 1H), 5.09-4.99 (m, 1H), 4.84-4.59 (m, 2H), 4.08-4.00 (m, 1H), 3.85-3.47 (m, 4H), 3.32-3.17 (m, 1H), 2.52-2.39 (m, 1H), 2.33-2.27 (m, 1H)

MS m/z: 497.34 [m+1]

Example 28: Preparation of (R)-4-(1-(1-acryloylpiperidin-3-yl)-4-amino-7-(1H-pyrazol-4-yl)-1H-pyrazolo[4,3-c]pyridin-3-yl)-N-phenylbenzamide

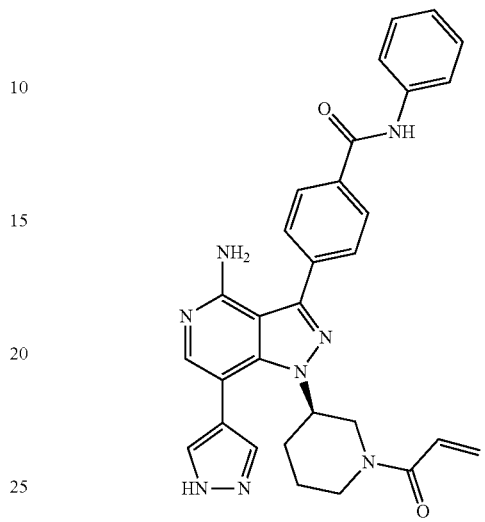

After (R)-4-(1-(1-acryloylpiperidin-3-yl)-4-amino-7-iodo-1H-pyrazolo[4,3-c]pyridin-3-yl)-N-phenylbenzamide (50.0 mg, 1.0 eq) obtained in step 25-3 of Example 25 was dissolved in 1,4-dioxane (3.3 mL) and water (0.7 mL), 4-(4,4,5,5-tetramethyl-1,3,2-dioxaborolan-2-yl)-1H-pyrazole (21.3 mg, 1.3 eq), [1,1'-bis(diphenylphosphino)ferrocene]dichloropalladium (II) (6.2 mg, 0.1 eq) and potassium carbonate (35.0 mg, 3.0 eq) were added thereto at room temperature. The reaction mixture was allowed to react at 130° C. for 15 minutes using a microwave reactor, then water was added and the mixture was extracted with ethyl acetate. The separated organic layer was dried over magnesium sulfate and then concentrated under reduced pressure. The resulting residue was purified by column chromatography (dichloromethane:methanol=10:1) to obtain 2.4 mg (5.3%) of the title compound.

$^1$H NMR (500 MHz, MeOD): 8.13 (d, 2H), 7.94-7.68 (m, 6H), 7.58 (s, 1H), 7.43-7.36 (m, 2H), 7.17 (t, 1H), 6.74-6.54 (m, 1H), 6.21-6.10 (m, 1H), 5.74-5.68 (m, 1H), 4.64-4.55 (m, 1H), 4.36-4.24 (m, 1H), 4.12-3.97 (m, 1H), 3.76-3.68 (m, 1H), 3.19-3.10 (m, 1H), 2.93-2.84 (m, 1H), 2.29-2.18 (m, 1H), 2.11-2.00 (m, 1H), 1.93-1.09 (m, 1H)

MS m/z: 533.60 [m+1]

Example 29: Preparation of (R)-4-(1-(1-acryloylpiperidin-3-yl)-4-amino-7-(1H-pyrazol-3-yl)-1H-pyrazolo[4,3-c]pyridin-3-yl)-N-phenylbenzamide

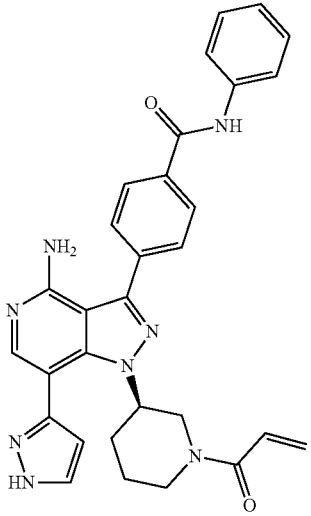 [SMILES: C=CC(=O)N1CCC[C@@H](n2nc(-c3ccc(C(=O)Nc4ccccc4)cc3)c3c(N)ncc(-c4cc[nH]n4)c32)C1]

A reaction was performed in the same manner as in Example 28 by using (R)-4-(1-(1-acryloylpiperidin-3-yl)-4-amino-7-iodo-1H-pyrazolo[4,3-c]pyridin-3-yl)-N-phenylbenzamide (50.0 mg, 1.0 eq) obtained in step 25-3 of Example 25, 1,4-dioxane (3.3 mL), water (0.7 mL), (1H-pyrazol-3-yl)boronic acid (21.3 mg, 1.5 eq), [1,1'-bis(diphenylphosphino)ferrocene]dichloropalladium (II) (6.2 mg, 0.1 eq), and potassium carbonate (35.0 mg, 3.0 eq) to obtain 3.6 mg (yield: 8.6%) of the title compound.

$^1$H NMR (500 MHz, MeOD): 8.12 (d, 2H), 7.85 (d, 2H), 7.82-7.69 (m, 3H), 7.43-7.36 (m, 2H), 7.147 (t, 1H), 6.76-6.53 (m, 2H), 6.18-6.07 (m, 1H), 5.76-5.65 (m, 1H), 4.63-4.52 (m, 1H), 4.35-4.28 (m, 1H), 4.08-3.95 (m, 1H), 3.73-3.63 (m, 1H), 3.48-3.17 (m, 1H), 3.20-3.11 (m, 1H), 2.92-2.84 (m, 1H), 2.28-2.00 (m, 2H), 1.98-1.89 (m, 1H)

MS m/z: 533.54 [m+1]

Example 30: Preparation of (R)-4-(1-(1-acryloylpiperidin-3-yl)-4-amino-7-(1H-pyrazol-5-yl)-1H-pyrazolo[4,3-c]pyridin-3-yl)-N-phenylbenzamide

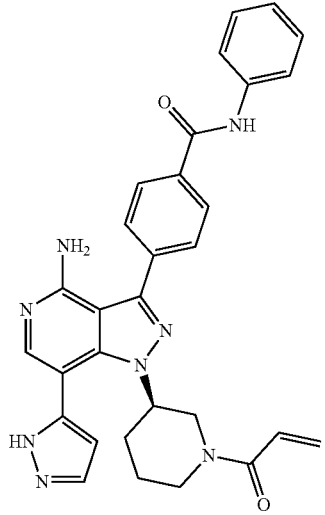 [SMILES: C=CC(=O)N1CCC[C@@H](n2nc(-c3ccc(C(=O)Nc4ccccc4)cc3)c3c(N)ncc(-c4ccn[nH]4)c32)C1]

A reaction was performed in the same manner as in Example 28 by using (R)-4-(1-(1-acryloylpiperidin-3-yl)-4-amino-7-iodo-1H-pyrazolo[4,3-c]pyridin-3-yl)-N-phenylbenzamide (50.0 mg, 1.0 eq) obtained in step 25-3 of Example 25, 1,4-dioxane (3.3 mL), water (0.7 mL), (1H-pyrazol-5-yl)boronic acid (21.3 mg, 1.5 eq), [1,1'-(diphenylphosphino)ferrocene]dichloropalladium (II) (6.2 mg, 0.1 eq) and potassium carbonate (35.0 mg, 30.eq) to obtain 5.1 mg (yield: 11.3%) of the title compound.

$^1$H NMR (500 MHz, MeOD): 8.14 (d, 2H), 7.86 (d, 2H), 7.82-7.65 (m, 4H), 7.42-7.37 (m, 2H), 7.17 (t, 1H), 6.74-6.53 (m, 2H), 6.17-6.09 (m, 1H), 5.73-5.66 (m, 1H), 4.63-4.54 (m, 1H), 4.36-4.27 (m, 1H), 4.09-3.95 (m, 1H), 3.73-3.65 (m, 1H), 3.22-3.10 (m, 1H), 2.93-2.84 (m, 1H), 2.29-2.01 (m, 2H), 1.92-1.85 (m, 1H)

MS m/z: 533.47 [m+1]

Example 31: Preparation of (R)-4-(1-(1-acryloylpiperidin-3-yl)-4-amino-7-(thiophen-3-yl)-1H-pyrazolo[4,3-c]pyridin-3-yl)-N-phenylbenzamide

Example 32: Preparation of (R)-4-(1-(1-acryloylpiperidin-3-yl)-4-amino-7-(2-methylthiazol-5-yl)-1H-pyrazolo[4,3-c]pyridin-3-yl)-N-phenylbenzamide

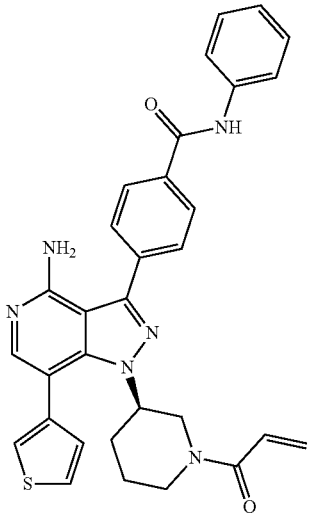 [SMILES: C=CC(=O)N1CCC[C@@H](n2nc(-c3ccc(C(=O)Nc4ccccc4)cc3)c3c(N)ncc(-c4ccsc4)c32)C1]

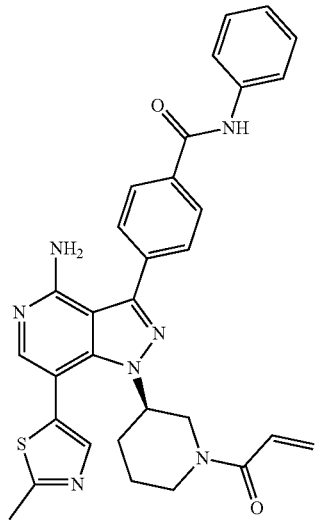 [SMILES: C=CC(=O)N1CCC[C@@H](n2nc(-c3ccc(C(=O)Nc4ccccc4)cc3)c3c(N)ncc(-c4cnc(C)s4)c32)C1]

A reaction was performed in the same manner as in Example 28 by using (R)-4-(1-(1-acryloylpiperidin-3-yl)-4-amino-7-iodo-1H-pyrazolo[4,3-c]pyridin-3-yl)-N-phenylbenzamide (50.0 mg, 1.0 eq) obtained in step 25-3 of Example 25, 1,4-dioxane (3.3 mL), water (0.7 mL), thiophen-3-yl boronic acid (14.0 mg, 1.5 eq), [1,1'-(diphenylphosphino)ferrocene]dichloropalladium (II) (6.2 mg, 0.1 eq) and potassium carbonate (35.0 mg, 3.0 eq) to obtain 2.0 mg (yield: 4.2%) of the title compound.

$^1$H NMR (500 MHz, MeOD): 8.13 (d, 2H), 7.85 (d, 2H), 7.73 (d, 2H), 7.60 (s, 1H), 7.59-7.48 (m, 2H), 7.43-7.36 (m, 2H), 7.22 (s, 1H), 7.17 (t, 1H), 6.74-6.58 (m, 1H), 6.21-6.10 (m, 1H), 5.76-5.69 (m, 1H), 4.63-4.53 (m, 1H), 4.38-4.27 (m, 1H), 4.04-3.92 (m, 1H), 3.73-3.63 (m, 1H), 3.16-2.78 (m, 1H), 2.27-2.13 (m, 1H), 2.00-1.81 (m, 2H), 1.40-1.30 (m, 1H)

MS m/z: 549.42 [m+1]

A reaction was performed in the same manner as in Example 28 by using (R)-4-(1-(1-acryloylpiperidin-3-yl)-4-amino-7-iodo-1H-pyrazolo[4,3-c]pyridin-3-yl)-N-phenylbenzamide (50.0 mg, 1.0 eq) obtained in step 25-3 of Example 25, 1,4-dioxane (3.3 mL), water (0.7 mL), 2-methyl-5-(4,4,5,5-tetramethyl-1,3,2-dioxaborolan-2-yl)thiazole (24.7 mg, 1.5 eq), [1,1'-(diphenylphosphino)ferrocene]dichloropalladium (II) (6.2 mg, 0.1 eq) and potassium carbonate (35.0 mg, 3.0 eq) to obtain 4.6 mg (yield: 9.7%) of the title compound.

$^1$H NMR (500 MHz, MeOD): 8.14 (d, 2H), 7.85 (d, 2H), 7.78-7.67 (m, 3H), 7.42-7.36 (m, 2H), 7.18 (t, 1H), 6.78-6.22 (m, 1H), 6.22-6.17 (m, 1H), 5.78-5.72 (m, 1H), 4.37-4.30 (m, 1H), 4.22-3.98 (m, 2H), 3.79-3.71 (m, 1H), 2.98-2.68 (m, 1H), 2.32-2.20 (m, 1H), 2.15-1.89 (m, 2H), 1.68-1.55 (m, 1H), 1.40-1.30 (s, 3H)

MS m/z: 564.53 [m+1]

Example 33: Preparation of (R)-4-(1-(1-acryloylpiperidin-3-yl)-4-amino-7-(1-(difluoromethyl)-1H-pyrazol-4-yl)-1H-pyrazolo[4,3-c]pyridin-3-yl)-N-phenylbenzamide

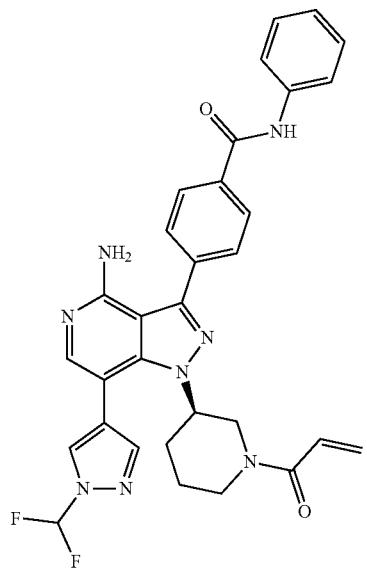 [SMILES: C=CC(=O)N1CCC[C@@H](n2nc(-c3ccc(C(=O)Nc4ccccc4)cc3)c3c(N)ncc(-c4cnn(C(F)F)c4)c32)C1]

A reaction was performed in the same manner as in Example 28 by using (R)-4-(1-(1-acryloylpiperidin-3-yl)-4-amino-7-iodo-1H-pyrazolo[4,3-c]pyridin-3-yl)-N-phenylbenzamide (50.0 mg, 1.0 eq) obtained in step 25-3 of Example 25, 1,4-dioxane (3.3 mL), water (0.7 mL), 1-(difluoro)-4-(4,4,5,5-tetramethyl-1,3,2-dioxaborolan-2-yl)-1H-pyrazole (24.6 mg, 1.5 eq), [1,1'-(diphenylphosphino)ferrocene]dichloropalladium (II) (6.2 mg, 0.1 eq) and potassium carbonate (35.0 mg, 3.0 eq) to obtain 8.2 mg (yield 16.7%) of the title compound.

$^1$H NMR (500 MHz, MeOD): 8.31 (s, 1H), 8.13 (d, 2H), 7.89 (s, 1H), 7.85 (d, 2H), 7.72 (d, 2H), 7.69-7.52 (m, 1H), 7.48-7.36 (m, 2H), 7.20-7.16 (m, 1H), 6.76-6.52 (m, 1H), 6.24-6.08 (m, 1H), 5.78-5.65 (m, 1H), 4.65-4.55 (m, 1H), 4.33-4.15 (m, 1H), 4.06-3.98 (m, 1H), 3.80-3.72 (m, 1H), 3.30-2.85 (m, 2H), 2.35-2.18 (m, 1H), 2.12-1.86 (m, 2H)

MS m/z: 583.43 [m+1]

Example 34: Preparation of (R)-4-(1-(1-acryloylpiperidin-3-yl)-4-amino-7-(1-(tetrahydro-2H-pyran-4-yl)-1H-pyrazol-4-yl)-1H-pyrazolo[4,3-c]pyridin-3-yl)-N-phenylbenzamide

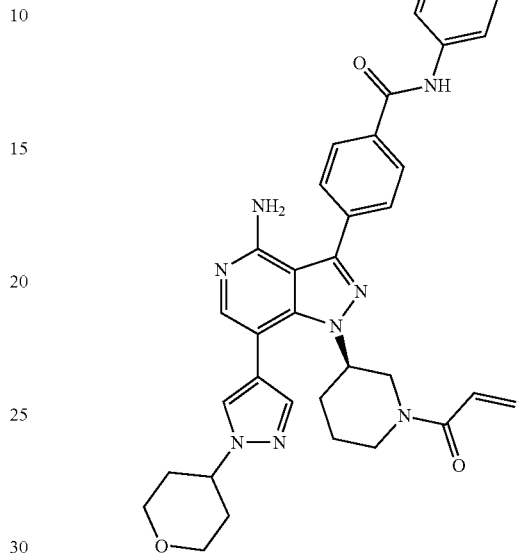

A reaction was performed in the same manner as in Example 28 by using (R)-4-(1-(1-acryloylpiperidin-3-yl)-4-amino-7-iodo-1H-pyrazolo[4,3-c]pyridin-3-yl)-N-phenylbenzamide (50.0 mg, 1.0 eq) obtained in step 25-3 of Example 25, 1,4-dioxane (3.3 mL), water (0.7 mL), 1-(tetrahydro-2H-pyran-4-yl)-4-(4,4,5,5-tetramethyl-1,3,2-dioxaborolan-2-yl)-1H-pyrazole (30.5 mg, 1.5 eq), [1,1'-(diphenylphosphino)ferrocene]dichloropalladium (II) (6.2 mg, 0.1 eq) and potassium carbonate (35.0 mg, 3.0 eq) to obtain 10.5 mg (yield: 20.2%) of the title compound.

$^1$H NMR (500 MHz, MeOD): 8.20-8.08 (m, 2H), 7.96-7.91 (m, 1H), 7.89-7.80 (m, 2H), 7.79-7.68 (m, 2H), 7.55 (d, 2H), 7.43-7.38 (m, 2H), 7.20-7.15 (m, 1H), 6.80-6.59 (m, 1H), 6.28-6.12 (m, 1H), 5.81-5.70 (m, 1H), 4.68-4.57 (m, 1H), 4.50-4.40 (m, 1H), 4.40-4.18 (m, 1H), 4.15-4.02 (m, 3H), 3.75-3.52 (m, 3H), 3.29-2.80 (m, 3H), 2.30-1.86 (m, 5H), 1.37-1.25 (m, 1H)

MS m/z: 617.53 [m+1]

Example 35: Preparation of (R)-4-(1-(1-acryloylpiperidin-3-yl)-4-amino-7-(1-(1-methylpiperidin-4-yl)-1H-pyrazol-4-yl)-1H-pyrazolo[4,3-c]pyridin-3-yl)-N-phenylbenzamide

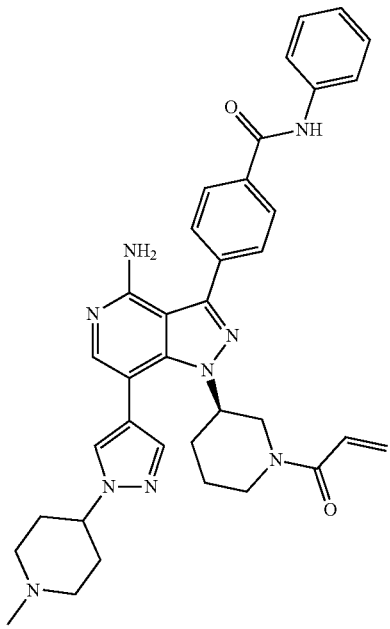 [SMILES: C=CC(=O)N1CCC[C@@H](n2nc(-c3ccc(C(=O)Nc4ccccc4)cc3)c3c(N)ncc(-c4cnn(C5CCN(C)CC5)c4)c32)C1]

A reaction was performed in the same manner as in Example 28 by using (R)-4-(1-(1-acryloylpiperidin-3-yl)-4-amino-7-iodo-1H-pyrazolo[4,3-c]pyridin-3-yl)-N-phenylbenzamide (50.0 mg, 1.0 eq) obtained in step 25-3 of Example 25, 1,4-dioxane (3.3 mL), water (0.7 mL), 1-methyl-4-(4-(4,4,5,5-tetramethyl-1,3,2-dioxaborolan-2-yl)-1H-pyrazol-1-yl)piperidine (32.0 mg, 1.5 eq), [1,1'-(diphenylphosphino)ferrocene]dichloropalladium (II) (6.2 mg, 0.1 eq) and potassium carbonate (35.0 mg, 3.0 eq) to obtain 9.8 mg (yield: 18.4%) of the title compound.

$^1$H NMR (500 MHz, MeOD): 8.11 (d, 2H), 7.92-7.86 (m, 1H), 7.83 (d, 2H), 7.72 (d, 2H), 7.55 (d, 2H), 7.41-7.36 (m, 2H), 7.16 (t, 1H), 6.78-6.56 (m, 1H), 6.27-6.10 (m, 1H), 5.80-5.56 (m, 1H), 4.66-4.57 (m, 1H), 4.50-4.00 (m, 5H), 3.80-3.55 (m, 1H), 3.30-2.76 (m, 4H), 2.45-1.82 (m, 7H)

MS m/z: 630.68 [m+1]

Example 36: Preparation of (R)-4-(1-(1-acryloylpiperidin-3-yl)-4-amino-7-(1-(2-(dimethylamino)ethyl)-1H-pyrazol-4-yl)-1H-pyrazolo[4,3-c]pyridin-3-yl)-N-phenylbenzamide

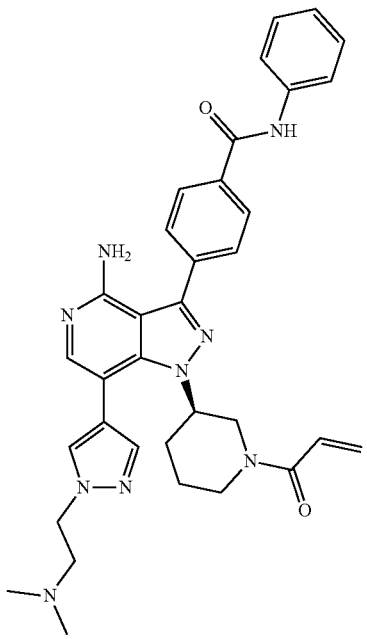 [SMILES: C=CC(=O)N1CCC[C@@H](n2nc(-c3ccc(C(=O)Nc4ccccc4)cc3)c3c(N)ncc(-c4cnn(CCN(C)C)c4)c32)C1]

A reaction was performed in the same manner as in Example 28 by using (R)-4-(1-(1-acryloylpiperidin-3-yl)-4-amino-7-iodo-1H-pyrazolo[4,3-c]pyridin-3-yl)-N-phenylbenzamide (50.0 mg, 1.0 eq) obtained in step 25-3 of Example 25, 1,4-dioxane (3.3 mL), water (0.7 mL), N,N-dimethyl-2-(4-(4,4,5,5-tetramethyl-1,3,2-dioxaborolan-2-yl)-1H-pyrazol-1-yl)ethane-1-amine (29.1 mg, 1.5 eq), [1,1'-(diphenylphosphino)ferrocene]dichloropalladium (II) (6.2 mg, 0.1 eq) and potassium carbonate (35.0 mg, 3.0 eq) to obtain 6.0 mg (yield: 11.8%) of the title compound.

$^1$H NMR (500 MHz, MeOD): 8.12 (d, 1H), 7.88-7.82 (m, 3H), 7.78-7.70 (m, 2H), 7.65 (s, 1H), 7.57 (s, 1H), 7.42-7.36 (m, 2H), 7.17 (t, 1H), 6.78-6.57 (m, 1H), 6.28-6.10 (m, 1H), 5.80-5.68 (m, 1H), 4.63-4.56 (m, 1H), 4.43-4.27 (m, 3H), 4.08-3.72 (m, 2H), 3.30-2.82 (m, 5H), 2.36 (s, 6H), 2.36-1.89 (m, 2H)

MS m/z: 604.64 [m+1]

Example 37: Preparation of (R)-4-(1-(1-acryloylpiperidin-3-yl)-4-amino-7-(1-(2-(pyrrolidin-1-yl)ethyl)-1H-pyrazol-4-yl)-1H-pyrazolo[4,3-c]pyridin-3-yl)-N-phenyl benzamide

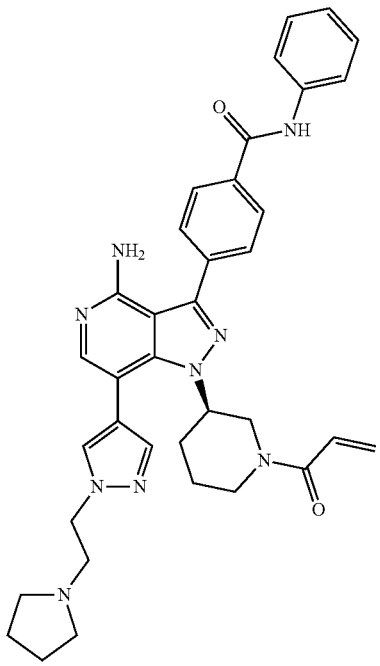 [SMILES: C=CC(=O)N1CCC[C@@H](n2nc(-c3ccc(C(=O)Nc4ccccc4)cc3)c3c(N)ncc(-c4cnn(CCN5CCCC5)c4)c32)C1]

A reaction was performed in the same manner as in Example 28 by using (R)-4-(1-(1-acryloylpiperidin-3-yl)-4-amino-7-iodo-1H-pyrazolo[4,3-c]pyridin-3-yl)-N-phenylbenzamide (50.0 mg, 1.0 eq) obtained in step 25-3 of Example 25, 1,4-dioxane (3.3 mL), water (0.7 mL), 1-(2-(pyrrolidin-1-yl)ethyl)-4-(4,4,5,5-tetramethyl-1,3,2-dioxaborolan-2-yl)-1H-pyrazole (24.1 mg, 1.5 eq), [1,1'-(diphenylphosphino)ferrocene]dichloropalladium (II) (6.2 mg, 0.1 eq) and potassium carbonate (35.0 mg, 3.0 eq) to obtain 4.9 mg (yield: 9.2%) of the title compound.

$^1$H NMR (500 MHz, MeOD): 8.11 (d, 2H), 7.91-7.08 (m, 3H), 7.72 (d, 2H), 7.65 (s, 1H), 7.46 (s, 1H), 7.42-7.35 (m, 2H), 7.16 (t, 1H), 6.80-6.56 (m, 1H), 6.27-6.10 (m, 1H), 5.80-5.68 (m, 1H), 4.82-4.57 (m, 1H), 4.46-4.28 (m, 3H), 4.08-3.68 (m, 2H), 3.30-3.00 (m, 2H), 2.78-2.55 (m, 3H), 2.38-1.78 (m, 7H), 1.38-1.25 (m, 2H)

MS m/z: 630.68 [m+1]

Example 38: Preparation of (R)-4-(1-(1-acryloylpiperidin-3-yl)-4-amino-7-(1-(2-morpholinoethyl)-1H-pyrazol-4-yl)-1H-pyrazolo[4,3-c]pyridin-3-yl)-N-phenyl benzamide

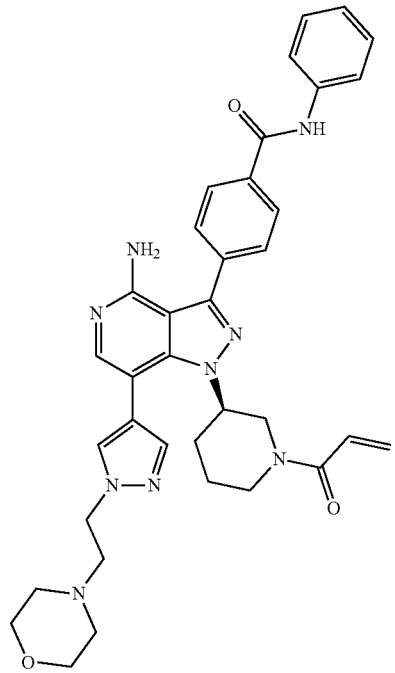 [SMILES: C=CC(=O)N1CCC[C@@H](n2nc(-c3ccc(C(=O)Nc4ccccc4)cc3)c3c(N)ncc(-c4cnn(CCN5CCOCC5)c4)c32)C1]

A reaction was performed in the same manner as in Example 28 by using (R)-4-(1-(1-acryloylpiperidin-3-yl)-4-amino-7-iodo-1H-pyrazolo[4,3-c]pyridin-3-yl)-N-phenylbenzamide (50.0 mg, 1.0 eq) obtained in step 25-3 of Example 25, 1,4-dioxane (3.3 mL), water (0.7 mL), 4-(2-(4-(4,4,5,5-tetramethyl-1,3,2-dioxaborolan-2-yl)-1H-pyrazol-1-yl)ethyl)morpholine (33.7 mg, 1.5 eq), [1,1'-(diphenylphosphino)ferrocene]dichloropalladium (II) (6.2 mg, 0.1 eq) and potassium carbonate (35.0 mg, 3.0 eq) to obtain 2.8 mg (yield: 5.1%) of the title compound.

$^1$H NMR (500 MHz, MeOD): 8.12 (d, 2H), 7.92-7.81 (m, 3H), 7.73 (d, 2H), 7.63 (s, 1H), 7.56 (s, 1H), 7.42-7.37 (m, 2H), 7.17 (t, 1H), 6.80-6.56 (m, 1H), 6.25-6.10 (m, 1H), 5.80-5.68 (m, 1H), 4.64-4.57 (m, 1H), 4.43-4.25 (m, 3H), 4.05-3.62 (m, 5H), 3.30-2.78 (m, 5H), 2.61-2.40 (m, 4H), 2.36-1.87 (m, 5H)

MS m/z: 646.63 [m+1]

Example 39: Preparation of (S)-4-(1-(1-acryloylpiperidin-3-yl)-4-amino-1H-pyrazolo[4,3-c]pyridin-3-yl)-N-(pyridin-2-yl)benzamide

Step 39-1: Preparation of tert-butyl (S)-3-(3-bromo-4-((2,4-dimethoxybenzyl)amino)-1H-pyrazolo[4,3-c]pyridin-1-yl)piperidine-1-carboxylate

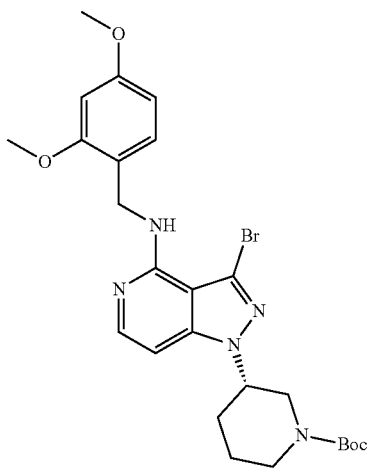 [SMILES: COc1ccc(CNc2nccc3c2c(Br)nn3[C@H]2CCCN(C(=O)OC(C)(C)C)C2)c(OC)c1]

After (R)-1-(tert-butoxycarbonyl)-3-hydroxypiperidine (1660.0 mg, 1.5 eq) was dissolved in tetrahydrofuran (55.0 mL), triphenylphosphine (2170.0 mg, 1.5 eq) was added at room temperature and diisopropyl azadicarboxylate (1630.0 uL, 1.5 eq) was added at 0° C. The reaction mixture was allowed to react at room temperature for 1 day, and then 3-bromo-N-(2,4-dimethoxybenzyl)-1H-pyrazolo[4,3-c]pyridin-4-amine (2000.0 mg, 1.0 eq) obtained in step 3-1 of Example 3 was added thereto. The reaction mixture was allowed to react at room temperature for 1 day, then water was added and the mixture was extracted with ethyl acetate. The separated organic layer was dried over magnesium sulfate and then concentrated under reduced pressure. The resulting residue was purified by column chromatography (ethyl acetate:hexane=1:1) to obtain 1700.0 mg (yield: 56.5%) of the title compound.

Step 39-2: Preparation of tert-butyl (S)-3-(4-((2,4-dimethoxybenzyl)amino)-3-(4-(pyridin-2-ylcarbamoyl)phenyl)-1H-pyrazolo[4,3-c]pyridin-1-yl)piperidine-1-carboxylate

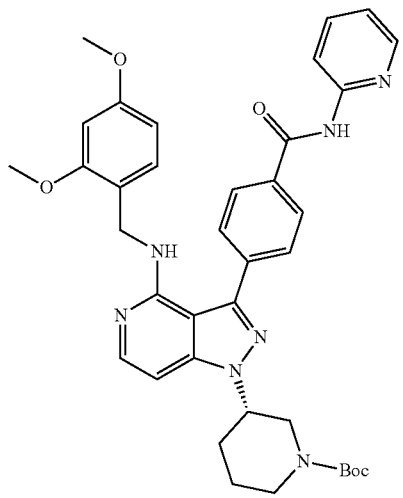 [SMILES: COc1ccc(CNc2nccc3c2c(-c2ccc(C(=O)Nc4ccccn4)cc2)nn3[C@H]2CCCN(C(=O)OC(C)(C)C)C2)c(OC)c1]

A reaction was performed in the same manner as in step 18-1 of Example 18 by using tert-butyl (S)-3-(3-bromo-4-((2,4-dimethoxybenzyl)amino)-1H-pyrazolo[4,3-c]pyridin-1-yl)piperidine-1-carboxylate (1500.0 mg, 1.0 eq) obtained in step 39-1, 1,4-dioxane (10.0 mL), water (2.0 mL), (4-(pyridin-2-ylcarbamoyl)phenyl)boronic acid (860.0 mg, 1.3 eq), [1,1'-(diphenylphosphino)ferrocene]dichloropalladium (II) (200.0 mg, 0.1 eq) and potassium carbonate (750.0 mg, 2.0 eq) to obtain 504.0 mg (yield: 27.6%) of the title compound.

Step 39-3: Preparation of (S)-4-(4-amino-1-(piperidin-3-yl)-1H-pyrazolo[4,3-c]pyridin-3-yl)-N-(pyridin-2-yl)benzamide A reaction was performed in the same manner as in step 18-2 of Example 18 by using tert-butyl (S)-3-(4-((2,4-dimethoxybenzyl)amino)-3-(4-(pyridin-2-ylcarbamoyl)phenyl)-1H-pyrazolo[4,3-c]pyridin-1-yl)piperidine-1-carboxylate (500.0 mg, 1.0 eq) obtained in step 39-2, trifluoroacetic acid (5.0 mL) and triethylsilane (239.9 uL, 2.0 eq) to obtain the title compound, which was used in the next reaction without purification.

Step 39-4: Preparation of (S)-4-(1-(1-acryloylpiperidin-3-yl)-4-amino-1H-pyrazolo[4,3-c]pyridin-3-yl)-N-(pyridin-2-yl)benzamide

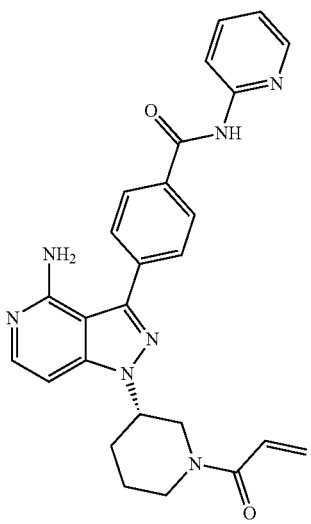 [SMILES: C=CC(=O)N1CCC[C@H](n2nc(-c3ccc(C(=O)Nc4ccccn4)cc3)c3c(N)nccc32)C1]

After (S)-4-(4-amino-1-(piperidin-3-yl)-1H-pyrazolo[4,3-c]pyridin-3-yl)-N-(pyridin-2-yl)benzamide (31.0 mg, 1.0 eq) obtained in step 39-3 was dissolved in tetrahydrofuran (10.0 mL) and water (2.0 mL), acryloyl chloride (60.9 uL, 1.0 eq) was added thereto. The reaction mixture was allowed to react at room temperature for 30 minutes, then water was added and the mixture was extracted with ethyl acetate. The separated organic layer was dried over magnesium sulfate and then concentrated under reduced pressure. The resulting residue was purified by column chromatography (dichloromethane:methanol=10:1) to obtain 160.0 mg (yield: 45.6%) of the title compound.

$^1$H NMR (500 MHz, CDCl$_3$): 8.80 (s, 1H), 8.41 (d, 1H), 8.33 (d, 1H), 8.14 (d, 2H), 7.79 (d, 2H), 7.65-7.57 (m, 1H), 7.15-7.09 (m, 1H), 6.99-6.96 (m, 1H), 6.68-6.60 (m, 1H), 6.40-6.33 (m, 1H), 5.82-5.76 (m, 1H), 4.95-4.86 (m, 1H), 4.77-4.60 (m, 1H), 4.48-4.38 (m, 1H), 3.30-3.15 (m, 1H), 2.52-2.00 (m, 4H)

MS m/z: 468.53 [m+1]

Example 40: Preparation of (R)-4-(1-(1-acryloylpiperidin-3-yl)-4-amino-1H-pyrazolo[4,3-c]pyridin-3-yl)-3-fluoro-N-(pyridin-2-yl)benzamide Step 40-1: Preparation of tert-butyl (R)-3-(4-((2,4-dimethoxybenzyl)amino)-3-(2-fluoro-4-(pyridin-2-ylcarbamoyl)phenyl)-1H-pyrazolo[4,3-c]pyridin-1-yl)piperidine-1-carboxylate

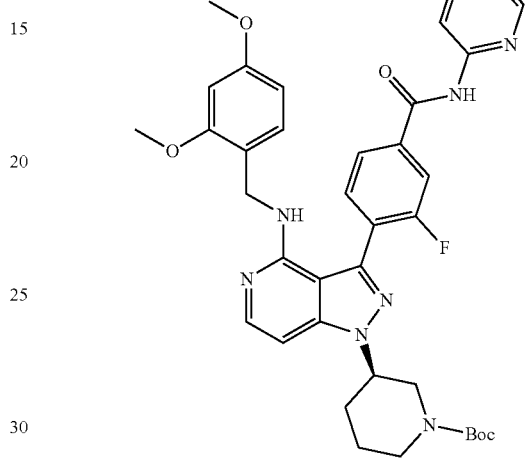

After tert-butyl (R)-3-(3-bromo-4-((2,4-dimethoxybenzyl)amino)-1H-pyrazolo[4,3-c]pyridin-1-yl)piperidine-1-carboxylate (300.0 mg, 1.0 eq) obtained in step 16-2 of Example 16 was dissolved in 1,4-dioxane (10.0 mL) and water (2.0 mL), (2-fluoro-4-(pyridin-2-ylcarbamoyl)phenyl) boronic acid (185.6 mg, 1.3 eq), [1,1'-(diphenylphosphino) ferrocene]dichloropalladium (II) (40.2 mg, 0.1 eq) and potassium carbonate (151.8 mg, 2.0 eq) were added thereto at room temperature. The reaction mixture was allowed to react at 120° C. for 15 minutes using a microwave reactor, then water was added and the mixture was extracted with ethyl acetate. The separated organic layer was dried over magnesium sulfate and then concentrated under reduced pressure. The resulting residue was purified by column chromatography (ethyl acetate:hexane=1:1) to obtain 30.0 mg (yield: 8.0%) of the title compound.

Step 40-2: Preparation of (R)-4-(4-amino-1-(piperidin-3-yl)-1H-pyrazolo[4,3-c]pyridin-3-yl)-3-fluoro-N-(pyridin-2-yl)benzamide

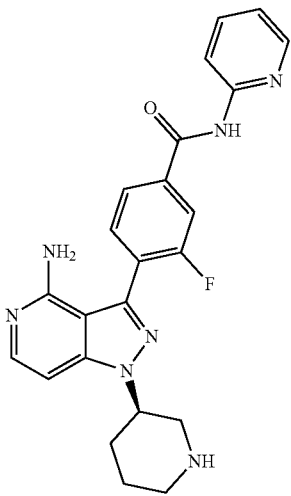 [SMILES: Nc1nccc2c1c(-c1ccc(C(=O)Nc3ccccn3)cc1F)nn2[C@@H]1CCCNC1]

A reaction was performed in the same manner as in step 18-2 of Example 18 by using tert-butyl (R)-3-(4-((2,4-dimethoxybenzyl)amino)-3-(2-fluoro-4-(pyridin-2-ylcarbamoyl)phenyl)-1H-pyrazolo[4,3-c]pyridin-1-yl)piperidine-1-carboxylate (30.0 mg, 1.0 eq) obtained in step 40-1, trifluoroacetic acid (2.0 mL) and triethylsilane (14.1 uL, 2.0 eq) to obtain the title compound, which was used in the next reaction without purification.

Step 40-3: Preparation of (R)-4-(1-(1-acryloylpiperidin-3-yl)-4-amino-1H-pyrazolo[4,3-c]pyridin-3-yl)-3-fluoro-N-(pyridin-2-yl)benzamide

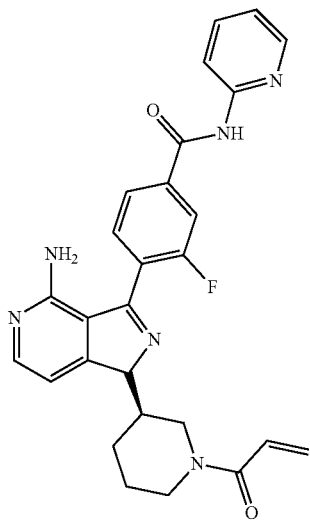 [SMILES: C=CC(=O)N1CCC[C@@H](C2N=C(c3ccc(C(=O)Nc4ccccn4)cc3F)c3c2ccnc3N)C1]

A reaction was performed in the same manner as in step 18-3 of Example 18 by using (R)-4-(4-amino-1-(piperidin-3-yl)-1H-pyrazolo[4,3-c]pyridin-3-yl)-3-fluoro-N-(pyridin-2-yl)benzamide (18.9 mg, 1.0 eq) obtained in step 40-2, sodium hydrogen carbonate (7.3 mg, 2.0 eq) and acryloyl chloride (7.1 uL, 2.0 eq) to obtain 2.3 mg (yield: 10.8%) of the title compound.

$^1$H NMR (500 MHz, MeOD): 8.42-8.38 (m, 1H), 8.30-8.22 (m, 1H), 8.02-7.98 (m, 2H), 6.86-6.78 (m, 1H), 6.30-6.10 (m, 1H), 5.80-5.63 (m, 1H), 4.75-4.63 (m, 1H), 4.45-4.33 (m, 1H), 3.94-3.80 (m, 1H), 3.28-3.10 (m, 1H), 2.80-2.66 (m, 1H), 2.40-2.25 (m, 1H), 2.13-2.02 (m, 1H), 1.81-1.65 (m, 1H)

MS m/z: 486.43 [m+1]

Example 41: Preparation of (R)-4-(1-(1-acryloylpiperidin-3-yl)-4-amino-1H-pyrazolo[4,3-c]pyridin-3-yl)-N-(4-fluoropyridin-2-yl)benzamide

Step 41-1: Preparation of 3-bromo-1H-pyrazolo[4,3-c]pyridin-4-amine

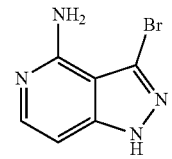

After 3-Bromo-N-(2,4-dimethoxybenzyl)-1H-pyrazolo[4,3-c]pyridin-4-amine (2000.0 mg, 1.0 eq) obtained in step 3-1 of Example 3 was dissolved in trifluoroacetic acid (10.0 mL) and triethylsilane (1640.0 uL, 2.0 eq) were added. The reaction mixture was allowed to react at room temperature for 12 hours, then neutralized by adding saturated aqueous sodium hydrogen carbonate solution, and extracted with ethyl acetate. The separated organic layer was dried over magnesium sulfate and then concentrated under reduced pressure. The resulting residue was purified by column chromatography (dichloromethane:methanol=10:1) to obtain 780.0 mg (yield: 66.4%) of the title compound.

Step 41-2: Preparation of tert-butyl (R)-3-(4-amino-3-bromo-1H-pyrazolo[4,3-c]pyridin-1-yl)piperidine-1-carboxylate

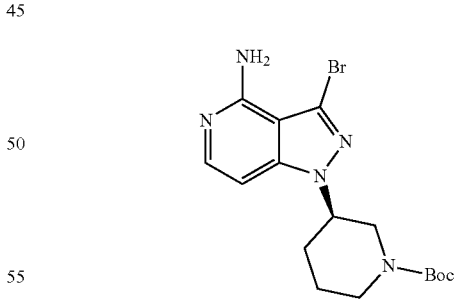

After (S)-1-(tert-butoxycarbonyl)-3-hydroxypiperidine (1100.0 mg, 1.5 eq) was dissolved in tetrahydrofuran (40.0 mL), triphenylphosphine (1440.0 mg, 1.5 eq) was added at room temperature and diisopropyl azodicarboxylate (1080.0 uL, 1.5 eq) was added at 0° C. The reaction mixture was allowed to react at room temperature for 10 minutes and then 3-bromo-1H-pyrazolo[4,3-c]pyridin-4-amine (780.0 mg, 1.0 eq) obtained in step 41-1 was added thereto. The reaction mixture was allowed to react at room temperature for 1 day, then water was added and the mixture was extracted with ethyl acetate. The separated organic layer was dried over magnesium sulfate and then concentrated under reduced pressure. The resulting residue was purified by column chromatography (ethyl acetate:hexane=1:1) to obtain 230.0 mg (yield: 15.9%) of the title compound.

Step 41-3: Preparation of tert-butyl (R)-3-(4-amino-3-(4-((4-fluoropyridin-2-yl)carbamoyl)phenyl)-1H-pyrazolo[4,3-c]pyridin-1-yl)piperidine-1-carboxylate

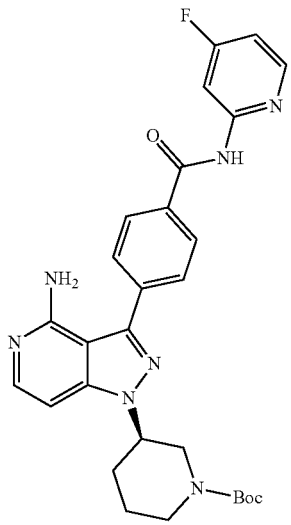 [SMILES: CC(C)(C)OC(=O)N1CCC[C@@H](n2nc(-c3ccc(C(=O)Nc4cc(F)ccn4)cc3)c3c(N)nccc32)C1]

After tert-butyl (R)-3-(4-amino-3-bromo-1H-pyrazolo[4,3-c]pyridin-1-yl)piperidine-1-carboxylate (200.0 mg, 1.0 eq) obtained in step 4-2 was dissolved in 1,4-dioxane (5.0 mL) and water (1.0 mL), (4-((4-fluoropyridin-2-yl)carbamoyl)phenyl)boronic acid (170.0 mg, 1.3 eq), [1,1'-(diphenylphosphino)ferrocene]dichloropalladium (II) (36.9 mg, 0.1 eq) and potassium carbonate (139.5 mg, 2.0 eq) were added thereto at room temperature. The reaction mixture was allowed to react at 120° C. for 15 minutes using a microwave reactor, then water was added and the mixture was extracted with ethyl acetate. The separated organic layer was dried over magnesium sulfate and then concentrated under reduced pressure. The resulting residue was purified by column chromatography (ethyl acetate:hexane=1:1) to obtain 91.0 mg (yield: 33.6%) of the title compound.

Step 41-4: Preparation of (R)-4-(4-amino-1-(piperidin-3-yl)-H-pyrazolo[4,3-c]pyridin-3-yl)-N-(4-fluoropyridin-2-yl)benzamide hydrochloride

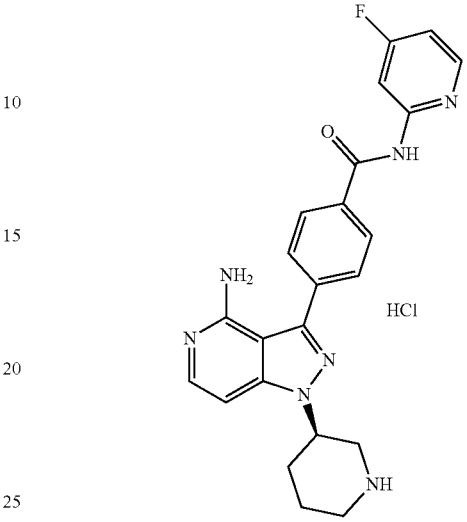

After tert-butyl (R)-3-(4-amino-3-(4-((4-fluoropyridin-2-yl)carbamoyl)phenyl)-1H-pyrazolo[4,3-c]pyridin-1-yl)piperidine-1-carboxylate (80.0 mg, 1.0 eq) obtained in step 41-3 was dissolved in ethyl acetate (2.0 mL), 1.0M hydrochloric acid ethyl acetate solution (300.0 uL, 2.0 eq) was added thereto at room temperature. The reaction mixture was reacted at room temperature for 3 hours. The obtained solid compound was filtered, washed with ethyl acetate and dried under reduced pressure to obtain 42.0 mg (yield: 59.8%) of the title compound.

Step 41-5: Preparation of (R)-4-(1-(1-acryloylpiperidin-3-yl)-4-amino-1H-pyrazolo[4,3-c]pyridin-3-yl)-N-(4-fluoropyridin-2-yl)benzamide

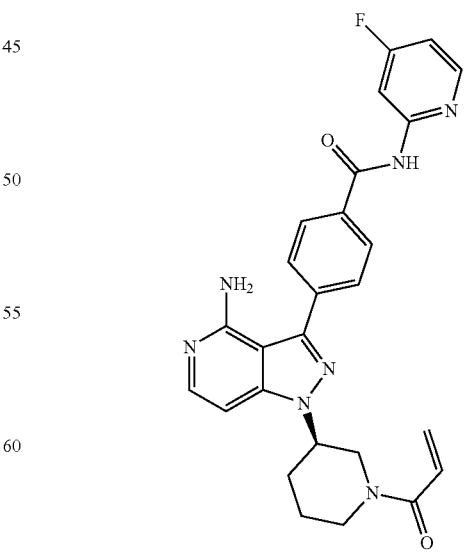

After (R)-4-(4-amino-1-(piperidin-3-yl)-1H-pyrazolo[4,3-c]pyridin-3-yl)-N-(4-fluoropyridin-2-yl)benzamide hydrochloride (20.0 mg, 1.0 eq) obtained in step 41-4 was dissolved in tetrahydrofuran (2.5 mL) and water (0.5 mL), sodium hydrogen carbonate (18.0 mg, 5.0 eq) was added thereto and the mixture was allowed to react at room temperature for 30 minutes. Acryloyl chloride (6.8 uL, 2.0 eq) was added to the mixture. The reaction mixture was allowed to react at room temperature for 10 minutes, then water was added and the mixture was extracted with ethyl acetate. The separated organic layer was dried over magnesium sulfate and then concentrated under reduced pressure. The resulting residue was purified by column chromatography (dichloromethane:methanol=10:1) to obtain 2.8 mg (yield: 13.4%) of the title compound.

$^1$H NMR (500 MHz, MeOD): 8.41-8.37 (m, 1H), 8.19-8.10 (m, 2H), 7.92-7.78 (m, 3H), 7.22-6.97 (m, 1H), 6.88-6.81 (m, 1H), 6.71-6.61 (m, 1H), 6.28-6.12 (m, 1H), 5.83-5.75 (m, 1H), 5.48-5.30 (m, 1H), 4.70-4.60 (m, 1H), 4.31-3.85 (m, 2H), 3.50-3.35 (m, 1H), 2.43-2.05 (m, 3H), 1.85-1.70 (m, 1H)

MS m/z: 486.23 [m+1]

Example 42: Preparation of (R)—N-acryloyl-4-(1-(1-acryloylpiperidin-3-yl)-4-amino-1H-pyrazolo[4,3-c]pyridin-3-yl)-N-(4-fluoropyridin-2-yl)benzamide

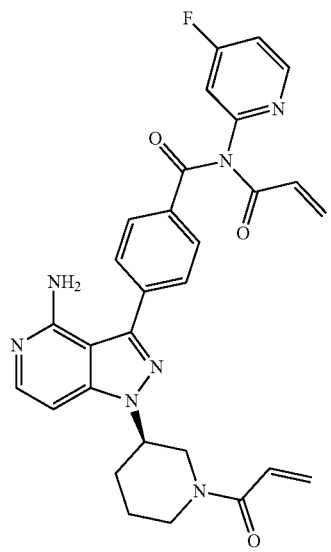 [SMILES: C=CC(=O)N1CCC[C@@H](n2nc(-c3ccc(C(=O)N(C(=O)C=C)c4cc(F)ccn4)cc3)c3c(N)nccc32)C1]

After (R)-4-(4-amino-1-(piperidin-3-yl)-1H-pyrazolo[4,3-c]pyridin-3-yl)-N-(4-fluoropyridin-2-yl)benzamide hydrochloride (20.0 mg, 1.0 eq) obtained in step 41-4 of Example 41 was dissolved in tetrahydrofuran (2.5 mL) and water (0.5 mL), sodium hydrogen carbonate (18.0 mg, 5.0 eq) was added thereto and the mixture was allowed to react at room temperature for 30 minutes. Acryloyl chloride (6.8 uL, 2.0 eq) was added to the mixture. The reaction mixture was allowed to react at room temperature for 10 minutes, then water was added and the mixture was extracted with ethyl acetate. The separated organic layer was dried over magnesium sulfate and then concentrated under reduced pressure. The resulting residue was purified by column chromatography (dichloromethane:methanol=10:1) to obtain 8.9 mg (yield: 38.4%) of the title compound.

$^1$H NMR (500 MHz, MeOD): 8.40-8.35 (m, 1H), 8.29 (d, 2H), 8.13 (d, 1H), 8.03 (d, 2H), 7.66 (d, 2H), 7.20 (d, 1H), 7.10-6.96 (m, 1H), 6.89-6.80 (m, 1H), 6.73-6.68 (m, 1H), 6.24 (d, 1H), 6.15 (d, 1H), 5.79 (d, 1H), 5.65 (d, 1H), 4.75-4.60 (m, 1H), 4.35-4.24 (m, 1H), 4.18-4.07 (m, 1H), 3.98-3.90 (m, 1H), 3.53-3.45 (m, 1H), 2.48-2.25 (m, 2H), 2.15-2.05 (m, 1H), 1.82-1.70 (m, 1H)

MS m/z: 540.26 [m+1]

Example 43: Preparation of (R)-4-(1-(1-acryloylpiperidin-3-yl)-4-amino-7-(phenylamino)-1H-pyrazolo[4,3-c]pyridin-3-yl)-N-(pyridin-2-yl)benzamide Step 43-1: Preparation of (R)-4-(4-amino-7-iodo-1-(piperidin-3-yl)-1H-pyrazolo[4,3-c]pyridin-3-yl)-N-(pyridin-2-yl)benzamide

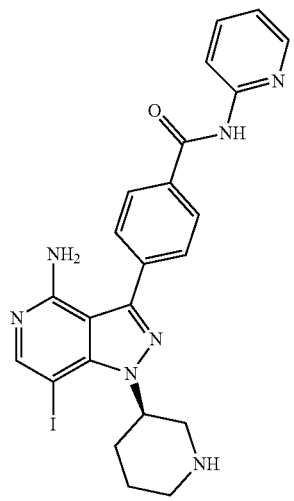 [SMILES: Nc1ncc(I)c2c1c(-c1ccc(C(=O)Nc3ccccn3)cc1)nn2[C@@H]1CCCNC1]

A reaction was performed in the same manner as in step 18-2 of Example 18 by using tert-butyl (R)-3-(4-((2,4-dimethoxybenzyl)amino)-7-iodo-3-(4-(pyridin-2-ylcarbamoyl)phenyl)-1H-pyrazolo[4,3-c]pyridin-1-yl)piperidine-1-carboxylate (45.2 mg, 1.0 eq) obtained in step 21-1 of Example 21, trifluoroacetic acid (1700.0 uL) and triethylsilane (18.3 uL, 2.0 eq) to obtain the title compound, which was used in the next reaction without purification.

Step 43-2: Preparation of tert-butyl (R)-3-(4-amino-7-iodo-3-(4-(pyridin-2-ylcarbamoyl)phenyl)-1H-pyrazolo[4,3-c]pyridin-1-yl)piperidine-1-carboxylate

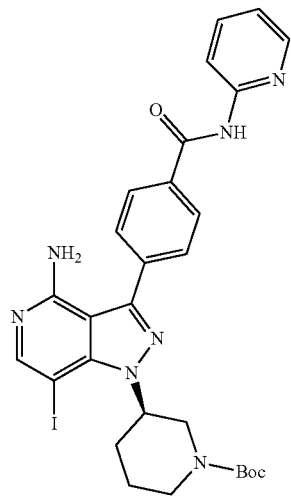 [SMILES: CC(C)(C)OC(=O)N1CCC[C@@H](n2nc(-c3ccc(C(=O)Nc4ccccn4)cc3)c3c(N)ncc(I)c32)C1]

After (R)-4-(4-amino-7-iodo-1-(piperidin-3-yl)-1H-pyrazolo[4,3-c]pyridin-3-yl)-N-(pyridin-2-yl)benzamide (60.0 mg, 1.0 eq) obtained in step 43-1 was dissolved in dichloromethane (10.0 mL), triethylamine (31.0 uL, 2.0 eq) and di-tert-butyldicarbonate (46.3 mg, 2.0 eq) were added thereto at room temperature. The reaction mixture was allowed to react at room temperature for 4 hours and then concentrated under reduced pressure. The resulting residue was purified by column chromatography (ethyl acetate:hexane=1:1) to obtain 52.0 mg (yield: 73.9%) of the title compound.

Step 43-3: Preparation of tert-butyl (R)-3-(4-amino-7-(phenylamino)-3-(4-(pyridin-2-ylcarbamoyl)phenyl)-1H-pyrazolo[4,3-c]pyridin-1-yl)piperidine-1-carboxylate

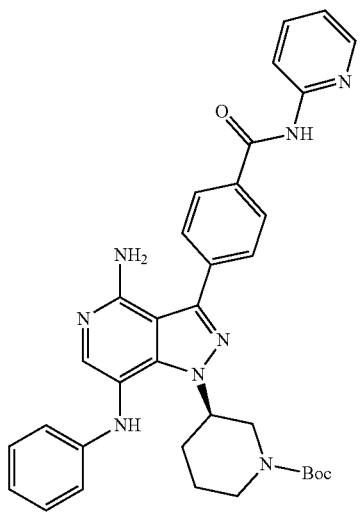 [SMILES: CC(C)(C)OC(=O)N1CCC[C@@H](n2nc(-c3ccc(C(=O)Nc4ccccn4)cc3)c3c(N)ncc(Nc4ccccc4)c32)C1]

After tert-butyl (R)-3-(4-amino-7-iodo-3-(4-(pyridin-2-ylcarbamoyl)phenyl)-1H-pyrazolo[4,3-c]pyridin-1-yl)piperidine-1-carboxylate (50.0 mg, 1.0 eq) obtained in step 43-2 was dissolved in 1,4-dioxane (3.0 mL), 2-aminopyridine (10.7 uL, 1.5 eq), bis(dibenzylideneacetone)palladium (0) (4.5 mg, 0.1 eq), Xantphos (9.1 mg, 0.2 eq) and cesium carbonate (50.9 mg, 2.0 eq) were added thereto at room temperature. The reaction mixture was allowed to react at 160° C. for 30 minutes using a microwave reactor, then water was added and the mixture was extracted with ethyl acetate. The separated organic layer was dried over magnesium sulfate and then concentrated under reduced pressure. The resulting residue was purified by column chromatography (ethyl acetate:hexane=1:1) to obtain 13.6 mg (yield: 27.6%) of the title compound.

Step 43-4: Preparation of (R)-4-(4-amino-7-(phenylamino)-1-(piperidin-3-yl)-1H-pyrazolo[4,3-c]pyridin-3-yl)-N-(pyridin-2-yl)benzamide hydrochloride

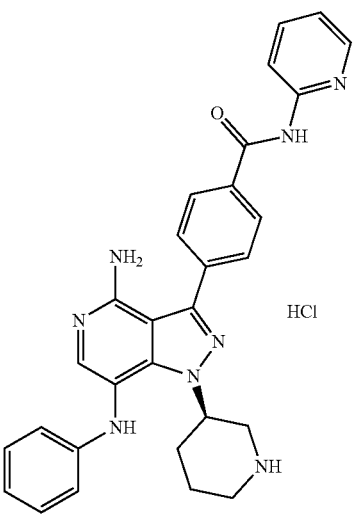 [SMILES: Nc1ncc(Nc2ccccc2)c2c1c(-c1ccc(C(=O)Nc3ccccn3)cc1)nn2[C@@H]1CCCNC1 ; Cl]

After tert-butyl (R)-3-(4-amino-7-(phenylamino)-3-(4-(pyridin-2-ylcarbamoyl)phenyl)-1H-pyrazolo[4,3-c]pyridin-1-yl)piperidine-1-carboxylate (13.0 mg, 1.0 eq) obtained in step 43-3 was dissolved in ethyl acetate (2.0 mL), 1.0M hydrochloric acid ethyl acetate solution (2.0 mL, excess) was added thereto at room temperature. The reaction mixture was allowed to react at room temperature for 12 hours and then concentrated under reduced pressure. The obtained title compound was used in a mixture state in the next reaction without purification.

Step 43-5: Preparation of (R)-4-(1-(1-acryloylpiperidin-3-yl)-4-amino-7-(phenylamino)-1H-pyrazolo[4,3-c]pyridin-3-yl)-N-(pyridin-2-yl)benzamide

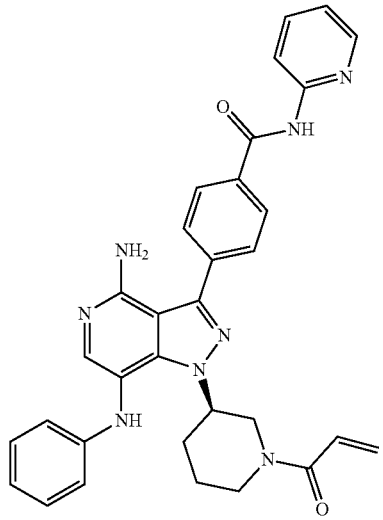 [SMILES: C=CC(=O)N1CCC[C@@H](n2nc(-c3ccc(C(=O)Nc4ccccn4)cc3)c3c(N)ncc(Nc4ccccc4)c32)C1]

A reaction was performed in the same manner as in step 18-3 of Example 18 by using (R)-4-(4-amino-7-(phenylamino)-1-(piperidin-3-yl)-1H-pyrazolo[4,3-c]pyridin-3-yl)-N-(pyridin-2-yl)benzamide hydrochloride (10.1 mg, 1.0 eq) obtained in step 43-4, sodium hydrogen carbonate (8.4 mg, 5.0 eq) and acryloyl chloride (1.9 uL, 1.2 eq) to obtain 3.2 mg (yield: 28.6%) of the title compound.

$^1$H NMR (500 MHz, MeOD): 8.41-8.38 (m, 1H), 8.28-8.19 (m, 1H), 8.12-8.07 (m, 1H), 7.90-7.85 (m, 1H), 7.47-7.41 (m, 3H), 7.35-7.28 (m, 1H), 7.26-7.14 (m, 3H), 7.06 (d, 1H), 6.97 (d, 1H), 6.79-6.75 (m, 1H), 6.17-6.05 (m, 1H), 5.57-5.50 (m, 1H), 4.89-4.75 (m, 1H), 4.65-4.50 (m, 1H), 3.90-3.40 (m, 2H), 3.30-3.15 (m, 2H), 2.10-2.02 (m, 1H), 1.15-1.10 (m, 1H), 0.99-0.80 (m, 1H)

MS m/z: 559.57 [m+1]

Example 44: Preparation of (R)-4-(1-(1-acryloylpiperidin-3-yl)-4-amino-7-methyl-1H-pyrazolo[4,3-c]pyridin-3-yl)-N-phenyl benzamide Step 44-1: Preparation of tert-butyl (R)-3-(4-((2,4-dimethoxybenzyl)amino)-7-methyl-3-(4-(phenylcarbamoyl)phenyl)-1H-pyrazolo[4,3-c]pyridin-1-yl)piperidine-1-carboxylate

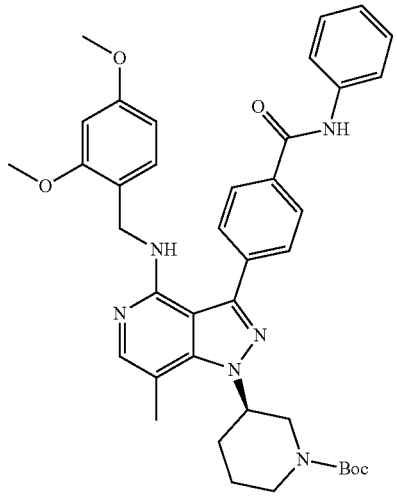 [SMILES: COc1ccc(CNc2ncc(C)c3c2c(-c2ccc(C(=O)Nc4ccccc4)cc2)nn3[C@@H]2CCCN(C(=O)OC(C)(C)C)C2)c(OC)c1]

After tert-butyl (R)-3-(4-((2,4-dimethoxybenzyl)amino)-7-iodo-3-(4-(phenylcarbamoyl)phenyl)-1H-pyrazolo[4,3-c]pyridin-1-yl)piperidine-1-carboxylate (50.0 mg, 1.0 eq) obtained in step 25-1 of Example 25 was dissolved in 1,4-dioxane (5.0 mL), methylboronic acid (7.6 mg, 1.5 eq), [1,1'-(diphenylphosphino)ferrocene]dichloropalladium(II) (6.1 mg, 0.1 eq) and cesium fluoride (25.6 mg, 1.2 eq) were added thereto at room temperature. The reaction mixture was allowed to react at 120° C. for 15 minutes using a microwave reactor, then water was added and the mixture was extracted with ethyl acetate. The separated organic layer was dried over magnesium sulfate and then concentrated under reduced pressure. The resulting residue was purified by column chromatography (ethyl acetate:hexane=1:1) to obtain 43.0 mg (yield: 74.0%) of the title compound.

Step 44-2: Preparation of (R)-4-(4-amino-7-methyl-1-(piperidin-3-yl)-1H-pyrazolo[4,3-c]pyridin-3-yl)-N-phenyl benzamide

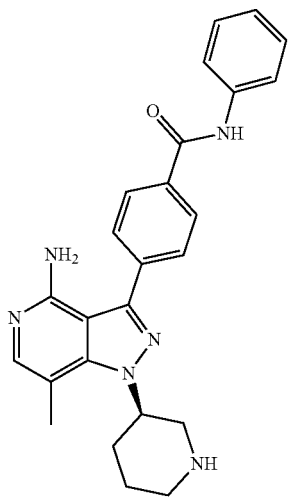 [SMILES: Cc1cnc(N)c2c(-c3ccc(C(=O)Nc4ccccc4)cc3)nn([C@@H]3CCCNC3)c12]

A reaction was performed in the same manner as in step 18-2 of Example 18 by using tert-butyl (R)-3-(4-((2,4-dimethoxybenzyl)amino)-7-methyl-3-(4-(phenylcarbamoyl)phenyl)-1H-pyrazolo[4,3-c]pyridin-1-yl)piperidine-1-carboxylate (41.0 mg, 1.0 eq) obtained in step 44-1, trifluoroacetic acid (1.0 mL) and triethylsilane (19.4 uL, 2.0 eq) to obtain the title compound, which was used in the next reaction without purification.

Step 44-3: Preparation of (R)-4-(1-(1-acryloylpiperidin-3-yl)-4-amino-7-methyl-1H-pyrazolo[4,3-c]pyridin-3-yl)-N-phenyl benzamide

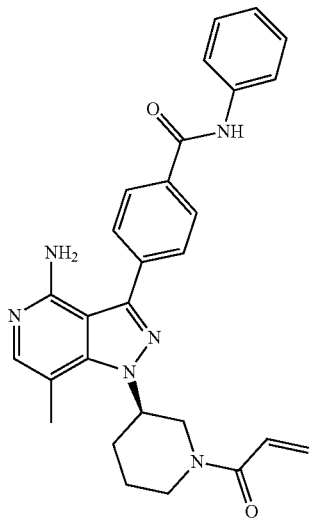 [SMILES: C=CC(=O)N1CCC[C@@H](n2nc(-c3ccc(C(=O)Nc4ccccc4)cc3)c3c(N)ncc(C)c32)C1]

A reaction was performed in the same manner as in step 18-3 of Example 18 by using (R)-4-(4-amino-7-methyl-1-(piperidin-3-yl)-1H-pyrazolo[4,3-c]pyridin-3-yl)-N-phenyl-benzamide (25.6 mg, 1.0 eq) obtained in step 44-2, sodium hydrogen carbonate (10.1 mg, 2.0 eq) and acryloyl chloride (5.9 uL, 1.2 eq) to obtain 26.7 mg (yield: 45.1%) of the title compound.

$^1$H NMR (500 MHz, MeOD): 8.12 (d, 2H), 7.84 (d, 2H), 7.73 (d, 2H), 7.51 (s, 1H), 7.43-7.38 (m, 2H), 7.17 (t, 1H), 6.88-6.65 (m, 1H), 6.28-6.14 (m, 1H), 5.82-5.66 (m, 1H), 4.80-4.75 (m, 1H), 4.37-4.31 (m, 1H), 4.18-4.10 (m, 1H), 3.95-3.86 (m, 1H), 3.42-3.30 (m, 1H), 2.67-2.48 (m, 4H), 2.35-2.27 (m, 1H), 2.11-2.05 (m, 1H), 1.80-1.68 (m, 1H)

MS m/z: 481.15 [m+1]

Example 45: Preparation of (R)-4-(1-(1-acryloylpiperidin-3-yl)-4-amino-7-methyl-1H-pyrazolo[4,3-c]pyridin-3-yl)-N-(pyridin-2-yl)benzamide

Step 45-1: Preparation of tert-butyl (R)-3-(4-((2,4-dimethoxybenzyl)amino)-7-methyl-3-(4-(pyridin-2-ylcarbamoyl)phenyl)-1H-pyrazolo[4,3-c]pyridin-1-yl)piperidine-1-carboxylate

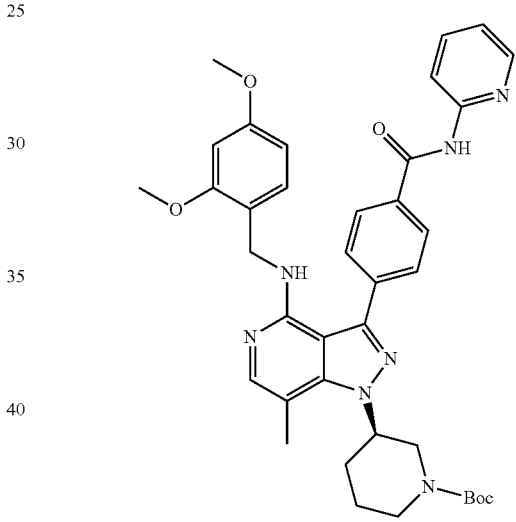

After tert-butyl (R)-3-(4-amino-7-iodo-3-(4-(pyridin-2-ylcarbamoyl)phenyl)-1H-pyrazolo[4,3-c]pyridin-1-yl)piperidine-1-carboxylate (50.0 mg, 1.0 eq) obtained in step 43-2 of Example 43 was dissolved in 1,4-dioxane (5.0 mL), methylboronic acid (5.7 mg, 1.5 eq), [1,1'-(diphenylphosphino)ferrocene]dichloropalladium (II) (4.6 mg, 0.1 eq) and cesium fluoride (11.5 mg, 1.2 eq) were added thereto at room temperature. The reaction mixture was allowed to react at 120° C. for 15 minutes using a microwave reactor, then water was added and the mixture was extracted with ethyl acetate. The separated organic layer was dried over magnesium sulfate and then concentrated under reduced pressure. The resulting residue was purified by column chromatography (ethyl acetate:hexane=1:1) to obtain 37.2 mg (yield: 87.1.0%) of the title compound.

Step 45-2: Preparation of (R)-4-(4-amino-7-methyl-1-(piperidin-3-yl)-1H-pyrazolo[4,3-c]pyridin-3-yl)-N-(pyridin-2-yl)benzamide

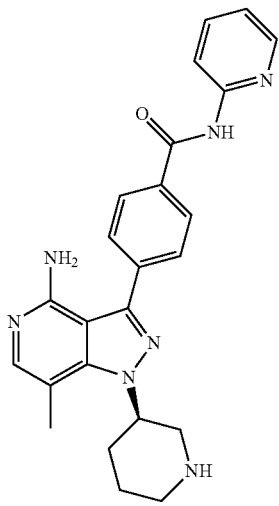 [SMILES: Cc1cnc(N)c2c(-c3ccc(C(=O)Nc4ccccn4)cc3)nn([C@@H]3CCCNC3)c12]

A reaction was performed in the same manner as in step 18-2 of Example 18 by using tert-butyl (R)-3-(4-((2,4-dimethoxybenzyl)amino)-7-methyl-3-(4-(pyridin-2-ylcarbamoyl)phenyl)-1H-pyrazolo[4,3-c]pyridin-1-yl)piperidine-1-carboxylate (36.0 mg, 1.0 eq) obtained in step 45-1, trifluoroacetic acid (1.0 mL) and triethylsilane (17.0 uL, 2.0 eq) to obtain the title compound, which was used in the next reaction without purification.

Step 45-3: Preparation of (R)-4-(1-(1-acryloylpiperidin-3-yl)-4-amino-7-methyl-1H-pyrazolo[4,3-c]pyridin-3-yl)-N-(pyridin-2-yl)benzamide

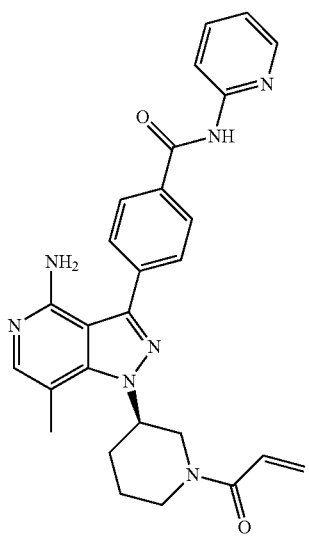 [SMILES: C=CC(=O)N1CCC[C@@H](n2nc(-c3ccc(C(=O)Nc4ccccn4)cc3)c3c(N)ncc(C)c32)C1]

A reaction was performed in the same manner as in step 18-3 of Example 18 by using (R)-4-(4-amino-7-methyl-1-(piperidin-3-yl)-1H-pyrazolo[4,3-c]pyridin-3-yl)-N-(pyridin-2-yl)benzamide (21.4 mg, 1.0 eq) obtained in step 45-2, sodium hydrogen carbonate (8.4 mg, 2.0 eq) and acryloyl chloride (4.9 uL, 1.2 eq) to obtain 18.2 mg (yield: 63.0%) of the title compound.

$^1$H NMR (500 MHz, MeOD): 8.43-8.37 (m, 2H), 8.26 (d, 1H), 8.17 (d, 2H), 7.91-7.80 (m, 3H), 7.51 (s, 1H), 7.22-7.17 (m, 1H), 6.86-6.80 (m, 1H), 6.30-6.20 (m, 1H), 6.33-6.25 (m, 1H), 4.99-4.09 (m, 1H), 4.63-4.55 (m, 1H), 3.68-3.62 (m, 1H), 3.50-3.43 (m, 1H), 3.28-3.15 (m, 1H), 2.68-2.55 (m, 1H), 2.38-2.20 (m, 2H), 2.20 (s, 1H), 1.81-1.68 (m, 1H)

MS m/z: 482.42 [m+1]

Example 46: Preparation of (S)-4-(1-(1-acryloylpyrrolidin-3-yl)-4-amino-7-(1-(difluoromethyl)-1H-pyrazol-4-yl)-1H-pyrazolo[4,3-c]pyridin-3-yl)-N-phenylbenzamide Step 46-1: Preparation of tert-butyl (S)-3-(3-bromo-4-((2,6-dimethoxybenzyl)amino)-1H-pyrazolo[4,3-c]pyridin-1-yl)pyrrolidine-1-carboxylate

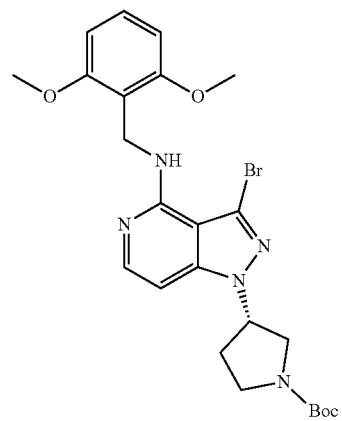 [SMILES: COc1cccc(OC)c1CNc1nccc2c1c(Br)nn2[C@H]1CCN(C(=O)OC(C)(C)C)C1]

After tert-butyl (R)-3-hydroxypyrrolidine-1-carboxylate (386.6 mg, 1.5 eq) was dissolved in tetrahydrofuran (10.0 mL), triphenylphosphine (541.6 mg, 1.5 eq) was added at room temperature and diisopropyl azodicarboxylate (400.0 uL, 1.5 eq) was added at 0° C. The reaction mixture was allowed to react at room temperature for 10 minutes and then 3 bromo-1H-pyrazolo[4,3-c]pyridin-4-amine (500.0 mg, 1.0 eq) obtained in step 41-1 was added thereto. The reaction mixture was allowed to react at room temperature for 1 day, then water was added and the mixture was extracted with ethyl acetate. The separated organic layer was dried over magnesium sulfate and then concentrated under reduced pressure. The resulting residue was purified by column chromatography (ethyl acetate:hexane=1:1) to obtain 651.0 mg (yield: 88.8%) of the title compound.

Step 46-2: Preparation of tert-butyl (S)-3-(3-bromo-4-((2,6-dimethoxybenzyl)amino)-1H-pyrazolo[4,3-c]pyridin-1-yl)pyrrolidine-1-carboxylate

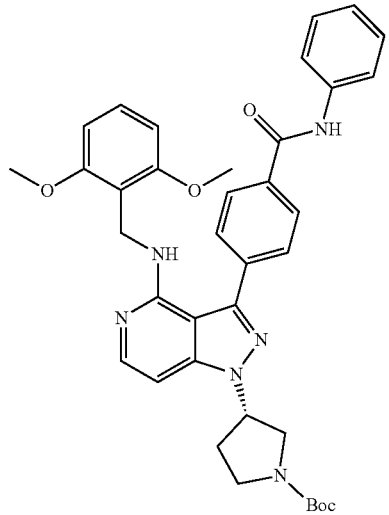 [SMILES: COc1cccc(OC)c1CNc1nccc2c1c(-c1ccc(C(=O)Nc3ccccc3)cc1)nn2[C@H]1CCN(C(=O)OC(C)(C)C)C1]

After tert-butyl (S)-3-(3-bromo-4-((2,6-dimethoxybenzyl)amino)-1H-pyrazolo[4,3-c]pyridin-1-yl)pyrrolidine-1-carboxylate (650.0 mg, 1.0 eq) obtained in step 46-1 was dissolved in 1,4-dioxane (10.0 mL) and water (1.0 mL), N-phenyl-4-(4,4,5,5-tetramethyl-1,3,2-dioxaborolan-2-yl)benzamide (493.2 mg, 1.3 eq), [1,1'-(diphenylphosphino)ferrocene]dichloropalladium(II) (62.5 mg, 0.1 eq) and potassium carbonate (843.6 mg, 2.0 eq) were added thereto at room temperature. The reaction mixture was allowed to react at 100° C. for 3 hours, then water was added and the mixture was extracted with ethyl acetate. The separated organic layer was dried over magnesium sulfate and then concentrated under reduced pressure. The resulting residue was purified by column chromatography (ethyl acetate: hexane=1:1) to obtain 556 mg (yield: 70.3%) of the title compound.

Step 46-3: Preparation of tert-butyl (S)-3-(4-((2,6-dimethoxybenzyl)amino)-7-iodo-3-(4-(phenylcarbamoyl)phenyl)-1H-pyrazolo[4,3-c]pyridin-1-yl)pyrrolidine-1-carboxylate

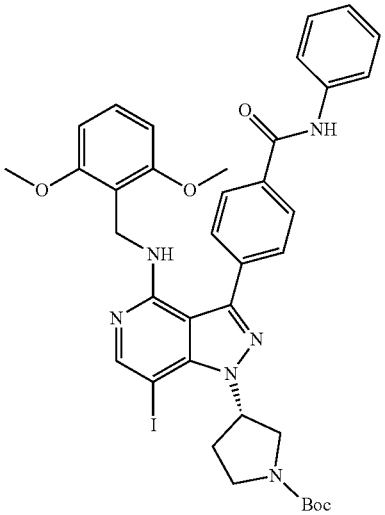 [SMILES: COc1cccc(OC)c1CNc1ncc(I)c2c1c(-c1ccc(C(=O)Nc3ccccc3)cc1)nn2[C@H]1CCN(C(=O)OC(C)(C)C)C1]

After tert-butyl (S)-3-(3-bromo-4-((2,6-dimethoxybenzyl)amino)-1H-pyrazolo[4,3-c]pyridin-1-yl)pyrrolidine-1-carboxylate (350.0 mg, 1.0 eq) obtained in step 46-2 was dissolved in formamide (3.0 mL), N-iodosuccinimide (24.0 mg, 1.1 eq) was added thereto at room temperature. The reaction mixture was allowed to react at room temperature for 2 hours, then water was added and the mixture was stirred for 30 minutes. The resulting solid was filtered to obtain 350.0 mg (yield: 83.3%) of the title compound.

Step 46-4: Preparation of tert-butyl (S)-3-(7-(1-(difluoromethyl)-1H-pyrazolo-4-yl)-4-((2,6-dimethoxybenzyl)amino)-3-(4-(phenylcarbamoyl)phenyl)-1H-pyrazolo[4,3-c]pyridin-1-yl)pyrrolidine-1-carboxylate

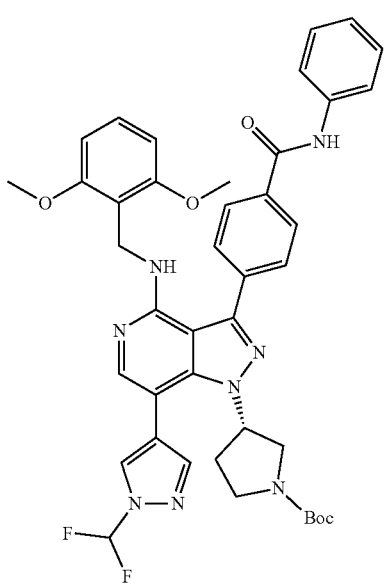 [SMILES: COc1cccc(OC)c1CNc1ncc(-c2cnn(C(F)F)c2)c2c1c(-c1ccc(C(=O)Nc3ccccc3)cc1)nn2[C@H]1CCN(C(=O)OC(C)(C)C)C1]

After tert-butyl (S)-3-(4-((2,6-dimethoxybenzyl)amino)-7-iodo-3-(4-(phenylcarbamoyl)phenyl)-1H-pyrazolo[4,3-c]pyridin-1-yl)pyrrolidine-1-carboxylate (150.0 mg, 1.0 eq) obtained in step 46-3 was dissolved in 1,4-dioxane (3.0 mL) and water (0.2 mL), 1-(difluoromethyl)-4-(4,4,5,5-tetramethyl-1,3,2-dioxaborolan-2-yl)-1H-pyrazole (54.3 mg, 1.0 eq), [1,1'-(diphenylphosphino)ferrocene]dichloropalladium (II) (7.3 mg, 0.1 eq), potassium carbonate (133.8 mg, 2.0 eq) was added thereto. The reaction mixture was allowed to react at 100° C. for 3 hours, then water was added and the mixture was extracted with ethyl acetate. The separated organic layer was dried over magnesium sulfate and then concentrated under reduced pressure. The resulting residue was purified by column chromatography (ethyl acetate: hexane=1:1) to obtain 100.0. mg (yield: 65.7%) of the title compound.

Step 46-5: Preparation of (S)-4-(4-amino-7-(1-(difluoromethyl)-1H-pyrazolo-4-yl)-1-(pyrrolidin-3-yl)-1H-pyrazolo[4,3-c]pyridin-3-yl)-N-phenylbenzamide

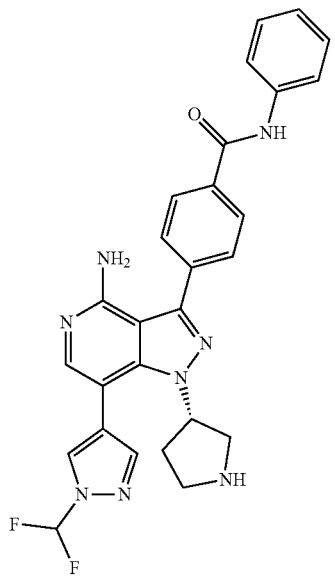 [SMILES: Nc1ncc(-c2cnn(C(F)F)c2)c2c1c(-c1ccc(C(=O)Nc3ccccc3)cc1)nn2[C@H]1CCNC1]

After tert-butyl (S)-3-(7-(1-(difluoromethyl)-1H-pyrazolo-4-yl)-4-((2,6-dimethoxybenzyl)amino)-3-(4-(phenylcarbamoyl)phenyl)-1H-pyrazolo[4,3-c]pyridin-1-yl)pyrrolidine-1-carboxylate (100.0 mg, 1.0 eq) obtained in step 46-4 was dissolved in trifluoroacetic acid (0.5 mL), triethylsilane (42.0 uL, 2.0 eq) was added thereto at room temperature. The reaction mixture was allowed to react at room temperature for 15 hours, neutralized with aqueous sodium hydrogen carbonate solution, and then extracted with ethyl acetate. The separated organic layer was dried over magnesium sulfate and then concentrated under reduced pressure. The obtained title compound was used in a mixture state in the next reaction without purification.

Step 46-6: Preparation of (S)-4-(1-(1-acryloylpyrrolidin-3-yl)-4-amino-7-(1-(difluoromethyl)-1H-pyrazol-4-yl)-1H-pyrazolo[4,3-c]pyridin-3-yl)-N-phenylbenzamide

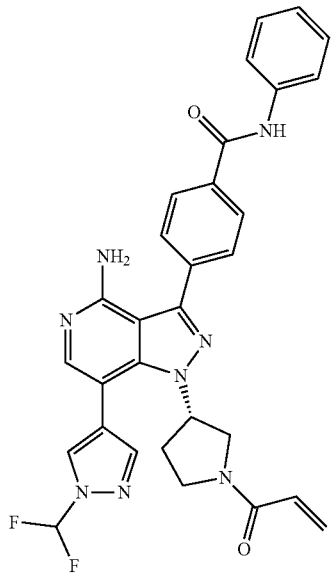 [SMILES: C=CC(=O)N1CC[C@H](n2nc(-c3ccc(C(=O)Nc4ccccc4)cc3)c3c(N)ncc(-c4cnn(C(F)F)c4)c32)C1]

After (S)-4-(4-amino-7-(1-(difluoromethyl)-1H-pyrazolo-4-yl)-1-(pyrrolidin-3-yl)-1H-pyrazolo[4,3-c]pyridin-3-yl)-N-phenylbenzamide (60.0 mg, 1.0 eq) obtained in step 46-5 was dissolved in tetrahydrofuran (1.0 mL) and water (0.06 mL), sodium hydrogen carbonate (20.0 mg, 2.0 eq) were added thereto at 0° C. and the mixture was allowed to react at 0° C. for 10 minutes. Acryloyl chloride (9.0 uL, 1.2 eq) was added thereto at 0° C. The reaction mixture was reacted at 0° C. for 30 minutes, then water was added and the mixture was extracted with ethyl acetate. The separated organic layer was dried over magnesium sulfate and then concentrated under reduced pressure. The resulting residue was purified by column chromatography (dichloromethane:methanol=10:1) to obtain 17.1 mg (yield: 25.8%) of the title compound.

$^1$H NMR (500 MHz, CDCl$_3$): 8.38 (d, 1H), 8.04-7.94 (m, 3H), 7.78-7.67 (m, 5H), 7.43-7.25 (m, 3H), 7.19-7.13 (m, 1H), 6.45-6.30 (m, 1H), 5.70-5.62 (m, 1H), 5.25-5.13 (m, 1H), 4.05-3.52 (m, 4H), 2.63-2.10 (m, 3H), MS m/z: 569.56 [m+1]

Example 47: Preparation of (S)-4-(1-(1-acryloylpyrrolidin-3-yl)-4-amino-1H-pyrazolo[4,3-c]pyridin-3-yl)-N-phenylbenzamide

Step 47-1: Preparation of (S)-4-(4-amino-1-(pyrrolidin-3-yl)-1H-pyrazolo[4,3-c]pyridin-3-yl)-N-phenyl benzamide

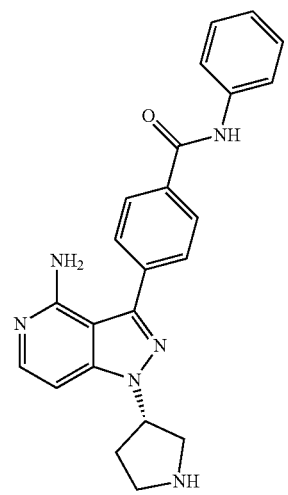 [SMILES: Nc1nccc2c1c(-c1ccc(C(=O)Nc3ccccc3)cc1)nn2[C@H]1CCNC1]

A reaction was performed in the same manner as in step 46-5 of Example 46 by using tert-butyl (S)-3-(3-bromo-4-((2,6-dimethoxybenzyl)amino)-1H-pyrazolo[4,3-c]pyridin-1-yl)pyrrolidine-1-carboxylate (150.0 mg, 1.0 eq) obtained in step 46-2 of Example 46, trifluoroacetic acid (1.0 mL) and triethylsilane (74.0 uL, 2.0 eq) to obtain the title compound, which was used in a mixture state in the next reaction without purification.

Step 47-2: Preparation of (S)-4-(1-(1-acryloylpyrrolidin-3-yl)-4-amino-1H-pyrazolo[4,3-c]pyridin-3-yl)-N-phenyl benzamide

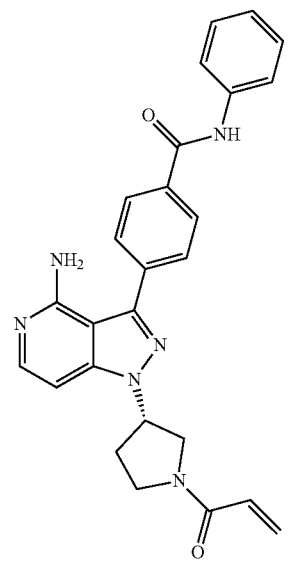 [SMILES: C=CC(=O)N1CC[C@H](n2nc(-c3ccc(C(=O)Nc4ccccc4)cc3)c3c(N)nccc32)C1]

A reaction was performed in the same manner as in step 46-6 of Example 46 by using (S)-4-(4-amino-1-(pyrrolidin-3-yl)-1H-pyrazolo[4,3-c]pyridin-3-yl)-N-phenylbenzamide (50.0 mg, 1.0 eq) obtained in step 47-1, sodium hydrogen carbonate (22.7 mg, 2.0 eq) and acryloyl chloride (10.1 uL, 1.2 eq) to obtain 2.0 mg (yield: 3.5%) of the title compound.

¹HNMR (500 MHz, CDCl₃): 8.69 (s, 1H), 8.05-7.97 (d, 2H), 7.84 (dd, 1H), 7.79-7.70 (m, 4H), 7.40-7.33 (m, 2H), 7.18-7.12 (m, 1H), 6.76 (dd, 1H), 5.40-5.30 (m, 1H), 5.18-5.08 (m, 1H), 4.18-4.10 (m, 1H), 4.00-3.95 (m, 1H), 3.89-3.79 (m, 1H), 3.70-3.60 (m, 1H), 3.20-2.68 (m, 1H), 2.65-2.57 (m, 1H), 2.50-2.40 (m, 1H)

MS m/z: 543.31 [m+1]

Example 48: Preparation of (S)-4-(4-amino-1-(1-but-2-ynoylpyrrolidin-3-yl)-1H-pyrazolo[4,3-c]pyridin-3-yl)-N-phenylbenzamide

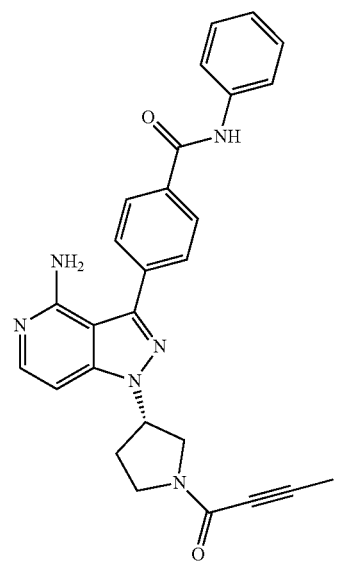 [SMILES: CC#CC(=O)N1CC[C@H](n2nc(-c3ccc(C(=O)Nc4ccccc4)cc3)c3c(N)nccc32)C1]

A reaction was performed in the same manner as in step 46-6 of Example 46 by using (S)-4-(4-amino-1-(pyrrolidin-3-yl)-1H-pyrazolo[4,3-c]pyridin-3-yl)-N-phenylbenzamide (50.0 mg, 1.0 eq) obtained in step 47-1, sodium hydrogen carbonate (22.7 mg, 2.0 eq) and but-2-enoyl chloride (15.4 mg, 1.2 eq) to obtain 17.2 mg (yield: 29.7) of the title compound.

1H NMR (500 MHz, CDCl₃): 8.04 (d, 2H), 7.91-7.78 (m, 3H), 7.68 (d, 2H), 7.46-7.38 (m, 2H), 6.78 (d, 1H), 6.46-6.39 (m, 1H), 5.28-5.12 (m, 1H), 4.19-3.98 (m, 2H), 3.88-3.75 (m, 1H), 2.82-2.73 (m, 1H), 2.67-2.43 (m, 2H), 2.36-2.30 (m, 1H), 2.08-1.98 (m, 3H)

MS m/z: 465.32 [m+1]

Example 49: Preparation of (R)-4-(1-(1-acryloylpiperidin-3-yl)-4-amino-7-chloro-1H-pyrazolo[4,3-c]pyridin-3-yl)-3-fluoro-N-(pyridin-2-yl)benzamide Step 49-1: Preparation of tert-butyl (R)-3-(4-amino-3-(2-fluoro-4-(pyridin-2-ylcarbamoyl)phenyl)-1H-pyrazolo[4,3-c]pyridin-1-yl)piperidine-1-carboxylate

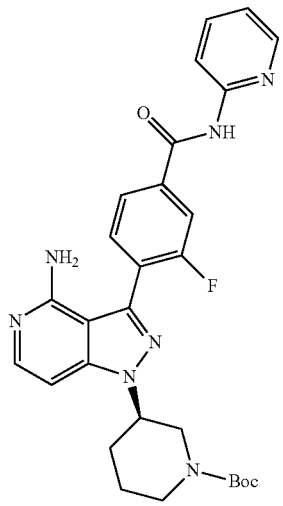 [SMILES: CC(C)(C)OC(=O)N1CCC[C@@H](n2nc(-c3ccc(C(=O)Nc4ccccn4)cc3F)c3c(N)nccc32)C1]

After tert-butyl (R)-3-(4-amino-3-bromo-1H-pyrazolo[4,3-c]pyridin-1-yl)piperidine-1-carboxylate (178.2 mg, 1.0 eq) obtained in step 41-2 of Example 41 was dissolved in 1,4-dioxane (10.0 mL) and water (2.0 mL), (2-fluoro-4-(pyridin-2-ylcarbamoyl)phenyl)boronic acid (200.0 mg, 1.5 eq), potassium carbonate (248.6 mg, 4.0 eq) and [1,1'-(diphenylphosphino)ferrocene]dichloropalladium(II) (32.9 mg, 0.1 eq) were added thereto. The reaction mixture was reacted at 120° C. for 15 minutes using a microwave reactor, then water was added and the mixture was extracted with ethyl acetate. The separated organic layer was dried over magnesium sulfate and then concentrated under reduced pressure. The resulting residue was purified by column chromatography (ethyl acetate:hexane=1:1) to obtain 230.0 mg (yield: 93.1%) of the title compound.

Step 49-2: Preparation of tert-butyl (R)-3-(4-amino-7-chloro-3-(2-fluoro-4-(pyridin-2-ylcarbamoyl)phenyl)-1H-pyrazolo[4,3-c]pyridin-1-yl)piperidine-1-carboxylate

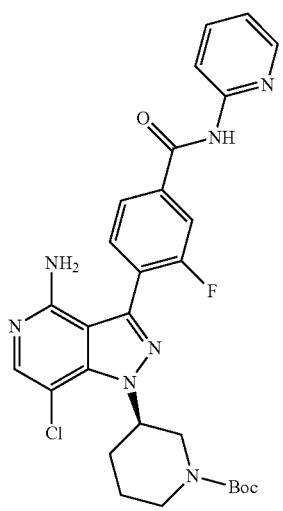 [SMILES: CC(C)(C)OC(=O)N1CCC[C@@H](n2nc(-c3ccc(C(=O)Nc4ccccn4)cc3F)c3c(N)ncc(Cl)c32)C1]

A reaction was performed in the same manner as in step 19-1 of Example 19 by using tert-butyl (R)-3-(4-amino-3-(2-fluoro-4-(pyridin-2-ylcarbamoyl)phenyl)-1H-pyrazolo[4,3-c]pyridin-1-yl)piperidine-1-carboxylate (100.0 mg, 1.0 eq) obtained in step 49-1, formamide (5.0 mL) and N-chlorosuccinimide (31.5 mg, 1.2 eq) to obtain 76.0 mg (yield: 71.4%) of the title compound.

Step 49-3: Preparation of (R)-4-(4-amino-7-chloro-1-(piperidin-3-yl)-1H-pyrazolo[4,3-c]pyridin-3-yl)-3-fluoro-N-(pyridin-2-yl)benzamide hydrochloride

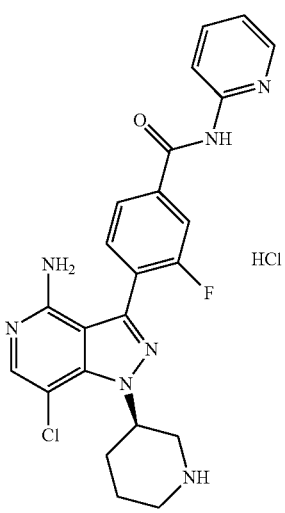 [SMILES: Nc1ncc(Cl)c2c1c(-c1ccc(C(=O)Nc3ccccn3)cc1F)nn2[C@@H]1CCCNC1 ; Cl]

A reaction was performed in the same manner as in step 43-4 of Example 43 by using tert-butyl (R)-3-(4-amino-7-chloro-3-(2-fluoro-4-(pyridin-2-ylcarbamoyl)phenyl)-1H-pyrazolo[4,3-c]pyridin-1-yl)piperidine-1-carboxylate (50.0 mg, 1.0 eq) obtained in step 49-2, ethyl acetate (2.0 mL) and 1.0M hydrochloric acid ethyl acetate solution (440.0 uL, 4.0 eq) to obtain 26.0 mg (yield: 57.5%) of the title compound.

Step 49-4: Preparation of (R)-4-(1-(1-acryloylpiperidin-3-yl)-4-amino-7-chloro-1H-pyrazolo[4,3-c]pyridin-3-yl)-3-fluoro-N-(pyridin-2-yl)benzamide

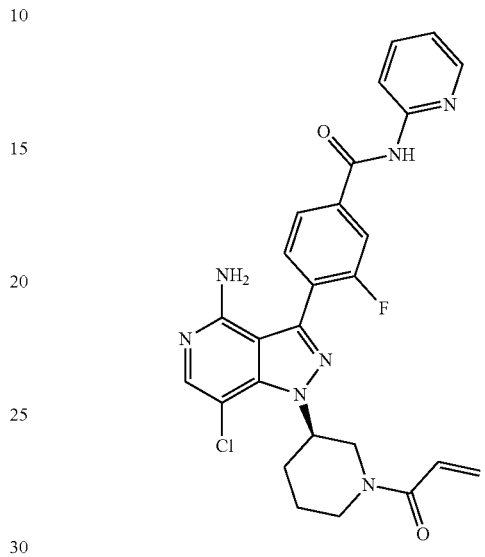

A reaction was performed in the same manner as in step 18-3 of Example 18 by using (R)-4-(4-amino-7-chloro-1-(piperidin-3-yl)-1H-pyrazolo[4,3-c]pyridin-3-yl)-3-fluoro-N-(pyridin-2-yl)benzamide hydrochloride (50.2 mg, 1.0 eq) obtained in step 49-3, tetrahydrofuran (2.5 mL), water (0.5 mL) and sodium hydrogen carbonate (33.6 mg, 4.0 eq) to obtain 12.0 mg (yield: 23.1%) of the title compound.

$^1$H NMR (500 MHz, MeOD): 8.39 (d, 1H), 8.25 (d, 1H), 7.98 (d, 1H), 7.93 (d, 1H), 7.86 (t, 1H), 7.74-7.71 (m, 2H), 7.19 (dd, 1H), 6.20 (ss, 1H), 5.72 (dd, 1H), 5.41-5.37 (m, 1H), 4.78-4.76 (m, 1H), 4.38-4.35 (m, 1H), 3.84-3.80 (m, 1H), 3.52-3.47 (m, 1H), 3.31-3.09 (m, 1H), 2.43-2.31 (m, 1H), 2.06-2.05 (m, 1H), 1.79-1.68 (m, 1H)

MS m/z: 520.36 [m+1]

Example 50: Preparation of (R)-4-(1-(1-acryloylpiperidin-3-yl)-4-amino-7-iodo-1H-pyrazolo[4,3-c]pyridin-3-yl)-3-fluoro-N-(pyridin-2-yl)benzamide Step 50-1: Preparation of tert-butyl (R)-3-(4-amino-3-(2-fluoro-4-(pyridin-2-ylcarbamoyl)phenyl)-7-iodo-1H-pyrazolo[4,3-c]pyridin-1-yl)piperidine-1-carboxylate

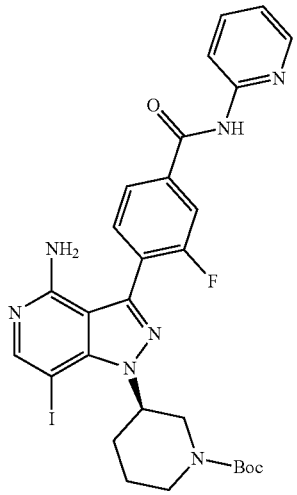 [SMILES: CC(C)(C)OC(=O)N1CCC[C@@H](n2nc(-c3ccc(C(=O)Nc4ccccn4)cc3F)c3c(N)ncc(I)c32)C1]

A reaction was performed in the same manner as in step 21-1 of Example 21 by using tert-butyl (R)-3-(4-amino-3-(2-fluoro-4-(pyridin-2-ylcarbamoyl)phenyl)-1H-pyrazolo[4,3-c]pyridin-1-yl)piperidine-1-carboxylate (100.0 mg, 1.0 eq) obtained in step 49-1 of Example 49, formamide (5.0 mL) and N-iodosuccinimide (225.0 mg, 1.2 eq) to obtain 85.0 mg (yield 68.8%) of the title compound.

Step 50-2: Preparation of (R)-4-(4-amino-7-iodo-1-(piperidin-3-yl)-1H-pyrazolo[4,3-c]pyridin-3-yl)-3-fluoro-N-(pyridin-2-yl)benzamide hydrochloride

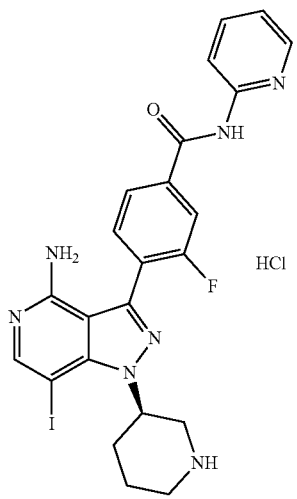 [SMILES: Nc1ncc(I)c2c1c(-c1ccc(C(=O)Nc3ccccn3)cc1F)nn2[C@@H]1CCCNC1 ; Cl]

A reaction was performed in the same manner as in step 43-4 of Example 43 by using tert-butyl (R)-3-(4-amino-3-(2-fluoro-4-(pyridin-2-ylcarbamoyl)phenyl)-7-iodo-1H-pyrazolo[4,3-c]pyridin-1-yl)piperidine-1-carboxylate (50.0 mg, 1.0 eq) obtained in step 50-1, ethyl acetate (2.0 mL) and 1.0M hydrochloric acid ethyl acetate solution (440.0 uL, 4.0 eq) to obtain 33.0 mg (yield: 73.0%) of the title compound.

Step 50-3: Preparation of (R)-4-(1-(1-acryloylpiperidin-3-yl)-4-amino-7-iodo-1H-pyrazolo[4,3-c]pyridin-3-yl)-3-fluoro-N-(pyridin-2-yl)benzamide

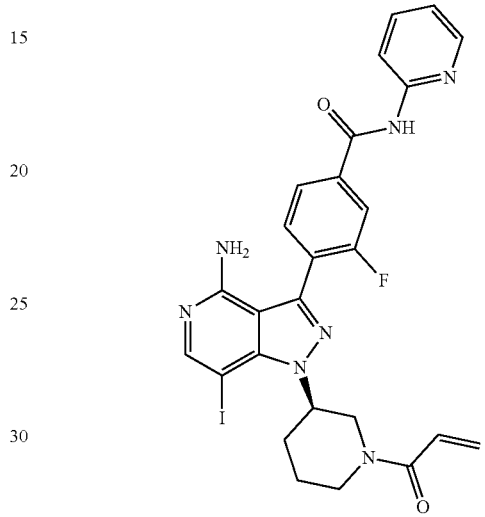

A reaction was performed in the same manner as in step 18-3 of Example 18 by using (R)-4-(4-amino-7-iodo-1-(piperidin-3-yl)-1H-pyrazolo[4,3-c]pyridin-3-yl)-3-fluoro-N-(pyridin-2-yl)benzamide hydrochloride (59.4 mg, 1.0 eq) obtained in step 50-2, sodium hydrogen carbonate (33.6 mg, 4.0 eq) and acryloyl chloride (8.9 uL, 1.1 eq) to obtain 13.2 mg (yield: 21.6%) of the title compound.

$^1$HNMR (500 MHz, MeOD): 8.39 (d, 1H), 8.25 (d, 1H), 8.06 (s, 1H), 7.98 (d, 1H), 7.93 (d, 1H), 7.86 (t, 1H), 7.27-7.23 (m, 1H), 7.23-7.18 (m, 1H), 6.88-6.25 (m, 1H), 6.25-6.15 (m, 1H), 6.30-6.12 (m, 1H), 4.85-4.75 (m, 1H), 4.48-4.15 (m, 1H), 4.20-4.11 (m, 1H), 3.90-3.81 (m, 1H), 3.58-3.45 (m, 1H), 3.09-3.01 (m, 1H), 2.42-2.30 (m, 2H), 2.10-1.98 (m, 1H), 1.79-1.65 (m, 1H)

MS m/z: 612.20 [m+1]

Example 51: Preparation of 4-(1-((6R)-2-acryloyl-2-azabicyclo[2.2.1]heptan-6-yl)-4-amino-1H-pyrazolo[4,3-c]pyridin-3-yl)-3-fluoro-N-(pyridin-2-yl)benzamide Step 51-1: Preparation of tert-butyl (6R)-6-(4-amino-3-bromo-1H-pyrazolo[4,3-c]pyridin-1-yl)-2-azabicyclo[2.2.1]heptane-2-carboxylate

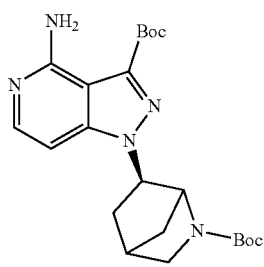 [SMILES: CC(C)(C)OC(=O)c1nn([C@@H]2CC3CC2N(C(=O)OC(C)(C)C)C3)c2ccnc(N)c12]

After tert-butyl (6S)-6-hydroxy-2-azabicyclo[2.2.1]heptane-2-carboxylate (750.0 mg, 1.5 eq) was dissolved in tetrahydrofuran (25.0 mL), triphenylphosphine (923.4 mg, 1.5 eq) was added at room temperature and diisopropyl azodicarboxylate (693.1 uL, 1.5 eq) was added at 0° C. The reaction mixture was allowed to react at room temperature for 10 minutes and then 3-bromo-1H-pyrazolo[4,3-c]pyridin-4-amine (500.0 mg, 1.0 eq) obtained in step 41-1 was added. The reaction mixture was allowed to react at room temperature for 1 day, then water was added and the mixture was extracted with ethyl acetate. The separated organic layer was dried over magnesium sulfate and then concentrated under reduced pressure. The resulting residue was purified by column chromatography (ethyl acetate:hexane=1:1) to obtain 220.0 mg (yield: 22.9%) of the title compound.

Step 51-2: Preparation of tert-butyl (6R)-6-(4-amino-3-(2-fluoro-4-(phenylcarbamoyl)phenyl)-1H-pyrazolo[4,3-c]pyridin-1-yl)-2-azabicyclo[2.2.1]heptan-2-carboxylate

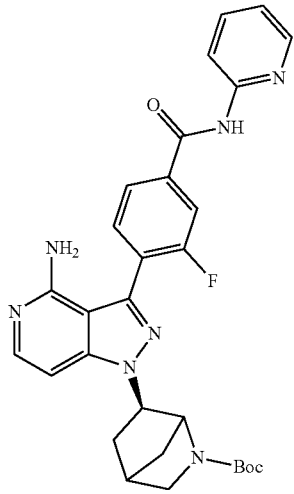 [SMILES: CC(C)(C)OC(=O)N1CC2CC1[C@H](n1nc(-c3ccc(C(=O)Nc4ccccn4)cc3F)c3c(N)nccc31)C2]

After tert-butyl (6R)-6-(4-amino-3-bromo-1H-pyrazolo[4,3-c]pyridin-1-yl)-2-azabicyclo[2.2.1]heptane-2-carboxylate (200.0 mg, 1.0 eq) obtained in step 51-1 was dissolved in 1,4-dioxane (1.0 mL) and water (2.0 mL), (2-fluoro-4-(phenylcarbamoyl)phenyl)boronic acid (217.8.0 mg, 1.3 eq), [1,1'-(diphenylphosphino)ferrocene]dichloropalladium (II) (35.8 mg, 0.1 eq) and potassium carbonate (135.4 mg, 2.0 eq) were added thereto at room temperature. The reaction mixture was allowed to react at 120° C. for 15 minutes using a microwave reactor, then water was added and the mixture was extracted with ethyl acetate. The separated organic layer was dried over magnesium sulfate and then concentrated under reduced pressure. The resulting residue was purified by column chromatography (ethyl acetate:hexane=1:1) to obtain 91.0 mg (yield: 30.0%) of the title compound.

Step 51-3: Preparation of 4-(1-(((6R)-2-acryloyl-2-azabicyclo[2.2.1]heptan-6-yl)-4-amino-1H-pyrazolo[4,3-c]pyridin-3-yl)-3-fluoro-N-(pyridin-2-yl)benzamide

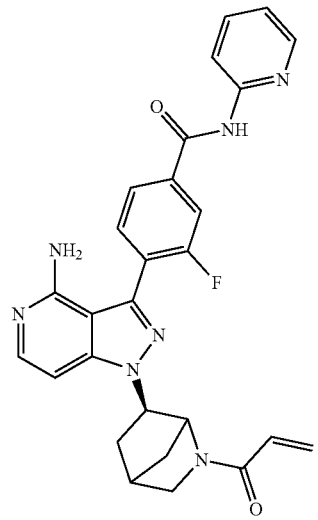 [SMILES: C=CC(=O)N1CC2CC1[C@H](n1nc(-c3ccc(C(=O)Nc4ccccn4)cc3F)c3c(N)nccc31)C2]

After tert-butyl (6R)-6-(4-amino-3-(2-fluoro-4-(phenylcarbamoyl)phenyl)-1H-pyrazolo[4,3-c]pyridin-1-yl)-2-azabicyclo[2.2.1]heptan-2-carboxylate (30.0 mg, 1.0 eq) obtained in step 51-2 was dissolved in ethyl acetate (5.0 mL), 1.0M hydrochloric acid ethyl acetate solution (1000.0 uL) was added thereto at room temperature. The reaction mixture was allowed to react at room temperature for 1 day. The obtained solid compound was filtered, then washed with ethyl acetate and dried under reduced pressure. The obtained title compound was dissolved in tetrahydrofuran (5.0 mL) and water (1.0 mL), and then odium hydrogen carbonate (18.48 mg, 4.0 eq) was added thereto and the mixture was allowed to react at room temperature for 30 minutes. Acryloyl chloride (4.5 uL, 1.0 eq) was added to the mixture. The reaction mixture was allowed to react at room temperature for 10 minutes, then methanol and water were added and the mixture was extracted with ethyl acetate. The separated organic layer was dried over magnesium sulfate and then concentrated under reduced pressure. The resulting residue was purified by column chromatography (dichloromethane:methanol=10:1) to obtain 3.9 mg (yield: 14.8%) of the title compound.

$^1$H NMR (500 MHz, MeOD): 8.39 (d, 1H), 8.25 (d, 1H), 7.98 (d, 1H), 7.94 (d, 1H), 7.68 (t, 1H), 7.80-7.78 (m, 1H), 7.47 (t, 1H), 7.21-7.18 (m, 1H), 7.13 (d, 1H), 6.78-6.73 (m, 1H), 6.59-6.53 (m, 1H), 6.39-6.35 (m, 1H), 5.84-5.80 (m, 1H), 3.63-3.62 (m, 1H), 3.46-3.41 (m, 1H), 2.91-2.85 (m, 1H), 2.27-2.19 (m, 1H), 1.70 (d, 1H), 1.33-1.25 (m, 1H)

MS m/z: 498.37 [m+1]

Example 52: Preparation of 4-(1-(1-acryloylazetidin-3-yl)-4-amino-7-chloro-1H-pyrazolo[4,3-c]pyridin-3-yl)-3-fluoro-N-(pyridin-2-yl)benzamide

Step 52-1: Preparation of tert-butyl 3-(3-bromo-4-((2,4-dimethoxybenzyl)amino)-1H-pyrazolo[4,3-c]pyridin-1-yl)azetidine-1-carboxylate

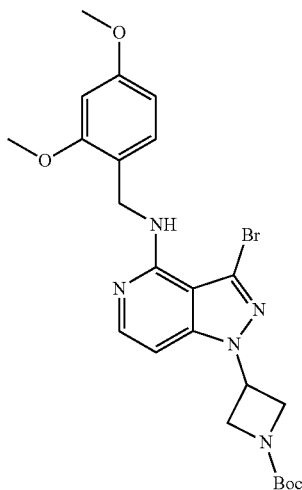 [SMILES: COc1ccc(CNc2nccc3c2c(Br)nn3C2CN(C(=O)OC(C)(C)C)C2)c(OC)c1]

After tert-butyl 3-hydroxyazetidine-1-carboxylate (500.0 mg, 1.5 eq) was dissolved in tetrahydrofuran (20.0 mL), triphenylphosphine (541.6 mg, 1.5 eq) was added at room temperature and diisopropyl azadicarboxylate (406.6 uL, 1.5 eq) was added at 0° C. The reaction mixture was allowed to react at room temperature for 10 minutes and then 3-bromo-N-(2,4-dimethoxybenzyl)-1H-pyrazolo[4,3-c]pyridin-4-amine (363.3 mg, 1.0 eq) obtained in step 3-1 of Example 3 was added thereto. The reaction mixture was allowed to react at room temperature for 1 day, then water was added and the mixture was extracted with ethyl acetate. The separated organic layer was dried over magnesium sulfate and then concentrated under reduced pressure. The resulting residue was purified by column chromatography (ethyl acetate:hexane=1:1) to obtain 105.1 mg (yield: 14.8%) of the title compound.

Step 52-2: Preparation of tert-butyl 3-(4-((2,4-dimethoxybenzyl)amino)-3-(2-fluoro-4-(pyridin-2-ylcarbamoyl)phenyl)-1H-pyrazolo[4,3-c]pyridin-1-yl)azetidine-1-carboxylate

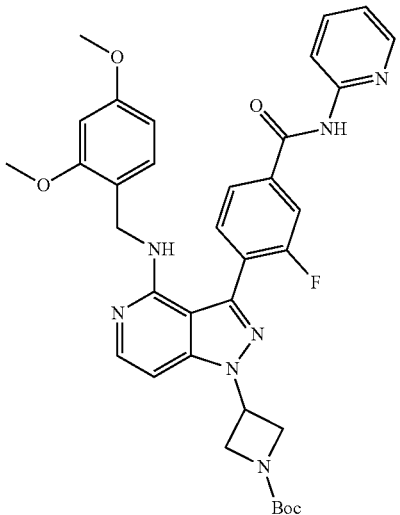

After tert-butyl 3-(3-bromo-4-((2,4-dimethoxybenzyl)amino)-1H-pyrazolo[4,3-c]pyridin-1-yl)azetidine-1-carboxylate (100.0 mg, 1.0 eq) obtained in step 52-1 was dissolved in 1,4-dioxane (10.0 mL) and water (1.0 mL), (2-fluoro-4-(pyridin-2-ylcarbamoyl)phenyl)boronic acid (85.8 mg, 1.5 eq), [1,1'-(diphenylphosphino)ferrocene]dichloropalladium (II) (14.1 mg, 0.1 eq) and potassium carbonate (138.2 mg, 2.0 eq) were added thereto at room temperature. The reaction mixture was allowed to react at 110° C. for 2 hours, then water was added and the mixture was extracted with ethyl acetate. The separated organic layer was dried over magnesium sulfate and then concentrated under reduced pressure. The resulting residue was purified by column chromatography (ethyl acetate:hexane=1:1) to obtain 82.0 mg (yield: 66.0%) of the title compound.

Step 52-3: Preparation of 4-(4-amino-1-(azetidin-3-yl)-1H-pyrazolo[4,3-c]pyridin-3-yl)-3-fluoro-N-(pyridin-2-yl)benzamide

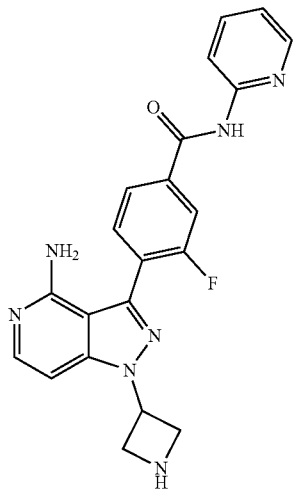 [SMILES: Nc1nccc2c1c(-c1ccc(C(=O)Nc3ccccn3)cc1F)nn2C1CNC1]

A reaction was performed in the same manner as in step 18-2 of Example 18 by using tert-butyl 3-(4-((2,4-dimethoxybenzyl)amino)-3-(2-fluoro-4-(pyridin-2-ylcarbamoyl)phenyl)-1H-pyrazolo[4,3-c]pyridin-1-yl)azetidine-1-carboxylate (80.0 mg, 1.0 eq) obtained in step 52-2, trifluoroacetic acid (2.0 mL) and triethylsilane (39.1 uL, 2.0 eq) to obtain the title compound, which was used in the next reaction without purification.

Step 52-4: Preparation of 4-(1-(1-acryloylazetidin-3-yl)-4-amino-7-chloro-1H-pyrazolo[4,3-c]pyridin-3-yl)-3-fluoro-N-(pyridin-2-yl)benzamide

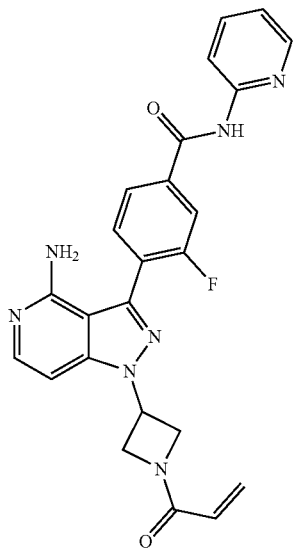 [SMILES: C=CC(=O)N1CC(n2nc(-c3ccc(C(=O)Nc4ccccn4)cc3F)c3c(N)nccc32)C1]

4-(4-Amino-1-(azetidin-3-yl)-1H-pyrazolo[4,3-c]pyridin-3-yl)-3-fluoro-N-(pyridin-2-yl)benzamide (48.0 mg, 1.0 eq) obtained in step 52-3 was dissolved in tetrahydrofuran (5.0 mL) and water (1.0 mL), and then sodium hydrogen carbonate (30.2 mg, 3.0 eq) was added thereto. The reaction mixture was stirred at room temperature for 30 minutes, then acryloyl chloride (9.75 uL, 1.0 eq) was added and stirred at room temperature for 10 minutes. Methanol was added to the reaction product and the mixture was extracted with water and ethyl acetate. The separated organic layer was dried over magnesium sulfate and then concentrated under reduced pressure. The resulting residue was purified by column chromatography (dichloromethane:methanol=10:1) to obtain 3.6 mg (yield: 6.6%) of the title compound.

$^1$H NMR (500 MHz, MeOD): 8.39 (d, 1H), 8.25 (d, 1H), 8.00 (d, 1H), 7.98 (d, 1H), 7.86 (t, 1H), 7.81-7.78 (m, 2H), 7.20-7.18 (m, 1H), 6.97 (d, 1H), 6.44-6.39 (m, 1H), 6.31-6.28 (m, 1H), 5.79-5.77 (m, 1H), 5.72-5.64 (m, 1H), 4.85-4.78 (m, 2H), 4.65-4.55 (m, 2H)

MS m/z: 458.32 [m+1]

Example 53: Preparation of (R)-4-(1-(1-acryloylpiperidin-3-yl)-4-amino-7-cyano-1H-pyrazolo[4,3-c]pyridin-3-yl)-3-fluoro-N-(pyridin-2-yl)benzamide Step 53-1: Preparation of tert-butyl (R)-3-(4-amino-7-cyano-3-(2-fluoro-4-(pyridin-2-ylcarbamoyl)phenyl)-1H-pyrazolo[4,3-c]pyridin-1-yl)piperidine-1-carboxylate

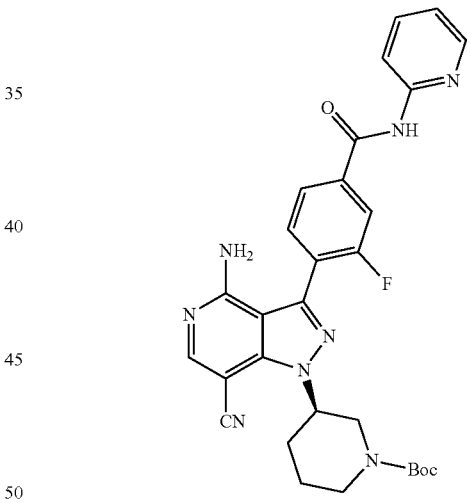

After tert-butyl (R)-3-(4-amino-3-(2-fluoro-4-(pyridin-2-ylcarbamoyl)phenyl)-7-iodo-1H-pyrazolo[4,3-c]pyridin-1-yl)piperidine-1-carboxylate (50.0 mg, 1.0 eq) obtained in step 50-1 of Example 50 was dissolved in dimethylformamide (10.0 mL), cyanocopper (13.6 mg, 2.0 eq) was added thereto at room temperature. The reaction mixture was allowed to react at 190° C. for 15 minutes using a microwave reactor, then water was added and the mixture was extracted with ethyl acetate. The separated organic layer was dried over magnesium sulfate and then concentrated under reduced pressure. The resulting residue was purified by column chromatography (ethyl acetate:hexane=1:1) to obtain 13.0 mg (yield: 28.7%) of the title compound.

Step 53-2: Preparation of (R)-4-(4-amino-7-cyano-1-(piperidin-3-yl)-1H-pyrazolo[4,3-c]pyridin-3-yl)-3-fluoro-N-(pyridin-2-yl)benzamide hydrochloride

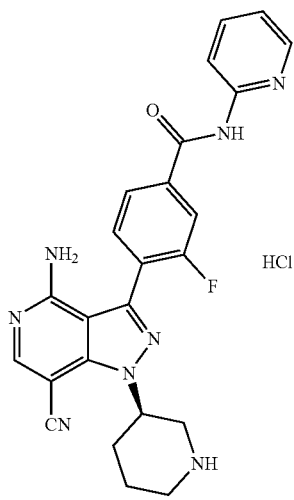 [SMILES: N#Cc1cnc(N)c2c(-c3ccc(C(=O)Nc4ccccn4)cc3F)nn([C@@H]3CCCNC3)c12 ; Cl]

A reaction was performed using tert-butyl (R)-3-(4-amino-7-cyano-3-(2-fluoro-4-(pyridin-2-ylcarbamoyl)phenyl)-1H-pyrazolo[4,3-c]pyridin-1-yl)piperidine-1-carboxylate (13.0 mg, 1.0 eq) obtained in step 53-1, ethyl acetate (2.0 mL) and 1.0M hydrochloric acid ethyl acetate solution (46.7 uL, 4.0 eq) at room temperature for 12 hours, and then concentrated under reduced pressure. The obtained title compound was used in a mixture state in the next reaction without purification.

Step 53-3: Preparation of (R)-4-(1-(1-acryloylpiperidin-3-yl)-4-amino-7-cyano-1H-pyrazolo[4,3-c]pyridin-3-yl)-3-fluoro-N-(pyridin-2-yl) benzamide

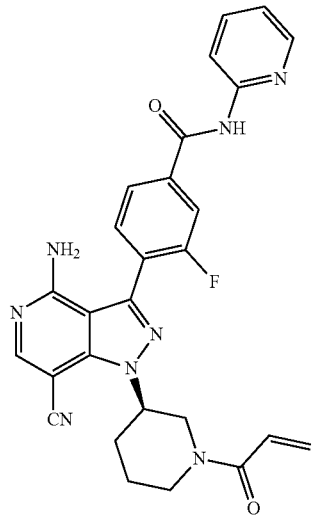 [SMILES: C=CC(=O)N1CCC[C@@H](n2nc(-c3ccc(C(=O)Nc4ccccn4)cc3F)c3c(N)ncc(C#N)c32)C1]

A reaction was performed in the same manner as in step 3-5 of Example 3 by using (R)-4-(4-amino-7-cyano-1-(piperidin-3-yl)-1H-pyrazolo[4,3-c]pyridin-3-yl)-3-fluoro-N-(pyridin-2-yl)benzamide hydrochloride (11.5 mg, 1.0 eq) obtained in step 53-2, sodium hydrogen carbonate (7.9 mg, 4.0 eq) and acryloyl chloride (2.3 uL, 1.2 eq) to obtain 5.3 mg (yield 44.4%) of the title compound.

$^1$H NMR (500 MHz, MeOD): 8.39 (d, 1H), 8.26-8.24 (2, 2H), 7.99 (d, 1H), 7.96 (d, 1H), 7.85 (t, 1H), 7.74 (t, 1H), 7.21-7.18 (m, 1H), 6.84-6.73 (m, 1H), 6.23-6.11 (m, 1H), 5.77-5.64 (m, 1H), 5.15-5.02 (m, 2H), 4.71-4.67 (m, 1H), 4.41-4.31 (m, 1H), 3.91-3.87 (m, 1H), 3.69-3.60 (m, 1H), 2.49-2.28 (m, 1H), 1.41-1.28 (m, 1H)

MS m/z: 511.11 [m+1]

Example 54: Preparation of (R)-4-(4-amino-1-(1-methacryloylpiperidin-3-yl)-1H-pyrazolo[4,3-c]pyridin-3-yl)-3-fluoro-N-(pyridin-2-yl)benzamide Step 54-1: Preparation of (R)-4-(4-amino-1-(piperidin-3-yl)-1H-pyrazolo[4,3-c]pyridin-3-yl)-3-fluoro-N-(pyridine-2-yl)benzamide hydrochloride

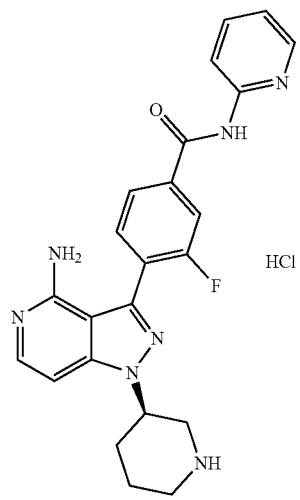 [SMILES: Nc1nccc2c1c(-c1ccc(C(=O)Nc3ccccn3)cc1F)nn2[C@@H]1CCCNC1 ; Cl]

A reaction was performed using tert-butyl (R)-3-(4-amino-3-(2-fluoro-4-(pyridin-2-ylcarbamoyl)phenyl)-1H-pyrazolo[4,3-c]pyridin-1-yl)piperidine-1-carboxylate (100.0 mg, 1.0 eq) obtained in step 49-1, ethyl acetate (2.0 mL) and 1.0M hydrochloric acid ethyl acetate solution (0.94 mL, 5.0 eq) at room temperature for 12 hours. The obtained solid compound was filtered, washed with ethyl acetate, and then dried to obtain 45.0 mg (yield: 51.1%) of the title compound.

Step 54-2: Preparation of (R)-4-(4-amino-1-(1-methacryloylpiperidin-3-yl)-1H-pyrazolo[4,3-c]pyridin-3-yl)-3-fluoro-N-(pyridin-2-yl)benzamide

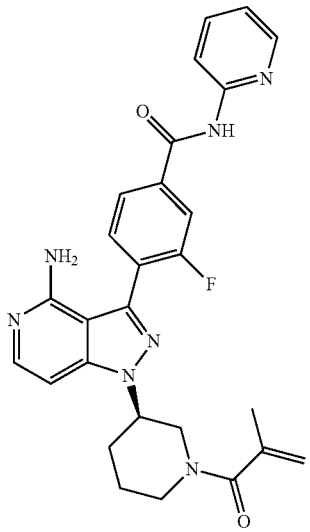 [SMILES: C=C(C)C(=O)N1CCC[C@@H](n2nc(-c3ccc(C(=O)Nc4ccccn4)cc3F)c3c(N)nccc32)C1]

A reaction was performed in the same manner as in step 52-4 of Example 52 by using (R)-4-(4-amino-1-(piperidin-3-yl)-1H-pyrazolo[4,3-c]pyridin-3-yl)-3-fluoro-N-(pyridine-2-yl)benzamide hydrochloride (15.0 mg, 1.0 eq) obtained in step 54-1, sodium hydrogen carbonate (10.0 mg, 4.0 eq) and acryloyl chloride (2.9 uL, 1.0 eq) to obtain 4.1 mg (yield: 27.5%) of the title compound.

$^1$H NMR (500 MHz, MeOD): 8.39 (d, 1H), 8.25 (d, 1H), 7.94 (d, 1H), 7.88 (t, 1H), 7.81-7.61 (m, 3H), 7.21-7.18 (m, 1H), 5.48-5.10 (m, 3H), 4.80-4.71 (m, 1H), 4.27-4.08 (m, 1H), 3.83-3.30 (m, 2H), 2.32-2.14 (m, 2H), 2.07-1.93 (m, 5H)

MS m/z: 500.39 [m+1]

Example 55: Preparation of (R)-4-(4-amino-7-chloro-1-(1-methacryloylpiperidin-3-yl)-1H-pyrazolo[4,3-c]pyridin-3-yl)-3-fluoro-N-(pyridin-2-yl)benzamide

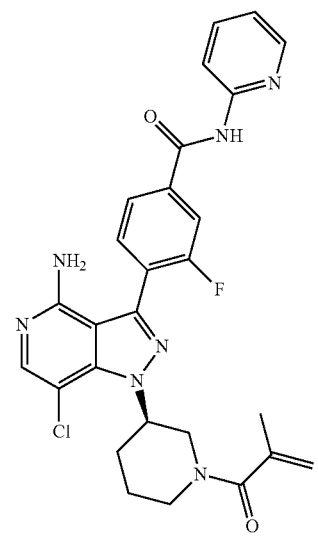 [SMILES: C=C(C)C(=O)N1CCC[C@@H](n2nc(-c3ccc(C(=O)Nc4ccccn4)cc3F)c3c(N)ncc(Cl)c32)C1]

A reaction was performed in the same manner as in step 52-4 of Example 52 by using (R)-4-(4-amino-7-chloro-1-(piperidin-3-yl)-1H-pyrazolo[4,3-c]pyridin-3-yl)-3-fluoro-N-(pyridin-2-yl)benzamide hydrochloride (20.0 mg, 1.0 eq) obtained in step 49-3, sodium hydrogen carbonate (13.3 mg, 4.0 eq) and acryloyl chloride (3.4 uL, 1.0 eq) to obtain 3.0 mg (yield: 14.1%) of the title compound.

$^1$H NMR (500 MHz, MeOD): 8.39 (s, 1H), 8.25 (d, 1H), 7.98 (d, 1H), 7.94 (d, 1H), 7.91-7.84 (m, 1H), 7.79-7.70 (m, 2H), 7.23-7.16 (m, 1H), 5.46-5.38 (m, 1H), 5.28-5.18 (m, 1H), 5.14-5.01 (m, 1H), 4.65-4.20 (m, 1H), 4.00-3.76 (m, 1H), 3.65-3.56 (m, 1H), 3.12-2.95 (m, 1H), 2.45-2.31 (m, 1H), 2.10-2.03 (m, 1H), 1.98-1.80 (m, 4H)

MS m/z: 535.33 [m+1]

Example 56: Preparation of (R)-4-(1-(1-acryloylpiperidin-3-yl)-4-amino-1H-pyrazolo[4,3-c]pyridin-3-yl)-3-chloro-N-(pyridin-2-yl)benzamide Step 56-1: Preparation of tert-butyl (R)-3-(4-amino-3-(2-chloro-4-(pyridin-2-ylcarbamoyl)phenyl)-1H-pyrazolo[4,3-c]pyridin-1-yl)piperidine-1-carboxylate

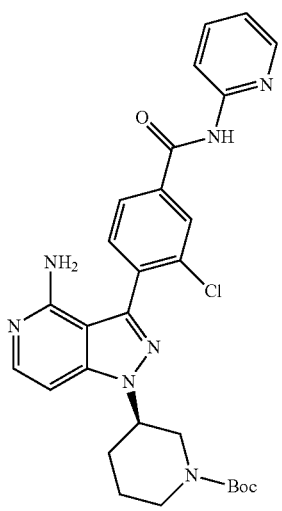 [SMILES: CC(C)(C)OC(=O)N1CCC[C@@H](n2nc(-c3ccc(C(=O)Nc4ccccn4)cc3Cl)c3c(N)nccc32)C1]

A reaction was performed in the same manner as in step 49-1 of Example 49 by using tert-butyl (R)-3-(4-amino-3-bromo-1H-pyrazolo[4,3-c]pyridin-1-yl)piperidine-1-carboxylate (50.0 mg, 1.0 eq) obtained in step 41-2, potassium carbonate (52.3 mg, 3.0 eq) and [1,1'-(diphenylphosphino)ferrocene] dichloropalladium (II) (9.2 mg, 0.1 eq) to obtain 57.0 mg (yield: 80.0%) of the title compound.

Step 56-2: Preparation of (R)-4-(4-amino-1-(piperidin-3-yl)-H-pyrazolo[4,3-c]pyridin-3-yl)-3-chloro-N-(pyridine-2-yl)benzamide hydrochloride

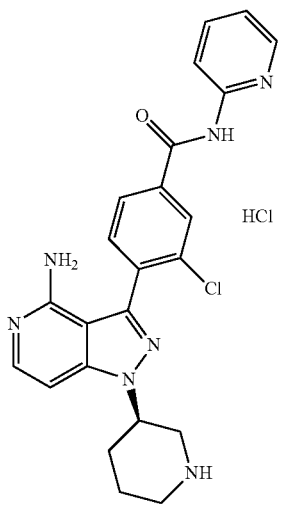 [SMILES: Nc1nccc2c1c(-c1ccc(C(=O)Nc3ccccn3)cc1Cl)nn2[C@@H]1CCCNC1 ; Cl]

A reaction was performed using tert-butyl (R)-3-(4-amino-3-(2-chloro-4-(pyridin-2-ylcarbamoyl)phenyl)-1H-pyrazolo[4,3-c]pyridin-1-yl)piperidine-1-carboxylate (25.0 mg, 1.0 eq) obtained in step 56-1, ethyl acetate (2.0 mL) and 1.0M hydrochloric ethyl acetate solution (0.46 mL, 10.0 eq) at room temperature for 12 hours. The obtained solid compound was filtered, washed with ethyl acetate and then dried to obtain 13.0 mg (yield: 58.3%) of the title compound.

Step 56-3: Preparation of (R)-4-(1-(1-acryloylpiperidin-3-yl)-4-amino-1H-pyrazolo[4,3-c]pyridin-3-yl)-3-chloro-N-(pyridin-2-yl)benzamide

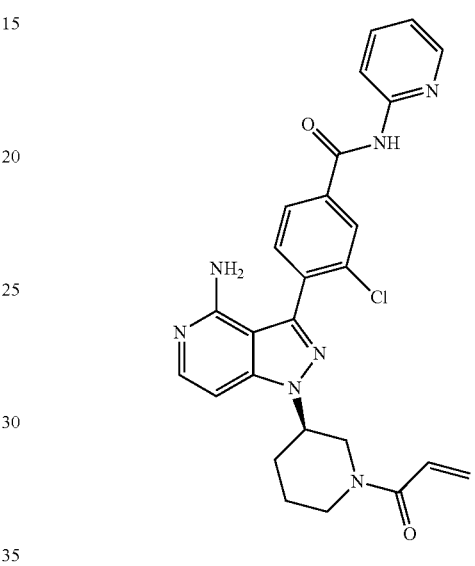

A reaction was performed in the same manner as in step 52-4 of Example 52 by using (R)-4-(4-amino-1-(piperidin-3-yl)-1H-pyrazolo[4,3-c]pyridin-3-yl)-3-chloro-N-(pyridine-2-yl)benzamide hydrochloride (13.0 mg, 1.0 eq) obtained in step 56-2, sodium hydrogen carbonate (16.8 mg, 4.0 eq) and acryloyl chloride (5.4 uL, 1.0 eq) to obtain 7.2 mg (yield: 9.0%) of the title compound.

$^1$H NMR (500 MHz, MeOD): 8.39 (d, 1H), 8.25-8.23 (m, 2H), 8.07 (d, 1H), 7.86 (d, 1H), 7.76-7.68 (m, 2H), 7.19 (t, 1H), 7.05-7.00 (m, 1H), 6.86-6.65 (m, 1H), 6.25-6.13 (m, 1H), 5.79-5.65 (m, 1H), 4.56-4.52 (m, 2H), 4.36-4.18 (m, 1H), 3.45-3.05 (m, 2H), 2.40-2.05 (m, 3H), 1.85-1.74 (m, 1H)

MS m/z: 502.47 [m+1]

Example 57: Preparation of (R)-4-(1-(1-acryloylpip-eridin-3-yl)-4-amino-1H-pyrazolo[4,3-c]pyridin-3-yl)-3-methoxy-N-(pyridin-2-yl)benzamide Step 57-1: Preparation of tert-butyl (R)-3-(4-amino-3-(2-methoxy-4-(pyridin-2-ylcarbamoyl)phenyl)-1H-pyrazolo[4,3-c]pyridin-1-yl)piperidine-1-carboxylate

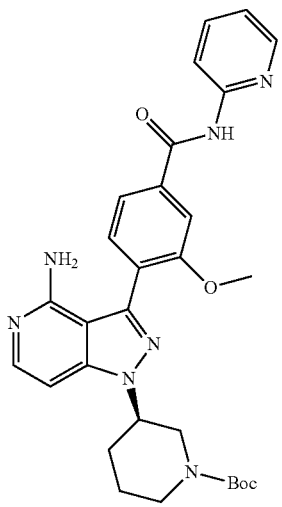 [SMILES: COc1cc(C(=O)Nc2ccccn2)ccc1-c1nn([C@@H]2CCCN(C(=O)OC(C)(C)C)C2)c2ccnc(N)c12]

A reaction was performed in the same manner as in step 49-1 of Example 49 by using tert-butyl (R)-3-(4-amino-3-bromo-1H-pyrazolo[4,3-c]pyridin-1-yl)piperidine-1-carboxylate (50.0 mg, 1.0 eq) obtained in step 41-2, (2-methoxy-4-(pyridin-2-ylcarbamoyl)phenyl)boronic acid (44.5 mg, 1.5 eq), potassium carbonate (52.3 mg, 3.0 eq) and [1,1'-(diphenylphosphino)ferrocene]dichloropalladium (II) (9.2 mg, 0.1 eq) to obtain 64.0 mg (yield: 90.6%) of the title compound.

Step 57-2: Preparation of (R)-4-(4-amino-1-(piperidin-3-yl)-1H-pyrazolo[4,3-c]pyridin-3-yl)-3-methoxy-N-(pyridin-2-yl)benzamide hydrochloride

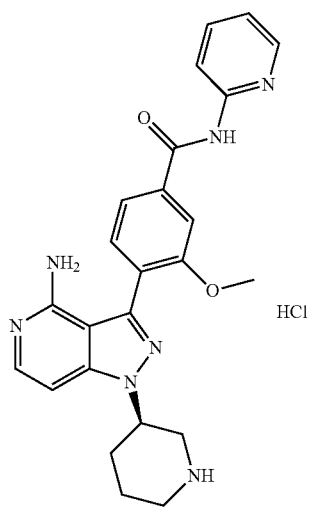 [SMILES: COc1cc(C(=O)Nc2ccccn2)ccc1-c1nn([C@@H]2CCCNC2)c2ccnc(N)c12 ; Cl]

A reaction was performed using tert-butyl (R)-3-(4-amino-3-(2-methoxy-4-(pyridin-2-ylcarbamoyl)phenyl)-1H-pyrazolo[4,3-c]pyridin-1-yl)piperidine-1-carboxylate (50.0 mg, 1.0 eq) obtained in step 57-1, ethyl acetate (2.0 mL) and 1.0M hydrochloric acid ethyl acetate solution (0.92 mL, 10.0 eq) at room temperature for 12 hours. The obtained solid compound was filtered, washed with ethyl acetate and dried to obtain 28.0 mg (yield: 61.1%) of the title compound.

Step 57-3: Preparation of (R)-4-(1-(1-acryloylpip-eridin-3-yl)-4-amino-1H-pyrazolo[4,3-c]pyridin-3-yl)-3-methoxy-N-(pyridin-2-yl)benzamide

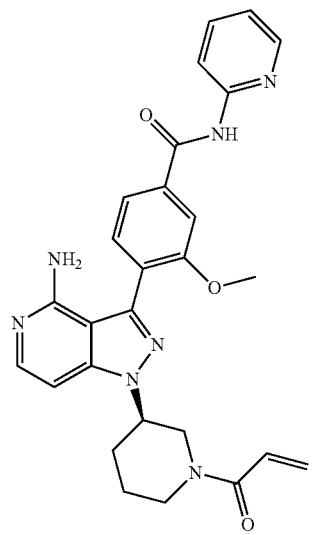 [SMILES: C=CC(=O)N1CCC[C@@H](n2nc(-c3ccc(C(=O)Nc4ccccn4)cc3OC)c3c(N)nccc32)C1]

A reaction was performed in the same manner as in step 52-4 of Example 52 by using (R)-4-(4-amino-1-(piperidin-3-yl)-1H-pyrazolo[4,3-c]pyridin-3-yl)-3-methoxy-N-(pyridin-2-yl)benzamide hydrochloride (20.0 mg, 1.0 eq) obtained in step 57-2, sodium hydrogen carbonate (14.0 mg, 4.0 eq) and acryloyl chloride (3.4 uL, 1.0 eq) to obtain 13.0 mg (yield: 62.2%) of the title compound.

$^1$H NMR (500 MHz, MeOD): 8.39 (d, 1H), 8.27 (d, 1H), 7.87 (t, 1H), 7.79 (s, 1H), 7.74-7.71 (m, 1H), 7.62-7.58 (m, 1H), 7.20-7.18 (m, 1H), 6.97-6.92 (m, 1H), 6.86-6.65 (m, 1H), 6.26-6.13 (m, 1H), 5.80-5.65 (m, 1H), 4.75-4.55 (m, 1H), 4.38-4.20 (m, 1H), 4.98-3.80 (m, 4H), 3.18-2.95 (m, 1H), 2.40-1.97 (m, 3H), 1.80-1.65 (m, 1H)

MS m/z: 498.51 [m+1]

Example 58: Preparation of (R)-4-(1-(1-acryloylpiperidin-3-yl)-4-amino-7-chloro-1H-pyrazolo[4,3-c]pyridin-3-yl)-3-chloro-N-(pyridin-2-yl)benzamide Step 58-1: Preparation of tert-butyl (R)-3-(4-amino-7-chloro-3-(2-chloro-4-(pyridin-2-ylcarbamoyl)phenyl)-1H-pyrazolo[4,3-c]pyridin-1-yl)piperidine-1-carboxylate

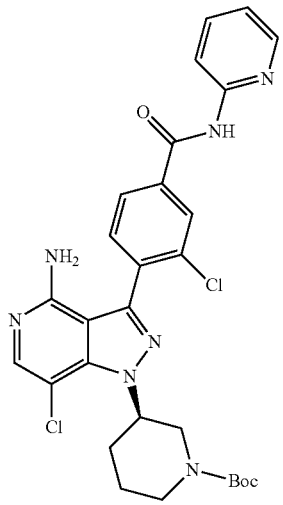 [SMILES: CC(C)(C)OC(=O)N1CCC[C@@H](n2nc(-c3ccc(C(=O)Nc4ccccn4)cc3Cl)c3c(N)ncc(Cl)c32)C1]

A reaction was performed in the same manner as in step 19-1 of Example 19 by using tert-butyl (R)-3-(4-amino-3-(2-chloro-4-(pyridin-2-ylcarbamoyl)phenyl)-1H-pyrazolo[4,3-c]pyridin-1-yl)piperidine-1-carboxylate (30.0 mg, 1.0 eq) obtained in step 56-1, formamide (5.0 mL) and N-chlorosuccinimide (8.0 mg, 1.1 eq) to obtain 17.9 mg (yield: 61.5%) of the title compound.

Step 58-2: Preparation of ((R)-4-(4-amino-7-chloro-1-(piperidin-3-yl)-1H-pyrazolo[4,3-c]pyridin-3-yl)-3-chloro-N-(pyridin-2-yl)benzamide hydrochloride

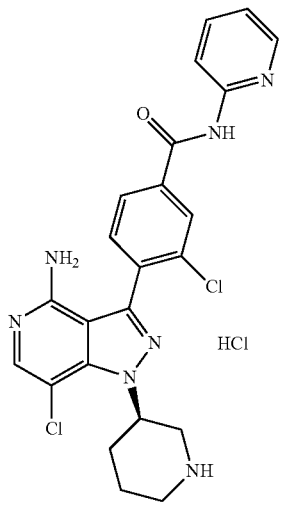 [SMILES: Nc1ncc(Cl)c2c1c(-c1ccc(C(=O)Nc3ccccn3)cc1Cl)nn2[C@@H]1CCCNC1 ; Cl]

A reaction was performed using tert-butyl (R)-3-(4-amino-7-chloro-3-(2-chloro-4-(pyridin-2-ylcarbamoyl)phenyl)-1H-pyrazolo[4,3-c]pyridin-1-yl)piperidine-1-carboxylate (16.0 mg, 1.0 eq) obtained in step 58-1, ethyl acetate (1.0 mL) and 1.0M hydrochloric acid ethyl acetate solution (0.27 mL, 10.0 eq) at room temperature for 12 hours, and then concentrated under reduced pressure. The obtained title compound was used in the next reaction without purification.

Step 58-3: Preparation of (R)-4-(1-(1-acryloylpiperidin-3-yl)-4-amino-7-chloro-1H-pyrazolo[4,3-c]pyridin-3-yl)-3-chloro-N-(pyridin-2-yl)benzamide

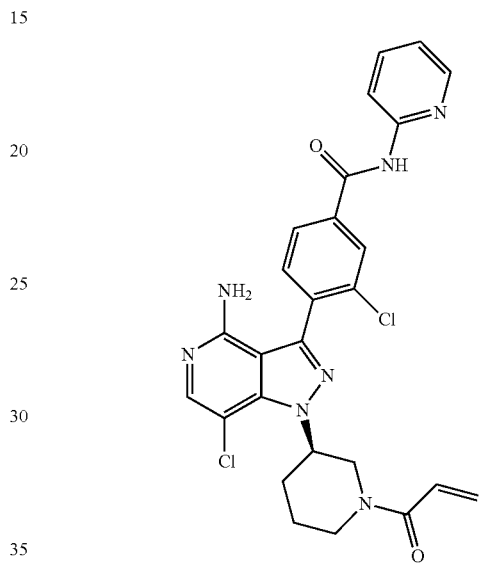

A reaction was performed in the same manner as in step 52-4 of Example 52 by using ((R)-4-(4-amino-7-chloro-1-(piperidin-3-yl)-1H-pyrazolo[4,3-c]pyridin-3-yl)-3-chloro-N-(pyridin-2-yl)benzamide hydrochloride (14.3 mg, 1.0 eq) obtained in step 58-2, sodium hydrogen carbonate (9.2 mg, 4.0 eq) and acryloyl chloride (2.5 uL, 1.1 eq) to obtain 2.3 mg (yield: 14.3%) of the title compound.

$^1$H NMR (500 MHz, MeOD): 8.39 (d, 1H), 8.25-8.23 (m, 1H), 8.12-8.07 (m, 1H), 7.86 (t, 1H), 7.74-7.70 (m, 2H), 7.63-7.61 (m, 1H), 7.21-7.18 (m, 1H), 6.23-6.14 (m, 1H), 5.78-5.67 (m, 1H), 5.37-5.31 (m, 1H), 4.40-4.20 (m, 2H), 3.84-3.58 (m, 2H), 3.20-3.08 (m, 1H), 2.48-2.31 (m, 2H), 2.20-1.98 (m, 2H)

MS m/z: 536.42 [m+1]

Example 59: Preparation of (R)-4-(1-(1-acryloylpiperidin-3-yl)-4-amino-7-chloro-1H-pyrazolo[4,3-c]pyridin-3-yl)-3-methoxy-N-(pyridin-2-yl)benzamide Step 59-1: Preparation of tert-butyl (R)-3-(4-amino-7-chloro-3-(2-methoxy-4-(pyridin-2-ylcarbamoyl)phenyl)-1H-pyrazolo[4,3-c]pyridin-1-yl)piperidine-1-carboxylate

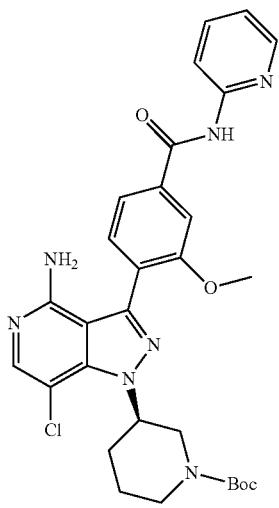 [SMILES: COc1cc(C(=O)Nc2ccccn2)ccc1-c1nn([C@@H]2CCCN(C(=O)OC(C)(C)C)C2)c2c(Cl)cnc(N)c12]

A reaction was performed in the same manner as in step 19-1 of Example 19 by using tert-butyl (R)-3-(4-amino-3-(2-methoxy-4-(pyridin-2-ylcarbamoyl)phenyl)-1H-pyrazolo[4,3-c]pyridin-1-yl)piperidine-1-carboxylate (29.8 mg, 1.0 eq) obtained in step 57-1, formamide (5.0 mL) and N-chlorosuccinimide (8.0 mg, 1.1 eq) to obtain 24.0 mg (yield 83.0%) of the title compound.

Step 59-2: Preparation of (R)-4-(4-amino-7-chloro-1-(piperidin-3-yl)-1H-pyrazolo[4,3-c]pyridin-3-yl)-3-methoxy-N-(pyridin-2-yl)benzamide hydrochloride

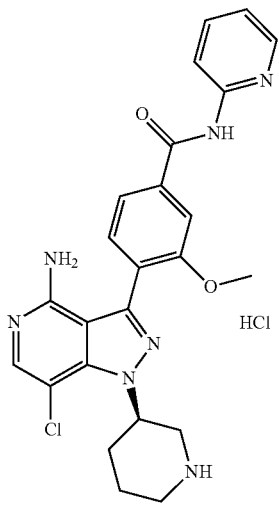 [SMILES: COc1cc(C(=O)Nc2ccccn2)ccc1-c1nn([C@@H]2CCCNC2)c2c(Cl)cnc(N)c12 ; Cl]

A reaction was performed using tert-butyl (R)-3-(4-amino-7-chloro-3-(2-methoxy-4-(pyridin-2-ylcarbamoyl)phenyl)-1H-pyrazolo[4,3-c]pyridin-1-yl)piperidine-1-carboxylate (23.0 mg, 1.0 eq) obtained in step 59-1, ethyl acetate (1.0 mL) and 1.0M hydrochloric acid ethyl acetate solution (0.40 mL, 10.0 eq) at room temperature for 12 hours and then concentrated under reduced pressure. The obtained title compound was used in the next reaction without purification.

Step 59-3: Preparation of (R)-4-(1-(1-acryloylpiperidin-3-yl)-4-amino-7-chloro-1H-pyrazolo[4,3-c]pyridin-3-yl)-3-methoxy-N-(pyridin-2-yl)benzamide

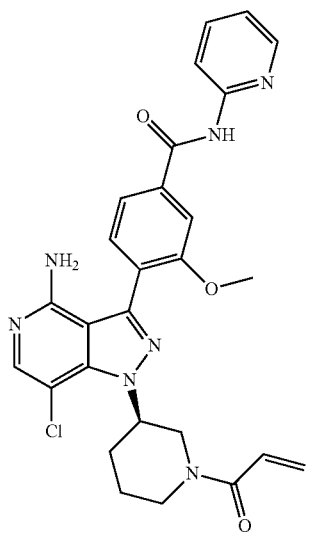

A reaction was performed in the same manner as in step 52-4 of Example 52 by using (R)-4-(4-amino-7-chloro-1-(piperidin-3-yl)-1H-pyrazolo[4,3-c]pyridin-3-yl)-3-methoxy-N-(pyridin-2-yl)benzamide hydrochloride (20.5 mg, 1.0 eq) obtained in step 58-2, sodium hydrogen carbonate (13.4 mg, 4.0 eq) and acryloyl chloride (3.6 uL, 1.1 eq) to obtain 7.0 mg (yield: 32.9%) of the title compound.

$^1$H NMR (500 MHz, MeOD): 8.39 (d, 1H), 8.27 (d, 1H), 7.87 (t, 1H), 7.79-7.68 (m, 2H), 7.63-7.56 (m, 2H), 7.21-7.18 (m, 1H), 6.85-6.71 (m, 1H), 6.24-6.14 (m, 1H), 5.78-5.66 (m, 1H), 5.42-5.32 (m, 1H), 4.42-4.08 (m, 2H), 4.01-3.80 (m, 4H), 3.47-3.10 (m, 2H), 2.45-1.95 (m, 2H), 1.80-1.67 (m, 1H)

MS m/z: 532.51 [m+1]

133

Example 60: Preparation of 4-(1-(1-acryloylazetidin-3-yl)-4-amino-7-chloro-1H-pyrazolo[4,3-c]pyridin-3-yl)-3-fluoro-N-(pyridin-2-yl)benzamide Step 60-1: Preparation of tert-butyl 3-(7-chloro-4-((2,4-dimethoxybenzyl)amino)-3-(2-fluoro-4-(pyridin-2-ylcarbamoyl)phenyl)-1H-pyrazolo[4,3-c]pyridin-1-yl)azetidine-1-carboxylate

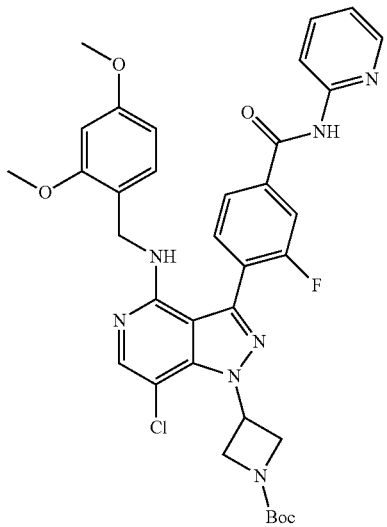 [SMILES: COc1ccc(CNc2ncc(Cl)c3c2c(-c2ccc(C(=O)Nc4ccccn4)cc2F)nn3C2CN(C(=O)OC(C)(C)C)C2)c(OC)c1]

Tert-butyl 3-(4-((2,4-dimethoxybenzyl)amino)-3-(2-fluoro-4-(pyridin-2-ylcarbamoyl)phenyl)-1H-pyrazolo[4,3-c]pyridin-1-yl)azetidine-1-carboxylate (230.0 mg, 1.0 eq) obtained in step 52-2 was dissolved in formamide (10.0 mL), and then N-chlorosuccinimide (61.0 mg, 1.0 eq) was added thereto. The reaction mixture was stirred at room temperature for 2 days, then water was added and the mixture was extracted with ethyl acetate. The separated organic layer was dried over magnesium sulfate and then concentrated under reduced pressure. The resulting residue was purified by column chromatography (ethyl acetate: hexane=1:1) to obtain 185.0 mg (yield: 59.0%) of the title compound.

134

Step 60-2: Preparation of 4-(4-amino-1-(azetidin-3-yl)-7-chloro-1H-pyrazolo[4,3-c]pyridin-3-yl)-3-fluoro-N-(pyridin-2-yl)benzamide

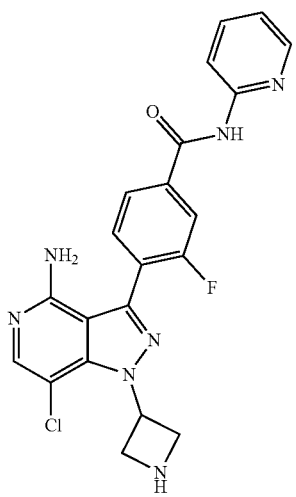 [SMILES: Nc1ncc(Cl)c2c1c(-c1ccc(C(=O)Nc3ccccn3)cc1F)nn2C1CNC1]

A reaction was performed in the same manner as in step 18-2 of Example 18 by using tert-butyl 3-(7-chloro-4-((2,4-dimethoxybenzyl)amino)-3-(2-fluoro-4-(pyridin-2-ylcarbamoyl)phenyl)-1H-pyrazolo[4,3-c]pyridin-1-yl)azetidine-1-carboxylate (80.0 mg, 1.0 eq) obtained in step 60-1, trifluoroacetic acid (2.0 mL) and triethylsilane (37.0 uL, 2.0 eq) to obtain the title compound, which was used in the next reaction without purification.

Step 60-3: Preparation of 4-(1-(1-acryloylazetidin-3-yl)-4-amino-7-chloro-1H-pyrazolo[4,3-c]pyridin-3-yl)-3-fluoro-N-(pyridin-2-yl)benzamide

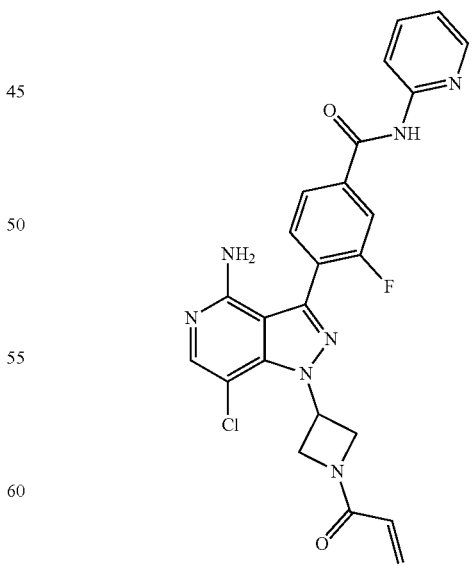

After 4-(4-amino-1-(azetidin-3-yl)-7-chloro-1H-pyrazolo[4,3-c]pyridin-3-yl)-3-fluoro-N-(pyridin-2-yl)benzamide (63.0 mg, 1.0 eq) obtained in step 60-2 was dissolved in tetrahydrofuran (5.0 mL) and water (1.0 mL), sodium hydrogen carbonate (24.4 mg, 2.0 eq) was added thereto. The reaction mixture was stirred at room temperature for 10 minutes, then acryloyl chloride (11.8 uL, 1.0 eq) was added and stirred at room temperature for 10 minutes. Methanol was added to the reaction mixture, followed by extraction with water and ethyl acetate. The separated organic layer was dried over magnesium sulfate and then concentrated under reduced pressure. The resulting residue was purified by column chromatography (dichloromethane:methanol=10:1) to obtain 32.0 mg (yield: 44.9%) of the title compound.

$^1$H NMR (500 MHz, MeOD): 8.39 (d, 1H), 8.25 (d, 1H), 7.99 (d, 1H), 7.94 (d, 1H), 7.86 (t, 1H), 7.79-7.76 (m, 2H), 7.20-7.19 (m, 1H), 6.43-6.34 (m, 2H), 6.28 (d, 1H), 5.79 (d, 1H), 4.88-4.86 (m, 2H), 4.68-4.60 (m, 2H)

MS m/z: 492.43 [m+1]

Example 61: Preparation of (R)-1-(3-(4-amino-3-(1-cyclopropyl-1H-pyrazol-4-ylamino)-1H-pyrazolo[4,3-c]pyridin-1-yl)piperidin-1-yl)prop-2-en-1-one Step 61-1: Preparation of tert-butyl (R)-3-(3-((1-cyclopropyl-1H-pyrazol-4-yl)amino)-4-((2,4-di methoxybenzyl)amino)-1H-pyrazolo[4,3-c]pyridin-1-yl)piperidine-1-carboxylate

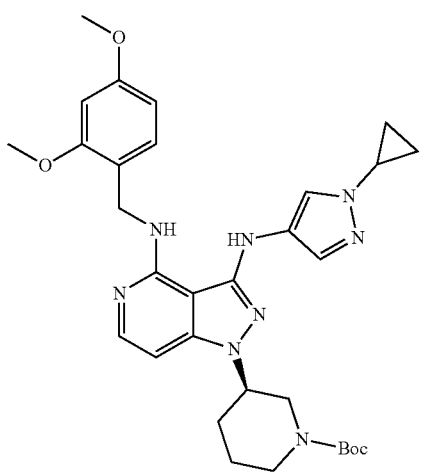 [SMILES: COc1ccc(CNc2nccc3c2c(Nc2cnn(C4CC4)c2)nn3[C@@H]2CCCN(C(=O)OC(C)(C)C)C2)c(OC)c1]

After tert-butyl (R)-3-(3-bromo-4-((2,4-dimethoxybenzyl)amino)-1H-pyrazolo[4,3-c]pyridin-1-yl)piperidine-1-carboxylate (30.0 mg, 1.0 eq) obtained in step 16-2 was dissolved in 1,4-dioxane (3000.0 uL), 1-cyclopropyl-1H-pyrazol-4-amine (10.1 mg, 1.5 eq), palladium acetate (1.2 mg. 0.1 eq), (±)-2,2''-bis(diphenylphosphino)-1,1''-binaphthalene (6.8 mg, 0.1 eq) and cesium carbonate (38.7 mg, 2.0 eq) were added thereto at room temperature. The reaction mixture was allowed to react at 150° C. under standard conditions for 30 minutes using a microwave reactor, and then water was added and the mixture was extracted with ethyl acetate. The separated organic layer was dried over magnesium sulfate and then concentrated under reduced pressure. The resulting residue was purified by column chromatography (ethyl acetate:hexane=1:1) to obtain 15.2 mg (yield: 43.0%) of the title compound as a brown solid.

Step 61-2: Preparation of (R)—N3-(1-cyclopropyl-1H-pyrazol-4-yl)-1-(piperidin-3-yl)-1H-pyrazolo[4,3-c]pyridine-3,4-diamine

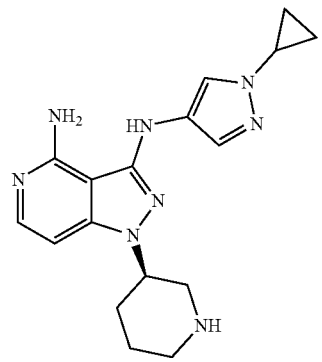 [SMILES: Nc1nccc2c1c(Nc1cnn(C3CC3)c1)nn2[C@@H]1CCCNC1]

After tert-butyl (R)-3-(3-((1-cyclopropyl-1H-pyrazol-4-yl)amino)-4-((2,4-dimethoxybenzyl)amino)-1H-pyrazolo[4,3-c]pyridin-1-yl)piperidine-1-carboxylate (15.2 mg, 1.0 eq) obtained in step 61-1 was dissolved in trifluoroacetic acid (1000.0 uL), triethylsilane (8.2 µL, 2.0 eq) was added thereto at room temperature. The reaction mixture was allowed to react at room temperature for 12 hours and then concentrated under reduced pressure. A saturated aqueous sodium hydrogen carbonate solution was added to the resulting residue, followed by extraction with ethyl acetate. The separated organic layer was dried over magnesium sulfate and then concentrated under reduced pressure. The obtained title compound was used in a mixture state in the next reaction without purification.

Step 61-3: Preparation of (R)-1-(3-(4-amino-3-(1-cyclopropyl-1H-pyrazol-4-ylamino)-1H-pyrazolo[4,3-c]pyridin-1-yl)piperidin-1-yl)prop-2-en-1-one

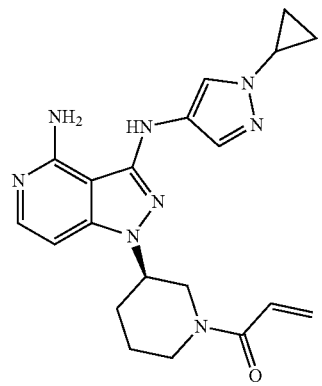 [SMILES: C=CC(=O)N1CCC[C@@H](n2nc(Nc3cnn(C4CC4)c3)c3c(N)nccc32)C1]

After (R)—N3-(1-cyclopropyl-1H-pyrazol-4-yl)-1-(piperidin-3-yl)-1H-pyrazolo[4,3-c]pyridine-3,4-diamine (8.9 mg, 1.0 eq) obtained in step 61-2 was dissolved in tetrahydrofuran (2500.0 uL) and water (500.0 uL), acryloyl chloride (4.2 µL, 1.0 eq) was added thereto. The reaction mixture was allowed to react at room temperature for 30 minutes, then water was added and the mixture was extracted with ethyl acetate. The separated organic layer was dried over magnesium sulfate and then concentrated under reduced pressure. The resulting residue was purified by column chromatography (dichloromethane:methanol=10:1) to obtain 1.6 mg (yield: 15.7%) of the title compound as a brown solid.

¹HNMR(500 MHz, MeOD): 8.78-8.50 (m, 1H), 7.72 (s, 1H), 7.32-7.17 (m, 2H), 6.71-6.55 (m, 1H), 6.38-6.25 (m, 1H), 5.80-5.69 (m, 1H), 5.42-5.30 (m, 1H), 4.80-4.63 (m, 1H), 4.29-3.97 (m, 2H), 3.60-3.53 (m, 1H), 3.27-3.13 (m, 2H), 2.40-1.11 (m, 7H)

MS m/z: 393.25 [m+1]

Example 62: Preparation of (R)-1-(3-(4-amino-3-bromo-1H-pyrazolo[4,3-c]pyridin-1-yl)piperidin-1-yl)prop-2-en-1-one Step 62-1: Preparation of (R)-3-bromo-1-(piperidin-3-yl)-1H-pyrazolo[4,3-c]pyridin-4-amine hydrochloride

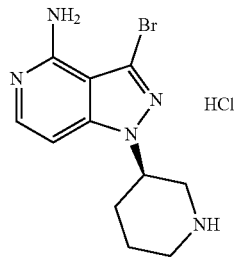 [SMILES: Nc1nccc2c1c(Br)nn2[C@@H]1CCCNC1 ; Cl]

After tert-butyl(R)-3-(4-amino-3-bromo-1H-pyrazolo[4,3-c]pyridin-1-yl)piperidine-1-carboxylate (25.0 mg, 1.0 eq) was dissolved in anhydrous ethyl acetate (2000.0 uL), 1.0M hydrochloric acid ethyl acetate solution (630.9 μL, 10.0 eq) was added thereto at room temperature. The reaction mixture was allowed to react at room temperature for 24 hours. The reaction mixture was concentrated under reduced pressure, and then washed with ethyl acetate to obtain 16.0 mg (yield: 76.4%) of the title compound as a brown solid.

Step 62-2: Preparation of (R)-1-(3-(4-amino-3-bromo-1H-pyrazolo[4,3-c]pyridin-1-yl)piperidin-1-yl)prop-2-en-1-one

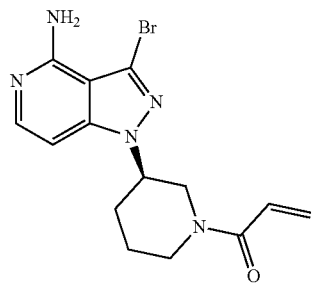 [SMILES: C=CC(=O)N1CCC[C@@H](n2nc(Br)c3c(N)nccc32)C1]

A reaction was performed in the same manner as in step 18-3 of Example 18 by using (R)-3-bromo-1-(piperidin-3-yl)-1H-pyrazolo[4,3-c]pyridin-4-amine hydrochloride (16.0 mg, 1.0 eq) obtained in step 62-1, sodium hydrogen carbonate (20.2 mg, 4.0 eq) and acryloyl chloride (6.5 μL, 1.1 eq) to obtain 3.7 mg (yield: 17.6%) of the title compound.

¹HNMR(500 MHz, MeOD): 7.71 (d, 1H), 6.91 (d, 1H), 6.87-6.65 (m, 1H), 6.28-6.15 (dd, 1H), 5.81-5.65 (m, 1H), 5.08-5.4.90 (m, 1H), 4.69-4.48 (m, 2H), 4.24-4.08 (m, 1H), 3.45-3.20 (m, 3H), 2.32-2.15 (m, 1H), 1.78-1.66 (m, 1H)

MS m/z:351.97 [m+1]

Example 63: Preparation of 4-(1-(1-acryloylazetidin-3-yl)-4-amino-1H-pyrazolo[4,3-c]pyridin-3-yl)-3-chloro-N-(pyridin-2-yl)benzamide Step 63-1: ylate Preparation of tert-butyl-3-(3-(2-chloro-4-(pyridin-2-ylcarbamoyl)phenyl)-4-((2,4-dimethoxybenzyl)amino)-1H-pyrazolo[4,3-c]pyridin-1-yl)azetidine-1-carboxylate

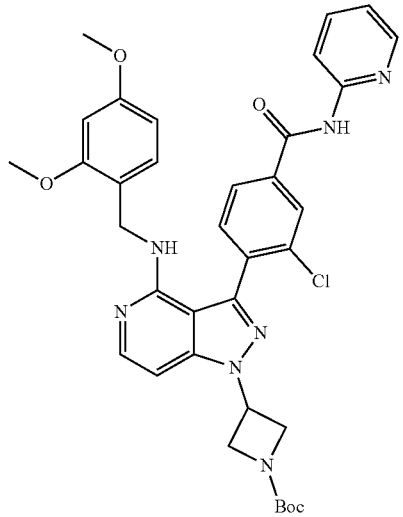 [SMILES: COc1ccc(CNc2nccc3c2c(-c2ccc(C(=O)Nc4ccccn4)cc2Cl)nn3C2CN(C(=O)OC(C)(C)C)C2)c(OC)c1]

After tert-butyl 3-(3-bromo-4-((2,4-dimethoxybenzyl)amino)-1H-pyrazolo[4,3-c]pyridin-1-yl)azetidine-1-carboxylate (400.0 mg, 1.0 eq) obtained in step 52-1 was dissolved in 1,4-dioxane (10.0 mL) and water (2.0 mL), (2-chloro-4-(pyridin-2-ylcarbamoyl)phenyl)boronic acid (285.3 mg, 1.5 eq), [1,1'-bis(diphenylphosphino)ferrocene]dichloro palladium (II) (56.5 mg, 0.1 eq) and potassium carbonate (213.3 mg, 2.0 eq) were added thereto at room temperature. The reaction mixture was allowed to react at 110° C. for 2 hours, then water was added and the mixture was extracted with ethyl acetate. The separated organic layer was dried over magnesium sulfate and then concentrated under reduced pressure. The resulting residue was purified by column chromatography (ethyl acetate:hexane=1:1) to obtain 195.0 mg (yield: 37.7%) of the title compound.

Step 63-2: Preparation of 4-(4-amino-1-(azetidin-3-yl)-1H-pyrazolo[4,3-c]pyridin-3-yl)-3-chloro-N-(pyridin-2-yl)benzamide

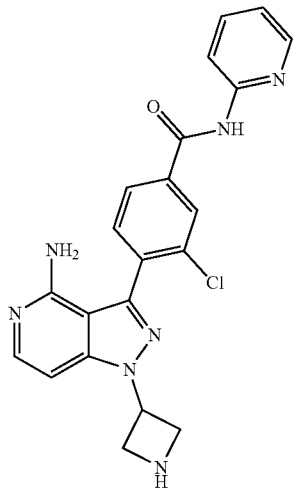 [SMILES: Nc1nccc2c1c(-c1ccc(C(=O)Nc3ccccn3)cc1Cl)nn2C1CNC1]

A reaction was performed in the same manner as in step 18-2 of Example 18 by using tert-butyl 3-(3-(2-chloro-4-(pyridin-2-ylcarbamoyl)phenyl)-4-((2,4-dimethoxybenzyl)amino)-1H-pyrazolo[4,3-c]pyridin-1-yl)azetidine-1-carboxylate (80.0 mg, 1.0 eq) obtained in step 63-1, trifluoroacetic acid (2.0 mL) and triethylsilane (38.0 μL, 2.0 eq) to obtain the title compound, which was used in the next reaction without purification.

Step 63-3: Preparation of 4-(1-(1-acryloylazetidin-3-yl)-4-amino-1H-pyrazolo[4,3-c]pyridin-3-yl)-3-chloro-N-(pyridin-2-yl)benzamide

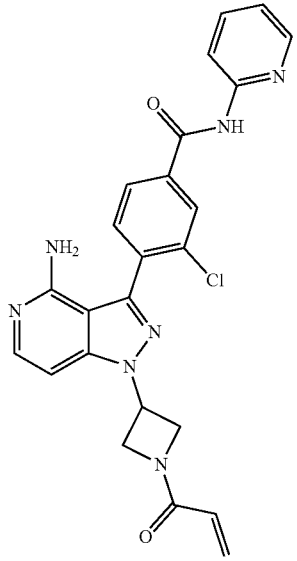 [SMILES: C=CC(=O)N1CC(n2nc(-c3ccc(C(=O)Nc4ccccn4)cc3Cl)c3c(N)nccc32)C1]

A reaction was performed in the same as in step 52-4 of Example 52 by using 4-(4-amino-1-(azetidin-3-yl)-1H-pyrazolo[4,3-c]pyridin-3-yl)-3-chloro-N-(pyridin-2-yl)benzamide (50.0 mg, 1.0 eq) obtained in step 63-2, sodium hydrogen carbonate (30.2 mg, 3.0 eq) and acryloyl chloride (9.7 μL, 1.0 eq) to obtain 32.0 mg (yield: 33.7%) of the title compound.

$^1$HNMR(500 MHz, MeOD):3.83 (s, 1H), 8.24 (d, 1H), 8.18-8.98 (m, 2H), 7.92-7.82 (m, 2H), 7.80-7.65 (m, 2H), 7.20-7.71 (m, 2H), 6.44-6.38 (m, 2H), 6.35-6.27 (m, 2H), 5.82-5.75 (m, 1H), 4.70-4.52 (m, 2H), 3.55-3.48 (m, 2H)

MS m/z: 474.43 [m+1]

Example 64: Preparation of 4-(1-(1-acryloylazetidin-3-yl)-4-amino-7-chloro-1H-pyrazolo[4,3-c]pyridin-3-yl)-3-chloro-N-(pyridin-2-yl)benzamide

Step 64-1: Preparation of tert-butyl 3-(7-chloro-3-(2-chloro-4-(pyridin-2-ylcarbamoyl)phenyl)-4-((2,4-di methoxybenzyl)amino)-1H-pyrazolo[4,3-c]pyridin-1-yl)azetidine-1-carboxylate

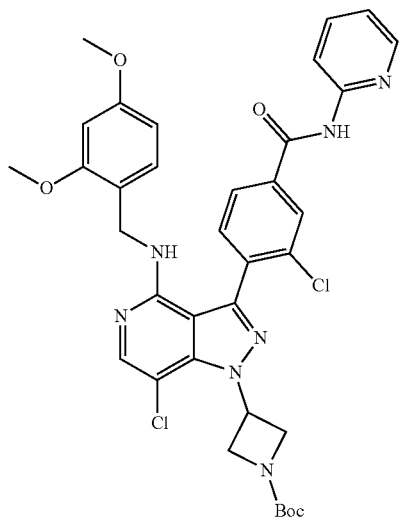 [SMILES: COc1ccc(CNc2ncc(Cl)c3c2c(-c2ccc(C(=O)Nc4ccccn4)cc2Cl)nn3C2CN(C(=O)OC(C)(C)C)C2)c(OC)c1]

After tert-butyl 3-(3-(2-chloro-4-(pyridin-2-ylcarbamoyl)phenyl)-4-((2,4-dimethoxybenzyl)amino)-1H-pyrazolo[4,3-c]pyridin-1-yl)azetidine-1-carboxylate (80.0 mg, 1.0 eq) obtained in step 63-1 was dissolved in anhydrous dimethylformamide (2000.0 uL), N-chlorosuccinimide (19.1 mg, 1.1 eq) was added thereto at room temperature. The reaction mixture was allowed to react at 80° C. for 2 hours and then water was added. The mixture was extracted with ethyl acetate. The separated organic layer was dried over magnesium sulfate and then concentrated under reduced pressure. The resulting residue was purified by column chromatography (ethyl acetate:hexane=1:1) to obtain 82.4 mg (yield: 98.0%) of the title compound as a brown oil.

Step 64-2: Preparation of 4-(4-amino-1-(azetidin-3-yl)-7-chloro-1H-pyrazolo[4,3-c]pyridin-3-yl)-3-chloro-N-(pyridine-2-yl)benzamide

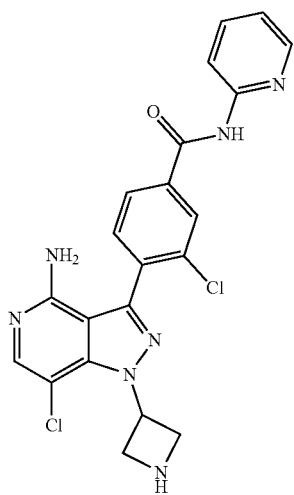 [SMILES: Nc1ncc(Cl)c2c1c(-c1ccc(C(=O)Nc3ccccn3)cc1Cl)nn2C1CNC1]

A reaction was performed in the same manner as in step 18-2 of Example 18 by using tert-butyl 3-(7-chloro-3-(2-chloro-4-(pyridin-2-ylcarbamoyl)phenyl)-4-((2,4-dimethoxybenzyl)amino)-1H-pyrazolo[4,3-c]pyridin-1-yl)azetidine-1-carboxylate (80.0 mg, 1.0 eq) obtained in step 64-1, trifluoroacetic acid (2.0 mL) and triethylsilane (36.2 μL, 2.0 eq) to obtain the title compound, which was used in the next reaction without purification.

Step 64-3: Preparation of 4-(1-(1-acryloylazetidin-3-yl)-4-amino-7-chloro-1H-pyrazolo[4,3-c]pyridin-3-yl)-3-chloro-N-(pyridin-2-yl)benzamide

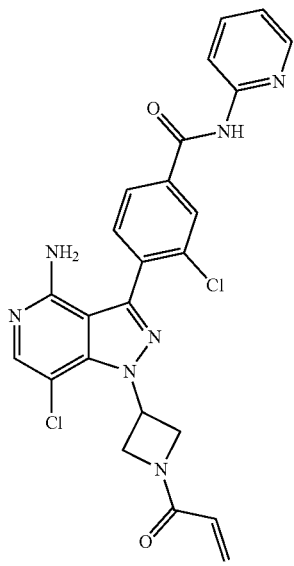 [SMILES: C=CC(=O)N1CC(n2nc(-c3ccc(C(=O)Nc4ccccn4)cc3Cl)c3c(N)ncc(Cl)c32)C1]

A reaction was performed in the same manner as in step 52-4 of Example 52 by using 4-(4-amino-1-(azetidin-3-yl)-7-chloro-1H-pyrazolo[4,3-c]pyridin-3-yl)-3-chloro-N-(pyridine-2-yl)benzamide (51.8 mg, 1.0 eq) obtained in step 64-2, sodium hydrogen carbonate (38.3 mg, 4.0 eq) and acryloyl chloride (9.3 μL, 1.0 eq) to obtain 24.5 mg (yield: 42.3%) of the title compound.

$^1$HNMR(500 MHz, CDCl$_3$):8.68 (s, 1H), 8.38 (d, 1H), 8.35 (d, 1H), 8.17 (s, 1H), 7.97 (d, 1H), 7.84 (d, 1H), 7.81 (t, 1H), 7.66 (d, 1H), 7.14 (t, 1H), 6.38 (d, 1H), 6.28-6.21 (m, 1H), 5.71 (d, 1H), 4.75-4.61 (m, 2H), 4.14-4.10 (m, 2H)

MS m/z: 510.31 [m+1]

Example 65: Preparation of (R)-4-(1-(1-acryloylpiperidin-3-yl)-4-amino-7-iodo-1H-pyrazolo[4,3-c]pyridin-3-yl)-3-chloro-N-(pyridin-2-yl)benzamide Step 65-1: Preparation of tert-butyl (R)-3-(4-amino-3-(2-chloro-4-(pyridin-2-ylcarbamoyl)phenyl)-7-iodo-1H-pyrazolo[4,3-c]pyridin-1-yl)piperidine-1-carboxylate

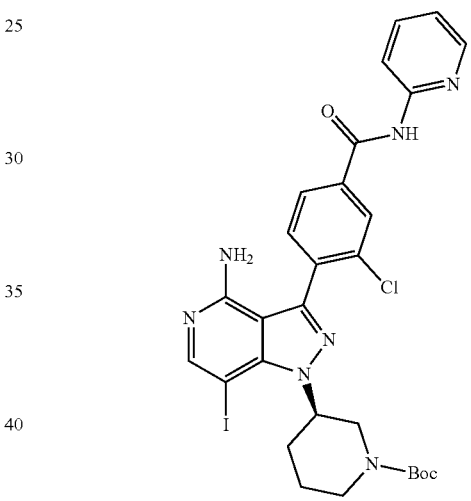

After tert-butyl(R)-3-(4-amino-3-(2-chloro-4-(pyridin-2-ylcarbamoyl)phenyl)-1H-pyrazolo[4,3-c]pyridin-1-yl)piperidine-1-carboxylate (300.0 mg, 1.0 eq) was dissolved in anhydrous dimethylformamide (10.0 mL), N-iodosuccinimide (147.8 mg, 1.2 eq) was added thereto at room temperature. The reaction mixture was allowed to react at room temperature for 1 hour and then water was added. The mixture was extracted with ethyl acetate. The separated organic layer was dried over magnesium sulfate and then concentrated under reduced pressure. The resulting residue was purified by column chromatography (dichloromethane:methanol=10:1) to obtain 141.0 mg (yield: 38.2%) of the title compound as a brown solid.

Step 65-2: Preparation of (R)-4-(4-amino-7-iodo-1-(piperidin-3-yl)-1H-pyrazolo[4,3-c]pyridin-3-yl)-3-chloro-N-(pyridin-2-yl)benzamide

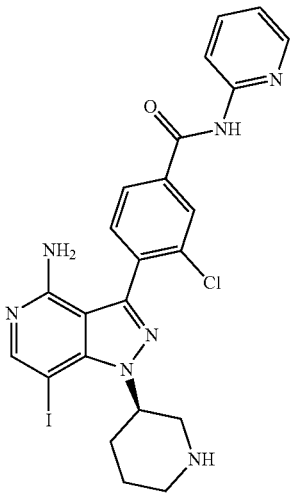 [SMILES: Nc1ncc(I)c2c1c(-c1ccc(C(=O)Nc3ccccn3)cc1Cl)nn2[C@@H]1CCCNC1]

After tert-butyl (R)-3-(4-amino-3-(2-chloro-4-(pyridin-2-ylcarbamoyl)phenyl)-7-iodo-1H-pyrazolo[4,3-c]pyridin-1-yl)piperidine-1-carboxylate (40.0 mg, 1.0 eq) obtained in step 65-1 was dissolved in anhydrous ethyl acetate (2.0 mL), 1.0M hydrochloric acid ethyl acetate solution (59.4 µL, 10.0 eq) was added thereto at room temperature. The reaction mixture was allowed to react at room temperature for 12 hours. The obtained solid compound was filtered and washed with ethyl acetate to obtain 25.0 mg (yield: 69.0%) of the title compound as a white solid.

Step 65-3: Preparation of (R)-4-(1-(1-acryloylpiperidin-3-yl)-4-amino-7-iodo-1H-pyrazolo[4,3-c]pyridin-3-yl)-3-chloro-N-(pyridin-2-yl)benzamide

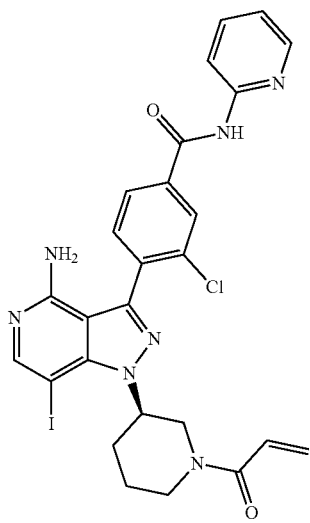 [SMILES: C=CC(=O)N1CCC[C@@H](n2nc(-c3ccc(C(=O)Nc4ccccn4)cc3Cl)c3c(N)ncc(I)c32)C1]

A reaction was performed in the same manner as in step 52-4 of Example 52 by using (R)-4-(4-amino-7-iodo-1-(piperidin-3-yl)-1H-pyrazolo[4,3-c]pyridin-3-yl)-3-chloro-N-(pyridin-2-yl)benzamide (25.0 mg, 1.0 eq) obtained in step 65-2, sodium hydrogen carbonate (13.8 mg, 4.0 eq) and acryloyl chloride (3.3 µL, 1.0 eq) to obtain 13.0 mg (yield: 50.5%) of the title compound.

$^1$HNMR(500 MHz, MeOD):8.39 (d, 1H), 8.25-8.23 (m, 2H), 8.08 (d, 1H), 8.04 (s, 1H), 7.88 (t, 1H), 7.71-7.68 (m, 1H), 7.20 (t, 1H), 6.86-6.80 (m, 1H), 6.21 (dd, 1H), 5.74 (dd, 1H), 4.97 (d, 1H), 4.43-4.35 (m, 1H), 4.18-4.10 (m, 1H), 3.84 (t, 1H), 3.58-3.48 (m, 1H), 3.07-3.00 (m, 1H), 2.40-2.38 (m, 1H), 2.09-2.01 (m, 1H), 1.80-1.67 (m, 1H)

MS m/z: 628.54 [m+1]

Example 66: Preparation of (R)-4-(1-(1-acryloylpiperidin-3-yl)-4-amino-7-cyano-1H-pyrazolo[4,3-c]pyridin-3-yl)-3-chloro-N-(pyridin-2-yl)benzamide

Step 66-1: Preparation of tert-butyl (R)-3-(4-amino-3-(2-chloro-4-(pyridin-2-ylcarbamoyl)phenyl)-7-cyano-1H-pyrazolo[4,3-c]pyridin-1-yl)piperidine-1-carboxylate

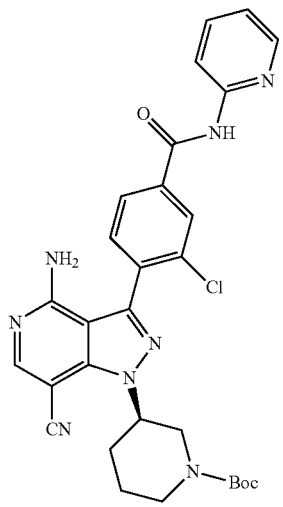

After tert-butyl (R)-3-(4-amino-3-(2-chloro-4-(pyridin-2-ylcarbamoyl)phenyl)-7-iodo-1H-pyrazolo[4,3-c]pyridin-1-yl)piperidine-1-carboxylate (80.0 mg, 1.0 eq) was dissolved in anhydrous dimethylformamide (3.0 mL), Cu(I)CN (21.3 mg, 2.0 eq) was added thereto at room temperature. The reaction mixture was allowed to react at 180° C. under standard conditions for 10 minutes using a microwave reactor, then water was added and the mixture was extracted with ethyl acetate. The separated organic layer was dried over magnesium sulfate and then concentrated under reduced pressure. The resulting residue was purified by column chromatography (dichloromethane:methanol=10:1) to obtain 23.0 mg (yield: 33.8%) of the title compound as a yellow solid.

Step 66-2: Preparation of (R)-4-(4-amino-7-cyano-1-(piperidin-3-yl)-1H-pyrazolo[4,3-c]pyridin-3-yl)-3-chloro-N-(pyridin-2-yl)benzamide

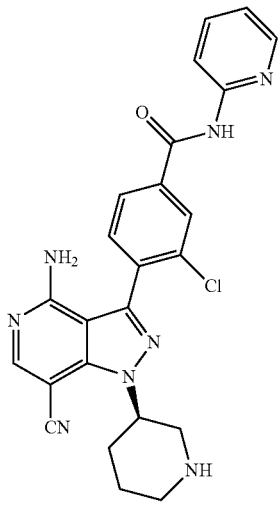 [SMILES: N#Cc1cnc(N)c2c(-c3ccc(C(=O)Nc4ccccn4)cc3Cl)nn([C@@H]3CCCNC3)c12]

After tert-butyl (R)-3-(4-amino-3-(2-chloro-4-(pyridin-2-ylcarbamoyl)phenyl)-7-cyano-1H-pyrazolo[4,3-c]pyridin-1-yl)piperidine-1-carboxylate (23.0 mg, 1.0 eq) obtained in step 66-1 was dissolved in ethyl acetate (2.0 mL), 1.0M hydrochloric acid ethyl acetate solution (0.4 mL, 10.0 eq) was added thereto at room temperature. The reaction mixture was allowed to react at room temperature for 12 hours. The obtained solid compound was filtered and then washed with ethyl acetate to obtain 8.0 mg (yield: 42.1%) of the title compound as a white solid.

Step 66-3: Preparation of (R)-4-(1-(1-acryloylpiperidin-3-yl)-4-amino-7-cyano-1H-pyrazolo[4,3-c]pyridin-3-yl)-3-chloro-N-(pyridin-2-yl)benzamide

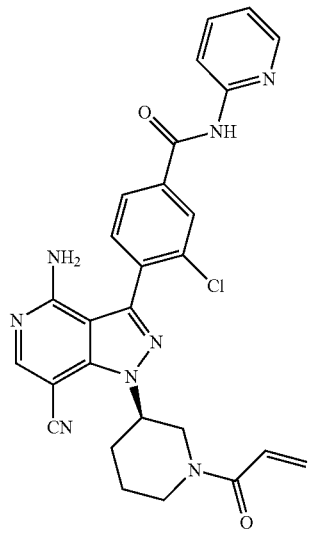 [SMILES: C=CC(=O)N1CCC[C@@H](n2nc(-c3ccc(C(=O)Nc4ccccn4)cc3Cl)c3c(N)ncc(C#N)c32)C1]

A reaction was performed in the same manner as step 52-4 in Example 52 by using (R)-4-(4-amino-7-cyano-1-(piperidin-3-yl)-1H-pyrazolo[4,3-c]pyridin-3-yl)-3-chloro-N-(pyridin-2-yl)benzamide (8.0 mg, 1.0 eq) obtained in step 66-2, sodium hydrogen carbonate (5.7 mg, 4.0 eq) and acryloyl chloride (1.4 μL, 1.0 eq) to obtain 3.5 mg (yield: 39.3%) of the title compound.

$^1$HNMR(500 MHz, MeOD): 8.39 (d, 1H), 8.25-8.23 (m, 2H), 8.02 (d, 1H), 7.88 (t, 1H), 7.75-7.68 (m, 1H), 7.20 (dd, 1H), 6.84-6.79 (m, 1H), 6.18 (dd, 1H), 5.72 (dd, 1H), 5.18-5.05 (m, 1H), 4.67 (d, 1H), 4.41-4.28 (m, 1H), 3.91-3.85 (m, 1H), 3.74-3.64 (m, 1H), 3.25-3.15 (m, 1H), 2.44-2.26 (m, 2H), 2.17-2.06 (m, 1H), 1.82-1.66 (m, 1H)

MS m/z: 527.60 [m+1]

Example 67: Preparation of (R)-4-(1-(1-acryloylpiperidin-3-yl)-4-amino-7-(1-methyl-1H-pyrazol-4-yl)-1H-pyrazolo[4,3-c]pyridin-3-yl)-3-chloro-N-(pyridin-2-yl)benzamide Step 67-1: Preparation of tert-butyl (R)-3-(4-amino-3-(2-chloro-4-(pyridin-2-ylcarbamoyl)phenyl)-7-(1-methyl-1H-pyrazol-4-yl)-1H-pyrazolo[4,3-c]pyridin-1-yl)piperidine-1-carboxylate

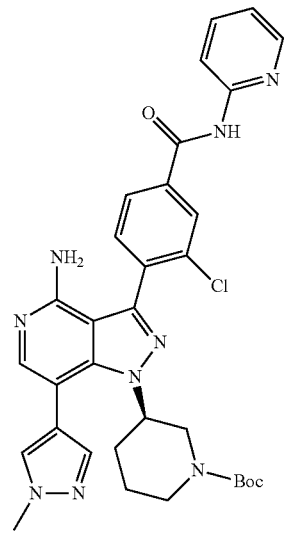 [SMILES: Cn1cc(-c2cnc(N)c3c(-c4ccc(C(=O)Nc5ccccn5)cc4Cl)nn([C@@H]4CCCN(C(=O)OC(C)(C)C)C4)c23)cn1]

After tert-butyl (R)-3-(4-amino-3-(2-chloro-4-(pyridin-2-ylcarbamoyl)phenyl)-7-iodo-1H-pyrazolo[4,3-c]pyridin-1-yl)piperidine-1-carboxylate (50.0 mg, 1.0 eq) was dissolved in 1,4-dioxane (5.0 mL) and water (1.0 mL), (4-((4-chloropyridin-2-yl)carbamoyl)phenyl)boronic acid (23.2 mg, 1.5 eq), [1,1'-bis(diphenylphosphino)ferrocene]dichloro palladium (II) (1.0 mg, 0.1 eq) and potassium carbonate (108.6 mg, 2.0 eq) were added thereto at room temperature. The reaction mixture was allowed to react at 110° C. for 1 hour, then water was added and extracted with ethyl acetate. The separated organic layer was dried over magnesium sulfate and then concentrated under reduced pressure. The resulting residue was purified by column chromatography (dichloromethane:methanol=10:1) to obtain 42.0 mg (yield: 90.1%) of the title compound as a brown oil.

Step 67-2: Preparation of (R)-4-(4-amino-7-(1-methyl-1H-pyrazol-4-yl)-1-(piperidin-3-yl)-1H-pyrazolo[4,3-c]pyridin-3-yl)-3-chloro-N-(pyridin-2-yl)benzamide

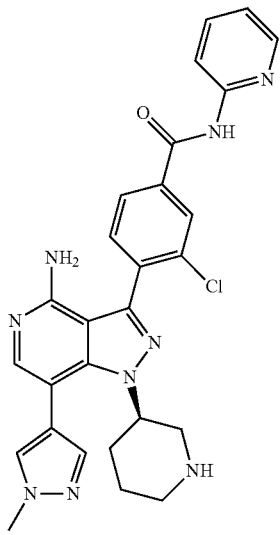 [SMILES: Cn1cc(-c2cnc(N)c3c(-c4ccc(C(=O)Nc5ccccn5)cc4Cl)nn([C@@H]4CCCNC4)c23)cn1]

After tert-butyl (R)-3-(4-amino-3-(2-chloro-4-(pyridin-2-ylcarbamoyl)phenyl)-7-(1-methyl-1H-pyrazol-4-yl)-1H-pyrazolo[4,3-c]pyridin-1-yl)piperidine-1-carboxylate (40.0 mg, 1.0 eq) obtained in step 67-1 was dissolved in anhydrous ethyl acetate (2.0 mL), 1.0M hydrochloric acid ethyl acetate solution (0.6 mL, 10.0 eq) was added thereto at room temperature. The reaction mixture was allowed to react at room temperature for 12 hours. The obtained solid compound was filtered and washed with ethyl acetate to obtain 19.0 mg (yield: 53.0%) of the title compound as a white solid.

Step 67-3: Preparation of (R)-4-(1-(1-acryloylpiperidin-3-yl)-4-amino-7-(1-methyl-1H-pyrazol-4-yl)-1H-pyrazolo[4,3-c]pyridin-3-yl)-3-chloro-N-(pyridin-2-yl)benzamide

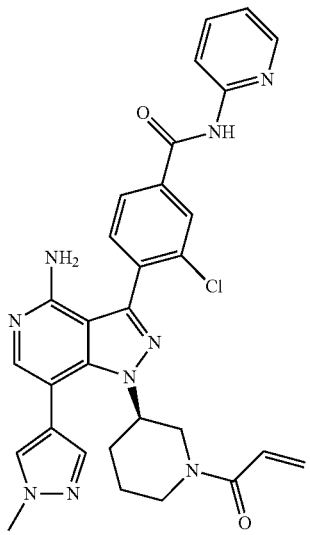 [SMILES: C=CC(=O)N1CCC[C@@H](n2nc(-c3ccc(C(=O)Nc4ccccn4)cc3Cl)c3c(N)ncc(-c4cnn(C)c4)c32)C1]

After (R)-4-(4-amino-7-(1-methyl-1H-pyrazol-4-yl)-1-(piperidin-3-yl)-1H-pyrazolo[4,3-c]pyridin-3-yl)-3-chloro-N-(pyridin-2-yl)benzamide (19.0 mg, 1.0 eq) obtained in step 67-2 was dissolved in tetrahydrofuran (5.0 mL) and water (1.0 mL), sodium hydrogen carbonate (11.3 mg, 4.0 eq) was added thereto at room temperature and reacted for 10 minutes. Acryloyl chloride (4.2 μL, 1.0 eq) was added to the mixture at room temperature. The reaction mixture was allowed to react at room temperature for 10 minutes, then methanol was added and the mixture was extracted with water and ethyl acetate. The separated organic layer was dried over magnesium sulfate and then concentrated under reduced pressure. The resulting residue was purified by column chromatography (dichloromethane:methanol=10:1) to obtain 4.2 mg (yield: 20.4%) of the title compound as a white solid.

$^1$HNMR(500 MHz, MeOD): 8.38 (d, 1H), 8.26-8.24 (m, 2H), 8.00 (d, 1H), 7.94-7.58 (m, 5H), 7.20 (t, 1H), 6.78-6.59 (m, 1H), 6.25-6.14 (m, 1H), 5.77-5.72 (m, 1H), 4.71-4.60 (m, 1H), 4.45-4.16 (m, 1H), 4.15-4.05 (m, 1H), 4.02 (s, 3H), 3.70-3.61 (m, 1H), 3.23-3.07 (m, 2H), 2.35-2.02 (m, 2H), 1.95-1.82 (m, 1H)

MS m/z: 582.64 [m+1]

149

Example 68: Preparation of (R)-4-(1-(1-acryloylpiperidin-3-yl)-4-amino-7-ethyl-1H-pyrazolo[4,3-c]pyridin-3-yl)-3-chloro-N-(pyridin-2-yl)benzamide Step 68-1: Preparation of tert-butyl (R)-3-(4-amino-3-(2-chloro-4-(pyridin-2-ylcarbamoyl)phenyl)-7-vinyl-1H-pyrazolo[4,3-c]pyridin-1-yl)piperidine-1-carboxylate

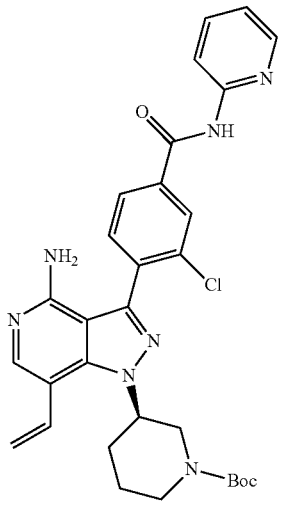 [SMILES: C=Cc1cnc(N)c2c(-c3ccc(C(=O)Nc4ccccn4)cc3Cl)nn([C@@H]3CCCN(C(=O)OC(C)(C)C)C3)c12]

After tert-butyl (R)-3-(4-amino-3-(2-chloro-4-(pyridin-2-ylcarbamoyl)phenyl)-7-iodo-1H-pyrazolo[4,3-c]pyridin-1-yl)piperidine-1-carboxylate (200.0 mg, 1.0 eq) obtained in step 65-1 was dissolved in 1,4-dioxane (10.0 mL) and water (2.0 mL), 4,4,5,5-tetramethyl-2-vinyl-1,3,2-dioxaborolane (76.2 µL, 1.5 eq), [1,1'-bis(diphenylphosphino)ferrocene]dichloro palladium (II) (21.7 mg, 0.1 eq) and potassium carbonate (82.0 mg, 2.0 eq) were added thereto at room temperature. The reaction mixture was allowed to react at 110° C. for 1 hour, then water was added and extracted with ethyl acetate. The separated organic layer was dried over magnesium sulfate and then concentrated under reduced pressure. The resulting residue was purified by column chromatography (dichloromethane:methanol=10:1) to obtain 152.0 mg (yield: 89.2%) of the title compound as a brown oil.

150

Step 68-2: Preparation of tert-butyl (R)-3-(4-amino-3-(2-chloro-4-(pyridin-2-ylcarbamoyl)phenyl)-7-ethyl-1H-pyrazolo[4,3-c]pyridin-1-yl)piperidine-1-carboxylate

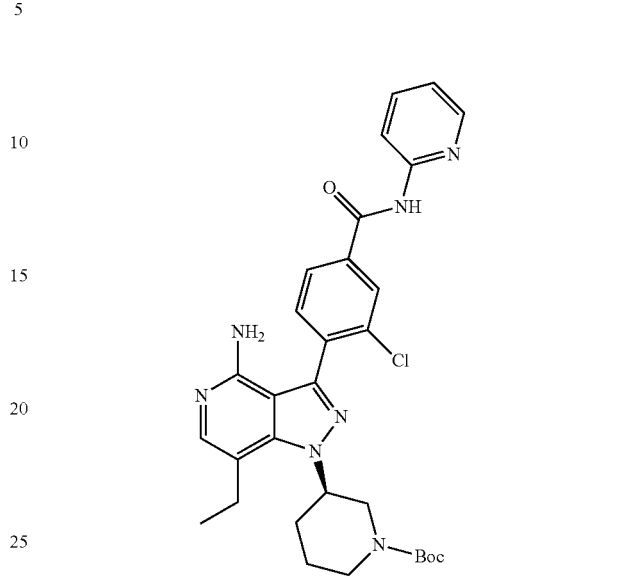

After tert-butyl (R)-3-(4-amino-3-(2-chloro-4-(pyridin-2-ylcarbamoyl)phenyl)-7-vinyl-1H-pyrazolo[4,3-c]pyridin-1-yl)piperidine-1-carboxylate (90.0 mg, 1.0 eq) obtained in step 68-1 was dissolved in anhydrous methanol (5.0 mL), Pd/C (palladium 10% on carbon) (16.7 mg, 0.1 eq) was added thereto at room temperature. The reaction mixture was allowed to react at room temperature for 1 hour while flowing hydrogen gas, filtered using Celite, and then concentrated under reduced pressure to obtain 65.0 mg (yield: 72.0%) of the title compound as a brown solid.

Step 68-3: Preparation of (R)-4-(4-amino-7-ethyl-1-(piperidin-3-yl)-1H-pyrazolo[4,3-c]pyridin-3-yl)-3-chloro-N-(pyridin-2-yl)benzamide

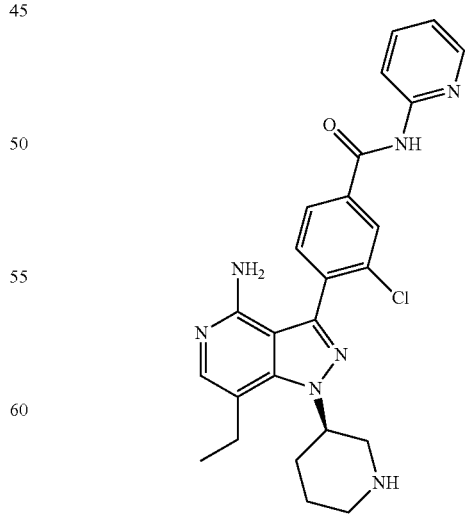

After tert-butyl (R)-3-(4-amino-3-(2-chloro-4-(pyridin-2-ylcarbamoyl)phenyl)-7-ethyl-1H-pyrazolo[4,3-c]pyridin-1- yl)piperidine-1-carboxylate (65.0 mg, 1.0 eq) obtained in step 68-2 was dissolved in anhydrous ethyl acetate (5.0 mL), 1.0M hydrochloric acid ethyl acetate solution (1128.3 μL, 10.0 eq) was added thereto at room temperature. The reaction mixture was allowed to react at room temperature for 12 hours. The obtained solid compound was filtered and then washed with ethyl acetate to obtain 41.0 mg (yield: 70.9%) of the title compound as a white solid.

Step 68-4: Preparation of (R)-4-(1-(1-acryloylpiperidin-3-yl)-4-amino-7-ethyl-1H-pyrazolo[4,3-c]pyridin-3-yl)-3-chloro-N-(pyridin-2-yl)benzamide

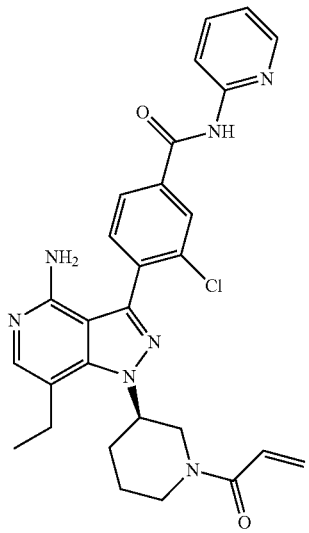 [SMILES: C=CC(=O)N1CCC[C@@H](n2nc(-c3ccc(C(=O)Nc4ccccn4)cc3Cl)c3c(N)ncc(CC)c32)C1]

A reaction was performed in the same manner as in step 52-4 of Example 52 by using (R)-4-(4-amino-7-ethyl-1-(piperidin-3-yl)-1H-pyrazolo[4,3-c]pyridin-3-yl)-3-chloro-N-(pyridin-2-yl)benzamide (40.0 mg, 1.0 eq) obtained in step 68-3, sodium hydrogen carbonate (26.2 mg, 4.0 eq) and acryloyl chloride (6.3 μL, 1.0 eq) to obtain 16.0 mg (yield: 38.7%) of the title compound.

¹HNMR(500 MHz, MeOD):3.38 (d, 1H), 8.33 (d, 1H), 8.15 (s, 1H), 7.95 (d, 1H), 7.79 (t, 1H), 7.65 (d, 1H), 7.61 (s, 1H), 7.12 (t, 1H), 7.86-7.43 (m, 2H), 4.89-4.75 (m, 1H), 4.68-4.58 (m, 1H), 4.43-4.32 (m, 1H), 4.28-4.19 (m, 1H), 3.39-3.28 (m, 1H), 2.9-2.89 (m, 1H), 2.85-2.76 (m, 1H), 2.42-2.31 (m, 1H), 2.29-2.10 (m, 4H), 1.94-1.85 (m, 1H), 1.78-1.62 (m, 1H), 1.36 (t, 3H)

MS m/z: 530.56[m+1]

Example 69: Preparation of (R)-4-(1-(1-acryloylpiperidin-3-yl)-4-amino-7-vinyl-1H-pyrazolo[4,3-c]pyridin-3-yl)-3-chloro-N-(pyridin-2-yl)benzamide Step 69-1: Preparation of (R)-4-(4-amino-1-(piperidin-3-yl)-7-vinyl-1H-pyrazolo[4,3-c]pyridin-3-yl)-3-chloro-N-(pyridin-2-yl)benzamide

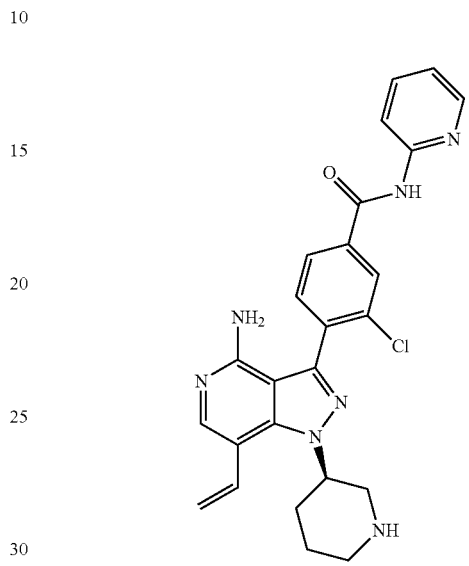

After tert-butyl (R)-3-(4-amino-3-(2-chloro-4-(pyridin-2-ylcarbamoyl)phenyl)-7-vinyl-1H-pyrazolo[4,3-c]pyridin-1-yl)piperidine-1-carboxylate (50.0 mg, 1.0 eq) obtained in step 68-1 was dissolved in anhydrous ethyl acetate (5.0 mL), 1.0M hydrochloric acid ethyl acetate solution (0.9 mL, 10.0 eq) was added thereto at room temperature. The reaction mixture was allowed to react at room temperature for 12 hours. The obtained solid compound was filtered and washed with ethyl acetate to obtain 22.0 mg (yield: 49.5%) of the title compound as a white solid.

Step 69-2: Preparation of (R)-4-(1-(1-acryloylpiperidin-3-yl)-4-amino-7-vinyl-1H-pyrazolo[4,3-c]pyridin-3-yl)-3-chloro-N-(pyridin-2-yl)benzamide

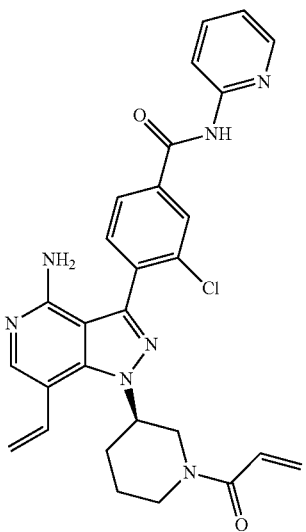 [SMILES: C=CC(=O)N1CCC[C@@H](n2nc(-c3ccc(C(=O)Nc4ccccn4)cc3Cl)c3c(N)ncc(C=C)c32)C1]

A reaction was performed in the same manner as in step 52-4 of Example 52 by using (R)-4-(4-amino-1-(piperidin-3-yl)-7-vinyl-1H-pyrazolo[4,3-c]pyridin-3-yl)-3-chloro-N-(pyridin-2-yl)benzamide (20.0 mg, 1.0 eq) obtained in step 69-1, sodium hydrogen carbonate (13.2 mg, 4.0 eq) and acryloyl chloride (3.2 μL, 1.0 eq) to obtain 10.2 mg (yield: 79.3%) of the title compound.

$^1$HNMR(500 MHz, CDCl$_3$): 8.69 (s, 1H), 8.39 (d, 1H), 8.16 (s, 1H), 7.95 (d, 1H), 7.82-7.78 (m, 2H), 7.66 (d, 1H), 7.16-7.12 (m, 2H), 5.63 (d, 1H), 5.38 (d, 1H), 4.90-4.81 (m, 2H), 4.72-4.65 (m, 1H), 4.48-4.18 (m, 2H), 3.28 (t, 1H), 2.87-2.75 (m, 1H), 4.90-4.81 (m, 2H), 2.43-2.28 (m, 1H), 2.28-2.18 (m, 1H), 1.91-1.86 (m, 1H)

MS m/z: 528.57 [m+1]

Example 70: Preparation of (R)-4-(1-(1-acryloylpiperidin-3-yl)-4-amino-7-(1H-pyrazol-4-yl)-1H-pyrazolo[4,3-c]pyridin-3-yl)-3-chloro-N-(pyridin-2-yl)benzamide

Step 70-1: Preparation of (R)-4-(1-(1-acryloylpiperidin-3-yl)-4-amino-7-(1H-pyrazol-4-yl)-1H-pyrazolo[4,3-c]pyridin-3-yl)-3-chloro-N-(pyridin-2-yl)benzamide

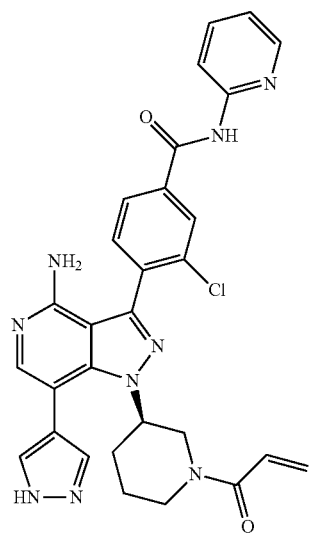 [SMILES: C=CC(=O)N1CCC[C@@H](n2nc(-c3ccc(C(=O)Nc4ccccn4)cc3Cl)c3c(N)ncc(-c4cn[nH]c4)c32)C1]

After (R)-4-(1-(1-acryloylpiperidin-3-yl)-4-amino-7-iodo-1H-pyrazolo[4,3-c]pyridin-3-yl)-3-chloro-N-(pyridin-2-yl)benzamide (50.0 mg, 1.0 eq) obtained in step 65-3 was dissolved in 1,4-dioxane (5.0 mL) and water (1.0 mL), 4-(4,4,5,5-tetramethyl-1,3,2-dioxaborolane-2-yl)-1H-pyrazole (23.2 μL, 1.5 eq), [1,1'-bis(diphenylphosphino)ferrocene] dichloropalladium (II) (5.8 mg, 0.1 eq) and potassium carbonate (22.0 mg, 2.0 eq) were added thereto at room temperature. The reaction mixture was allowed to react at 110° C. for 1 hour, then water was added and the mixture was extracted with ethyl acetate. The separated organic layer was dried over magnesium sulfate and then concentrated under reduced pressure. The resulting residue was purified by column chromatography (dichloromethane:methanol=10:1) to obtain 5.2 mg (yield: 11.5%) of the title compound as a brown oil.

$^1$HNMR(500 MHz, MeOD): 8.39 (d, 1H), 8.26-8.20 (m, 2H), 8.08 (d, 1H), 7.90-7.65 (m, 4H), 7.51 (s, 1H), 7.20 (t, 1H), 6.78-6.55 (m, 1H), 6.22-6.11 (m, 1H), 5.74-5.70 (m, 1H), 4.70-4.54 (m, 2H), 4.38-4.20 (m, 1H), 4.05-3.97 (m, 1H), 3.65 (t, 1H), 3.20-3.18 (m, 1H), 3.90-3.75 (m, 1H), 2.39-2.15 (m, 2H), 1.92-1.87 (m, 1H)

MS m/z: 566.50 [m−1]

Example 71: Preparation of (R)-1-(1-acryloylpiperidin-3-yl)-4-amino-N-(5-chlorobenzo[d]oxazol-2-yl)-1H-pyrazolo[4,3-c]pyridine-3-carboxamide

Step 71-1: Preparation of methyl (R)-4-amino-1-(1-(tert-butoxycarbonyl)piperidin-3-yl)-1H-pyrazolo[4,3-c]pyridine-3-carboxylate

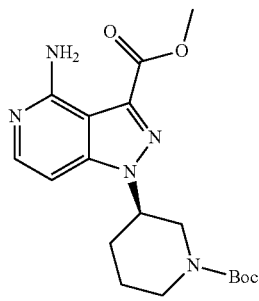 [SMILES: COC(=O)c1nn([C@@H]2CCCN(C(=O)OC(C)(C)C)C2)c2ccnc(N)c12]

Tert-butyl (R)-3-(4-amino-3-iodo-1H-pyrazolo [4,3-c]pyridin-1-yl)piperidine-1-carboxylate (1000.0 mg, 1.0 eq) was dissolved in anhydrous dimethylformamide (6.7 mL) and anhydrous methanol (6.7 mL), and then triethylamine (6.7 mL, 3.0 mL/mmol) was added thereto at room temperature. The reaction vessel was replaced with nitrogen gas, to which palladium acetate (50.6 mg, 0.1 eq) and Xantphos (261.1 mg, 0.2 eq) were added, and the reaction vessel was replaced with carbon dioxide gas. The reaction mixture was allowed to react at 70° C. for 3 hours, then water was added and the mixture was extracted with ethyl acetate. The separated organic layer was dried over magnesium sulfate and then concentrated under reduced pressure. The resulting residue was purified by column chromatography (ethyl acetate:hexane=1:1>1:0) to obtain 700.0 mg (yield: 90.5%) of the title compound as a yellow solid.

Step 71-2: Preparation of (R)-4-amino-1-(1-(tert-butoxycarbonyl)piperidin-3-yl)-1H-pyrazolo[4,3-c]pyridine-3-carboxylic acid

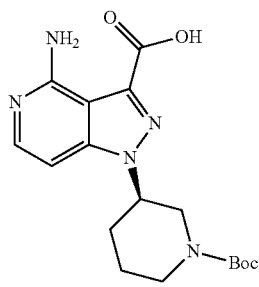 [SMILES: CC(C)(C)OC(=O)N1CCC[C@@H](n2nc(C(=O)O)c3c(N)nccc32)C1]

After methyl (R)-4-amino-1-(1-(tert-butoxycarbonyl)piperidin-3-yl)-1H-pyrazolo[4,3-c]pyridine-3-carboxylate (600.0 mg, 1.0 eq) obtained in step 71-1 was dissolved in water (5.0 mL) and methanol (5.0 mL), sodium hydroxide (369.3 mg, 10.0 eq) was added thereto at room temperature. The reaction mixture was allowed to react at room temperature for 4 hours and then concentrated under reduced pressure. The resulting compound was adjusted to pH 4.0 using 1N aqueous hydrochloric acid solution, and then the obtained solid compound was filtered and washed with water to obtain 250.0 mg (yield: 43.2%) of a brown title compound.

Step 71-3: Preparation of tert-butyl(R)-3-(4-amino-3-((5-chlorobenzo[d]oxazol-2-yl)carbamoyl)-1H-pyrazolo[4,3-c]pyridine-1-yl)piperidine-1-carboxylate

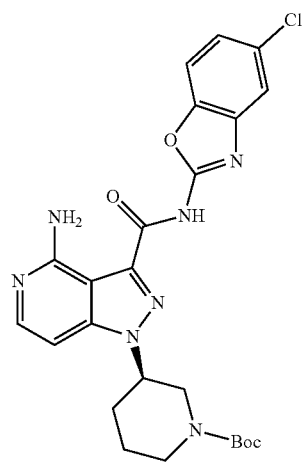 [SMILES: CC(C)(C)OC(=O)N1CCC[C@@H](n2nc(C(=O)Nc3nc4cc(Cl)ccc4o3)c3c(N)nccc32)C1]

After (R)-4-amino-1-(1-(tert-butoxycarbonyl)piperidin-3-yl)-1H-pyrazolo[4,3-c]pyridine-3-carboxylic acid (150.0 mg, 1.0 eq) obtained in step 71-2 was dissolved in anhydrous dimethylformamide (5.0 mL), 1,1'-carbonyldiimidazole (100.9 mg, 1.5 eq) was added thereto at room temperature. The reaction mixture was allowed to react at room temperature for 1 hour, to which 5-chlorobenzo[d]oxazol-2-amine (104.9 mg, 1.5 eq) and sodium tert-butoxide (59.8 mg, 1.5 eq) were added and reacted at room temperature for 1 hour, then water was added and the mixture was extracted with ethyl acetate. The separated organic layer was dried over magnesium sulfate and then concentrated under reduced pressure. The resulting residue was purified by column chromatography (dichloromethane:methanol=10:1) to obtain 80.0 mg (yield: 37.7%) of the title compound as a brown solid.

Step 71-4: Preparation of (R)-4-amino-N-(5-chlorobenzo[d]oxazol-2-yl)-1-(piperidin-3-yl)-1H-pyrazolo[4,3-c]pyridine-3-carboxamide

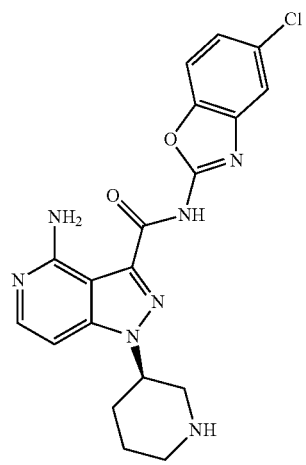 [SMILES: Nc1nccc2c1c(C(=O)Nc1nc3cc(Cl)ccc3o1)nn2[C@@H]1CCCNC1]

After tert-butyl(R)-3-(4-amino-3-((5-chlorobenzo[d]oxazol-2-yl)carbamoyl)-1H-pyrazolo[4,3-c]pyridine-1-yl)piperidine-1-carboxylate (60.0 mg, 1.0 eq) obtained in step 71-3 was dissolved in anhydrous ethyl acetate (5.0 mL), 1.0M hydrochloric acid ethyl acetate solution (0.6 mL, 5.0 eq) was added thereto at room temperature. The reaction mixture was allowed to react at room temperature for 12 hours, and then concentrated under reduced pressure. The obtained title compound was used in the next reaction without filtration.

Step 71-5: Preparation of (R)-1-(1-acryloylpiperidin-3-yl)-4-amino-N-(5-chlorobenzo[d]oxazol-2-yl)-1H-pyrazolo[4,3-c]pyridine-3-carboxamide

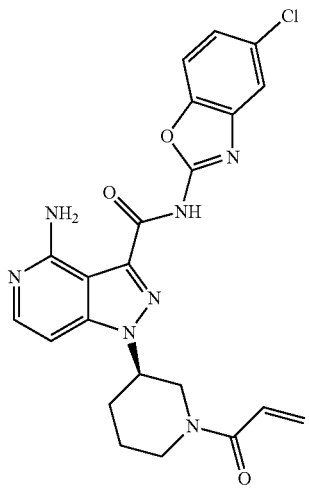 [SMILES: C=CC(=O)N1CCC[C@@H](n2nc(C(=O)Nc3nc4cc(Cl)ccc4o3)c3c(N)nccc32)C1]

After (R)-4-amino-N-(5-chlorobenzo[d]oxazol-2-yl)-1-(piperidin-3-yl)-1H-pyrazolo[4,3-c]pyridine-3-carboxamide (52.5 mg, 1.0 eq) obtained in step 71-4 was dissolved in tetrahydrofuran (5.0 mL) and water (1.0 mL), sodium hydrogen carbonate (39.3 mg, 4.0 eq) was added thereto at room temperature and allowed to react for 30 minutes. Acryloyl chloride (9.5 μL, 1.0 eq) was added to the mixture at room temperature. The reaction mixture was allowed to react at room temperature for 10 minutes, then methanol was added and the mixture was extracted with water and ethyl acetate. The separated organic layer was dried over magnesium sulfate and then concentrated under reduced pressure. The resulting residue was purified by column chromatography (dichloromethane:methanol=10:1) to obtain 3.5 mg (yield: 6.4%) of the title compound as a white solid.

$^1$HNMR(500 MHz, MeOD): 7.74 (d, 1H), 7.58 (s, 1H), 7.52 (d, 1H), 7.29 (d, 1H), 7.72-6.95 (m, 1H), 6.90-6.81 (m, 1H), 6.30-6.20 (m, 1H), 5.81-5.69 (m, 1H), 5.37-5.33 (m, 1H), 4.72-4.66 (m, 1H), 4.9-4.30 (m, 1H), 4.00-3.88 (m, 1H), 3.60-3.51 (m, 1H), 3.35-3.03 (m, 1H), 2.50-2.41 (m, 1H), 2.31-2.25 (m, 1H), 2.08-2.01 (m, 1H)

MS m/z: 466.33 [m+1]

Example 72: Preparation of (R)-tert-butyl 1-(1-acryloylpiperidin-3-yl)-4-amino-1H-pyrazolo[4,3-c]pyridine-3-carboxylate Step 72-1: Preparation of tert-butyl (R)-4-amino-1-(1-(tert-butoxycarbonyl)piperidin-3-yl)-1H-pyrazolo[4,3-c]pyridine-3-carboxylate

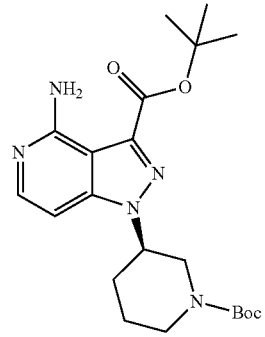 [SMILES: CC(C)(C)OC(=O)c1nn([C@@H]2CCCN(C(=O)OC(C)(C)C)C2)c2ccnc(N)c12]

After (R)-4-amino-1-(1-(tert-butoxycarbonyl)piperidin-3-yl)-1H-pyrazolo[4,3-c]pyridine-3-carboxylic acid (150.0 mg, 1.0 eq) obtained in step 71-2 was dissolved in anhydrous dimethylformamide (5.0 mL), 1,1'-carbonyldiimidazole (100.9 mg, 1.5 eq) was added thereto at room temperature. The reaction mixture was allowed to react at room temperature for 1 hour, and then 5-bromobenzo[d]oxazol-2-amine (88.4 mg, 1.5 eq) and sodium tert-butoxide (39.9 mg, 1.5 eq) was added and reacted at room temperature for 1 hour, followed by addition of water and extraction with ethyl acetate. The separated organic layer was dried over magnesium sulfate and then concentrated under reduced pressure. The resulting residue was purified by column chromatography (dichloromethane:methanol=10:1) to obtain 12.0 mg (yield: 10.4%) of the title compound as a brown solid.

Step 72-2: Preparation of tert-butyl(R)-4-amino-1-(piperidin-3-yl)-1H-pyrazolo[4,3-c]pyridine-3-carboxylate

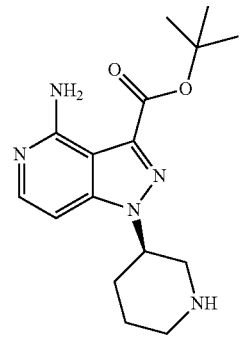 [SMILES: CC(C)(C)OC(=O)c1nn([C@@H]2CCCNC2)c2ccnc(N)c12]

After tert-butyl (R)-4-amino-1-(1-(tert-butoxycarbonyl)piperidin-3-yl)-1H-pyrazolo[4,3-c]pyridine-3-carboxylate (12.0 mg, 1.0 eq) obtained in step 72-1 was dissolved in anhydrous ethyl acetate (5.0 mL), 1.0M hydrochloric acid ethyl acetate solution (0.3 mL, 10.0 eq) was added thereto at room temperature. The reaction mixture was allowed to react at room temperature for 12 hours and then concentrated under reduced pressure. The obtained title compound was used in the next reaction without filtration.

Step 72-3: Preparation of (R)-tert-butyl 1-(1-acryloylpiperidin-3-yl)-4-amino-1H-pyrazolo[4,3-c]pyridine-3-carboxylate

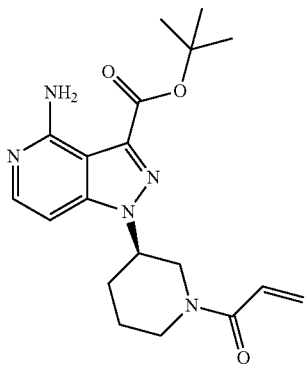 [SMILES: C=CC(=O)N1CCC[C@@H](n2nc(C(=O)OC(C)(C)C)c3c(N)nccc32)C1]

After tert-butyl(R)-4-amino-1-(piperidin-3-yl)-1H-pyrazolo[4,3-c]pyridine-3-carboxylate (8.8 mg, 1.0 eq) obtained in step 72-2 was dissolved in tetrahydrofuran (5.0 mL) and water (1.0 mL), sodium hydrogen carbonate (8.4 mg, 4.0 eq) was added thereto at room temperature and reacted for 30 minutes. Acryloyl chloride (2.0 μL, 1.0 eq) was added to the mixture at room temperature. The reaction mixture was allowed to react at room temperature for 10 minutes, then methanol was added and the mixture was extracted with water and ethyl acetate. The separated organic layer was dried over magnesium sulfate and then concentrated under reduced pressure. The resulting residue was purified by column chromatography (dichloromethane:methanol=10:1) to obtain 2.3 mg (yield: 24.8%) of the title compound as a white solid.

$^1$HNMR(500 MHz, MeOD): 8.09 (d, 1H), 7.79 (d, 1H), 6.99-6.89 (m, 1H), 6.38-6.20 (m, 1H), 5.86-5.79 (m, 1H), 4.85-4.58 (m, 2H), 4.36-4.20 (m, 2H), 3.96-3.89 (m, 1H), 3.67-3.58 (m, 1H), 3.50-3.41 (m, 1H), 2.33-2.26 (m, 1H), 2.10-2.08 (m, 1H), 1.30 (s, 3H)

MS m/z: 373.29 [m+1]

Example 73: Preparation of (R)-1-(1-acryloylpiperidin-3-yl)-4-amino-N-(6-bromobenzo[d]oxazol-2-yl)-1H-pyrazolo[4,3-c]pyridine-3-carboxamide

Step 73-1: Preparation of tert-butyl(R)-3-(4-amino-3-((6-bromobenzo[d]oxazol-2-yl)carbamoyl)-1H-pyrazolo[4,3-c]pyridin-1-yl)piperidine-1-carboxylate

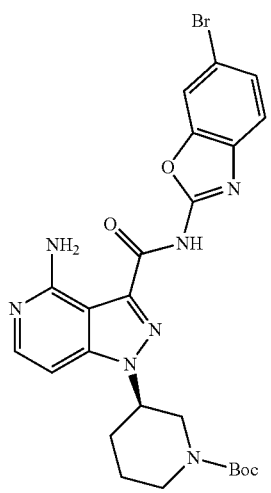 [SMILES: CC(C)(C)OC(=O)N1CCC[C@@H](n2nc(C(=O)Nc3nc4ccc(Br)cc4o3)c3c(N)nccc32)C1]

After (R)-4-amino-1-(1-(tert-butoxycarbonyl)piperidin-3-yl)-1H-pyrazolo[4,3-c]pyridine-3-carboxylic acid (40.0 mg, 1.0 eq) obtained in step 71-2 was dissolved in anhydrous dimethylacetamide (5.0 mL) in a reaction vessel 1,1,1'-carbonyldiimidazole (23.3 mg, 1.3 eq) was added thereto at room temperature and the reaction mixture was allowed to react at room temperature for 1 hour. After 6-bromobenzo[d]oxazol-2-amine (30.6 mg, 1.3 eq) was dissolved in anhydrous dimethylacetamide (5.0 mL) in a reaction vessel 2, sodium hydride (5.7 mg, 1.3 eq) was added thereto at room temperature and the reaction mixture was allowed to react at room temperature for 1 hour. The mixture that was reacted in the reaction vessel 2 was added to the reaction vessel 1 and reacted at room temperature for 1 hour. Water was added and the mixture was extracted with ethyl acetate. The separated organic layer was dried over magnesium sulfate and then concentrated under reduced pressure. The resulting residue was purified by column chromatography (dichloromethane:methanol=10:1) to obtain 15.0 mg (yield: 24.5%) of the title compound as a brown solid.

Step 73-2: Preparation of (R)-4-amino-N-(6-bromobenzo[d]oxazol-2-yl)-1-(piperidin-3-yl)-1H-pyrazolo[4,3-c]pyridine-3-carboxamide

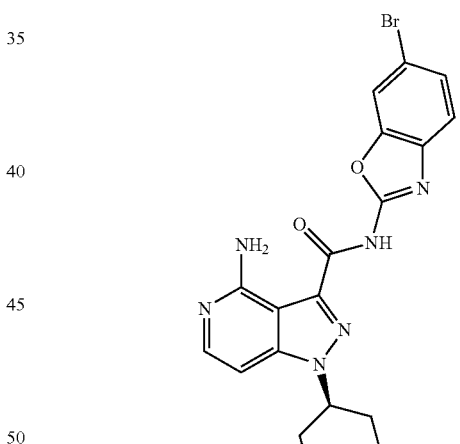

After tert-butyl(R)-3-(4-amino-3-((6-bromobenzo[d]oxazol-2-yl)carbamoyl)-1H-pyrazolo[4,3-c]pyridin-1-yl)piperidine-1-carboxylate (15.0 mg, 1.0 eq) obtained in step 73-1 was dissolved in anhydrous ethyl acetate (5.0 mL), 1.0M hydrochloric acid ethyl acetate solution (135.0 μL, 5.0 eq) was added thereto at room temperature. The reaction mixture was allowed to react at room temperature for 12 hours, then concentrated under reduced pressure and the obtained title compound was used in the next reaction without filtration.

Step 73-3: Preparation of (R)-1-(1-acryloylpiperidin-3-yl)-4-amino-N-(6-bromobenzo[d]oxazol-2-yl)-1H-pyrazolo[4,3-c]pyridine-3-carboxamide

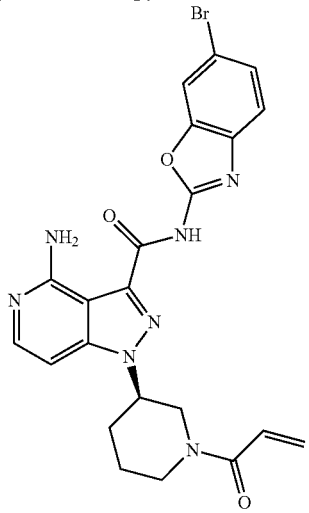

After (R)-4-amino-N-(6-bromobenzo[d]oxazol-2-yl)-1-(piperidin-3-yl)-1H-pyrazolo[4,3-c]pyridine-3-carboxamide (13.3 mg, 1.0 eq) obtained in step 73-2 was dissolved in tetrahydrofuran (5.0 mL) and water (1.0 mL), sodium hydrogen carbonate (9.1 mg, 4.0 eq) was added thereto at room temperature and reacted for 30 minutes. Acryloyl chloride (2.2 μL, 1.0 eq) was added to the mixture at room temperature. The reaction mixture was allowed to react at room temperature for 10 minutes, then methanol was added and the mixture was extracted with water and ethyl acetate. The separated organic layer was dried over magnesium sulfate and then concentrated under reduced pressure. The resulting residue was purified by column chromatography (dichloromethane:methanol=10:1) to obtain 3.2 mg (yield: 23.2%) of the title compound as a white solid.

¹HNMR(500 MHz, MeOD): 7.78-7.59 (m, 3H), 7.66-7.59 (m, 2H), 6.90-6.81 (m, 1H), 6.29-6.20 (m, 1H), 5.83-5.78 (m, 1H), 5.34 (t, 1H), 4.65-4.59 (m, 1H), 3.89-3.70 (m, 2H), 3.50-3.40 (m, 1H), 3.00-2.95 (m, 1H), 2.50-2.42 (m, 1H), 2.30-2.13 (m, 3H), 1.73-1.58 (m, 1H)

MS m/z: 373.29 [m+1]

Example 74: Preparation of (R)-1-(1-acryloylpiperidin-3-yl)-4-amino-7-chloro-N-(5-chlorobenzo[d]oxazol-2-yl)-1H-pyrazolo[4,3-c]pyridine-3-carboxamide

Step 74-1: Preparation of methyl (R)-4-amino-1-(1-(tert-butoxycarbonyl)piperidin-3-yl)-7-chloro-1H-pyrazolo[4,3-c]pyridine-3-carboxylate

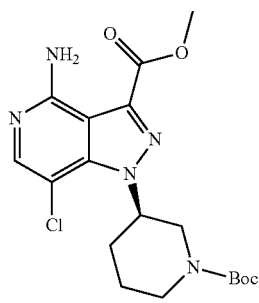 [SMILES: COC(=O)c1nn([C@@H]2CCCN(C(=O)OC(C)(C)C)C2)c2c(Cl)cnc(N)c12]

After methyl (R)-4-amino-1-(1-(tert-butoxycarbonyl)piperidin-3-yl)-1H-pyrazolo[4,3-c]pyridine-3-carboxylate (1000.0 mg, 1.0 eq) was dissolved in anhydrous dimethylformamide (10.0 mL), N-chlorosuccinimide (391.2 mg, 1.1 eq) was added thereto at room temperature, and the reaction mixture was allowed to react at room temperature for 4 hours. Then, water was added and the mixture was extracted with ethyl acetate. The separated organic layer was dried over magnesium sulfate and then concentrated under reduced pressure. The resulting residue was purified by column chromatography (ethyl acetate:hexane=1:1>1:0) to obtain 600.0 mg (yield: 55.0%) of the title compound as a yellow solid.

Step 74-2: Preparation of (R)-4-amino-1-(1-(tert-butoxycarbonyl)piperidin-3-yl)-7-chloro-1H-pyrazolo[4,3-c]pyridine-3-carboxylic acid

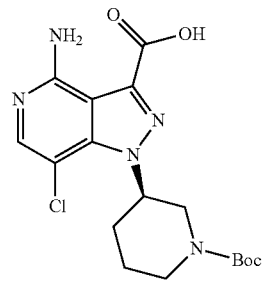 [SMILES: CC(C)(C)OC(=O)N1CCC[C@@H](n2nc(C(=O)O)c3c(N)ncc(Cl)c32)C1]

After methyl (R)-4-amino-1-(1-(tert-butoxycarbonyl)piperidin-3-yl)-7-chloro-1H-pyrazolo[4,3-c]pyridine-3-carboxylate (600.0 mg, 1.0 eq) obtained in step 74-1 was dissolved in water (5.0 mL) and methanol (5.0 mL), sodium hydroxide (585.6 mg, 10.0 eq) was added thereto at room temperature. The reaction mixture was allowed to react at room temperature for 4 hours and then concentrated under reduced pressure. The obtained compound was adjusted to pH 4.0 using 1N aqueous hydrochloric acid solution, and then the obtained solid compound was filtered and washed with water to obtain 490.0 mg (yield: 84.8%) of a white title compound.

Step 74-3: Preparation of tert-butyl (R)-3-(4-amino-7-chloro-3-((5-chlorobenzo[d]oxazol-2-yl)carbamoyl)-1H-pyrazolo[4,3-c]pyridin-1-yl)piperidine-1-carboxylate

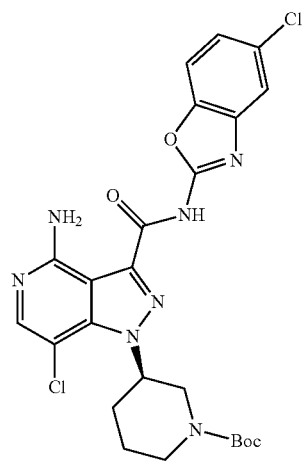 [SMILES: CC(C)(C)OC(=O)N1CCC[C@@H](n2nc(C(=O)Nc3nc4cc(Cl)ccc4o3)c3c(N)ncc(Cl)c32)C1]

After (R)-4-amino-1-(1-(tert-butoxycarbonyl)piperidin-3-yl)-7-chloro-1H-pyrazolo[4,3-c]pyridine-3-carboxylic acid (200.0 mg, 1.0 eq) obtained in step 74-2 was dissolved in anhydrous dimethylacetamide (5.0 mL) in a reaction vessel 1,1,1'-carbonyldiimidazole (106.5 mg, 1.3 eq) was added thereto at room temperature and the reaction mixture was allowed to react at room temperature for 1 hour. After 5-chlorobenzo[d]oxazol-2-amine (110.7 mg, 1.3 eq) was dissolved in anhydrous dimethylacetamide (5.0 mL) in a reaction vessel 2, sodium hydride (26.3 mg, 1.3 eq) was added thereto at room temperature and the reaction mixture was allowed to react at room temperature for 1 hour. The mixture that was reacted in the reaction vessel 2 was added to the reaction vessel 1 and reacted at room temperature for 1 hour. Water was added and the mixture was extracted with ethyl acetate. The separated organic layer was dried over magnesium sulfate and then concentrated under reduced pressure. The resulting residue was purified by column chromatography (dichloromethane:methanol=10:1) to obtain 35.0 mg (yield: 12.6%) of the title compound as a brown solid.

Step 74-4: Preparation of (R)-1-(1-acryloylpiperidin-3-yl)-4-amino-7-chloro-N-(5-chlorobenzo[d]oxazol-2-yl)-1H-pyrazolo[4,3-c]pyridine-3-carboxamide

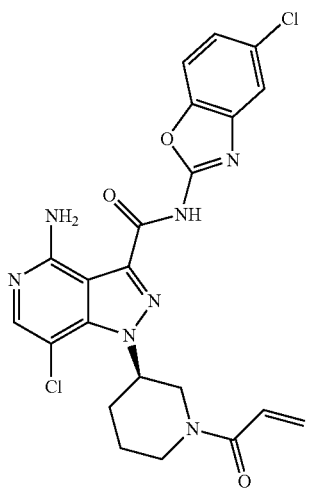 [SMILES: C=CC(=O)N1CCC[C@@H](n2nc(C(=O)Nc3nc4cc(Cl)ccc4o3)c3c(N)ncc(Cl)c32)C1]

After tert-butyl (R)-3-(4-amino-7-chloro-3-((5-chlorobenzo[d]oxazol-2-yl)carbamoyl)-1H-pyrazolo[4,3-c]pyridin-1-yl)piperidine-1-carboxylate (35.0 mg, 1.0 eq) obtained in step 74-3 was dissolved in anhydrous 1,4-dioxane (5.0 mL), 1.0M hydrochloric acid 1,4-dioxane solution (160.0 μL, 5.0 eq) was added thereto at room temperature. The reaction mixture was allowed to react at room temperature for 1 hour, then concentrated under reduced pressure, dissolved in chloroform (5.0 mL), to which triethylamine (89.2 μL, 1.0 eq) and acryloyl chloride (5.2 μL, 1.0 eq) were added at room temperature. The reaction mixture was allowed to react at room temperature for 1 hour, and then concentrated under reduced pressure, and the resulting residue was purified by column chromatography (dichloromethane:methanol=10:1) to obtain 7.8 mg (yield: 24.4%) of the title compound as a brown solid.

$^1$HNMR(500 MHz, MeOD): 7.78-7.60 (m, 2H), 7.49-7.38 (m, 1H), 7.28-7.10 (m, 1H), 6.89-6.73 (m, 1H), 6.30-6.13 (m, 1H), 5.84-5.70 (m, 1H), 5.24-5.28 (m, 1H), 4.58-4.36 (m, 2H), 4.23-4.19 (m, 1H), 3.80-3.61 (m, 1H), 2.40-2.13 (m, 3H), 1.73-1.58 (m, 1H)

MS m/z: 502.14 [m+1]

Example 75: Preparation of (R)-1-(1-acryloylpiperidin-3-yl)-4-amino-N-(benzo[d]oxazol-2-yl)-7-chloro-1H-pyrazolo[4,3-c]pyridine-3-carboxamide Step 75-1: Preparation of tert-butyl (R)-3-(4-amino-3-(benzo[d]oxazol-2-ylcarbamoyl)-7-chloro-1H-pyrazolo[4,3-c]pyridin-1-yl)piperidine-1-carboxylate

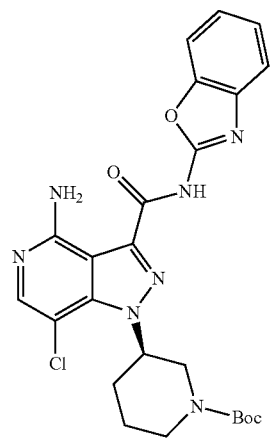 [SMILES: CC(C)(C)OC(=O)N1CCC[C@@H](n2nc(C(=O)Nc3nc4ccccc4o3)c3c(N)ncc(Cl)c32)C1]

After (R)-4-amino-1-(1-(tert-butoxycarbonyl)piperidin-3-yl)-7-chloro-1H-pyrazolo[4,3-c]pyridine-3-carboxylic acid (200.0 mg, 1.0 eq) obtained in step 74-2 was dissolved in anhydrous dimethylacetamide (5.0 mL) in a reaction vessel 1,1,1'-carbonyldiimidazole (122.9 mg, 1.5 eq) was added thereto at room temperature and the reaction mixture was allowed to react at room temperature for 2 hours. After benzo[d]oxazol-2-amine (101.7 mg, 1.5 eq) was dissolved in anhydrous dimethylacetamide (5.0 mL) in a reaction vessel 2, sodium hydride (30.0 mg, 1.5 eq) was added thereto at room temperature and the reaction mixture was allowed to react at room temperature for 2 hours. The mixture that was reacted in the reaction vessel 2 was added to the reaction vessel 1 and reacted at room temperature for 1 hour. Water was added and the mixture was extracted with ethyl acetate. The separated organic layer was dried over magnesium sulfate and then concentrated under reduced pressure. The resulting residue was purified by column chromatography (dichloromethane:methanol=10:1) to obtain 131.0 mg (yield: 50.2%) of the title compound as a brown solid.

Step 75-2: Preparation of (R)-1-(1-acryloylpiperidin-3-yl)-4-amino-N-(benzo[d]oxazol-2-yl)-7-chloro-1H-pyrazolo[4,3-c]pyridine-3-carboxamide

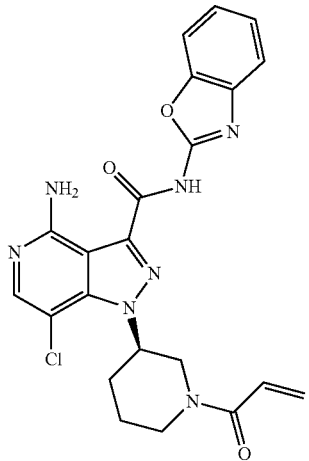 [SMILES: C=CC(=O)N1CCC[C@@H](n2nc(C(=O)Nc3nc4ccccc4o3)c3c(N)ncc(Cl)c32)C1]

After tert-butyl (R)-3-(4-amino-3-(benzo[d]oxazol-2-ylcarbamoyl)-7-chloro-1H-pyrazolo[4,3-c]pyridin-1-yl)piperidine-1-carboxylate (120.0 mg, 1.0 eq) obtained in step 75-1 was dissolved in anhydrous 1,4-dioxane (5.0 mL), 4.0M hydrochloric acid 1,4-dioxane solution (0.6 mL, 10.0 eq) was added thereto at room temperature. The reaction mixture was allowed to react at room temperature for 4 hours, concentrated under reduced pressure, dissolved in chloroform (5.0 mL), and then triethylamine (163.3 µL, 1.0 eq) and acryloyl chloride (19.1 µL, 1.0 eq) were added thereto at 0° C. The reaction mixture was reacted at 0° C. for 90 minutes, concentrated under reduced pressure, and the residue was purified by column chromatography (dichloromethane:methanol=10:1) to obtain 35.0 mg (yield: 32.7%) of the title compound as a brown solid.

$^1$HNMR(500 MHz, MeOD): 7.94 (s, 1H), 7.71-7.37 (m, 5H), 6.68-6.83 (m, 1H), 6.29-6.23 (m, 1H), 5.81-5.74 (m, 1H), 5.47-5.39 (m, 1H), 4.85-4.76 (m, 1H), 4.63-4.50 (m, 1H), 4.18-4.05 (m, 1H), 3.78-3.68 (m, 1H), 3.10-2.96 (m, 1H), 2.57-2.30 (m, 2H), 2.1-2.04 (m, 1H)

MS m/z: 466.13 [m+1]

Example 76: Preparation of (R)-1-(1-acryloylpiperidin-3-yl)-4-amino-7-chloro-N-(5-fluorobenzo[d]oxazol-2-yl)-1H-pyrazolo[4,3-c]pyridine-3-carboxamide Step 76-1: Preparation of tert-butyl (R)-3-(4-amino-7-chloro-3-((5-fluorobenzo[d]oxazol-2-yl)carbamoyl)-1H-pyrazolo[4,3-c]pyridin-1-yl)piperidine-1-carboxylate

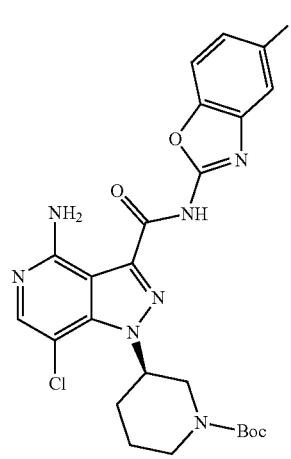

After (R)-4-amino-1-(1-(tert-butoxycarbonyl)piperidin-3-yl)-7-chloro-1H-pyrazolo[4,3-c]pyridine-3-carboxylic acid (200.0 mg, 1.0 eq) obtained in step 74-2 was dissolved in anhydrous dimethylacetamide (5.0 mL) in a reaction vessel 1,1,1'-carbonyldiimidazole (122.9 mg, 1.5 eq) was added thereto at room temperature and the reaction mixture was allowed to react at room temperature for 2 hours. After 5-fluorobenzo[d]oxazol-2-amine (115.3 mg, 1.5 eq) was dissolved in anhydrous dimethylacetamide (5.0 mL) in a reaction vessel 2, sodium hydride (30.0 mg, 1.5 eq) was added thereto at room temperature and the reaction mixture was allowed to react at room temperature for 2 hours. The mixture that was reacted in the reaction vessel 2 was added to the reaction vessel 1 and reacted at room temperature for 1 hour. Water was added and the mixture was extracted with ethyl acetate. The separated organic layer was dried over magnesium sulfate and then concentrated under reduced pressure. The resulting residue was purified by column chromatography (dichloromethane:methanol=10:1) to obtain 45.0 mg (yield: 16.6%) of the title compound as a white solid.

Step 76-2: Preparation of (R)-4-amino-7-chloro-N-(5-fluorobenzo[d]oxazol-2-yl)-1-(piperidin-3-yl)-1H-pyrazolo[4,3-c]pyridine-3-carboxamide

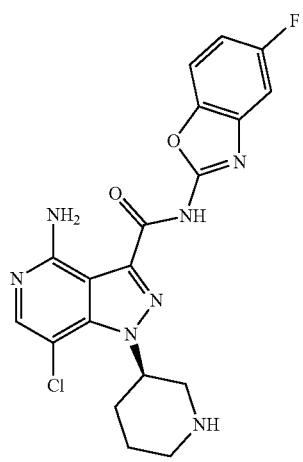 [SMILES: Nc1ncc(Cl)c2c1c(C(=O)Nc1nc3cc(F)ccc3o1)nn2[C@@H]1CCCNC1]

After tert-butyl (R)-3-(4-amino-7-chloro-3-((5-fluorobenzo[d]oxazol-2-yl)carbamoyl)-1H-pyrazolo[4,3-c]pyridin-1-yl)piperidine-1-carboxylate (45.0 mg, 1.0 eq) obtained in step 76-1 was dissolved in anhydrous ethyl acetate (5.0 mL), 1.0M hydrochloric acid ethyl acetate solution (0.9 mL, 10.0 eq) was added thereto at room temperature. The reaction mixture was allowed to react at room temperature for 12 hours, then concentrated under reduced pressure, and the obtained title compound was used in the next reaction without filtration.

Step 76-3: Preparation of (R)-1-(1-acryloylpiperidin-3-yl)-4-amino-7-chloro-N-(5-fluorobenzo[d]oxazol-2-yl)-1H-pyrazolo[4,3-c]pyridine-3-carboxamide

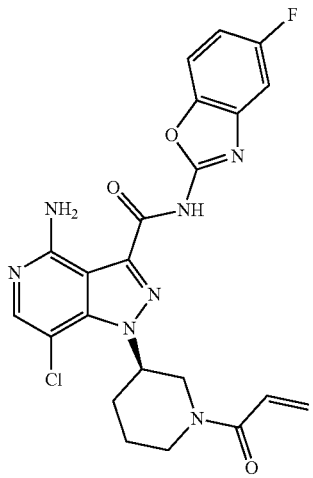 [SMILES: C=CC(=O)N1CCC[C@@H](n2nc(C(=O)Nc3nc4cc(F)ccc4o3)c3c(N)ncc(Cl)c32)C1]

After (R)-4-amino-7-chloro-N-(5-fluorobenzo[d]oxazol-2-yl)-1-(piperidin-3-yl)-1H-pyrazolo[4,3-c]pyridine-3-carboxamide (39.6 mg, 1.0 eq) obtained in step 76-2 was dissolved in chloroform (5.0 mL), triethylamine (35.6 μL, 3.0 eq) was added thereto at room temperature. Acryloyl chloride (6.9 μL, 1.0 eq) was added to the mixture at 0° C., and the reaction mixture was allowed to react at 0° C. for 1 hour, followed by extraction with water and ethyl acetate. The separated organic layer was dried over magnesium sulfate and then concentrated under reduced pressure. The resulting residue was purified by column chromatography (dichloromethane:methanol=10:1) to obtain 4.8 mg (yield: 11.7%) of the title compound as a brown solid.

$^1$H NMR (500 MHz, CDCl$_3$): 7.83 (d, 1H), 7.61-7.48 (m, 2H), 7.22-6.97 (m, 1H), 6.75 (t, 1H), 6.72-6.20 (m, 2H), 5.82-5.25 (m, 2H), 4.48-4.15 (m, 1H), 4.05-3.60 (m, 2H), 3.39-3.18 (m, 1H), 2.72-2.41 (m, 1H), 2.38-2.08 (m, 2H), 1.85-1.50 (m, 1H)

MS m/z: 484.20 [m+1]

Example 77: Preparation of (R)-1-(1-acryloylpiperidin-3-yl)-4-amino-N-(benzo[d]oxazol-2-yl)-1H-pyrazolo[4,3-c]pyridine-3-carboxamide Step 77-1: Preparation of tert-butyl (R)-3-(4-amino-3-(benzo[d]oxazol-2-ylcarbamoyl)-1H-pyrazolo[4,3-c]pyridin-1-yl)piperidine-1-carboxylate

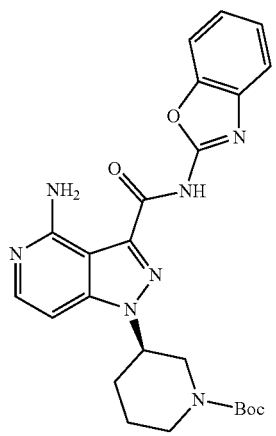 [SMILES: CC(C)(C)OC(=O)N1CCC[C@@H](n2nc(C(=O)Nc3nc4ccccc4o3)c3c(N)nccc32)C1]

After (R)-4-amino-1-(1-(tert-butoxycarbonyl)piperidin-3-yl)-1H-pyrazolo[4,3-c]pyridine-3-carboxylic acid (50.0 mg, 1.0 eq) obtained in step 71-2 was dissolved in anhydrous dimethylacetamide (5.0 mL) in a reaction vessel 1,1,1'-carbonyldiimidazole (29.2 mg, 1.3 eq) was added thereto at room temperature and the reaction mixture was allowed to react at room temperature for 1 hour. After benzo[d]oxazol-2-amine (24.1 mg, 1.3 eq) was dissolved in anhydrous dimethylacetamide (5.0 mL) in a reaction vessel 2, sodium hydride (7.2 mg, 1.3 eq) was added thereto at room temperature and the reaction mixture was allowed to react at room temperature for 1 hour. The mixture that was reacted in the reaction vessel 2 was added to the reaction vessel 1 and then reacted at room temperature for 1 hour. Water was added and the mixture was extracted with ethyl acetate. The separated organic layer was dried over magnesium sulfate and then concentrated under reduced pressure. The resulting residue was purified by column chromatography (dichloromethane:methanol=10:1) to obtain 11.0 mg (yield: 16.7%) of the title compound as a brown solid.

Step 77-2: Preparation of (R)-4-amino-N-(benzo[d]oxazol-2-yl)-1-(piperidin-3-yl)-1H-pyrazolo[4,3-c]pyridine-3-carboxamide

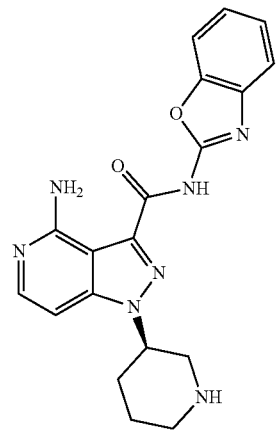 [SMILES: Nc1nccc2c1c(C(=O)Nc1nc3ccccc3o1)nn2[C@@H]1CCCNC1]

After tert-butyl (R)-3-(4-amino-3-(benzo[d]oxazol-2-ylcarbamoyl)-1H-pyrazolo[4,3-c]pyridin-1-yl)piperidine-1-carboxylate (11.0 mg, 1.0 eq) obtained in step 77-1 was dissolved in anhydrous ethyl acetate (5.0 mL), 1.0M hydrochloric acid ethyl acetate solution (230.0 μL, 10.0 eq) was added thereto at room temperature. The reaction solution was allowed to react at room temperature for 12 hours and then concentrated under reduced pressure, and the obtained compound was used in the next reaction without filtration.

Step 77-3: Preparation of (R)-1-(1-acryloylpiperidin-3-yl)-4-amino-7-chloro-N-phenyl-1H-pyrazolo[4,3-c]pyridine-3-carboxamide

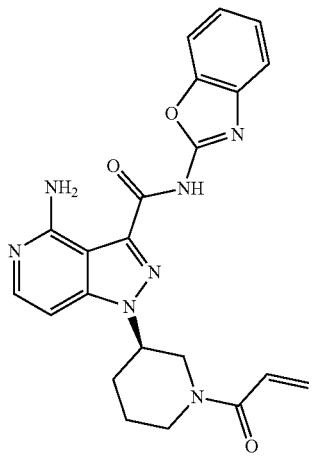 [SMILES: C=CC(=O)N1CCC[C@@H](n2nc(C(=O)Nc3nc4ccccc4o3)c3c(N)nccc32)C1]

After (R)-4-amino-N-(benzo[d]oxazol-2-yl)-1-(piperidin-3-yl)-1H-pyrazolo[4,3-c]pyridine-3-carboxamide (9.5 mg, 1.0 eq) obtained in step 77-2 was dissolved in dichloromethane (5.0 mL), triethylamine (12.8 µL, 3.0 eq) was added thereto at room temperature and allowed to react for 30 minutes. Acryloyl chloride (1.9 µL, 1.0 eq) was added to the mixture at room temperature. The reaction mixture was allowed to react at room temperature for 30 minutes, then methanol was added and the mixture was extracted with water and ethyl acetate. The separated organic layer was dried over magnesium sulfate and then concentrated under reduced pressure. The resulting residue was purified by column chromatography (dichloromethane:methanol=10:1) to obtain 3.5 mg (yield: 20.2%) of the title compound as a white solid.

$^1$HNMR(500 MHz, CDCl$_3$): 7.83 (d, 1H), 7.61-7.48 (m, 2H), 7.22-6.97 (m, 1H), 6.75 (t, 1H), 6.72-6.20 (m, 2H), 5.82-5.25 (m, 2H), 4.48-4.15 (m, 1H), 4.05-3.60 (m, 2H), 3.39-3.18 (m, 1H), 2.72-2.41 (m, 1H), 2.38-2.08 (m, 2H), 1.85-1.50 (m, 1H)

MS m/z: 430.21 [m+1]

Example 78: Preparation of (R)-1-(1-acryloylpiperidin-3-yl)-4-amino-7-chloro-N-phenyl-1H-pyrazolo[4,3-c]pyridine-3-carboxamide

Step 78-1: Preparation of tert-butyl (R)-3-(4-amino-7-chloro-3-(phenylcarbamoyl)-1H-pyrazolo[4,3-c]pyridin-1-yl)piperidine-1-carboxylate

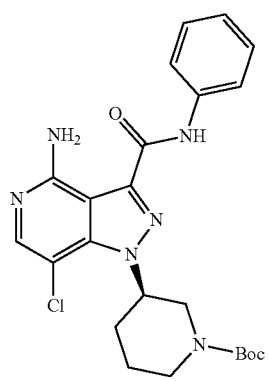 [SMILES: CC(C)(C)OC(=O)N1CCC[C@@H](n2nc(C(=O)Nc3ccccc3)c3c(N)ncc(Cl)c32)C1]

After (R)-4-amino-1-(1-(tert-butoxycarbonyl)piperidin-3-yl)-7-chloro-1H-pyrazolo[4,3-c]pyridine-3-carboxylic acid (100.0 mg, 1.0 eq) obtained in step 74-2 was dissolved in in anhydrous dimethylacetamide (5.0 mL) in a reaction vessel 1,1,1'-carbonyldiimidazole (53.3 mg, 1.3 eq) was added thereto at room temperature and the reaction mixture was allowed to react at room temperature for 1 hour. After aniline (29.9 µL, 1.3 eq) was dissolved in anhydrous dimethylacetamide (5.0 mL) in a reaction vessel 2, sodium hydride (13.1 mg, 1.3 eq) was added thereto at room temperature and the reaction mixture was allowed to react at room temperature for 1 hour. The mixture that was reacted in the reaction vessel 2 was added to the reaction vessel 1 and reacted at room temperature for 1 hour. Water was added and the mixture was extracted with ethyl acetate. The separated organic layer was dried over magnesium sulfate and then concentrated under reduced pressure. The resulting residue was purified by column chromatography (dichloromethane:methanol=10:1) to obtain 8.0 mg (yield: 6.8%) of the title compound as a brown solid.

Step 78-2: Preparation of (R)-4-amino-7-chloro-N-phenyl-1-(piperidin-3-yl)-1H-pyrazolo[4,3-c]pyridine-3-carboxamide

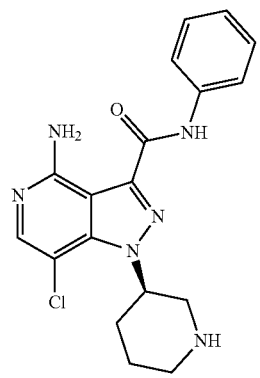 [SMILES: Nc1ncc(Cl)c2c1c(C(=O)Nc1ccccc1)nn2[C@@H]1CCCNC1]

After tert-butyl (R)-3-(4-amino-7-chloro-3-(phenylcarbamoyl)-1H-pyrazolo[4,3-c]pyridin-1-yl)piperidine-1-carboxylate (8.0 mg, 1.0 eq) obtained in step 78-1 was dissolved in anhydrous ethyl acetate (5.0 mL), 1.0M hydrochloric acid ethyl acetate solution (84.9 µL, 5.0 eq) was added thereto at room temperature. The reaction mixture was allowed to react at room temperature for 12 hours, then concentrated under reduced pressure and the obtained title compound was used in the next reaction without filtration.

Step 78-3: Preparation of (R)-1-(1-acryloylpiperidin-3-yl)-4-amino-7-chloro-N-phenyl-1H-pyrazolo[4,3-c]pyridine-3-carboxamide

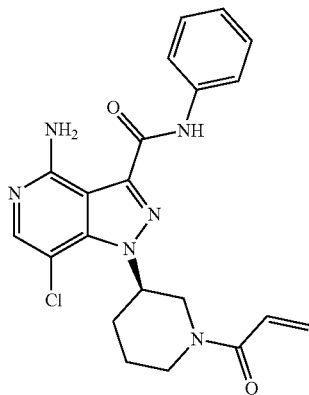 [SMILES: C=CC(=O)N1CCC[C@@H](n2nc(C(=O)Nc3ccccc3)c3c(N)ncc(Cl)c32)C1]

After (R)-4-amino-7-chloro-N-phenyl-1-(piperidin-3-yl)-1H-pyrazolo[4,3-c]pyridine-3-carboxamide (6.9 mg, 1.0 eq) obtained in step 78-2 was dissolved in tetrahydrofuran (2.5 mL) and water (0.5 mL), sodium hydrogen carbonate (5.7 mg, 4.0 eq) was added thereto at room temperature and reacted for 30 minutes. Acryloyl chloride (1.5 µL, 1.1 eq) was added to the mixture at room temperature. The reaction mixture was allowed to react at room temperature for 10 minutes, then methanol was added and the mixture was extracted with water and ethyl acetate. The separated organic layer was dried over magnesium sulfate and then concentrated under reduced pressure. The resulting residue was purified by column chromatography (dichloromethane:methanol=10:1) to obtain 0.8 mg (yield: 2.7%) of the title compound as a brown solid.

$^1$HNMR(500 MHz, MeOD): 7.83-7.79 (m, 1H), 7.75-7.70 (m, 1H), 7.68-7.60 (m, 2H), 7.48-7.38 (m, 1H), 7.36-7.30 (m, 1H), 7.15-7.10 (t, 1H), 6.34 (d, 1H), 5.77 (d, 1H), 4.60-4.51 (m, 1H), 4.80-4.68 (m, 1H), 4.15-3.88 (m, 2H), 2.50-2.25 (m, 2H), 2.10-1.56 (m, 2H)

MS m/z: 425.44 [m+1]

Example 79: Preparation of (R)-1-(1-acryloylpiperidin-3-yl)-4-amino-7-chloro-N-(2,3-di hydrobenzo[b][1,4]dioxin-6-yl)-1H-pyrazolo[4,3-c]pyridine-3-carboxamide

Step 79-1: Preparation of tert-butyl (R)-3-(4-amino-7-chloro-3-((2,3-dihydrobenzo[b][1,4]dioxin-6-yl)carbamoyl)-1H-pyrazolo[4,3-c]pyridin-1-yl)piperidine-1-carboxylate

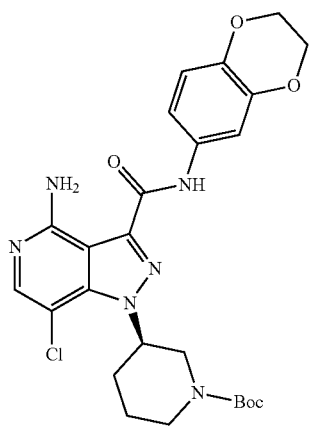 [SMILES: CC(C)(C)OC(=O)N1CCC[C@@H](n2nc(C(=O)Nc3ccc4c(c3)OCCO4)c3c(N)ncc(Cl)c32)C1]

After (R)-4-amino-1-(1-(tert-butoxycarbonyl)piperidin-3-yl)-7-chloro-1H-pyrazolo[4,3-c]pyridine-3-carboxylic acid (100.0 mg, 1.0 eq) obtained in step 74-2 was dissolved in anhydrous dimethylacetamide (5.0 mL) in a reaction vessel 1,1,1'-carbonyldiimidazole (53.3 mg, 1.3 eq) was added thereto at room temperature and the reaction mixture was allowed to react at room temperature for 1 hour. After 2,3-dihydrobenzo[b][1,4]dioxin-6-amine (49.7 mg, 1.3 eq) was dissolved in anhydrous dimethylacetamide (5.0 mL) in a reaction vessel 2, sodium hydride (13.1 mg, 1.3 eq) was added thereto at room temperature and the reaction mixture was allowed to react at room temperature for 1 hour. The mixture that was reacted in the reaction vessel 2 was added to the reaction vessel 1 and then reacted at room temperature for 1 hour. Water was added and the mixture was extracted with ethyl acetate. The separated organic layer was dried over magnesium sulfate and then concentrated under reduced pressure. The resulting residue was purified by column chromatography (dichloromethane:methanol=10:1) to obtain 28.0 mg (yield: 21.2%) of the title compound as a brown solid.

Step 79-2: Preparation of (R)-4-amino-7-chloro-N-(2,3-dihydrobenzo[b][1,4]dioxin-6-yl)-1-(piperidin-3-yl)-1H-pyrazolo[4,3-c]pyridine-3-carboxamide

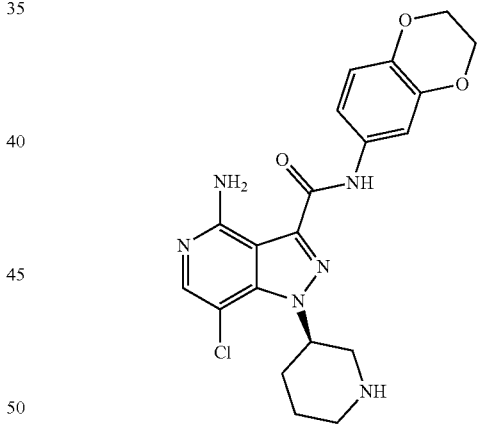

After tert-butyl (R)-3-(4-amino-7-chloro-3-((2,3-dihydrobenzo[b][1,4]dioxin-6-yl)carbamoyl)-1H-pyrazolo[4,3-c]pyridin-1-yl)piperidine-1-carboxylate (28.0 mg, 1.0 eq) obtained in step 79-1 was dissolved in anhydrous ethyl acetate (5.0 mL), 1.0M hydrochloric acid ethyl acetate solution (0.3 mL, 5.0 eq) was added thereto at room temperature. The reaction mixture was allowed to react at room temperature for 12 hours and then concentrated under reduced pressure, and the obtained title compound was used in the next reaction without filtration.

Step 79-3: Preparation of (R)-1-(1-acryloylpiperidin-3-yl)-4-amino-7-chloro-N-(2,3-dihydrobenzo[b][1,4]dioxin-6-yl)-1H-pyrazolo[4,3-c]pyridine-3-carboxamide

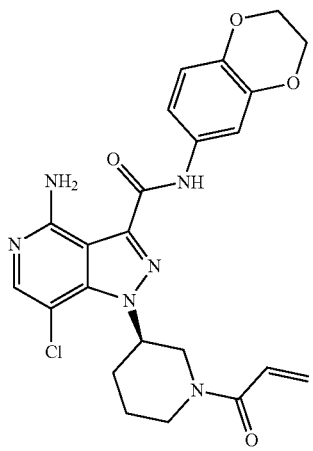 [SMILES: C=CC(=O)N1CCC[C@@H](n2nc(C(=O)Nc3ccc4c(c3)OCCO4)c3c(N)ncc(Cl)c32)C1]

After (R)-4-amino-7-chloro-N-(2,3-dihydrobenzo[b][1,4]dioxin-6-yl)-1-(piperidin-3-yl)-1H-pyrazolo[4,3-c]pyridine-3-carboxamide (24.6 mg, 1.0 eq) obtained in step 79-2 was dissolved in tetrahydrofuran (2.5 mL) and water (0.5 mL), sodium hydrogen carbonate (17.8 mg, 4.0 eq) was added thereto at room temperature and reacted for 30 minutes. Acryloyl chloride (4.7 μL, 1.1 eq) was added to the mixture at room temperature. The reaction mixture was allowed to react at room temperature for 10 minutes, then methanol was added thereto and the mixture was extracted with water and ethyl acetate. The separated organic layer was dried over magnesium sulfate and then concentrated under reduced pressure. The resulting residue was purified by column chromatography (dichloromethane:methanol=10:1) to obtain 1.7 mg (yield: 6.7%) of the title compound as a brown solid.

$^1$HNMR(500 MHz, MeOD): 7.72-7.61 (m, 2H), 7.89-6.73 (m, 2H), 6.27-6.18 (m, 1H), 5.80-5.65 (m, 1H), 5.51-5.35 (m, 1H), 4.58-4.51 (m, 1H), 4.32-4.15 (m, 5H), 4.03-3.92 (m, 1H), 3.56-3.41 (m, 1H), 2.47-2.30 (m, 2H), 2.48-1.90 (m, 2H), 1.79-1.66 (m, 1H)

MS m/z: 483.28 [m+1]

Experimental Example: BTK and ITK Inhibitory Activity

The inhibitory activity against BTK and ITK of the compounds prepared in Examples above were measured as follows.

The inhibitory activity against BTK was evaluated using 'ADP-Glo™+BTK Kinase enzyme system' kit from Promega. In white 96-well plate, 10 uL of BTK enzyme prepared at a final concentration of 1 ng/uL was mixed with 5 μL of compounds with a final compound concentration of 1 uM for a single concentration evaluation of compounds, or with concentrations of 1000, 300, 100, 30, 10, 3, 1, 0.3, 0.1, 0.03 nM for IC$_{50}$ evaluation and then allowed to react at room temperature for 15 minutes. 5 uL of substrate and 5 uL of ATP prepared at a final concentration of 10 uM were added to all wells of the plate after completion of the reaction, and allowed to react at 30° C. for 1 hour. All wells of the plate after completion of the reaction were treated with 25 uL of ADP-Glo™ reagent and reacted at 30° C. for 40 minutes. Then, 50 uL of the kinase detection buffer was applied to all wells of the plate, and then the light was blocked and reacted at 30° C. for 30 minutes. For the plate for which all reactions were completed, the luminescence was measured and the results were calculated. The evaluation was performed in duplicate. The respective values of negative and positive controls, depending on whether the enzymes were added without treatment of the compound, were determined, and IC$_{50}$ was calculated based on the values.

The inhibitory activity against ITK was evaluated using 'ADP-Glo™+ITK Kinase enzyme system' kit from Promega. In white 96-well plate, 10 uL of ITK enzyme prepared at a final concentration of 0.4 ng/uL was mixed with 5 μL of compounds with a final concentration of 1 uM for a single concentration evaluation of compounds, or with concentrations of 1000, 300, 100, 30, 10, 3, 1, 0.3, 0.1, 0.03 nM for IC$_{50}$ evaluation and then allowed to react at room temperature for 15 minutes. 5 uL of substrate and 5 uL of ATP prepared at a final concentration of 25 uM were added to all wells of the plate after completion of the reaction, and allowed to react at 30° C. for 1 hour. All wells of the plate after completion of the reaction were treated with 25 uL of ADP-Glo™ reagent and reacted at 30° C. for 40 minutes. Then, 50 uL of the kinase detection buffer was applied to all wells of the plate, and then the light was blocked and reacted at 30° C. for 30 minutes. For the plate for which all reactions were completed, the luminescence was measured and the results were calculated. The evaluation was performed in duplicate. The respective values of negative and positive controls, depending on whether the enzymes were added without treatment of the compound, were determined, and IC$_{50}$ was calculated based on the values. The results are shown in Table 1 below.

TABLE 1

| | BTK IC$_{50}$ (nM) | ITK IC$_{50}$ (nM) |
| --- | --- | --- |
| Example 1 | 1.4 | 37.7 |
| Example 2 | 3.5 | 15.7 |
| Example 3 | 2.7 | >1000 |
| Example 4 | 5.5 | 276.7 |
| Example 5 | 6.7 | 19.5 |
| Example 6 | 29.9 | 287.6 |
| Example 7 | 3.0 | 36.4 |
| Example 8 | 7.3 | >500 |
| Example 9 | 1.5 | 11.3 |
| Example 10 | 2.1 | 10.8 |
| Example 11 | 11.4 | 223.6 |
| Example 12 | 7.7 | >1000 |
| Example 13 | 5.1 | >1000 |
| Example 14 | 4.1 | 38.4 |
| Example 15 | 3.7 | >500 |
| Example 16 | 1.0 | 2.7 |
| Example 17 | 14.0 | 13.4 |
| Example 18 | 1.0 | 26.4 |
| Example 19 | 1.7 | 7.8 |
| Example 20 | 15.2 | >1000 |
| Example 21 | 10.7 | >1000 |
| Example 22 | 2.5 | 130.6 |
| Example 23 | 1.2 | 48.0 |
| Example 24 | 1.2 | 36.8 |
| Example 25 | 1.5 | 39.5 |
| Example 26 | 2.7 | 59.3 |
| Example 27 | 8.0 | >500 |
| Example 28 | 4.4 | 180.8 |
| Example 29 | 3.1 | 555.7 |
| Example 30 | 3.0 | 490.2 |
| Example 31 | 15.9 | 375.6 |
| Example 32 | 6.2 | 199.5 |
| Example 33 | 10.2 | 306.8 |

TABLE 1-continued

| | BTK IC$_{50}$ (nM) | ITK IC$_{50}$ (nM) |
|---|---|---|
| Example 34 | 2.3 | 293.4 |
| Example 35 | 1.9 | 61 |
| Example 36 | 1.5 | 89 |
| Example 37 | 3.0 | 91.3 |
| Example 38 | 2.6 | 186.4 |
| Example 39 | 3.5 | >1000 |
| Example 40 | 2.7 | 6.4 |
| Example 41 | 1.5 | 10.1 |
| Example 42 | 66.3 | 240.8 |
| Example 43 | 2.5 | 146.3 |
| Example 44 | >1.56 | 104.6 |
| Example 45 | 11.2 | 66.8 |
| Example 46 | >400 | >1000 |
| Example 47 | 179.8 | >1000 |
| Example 48 | >400 | >1000 |
| Example 49 | 1.2 | 3.3 |
| Example 50 | 1.3 | 2.1 |
| Example 51 | 0.5 | 30.8 |
| Example 52 | 1.6 | 51.6 |
| Example 53 | 0.5 | 4.3 |
| Example 54 | 77.5 | >1000 |
| Example 55 | 6.4 | 124.1 |
| Example 56 | 0.4 | 0.6 |
| Example 57 | 0.5 | 11.4 |
| Example 58 | 8.8 | 9.3 |
| Example 59 | 3.7 | 26.0 |
| Example 60 | 0.4 | 263.0 |
| Example 61 | 187.1 | >1000 |
| Example 62 | 6.3 | 8.1 |
| Example 63 | 3.1 | 30.1 |
| Example 64 | 1.1 | 22.5 |
| Example 65 | 0.4 | 1.3 |
| Example 66 | 1.3 | 1.3 |
| Example 67 | 2 | 2.7 |
| Example 68 | 0.9 | 1.7 |
| Example 69 | 2 | 2.9 |
| Example 70 | 2 | 5.2 |
| Example 71 | 3.4 | 4.1 |
| Example 72 | 88.9 | 68.2 |
| Example 73 | 32 | 140.8 |
| Example 74 | 3.3 | 6.4 |
| Example 75 | 2.2 | 2.4 |
| Example 76 | 1.5 | 2.1 |
| Example 77 | 5 | 13.1 |
| Example 78 | 22.1 | 27 |
| Example 79 | 100.1 | 54.9 |

The invention claimed is:

1. A compound represented by the following Chemical Formula 1, or a pharmaceutically acceptable salt thereof:

[Chemical Formula 1]

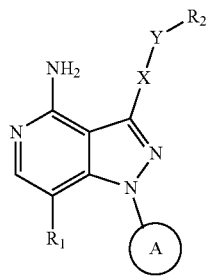

wherein in Chemical Formula 1,
X is a bond, or

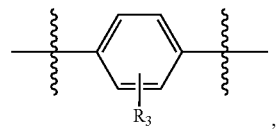

Y is a bond, O, NH, COO, CONH, or CONCO(C$_{2-4}$ alkenyl),
A is

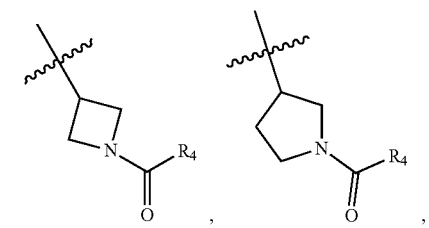

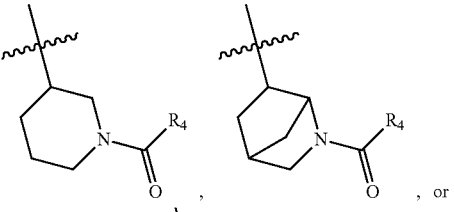

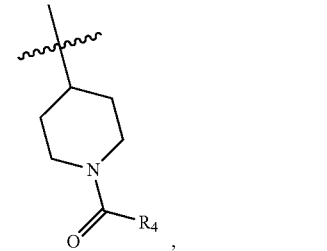

R$_1$ is hydrogen, halogen, C$_{1-4}$ alkyl, C$_{1-4}$ alkyl substituted with hydroxy, C$_{2-4}$ alkenyl, cyano, or -L-R',
wherein L is a bond, NH, C$_{1-4}$ alkylene, or C$_{2-4}$ alkenylene; R' is C$_{6-10}$ aryl, pyrazolyl, thiophenyl, or thiazolyl,
R' is unsubstituted or substituted with halogen, C$_{1-4}$ alkyl, C$_{1-4}$ haloalkyl, tetrahydropyranyl, piperidinyl substituted with C$_{1-4}$ alkyl, —(C$_{1-4}$ alkylene)-N(C$_{1-4}$ alkyl)$_2$, —(C$_{1-4}$ alkylene)-pyrrolidinyl, or —(C$_{1-4}$ alkylene)-morpholino,
R$_2$ is bromo, tert-butyl, unsubstituted phenyl, pyrazolyl substituted with cyclopropyl, unsubstituted benzoxazolyl, benzoxazolyl substituted with halogen, or unsubstituted dihydrobenzodioxinyl,
R$_3$ is hydrogen, halogen, or C$_{1-4}$ alkoxy, and
R$_4$ is C$_{2-4}$ alkenyl, or C$_{2-4}$ alkynyl.

2. The compound, or a pharmaceutically acceptable salt thereof according to claim 1, wherein Y is a bond, O, NH, COO, CONH, or CONCO(CH=CH$_2$).

3. The compound, or a pharmaceutically acceptable salt thereof according to claim 1, wherein
R$_1$ is hydrogen, bromo, chloro, iodo, methyl, ethyl, hydroxymethyl, vinyl, cyano, or -L-R',
wherein L is a bond, NH, CH$_2$, CH=CH, or CH=CHCH$_2$, R' is phenyl unsubstituted or substituted with fluoro; unsubstituted thiophenyl; thiazolyl substituted with methyl; or pyrazolyl unsubstituted or substituted with methyl, difluoromethyl, tetrahydropyranyl, methylpiperidinyl, dimethylaminoethyl, pyrrolidinylethyl, or morpholinoethyl.

4. A compound represented by the following Chemical Formula 1, or a pharmaceutically acceptable salt thereof:

[Chemical Formula 1]

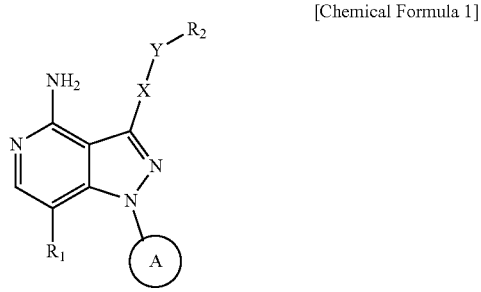

wherein,
X is a bond, or

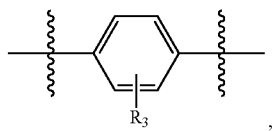

Y is a bond, O, NH, COO, CONH, or CONCO($C_{2-4}$ alkenyl),
A is

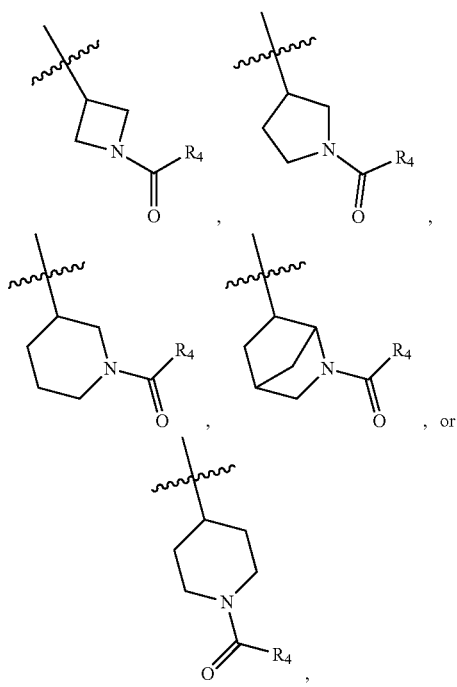

$R_1$ is hydrogen, halogen, $C_{1-4}$ alkyl, $C_{1-4}$ alkyl substituted with hydroxy, $C_{2-4}$ alkenyl, cyano, or -L-R', wherein L is a bond, NH, $C_{1-4}$ alkylene, or $C_{2-4}$ alkenylene; R' is $C_{6-10}$ aryl, pyrazolyl, thiophenyl, or thiazolyl, R' is unsubstituted or substituted with halogen, $C_{1-4}$ alkyl, $C_{1-4}$ haloalkyl, tetrahydropyranyl, piperidinyl substituted with $C_{1-4}$ alkyl, —($C_{1-4}$ alkylene)-N($C_{1-4}$ alkyl)$_2$, —($C_{1-4}$ alkylene)-pyrrolidinyl, or —($C_{1-4}$ alkylene)-morpholino, $R_2$ is unsubstituted pyridinyl or pyridinyl substituted with fluoro, $R_3$ is halogen or $C_{1-4}$ alkoxy, and $R_4$ is $C_{2-4}$ alkenyl, or $C_{2-4}$ alkynyl.

5. The compound, or a pharmaceutically acceptable salt thereof according to claim 1, wherein $R_3$ is hydrogen, fluoro, chloro, or methoxy.

6. The compound, or a pharmaceutically acceptable salt thereof according to claim 1, wherein $R_4$ is —CH=CH$_2$, —C(CH$_3$)=CH$_2$, —C≡CH, or —C≡CCH$_3$.

7. A compound, or a pharmaceutically acceptable salt thereof, wherein the compound is any one selected from the group consisting of:

1) 1-(3-(4-amino-3-(4-phenoxyphenyl)-1H-pyrazolo[4,3-c]pyridin-1-yl)piperidin-1-yl)prop-2-en-1-one,
2) 1-(3-(4-amino-3-(4-phenoxyphenyl)-1H-pyrazolo[4,3-c]pyridin-1-yl)piperidin-1-yl)prop-2-yn-1-one,
3) 1-(4-(4-amino-3-(4-phenoxyphenyl)-1H-pyrazolo[4,3-c]pyridin-1-yl)piperidin-1-yl)prop-2-en-1-one,
4) 1-(4-(4-amino-3-(4-phenoxyphenyl)-1H-pyrazolo[4,3-c]pyridin-1-yl)piperidin-1-yl)prop-2-yn-1-one,
5) 1-(3-(4-amino-7-iodo-3-(4-phenoxyphenyl)-1H-pyrazolo[4,3-c]pyridin-1-yl)piperidin-1-yl)prop-2-en-1-one,
6) 1-(3-(4-amino-7-benzyl-3-(4-phenoxyphenyl)-1H-pyrazolo[4,3-c]pyridin-1-yl)piperidin-1-yl)prop-2-en-1-one,
7) 1-(3-(4-amino-7-(1-methyl-1H-pyrazol-4-yl)-3-(4-phenoxyphenyl)-1H-pyrazolo[4,3-c]pyridin-1-yl)piperidin-1-yl)prop-2-en-1-one,
8) 1-(6-(4-amino-7-(1-methyl-1H-pyrazol-4-yl)-3-(4-phenoxyphenyl)-1H-pyrazolo[4,3-c]pyridin-1-yl)-2-azabicyclo[2.2.1]heptan-2-yl)prop-2-en-1-one,
9) 1-(3-(4-amino-7-chloro-3-(4-phenoxyphenyl)-1H-pyrazolo[4,3-c]pyridin-1-yl)piperidin-1-yl)prop-2-en-1-one,
10) 1-(3-(4-amino-7-bromo-3-(4-phenoxyphenyl)-1H-pyrazolo[4,3-c]pyridin-1-yl)piperidin-1-yl)prop-2-en-1-one,
11) 1-(3-(4-amino-3-(4-phenoxyphenyl)-7-phenyl-1H-pyrazolo[4,3-c]pyridin-1-yl)piperidin-1-yl)prop-2-en-1-one,
12) 1-(4-(4-amino-7-iodo-3-(4-phenoxyphenyl)-1H-pyrazolo[4,3-c]pyridin-1-yl)piperidin-1-yl)prop-2-en-1-one,
13) 1-(4-(4-amino-7-(1-methyl-1H-pyrazol-4-yl)-3-(4-phenoxyphenyl)-1H-pyrazolo[4,3-c]pyridin-1-yl)piperidin-1-yl)prop-2-en-1-one,
14) (E)-1-(3-(4-amino-7-(4-fluorostyryl)-3-(4-phenoxyphenyl)-1H-pyrazolo[4,3-c]pyridin-1-yl)piperidin-1-yl)prop-2-en-1-one,
15) (E)-1-(4-(4-amino-7-(4-fluorostyryl)-3-(4-phenoxyphenyl)-1H-pyrazolo[4,3-c]pyridin-1-yl)piperidin-1-yl)prop-2-en-1-one,
16) (R)-1-(3-(4-amino-7-iodo-3-(4-phenoxyphenyl)-1H-pyrazolo[4,3-c]pyridin-1-yl)piperidin-1-yl)prop-2-en-1-one, 17) (E)-1-(3-(4-amino-3-(4-phenoxyphenyl)-7-(3-phenylprop-1-enyl)-1H-pyrazolo[4,3-c]pyridin-1-yl)piperidin-1-yl)prop-2-en-1-one,
20) (R)-4-(1-(1-acryloylpiperidin-3-yl)-4-amino-7-bromo-1H-pyrazolo[4,3-c]pyridin-3-yl)-N-(pyridin-2-yl)benzamide,
21) (R)-4-(1-(1-acryloylpiperidin-3-yl)-4-amino-7-iodo-1H-pyrazolo[4,3-c]pyridin-3-yl)-N-(pyridin-2-yl)benzamide,
22) (R)-4-(1-(1-acryloylpiperidin-3-yl)-4-amino-1H-pyrazolo[4,3-c]pyridin-3-yl)-N-phenylbenzamide,
23) (R)-4-(1-(1-acryloylpiperidin-3-yl)-4-amino-7-chloro-1H-pyrazolo[4,3-c]pyridin-3-yl)-N-phenylbenzamide,
24) (R)-4-(1-(1-acryloylpiperidin-3-yl)-4-amino-7-bromo-1H-pyrazolo[4,3-c]pyridin-3-yl)-N-phenylbenzamide,
25) (R)-4-(1-(1-acryloylpiperidin-3-yl)-4-amino-7-iodo-1H-pyrazolo[4,3-c]pyridin-3-yl)-N-phenylbenzamide,
26) (R)-4-(1-(1-acryloylpiperidin-3-yl)-4-amino-7-(1-methyl-1H-pyrazol-4-yl)-1H-pyrazolo[4,3-c]pyridin-3-yl)-N-phenylbenzamide,
27) (R)-4-(1-(1-acryloylpiperidin-3-yl)-4-amino-7-(hydroxymethyl)-1H-pyrazolo[4,3-c]pyridin-3-yl)-N-phenylbenzamide,
28) (R)-4-(1-(1-acryloylpiperidin-3-yl)-4-amino-7-(1H-pyrazol-4-yl)-1H-pyrazolo[4,3-c]pyridin-3-yl)-N-phenylbenzamide,
29) (R)-4-(1-(1-acryloylpiperidin-3-yl)-4-amino-7-(1H-pyrazol-3-yl)-1H-pyrazolo[4,3-c]pyridin-3-yl)-N-phenylbenzamide,
30) (R)-4-(1-(1-acryloylpiperidin-3-yl)-4-amino-7-(1H-pyrazol-5-yl)-1H-pyrazolo[4,3-c]pyridin-3-yl)-N-phenylbenzamide,
31) (R)-4-(1-(1-acryloylpiperidin-3-yl)-4-amino-7-(thiophen-3-yl)-1H-pyrazolo[4,3-c]pyridin-3-yl)-N-phenylbenzamide,
32) (R)-4-(1-(1-acryloylpiperidin-3-yl)-4-amino-7-(2-methylthiazol-5-yl)-1H-pyrazolo[4,3-c]pyridin-3-yl)-N-phenylbenzamide,
33) (R)-4-(1-(1-acryloylpiperidin-3-yl)-4-amino-7-(1-(difluoromethyl)-1H-pyrazol-4-yl)-1H-pyrazolo[4,3-c]pyridin-3-yl)-N-phenylbenzamide,
34) (R)-4-(1-(1-acryloylpiperidin-3-yl)-4-amino-7-(1-(tetrahydro-2H-pyran-4-yl)-1H-pyrazol-4-yl)-1H-pyrazolo[4,3-c]pyridin-3-yl)-N-phenylbenzamide,
35) (R)-4-(1-(1-acryloylpiperidin-3-yl)-4-amino-7-(1-(1-methylpiperidin-4-yl)-1H-pyrazol-4-yl)-1H-pyrazolo[4,3-c]pyridin-3-yl)-N-phenylbenzamide,
36) (R)-4-(1-(1-acryloylpiperidin-3-yl)-4-amino-7-(1-(2-(dimethylamino)ethyl)-1H-pyrazol-4-yl)-1H-pyrazolo[4,3-c]pyridin-3-yl)-N-phenylbenzamide,
37) (R)-4-(1-(1-acryloylpiperidin-3-yl)-4-amino-7-(1-(2-(pyrrolidin-1-yl)ethyl)-1H-pyrazol-4-yl)-1H-pyrazolo[4,3-c]pyridin-3-yl)-N-phenylbenzamide,
38) (R)-4-(1-(1-acryloylpiperidin-3-yl)-4-amino-7-(1-(2-morpholinoethyl)-1H-pyrazol-4-yl)-1H-pyrazolo[4,3-c]pyridin-3-yl)-N-phenylbenzamide,
39) (S)-4-(1-(1-acryloylpiperidin-3-yl)-4-amino-1H-pyrazolo[4,3-c]pyridin-3-yl)-N-(pyridin-2-yl)benzamide,
40) (R)-4-(1-(1-acryloylpiperidin-3-yl)-4-amino-1H-pyrazolo[4,3-c]pyridin-3-yl)-3-fluoro-N-(pyridin-2-yl)benzamide,
41) (R)-4-(1-(1-acryloylpiperidin-3-yl)-4-amino-1H-pyrazolo[4,3-c]pyridin-3-yl)-N-(4-fluoropyridin-2-yl)benzamide,
42) (R)—N-acryloyl-4-(1-(1-acryloylpiperidin-3-yl)-4-amino-1H-pyrazolo[4,3-c]pyridin-3-yl)-N-(4-fluoropyridin-2-yl)benzamide,
43) (R)-4-(1-(1-acryloylpiperidin-3-yl)-4-amino-7-(phenylamino)-1H-pyrazolo[4,3-c]pyridin-3-yl)-N-(pyridin-2-yl)benzamide,
44) (R)-4-(1-(1-acryloylpiperidin-3-yl)-4-amino-7-methyl-1H-pyrazolo[4,3-c]pyridin-3-yl)-N-phenylbenzamide,
45) (R)-4-(1-(1-acryloylpiperidin-3-yl)-4-amino-7-methyl-1H-pyrazolo[4,3-c]pyridin-3-yl)-N-(pyridin-2-yl)benzamide,
46) 4-(1-(1-acryloylpyrrolidin-3-yl)-4-amino-7-(1-(difluoromethyl)-1H-pyrazol-4-yl)-1H-pyrazolo[4,3-c]pyridin-3-yl)-N-phenylbenzamide,
47) 4-(1-(1-acryloylpyrrolidin-3-yl)-4-amino-1H-pyrazolo[4,3-c]pyridin-3-yl)-N-phenylbenzamide,
48) 4-(4-amino-1-(1-but-2-ynoylpyrrolidin-3-yl)-1H-pyrazolo[4,3-c]pyridin-3-yl)-N-phenylbenzamide,
49) (R)-4-(1-(1-acryloylpiperidin-3-yl)-4-amino-7-chloro-1H-pyrazolo[4,3-c]pyridin-3-yl)-3-fluoro-N-(pyridin-2-yl)benzamide,
50) (R)-4-(1-(1-acryloylpiperidin-3-yl)-4-amino-7-iodo-1H-pyrazolo[4,3-c]pyridin-3-yl)-3-fluoro-N-(pyridin-2-yl)benzamide,
51) 4-(1-((6R)-2-acryloyl-2-azabicyclo[2.2.1]heptan-6-yl)-4-amino-1H-pyrazolo[4,3-c]pyridin-3-yl)-3-fluoro-N-(pyridin-2-yl)benzamide,
52) 4-(1-(1-acryloylazetidin-3-yl)-4-amino-7-chloro-1H-pyrazolo[4,3-c]pyridin-3-yl)-3-fluoro-N-(pyridin-2-yl)benzamide,
53) (R)-4-(1-(1-acryloylpiperidin-3-yl)-4-amino-7-cyano-1H-pyrazolo[4,3-c]pyridin-3-yl)-3-fluoro-N-(pyridin-2-yl)benzamide,
54) (R)-4-(4-amino-1-(1-methacryloylpiperidin-3-yl)-1H-pyrazolo[4,3-c]pyridin-3-yl)-3-fluoro-N-(pyridin-2-yl)benzamide,
55) (R)-4-(4-amino-7-chloro-1-(1-methacryloylpiperidin-3-yl)-1H-pyrazolo[4,3-c]pyridin-3-yl)-3-fluoro-N-(pyridin-2-yl)benzamide,
56) (R)-4-(1-(1-acryloylpiperidin-3-yl)-4-amino-1H-pyrazolo[4,3-c]pyridin-3-yl)-3-chloro-N-(pyridin-2-yl)benzamide,
57) (R)-4-(1-(1-acryloylpiperidin-3-yl)-4-amino-1H-pyrazolo[4,3-c]pyridin-3-yl)-3-methoxy-N-(pyridin-2-yl)benzamide,
58) (R)-4-(1-(1-acryloylpiperidin-3-yl)-4-amino-7-chloro-1H-pyrazolo[4,3-c]pyridin-3-yl)-3-chloro-N-(pyridin-2-yl)benzamide,
59) (R)-4-(1-(1-acryloylpiperidin-3-yl)-4-amino-7-chloro-1H-pyrazolo[4,3-c]pyridin-3-yl)-3-methoxy-N-(pyridin-2-yl)benzamide,
60) 4-(1-(1-acryloylazetidin-3-yl)-4-amino-7-chloro-1H-pyrazolo[4,3-c]pyridin-3-yl)-3-fluoro-N-(pyridin-2-yl)benzamide,
61) (R)-1-(3-(4-amino-3-(1-cyclopropyl-1H-pyrazol-4-ylamino)-1H-pyrazolo[4,3-c]pyridin-1-yl)piperidin-1-yl)prop-2-en-1-one,
62) (R)-1-(3-(4-amino-3-bromo-1H-pyrazolo[4,3-c]pyridin-1-yl)piperidin-1-yl)prop-2-en-1-one,
63) 4-(1-(1-acryloylazetidin-3-yl)-4-amino-1H-pyrazolo[4,3-c]pyridin-3-yl)-3-chloro-N-(pyridin-2-yl)benzamide,
64) 4-(1-(1-acryloylazetidin-3-yl)-4-amino-7-chloro-1H-pyrazolo[4,3-c]pyridin-3-yl)-3-chloro-N-(pyridin-2-yl)benzamide, 65) (R)-4-(1-(1-acryloylpiperidin-3-yl)-4-amino-7-iodo-1H-pyrazolo[4,3-c]pyridin-3-yl)-3-chloro-N-(pyridin-2-yl)benzamide,
66) (R)-4-(1-(1-acryloylpiperidin-3-yl)-4-amino-7-cyano-1H-pyrazolo[4,3-c]pyridin-3-yl)-3-chloro-N-(pyridin-2-yl)benzamide,
67) (R)-4-(1-(1-acryloylpiperidin-3-yl)-4-amino-7-(1-methyl-1H-pyrazol-4-yl)-1H-pyrazolo[4,3-c]pyridin-3-yl)-3-chloro-N-(pyridin-2-yl)benzamide,
68) (R)-4-(1-(1-acryloylpiperidin-3-yl)-4-amino-7-ethyl-1H-pyrazolo[4,3-c]pyridin-3-yl)-3-chloro-N-(pyridin-2-yl)benzamide,
69) (R)-4-(1-(1-acryloylpiperidin-3-yl)-4-amino-7-vinyl-1H-pyrazolo[4,3-c]pyridin-3-yl)-3-chloro-N-(pyridin-2-yl)benzamide,
70) (R)-4-(1-(1-acryloylpiperidin-3-yl)-4-amino-7-(1H-pyrazol-4-yl)-1H-pyrazolo[4,3-c]pyridin-3-yl)-3-chloro-N-(pyridin-2-yl)benzamide,
71) (R)-1-(1-acryloylpiperidin-3-yl)-4-amino-N-(5-chlorobenzo[d]oxazol-2-yl)-1H-pyrazolo[4,3-c]pyridine-3-carboxamide,
72) (R)-tert-butyl 1-(1-acryloylpiperidin-3-yl)-4-amino-1H-pyrazolo[4,3-c]pyridine-3-carboxylate,
73) (R)-1-(1-acryloylpiperidin-3-yl)-4-amino-N-(6-bromobenzo[d]oxazol-2-yl)-1H-pyrazolo[4,3-c]pyridine-3-carboxamide,
74) (R)-1-(1-acryloylpiperidin-3-yl)-4-amino-7-chloro-N-(5-chlorobenzo[d]oxazol-2-yl)-1H-pyrazolo[4,3-c]pyridine-3-carboxamide,
75) (R)-1-(1-acryloylpiperidin-3-yl)-4-amino-N-(benzo[d]oxazol-2-yl)-7-chloro-1H-pyrazolo[4,3-c]pyridine-3-carboxamide,
76) (R)-1-(1-acryloylpiperidin-3-yl)-4-amino-7-chloro-N-(5-fluorobenzo[d]oxazol-2-yl)-1H-pyrazolo[4,3-c]pyridine-3-carboxamide,
77) (R)-1-(1-acryloylpiperidin-3-yl)-4-amino-N-(benzo[d]oxazol-2-yl)-1H-pyrazolo[4,3-c]pyridine-3-carboxamide,
78) (R)-1-(1-acryloylpiperidin-3-yl)-4-amino-7-chloro-N-phenyl-1H-pyrazolo[4,3-c]pyridine-3-carboxamide, and
79) (R)-1-(1-acryloylpiperidin-3-yl)-4-amino-7-chloro-N-(2,3-dihydrobenzo[b][1,4]dioxin-6-yl)-1H-pyrazolo[4,3-c]pyridine-3-carboxamide.

8. A pharmaceutical composition comprising a compound of claim 1, or a pharmaceutically acceptable salt thereof as an active ingredient and a pharmaceutically acceptable diluent.

9. A method of inhibiting Bruton's tyrosine kinase (BTK) and Interleukin-2 tyrosine kinase (ITK), comprising administering a compound of claim 1, or a pharmaceutically acceptable salt thereof to a subject in need thereof.

* * * * *